US012667431B2

(12) United States Patent
Shelton, IV et al.

(10) Patent No.: US 12,667,431 B2
(45) Date of Patent: Jun. 30, 2026

(54) SITUATION ADAPTABLE SURGICAL INSTRUMENT CONTROL

(71) Applicant: Cilag GmbH International, Zug (CH)

(72) Inventors: Frederick E. Shelton, IV, Hillsboro, OH (US); Jason L. Harris, Lebanon, OH (US); Kevin M. Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 906 days.

(21) Appl. No.: 17/156,300

(22) Filed: Jan. 22, 2021

(65) Prior Publication Data

US 2022/0233253 A1 Jul. 28, 2022

(51) Int. Cl.
A61B 34/00 (2016.01)
A61B 90/00 (2016.01)
(Continued)

(52) U.S. Cl.
CPC .............. A61B 34/25 (2016.02); A61B 90/08 (2016.02); G16H 40/20 (2018.01); G16H 40/60 (2018.01);
(Continued)

(58) Field of Classification Search
CPC ... A61B 34/25; A61B 90/08; A61B 2034/252; A61B 2090/0807; G16H 40/20; G16H 40/60; G16H 20/40
See application file for complete search history.

(56) References Cited

U.S. PATENT DOCUMENTS 5,406,914 A 4/1995 Hyppanen
5,494,546 A 2/1996 Horvath
(Continued)

FOREIGN PATENT DOCUMENTS

CA 3032139 A1 2/2018
CA 3080325 A1 5/2019
(Continued)

OTHER PUBLICATIONS

U.S. Appl. No. 17/156,287, filed Jan. 22, 2021, Shelton, et al.
U.S. Appl. No. 17/156,296, filed Jan. 22, 2021, Shelton, et al.
U.S. Appl. No. 17/156,304, filed Jan. 22, 2021, Shelton, et al.
U.S. Appl. No. 17/156,266, filed Jan. 22, 2021, Shelton, et al.
(Continued)

*Primary Examiner* — Christopher L Gilligan
(74) *Attorney, Agent, or Firm* — Condo Roccia Koptiw LLP

(57) ABSTRACT

A surgical computing system and/or a surgical instrument may determine situational awareness about a surgical procedure based on information provided by one or more sensors and dynamically adapt operation and/or control of surgical instruments and/or communication of information to healthcare professionals based on the determined situational awareness. Situational awareness may include, for example, an importance level (e.g., a stress level or attention) of a health care provider, possession of a controllable surgical instrument by a health care provider, and/or body positioning of a health care provider. Situational awareness may be determined based on information provided by one or more personnel (e.g., wearable) sensing systems, environmental sensing systems, and/or surgical instruments, such as one or more of healthcare provider data (e.g., position, posture, balance, motion, attention, physiologic states), environmental data (e.g., operating room noise level, patient data, healthcare provider data), and/or surgical instrument data (e.g., position, motion, possession, and/or usage).

11 Claims, 33 Drawing Sheets

(51) Int. Cl.
　　 *G16H 40/20* 　　　(2018.01)
　　 *G16H 40/60* 　　　(2018.01)
(52) U.S. Cl.
　　 CPC . *A61B 2034/252* (2016.02); *A61B 2090/0807*
　　　　　　　　　　　　　　　　　　　(2016.02)

(56) References Cited

U.S. PATENT DOCUMENTS

| | | | |
|---|---|---|---|
| 6,036,446 | A | 3/2000 | Goodman |
| 6,317,731 | B1 | 11/2001 | Luciano |
| 6,491,701 | B2 | 12/2002 | Tierney et al. |
| 6,840,913 | B2 | 1/2005 | Mansy et al. |
| 7,321,862 | B2 | 1/2008 | Rosenfeld et al. |
| 8,512,260 | B2 | 8/2013 | Grudic et al. |
| 8,583,224 | B2 | 11/2013 | Lee et al. |
| 8,696,616 | B2 | 4/2014 | Baynham et al. |
| 8,864,009 | B2 | 10/2014 | Shelton et al. |
| 9,011,427 | B2 | 4/2015 | Price et al. |
| 9,028,407 | B1 | 5/2015 | Bennett-guerrero |
| 9,072,535 | B2 | 7/2015 | Shelton et al. |
| 9,123,155 | B2 | 9/2015 | Cunningham et al. |
| 9,345,481 | B2 | 5/2016 | Hall et al. |
| 9,525,482 | B1 | 12/2016 | Tse |
| 9,621,357 | B2 | 4/2017 | Williams et al. |
| 9,700,317 | B2 | 7/2017 | Aronhalt et al. |
| 9,855,431 | B2 | 1/2018 | Ternes et al. |
| 9,974,903 | B1 | 5/2018 | Davis et al. |
| 10,065,658 | B2 | 9/2018 | Deligianni et al. |
| 10,194,873 | B2 | 2/2019 | Colman et al. |
| 10,467,327 | B1 | 11/2019 | Arazi |
| 10,535,020 | B2 | 1/2020 | Experton |
| 10,813,710 | B2 | 10/2020 | Grubbs |
| 10,943,692 | B1 | 3/2021 | Lynn et al. |
| 10,993,645 | B2 | 5/2021 | Naseri et al. |
| 11,099,647 | B2 | 8/2021 | Ang et al. |
| 11,182,576 | B1 | 11/2021 | Bhushan et al. |
| 11,238,012 | B1 | 2/2022 | Liang et al. |
| 11,240,404 | B2 | 2/2022 | Bangs et al. |
| 11,543,887 | B2 | 1/2023 | Ang et al. |
| 11,728,033 | B2 * | 8/2023 | Spenciner ............... G16H 40/20 |
| | | | 705/2 |
| 2002/0111830 | A1 | 8/2002 | Tahan |
| 2003/0139942 | A1 | 7/2003 | Rakshit et al. |
| 2004/0071323 | A1 | 4/2004 | Darzi et al. |
| 2005/0021369 | A1 | 1/2005 | Cohen et al. |
| 2007/0136218 | A1 * | 6/2007 | Bauer ................... G16H 50/20 |
| | | | 700/83 |
| 2008/0064965 | A1 | 3/2008 | Jay et al. |
| 2008/0300915 | A1 | 12/2008 | Molmenti et al. |
| 2009/0299924 | A1 | 12/2009 | Bauer et al. |
| 2011/0152759 | A1 | 6/2011 | Clymer et al. |
| 2011/0319746 | A1 | 12/2011 | Kochba et al. |
| 2012/0116365 | A1 | 5/2012 | Price et al. |
| 2012/0132211 | A1 | 5/2012 | Halperin et al. |
| 2012/0265549 | A1 | 10/2012 | Virolainen |
| 2012/0310670 | A1 | 12/2012 | Pruitt |
| 2013/0038707 | A1 | 2/2013 | Cunningham et al. |
| 2013/0137941 | A1 | 5/2013 | Schardey |
| 2013/0245481 | A1 | 9/2013 | Tremper |
| 2013/0265919 | A1 | 10/2013 | Pochiraju et al. |
| 2014/0051921 | A1 | 2/2014 | Miller et al. |
| 2014/0081659 | A1 | 3/2014 | Nawana et al. |
| 2014/0157288 | A1 | 6/2014 | Wong |
| 2014/0236159 | A1 | 8/2014 | Haider et al. |
| 2014/0263541 | A1 | 9/2014 | Leimbach et al. |
| 2014/0263551 | A1 | 9/2014 | Hall et al. |
| 2014/0263552 | A1 | 9/2014 | Hall et al. |
| 2014/0287393 | A1 | 9/2014 | Kumar et al. |
| 2015/0109196 | A1 | 4/2015 | Grass et al. |
| 2015/0173697 | A1 | 6/2015 | Parks et al. |
| 2015/0199010 | A1 | 7/2015 | Coleman et al. |
| 2015/0289929 | A1 | 10/2015 | Toth et al. |
| 2015/0302536 | A1 | 10/2015 | Wahl et al. |
| 2015/0302538 | A1 | 10/2015 | Mazar et al. |
| 2015/0317230 | A1 | 11/2015 | Le Grand |
| 2016/0000631 | A1 * | 1/2016 | Becker ................... A61G 13/10 |
| | | | 700/60 |
| 2016/0030240 | A1 | 2/2016 | Gonenc et al. |
| 2016/0110504 | A1 | 4/2016 | Fialkov |
| 2016/0239611 | A1 | 8/2016 | Heldt et al. |
| 2016/0303340 | A1 | 10/2016 | Sinderby et al. |
| 2016/0331248 | A1 | 11/2016 | Satish et al. |
| 2017/0041688 | A1 | 2/2017 | Pitigoi-aron et al. |
| 2017/0068785 | A1 | 3/2017 | Experton et al. |
| 2017/0119300 | A1 | 5/2017 | Conner |
| 2017/0143268 | A1 | 5/2017 | Kovacs et al. |
| 2017/0228501 | A1 | 8/2017 | Turner, Jr. et al. |
| 2017/0258408 | A1 | 9/2017 | Stapelfeldt |
| 2017/0281064 | A1 | 10/2017 | Bayon |
| 2017/0296139 | A1 | 10/2017 | Giaya et al. |
| 2017/0296213 | A1 | 10/2017 | Swensgard et al. |
| 2017/0331881 | A1 | 11/2017 | Chandramouli et al. |
| 2017/0360358 | A1 | 12/2017 | Amiot et al. |
| 2018/0028088 | A1 | 2/2018 | Garbey et al. |
| 2018/0042681 | A1 | 2/2018 | Jagga |
| 2018/0090029 | A1 | 3/2018 | Fisher et al. |
| 2018/0102960 | A1 | 4/2018 | Rickert et al. |
| 2018/0168579 | A1 | 6/2018 | Aronhalt et al. |
| 2018/0256051 | A1 | 9/2018 | Stone et al. |
| 2018/0262656 | A1 | 9/2018 | Uchida et al. |
| 2018/0286521 | A1 | 10/2018 | Fong |
| 2018/0360451 | A1 | 12/2018 | Shelton et al. |
| 2018/0360452 | A1 | 12/2018 | Shelton et al. |
| 2019/0013099 | A1 | 1/2019 | Esterberg et al. |
| 2019/0014992 | A1 | 1/2019 | Mestek et al. |
| 2019/0059932 | A1 | 2/2019 | Isosaki et al. |
| 2019/0069957 | A1 * | 3/2019 | Barral ................... A61B 34/20 |
| 2019/0079916 | A1 | 3/2019 | Eyigoz |
| 2019/0090969 | A1 | 3/2019 | Jarc et al. |
| 2019/0104919 | A1 | 4/2019 | Shelton, IV et al. |
| 2019/0113973 | A1 | 4/2019 | Coleman et al. |
| 2019/0190635 | A1 | 6/2019 | Goel et al. |
| 2019/0192072 | A1 | 6/2019 | Bailey et al. |
| 2019/0200844 | A1 | 7/2019 | Shelton et al. |
| 2019/0200981 | A1 | 7/2019 | Harris et al. |
| 2019/0201033 | A1 | 7/2019 | Yates et al. |
| 2019/0201043 | A1 | 7/2019 | Shelton, IV et al. |
| 2019/0201102 | A1 | 7/2019 | Shelton, IV et al. |
| 2019/0201104 | A1 | 7/2019 | Shelton, IV et al. |
| 2019/0201115 | A1 | 7/2019 | Shelton et al. |
| 2019/0201129 | A1 | 7/2019 | Shelton, IV et al. |
| 2019/0201136 | A1 | 7/2019 | Shelton et al. |
| 2019/0201137 | A1 | 7/2019 | Shelton et al. |
| 2019/0201140 | A1 | 7/2019 | Yates et al. |
| 2019/0204201 | A1 | 7/2019 | Shelton, IV et al. |
| 2019/0206050 | A1 | 7/2019 | Yates et al. |
| 2019/0206562 | A1 | 7/2019 | Shelton, IV et al. |
| 2019/0206563 | A1 | 7/2019 | Shelton, IV et al. |
| 2019/0206569 | A1 | 7/2019 | Shelton et al. |
| 2019/0216452 | A1 | 7/2019 | Nawana et al. |
| 2019/0223961 | A1 | 7/2019 | Barral et al. |
| 2019/0228859 | A1 * | 7/2019 | Moctezuma de la Barrera .......... |
| | | | G16H 40/63 |
| 2019/0258672 | A1 | 8/2019 | Sadrieh |
| 2019/0259476 | A1 | 8/2019 | Armijos |
| 2019/0392162 | A1 | 12/2019 | Stern et al. |
| 2020/0143594 | A1 | 5/2020 | Lal et al. |
| 2020/0168313 | A1 | 5/2020 | Westerhoff |
| 2020/0168334 | A1 | 5/2020 | Mowery |
| 2020/0184850 | A1 | 6/2020 | Pugh |
| 2020/0188028 | A1 | 6/2020 | Feiner et al. |
| 2020/0204631 | A1 | 6/2020 | Subramaniam et al. |
| 2020/0237452 | A1 | 7/2020 | Wolf et al. |
| 2020/0246081 | A1 | 8/2020 | Johnson et al. |
| 2020/0268472 | A1 | 8/2020 | Wolf et al. |
| 2020/0273575 | A1 | 8/2020 | Wolf et al. |
| 2020/0273581 | A1 | 8/2020 | Wolf et al. |
| 2020/0315454 | A1 | 10/2020 | Gregg |
| 2020/0315734 | A1 | 10/2020 | El Amm |
| 2020/0394334 | A1 | 12/2020 | Bulut et al. |
| 2020/0397515 | A1 | 12/2020 | Frimer et al. |
| 2021/0000558 | A1 | 1/2021 | Penny et al. |
| 2021/0005321 | A1 | 1/2021 | Hwang |
| 2021/0007774 | A1 | 1/2021 | Rodrigues et al. |

(56)        References Cited

U.S. PATENT DOCUMENTS

| | | | |
|---|---|---|---|
| 2021/0015432 A1 | 1/2021 | Konno et al. | |
| 2021/0098088 A1 | 4/2021 | Hashimoto et al. | |
| 2021/0117868 A1 | 4/2021 | Sriharsha | |
| 2021/0158955 A1 | 5/2021 | Azizian et al. | |
| 2021/0196384 A1 | 7/2021 | Shelton, IV et al. | |
| 2021/0196423 A1 | 7/2021 | Shelton, IV et al. | |
| 2021/0196425 A1 | 7/2021 | Shelton, IV et al. | |
| 2021/0241869 A1 | 8/2021 | Muse et al. | |
| 2021/0257095 A1 | 8/2021 | Zacharia | |
| 2021/0313052 A1 | 10/2021 | Makrinich et al. | |
| 2021/0346583 A1 | 11/2021 | Diaz-chiosa et al. | |
| 2021/0346853 A1 | 11/2021 | Hull et al. | |
| 2021/0386489 A1 | 12/2021 | Wright et al. | |
| 2022/0022982 A1 | 1/2022 | Hares et al. | |
| 2022/0079675 A1 * | 3/2022 | Lang | G02B 30/52 |
| 2022/0104896 A1 | 4/2022 | Shelton, IV et al. | |
| 2022/0409285 A1 | 12/2022 | Chow et al. | |
| 2023/0145790 A1 | 5/2023 | Walker et al. | |

FOREIGN PATENT DOCUMENTS

| | | | |
|---|---|---|---|
| CA | 3101092 A1 | 10/2019 | |
| CN | 109575143 A | 4/2019 | |
| CN | 111616803 A | 9/2020 | |
| CN | 112220562 A | 1/2021 | |
| EP | 3501459 A2 | 6/2019 | |
| EP | 3671305 A1 * | 6/2020 | |
| EP | 3671759 A1 | 6/2020 | |
| EP | 3 895 613 A1 | 10/2021 | |
| GB | 2333882 A | 8/1999 | |
| JP | 2019-525276 A | 9/2019 | |
| JP | 2019-177134 A | 10/2019 | |
| WO | 2007/025218 A2 | 3/2007 | |
| WO | 2007/096931 A2 | 8/2007 | |
| WO | 2010/017192 A1 | 2/2010 | |
| WO | 2016/046634 A1 | 3/2016 | |
| WO | 2017/098503 A1 | 6/2017 | |
| WO | 2017/147652 A1 | 9/2017 | |
| WO | 2018/023037 A1 | 2/2018 | |
| WO | 2019/084469 A1 | 5/2019 | |
| WO | 2019/130075 A1 | 7/2019 | |
| WO | 2019/130085 A1 | 7/2019 | |
| WO | 2019/147718 A1 | 8/2019 | |
| WO | 2019/181432 A1 | 9/2019 | |
| WO | 2019200222 A1 | 10/2019 | |
| WO | 2020/075546 A1 | 4/2020 | |
| WO | 2020/092701 A2 | 5/2020 | |
| WO | 2020/180917 A1 | 9/2020 | |
| WO | 2020/191494 A1 | 10/2020 | |
| WO | 2021/007418 A2 | 1/2021 | |
| WO | 2021/126163 A1 | 6/2021 | |

OTHER PUBLICATIONS

U.S. Appl. No. 17/156,318, filed Jan. 22, 2021, Shelton, et al.
U.S. Appl. No. 17/156,309, filed Jan. 22, 2021, Shelton, et al.
U.S. Appl. No. 17/156,306, filed Jan. 22, 2021, Shelton, et al.
U.S. Appl. No. 17/156,321, filed Jan. 22, 2021, Shelton, et al.
U.S. Appl. No. 17/156,281, filed Jan. 22, 2021, Shelton, et al.
U.S. Appl. No. 17/156,272, filed Jan. 22, 2021, Shelton, et al.
U.S. Appl. No. 17/156,279, filed Jan. 22, 2021, Shelton, et al.
U.S. Appl. No. 17/156,284, filed Jan. 22, 2021, Shelton, et al.
U.S. Appl. No. 17/156,282, filed Jan. 22, 2021, Shelton, et al.
U.S. Appl. No. 17/156,269, filed Jan. 22, 2021, Shelton, et al.
U.S. Appl. No. 17/156,286, filed Jan. 22, 2021, Shelton, et al.
U.S. Appl. No. 17/156,324, filed Jan. 22, 2021, Shelton, et al.
U.S. Appl. No. 17/156,329, filed Jan. 22, 2021, Shelton, et al.
U.S. Appl. No. 17/156,289, filed Jan. 22, 2021, Shelton, et al.
U.S. Appl. No. 17/156,293, filed Jan. 22, 2021, Shelton, et al.
U.S. Appl. No. 17/156,298, filed Jan. 22, 2021, Shelton, et al.
U.S. Appl. No. 17/156,274, filed Jan. 22, 2021, Shelton, et al.

U.S. Appl. No. 17/156,278, filed Jan. 22, 2021, Shelton, et al.
U.S. Appl. No. 17/062,509, filed Oct. 2, 2020, Shelton, et al.
U.S. Appl. No. 62/611,341, filed Dec. 28, 2017, Shelton, et al.
Aliverti, et al., "Wearable technology: role in respiratory health and disease", Breathe, 2017, 10 pages.
Kazamias, et al., "Blood pressure measurement with Doppler ultrasonic flowmeter", Journal of Applied Physiology vol. 30, No. 4, Apr. 1971, 1 page.
Cerfolio, et a., "Prospective Randomized Trial Compares Suction Versus Water Seal for Air Leaks", General Thoracic, May 1, 2001, 5 pages.
Brunelli, et al., "A Scoring System to Predict the Risk of Prolonged Air Leak After Lobectomy", General Thoracic, 2010, 6 pages.
Jacob, et al., "Clinical applications of magnets on cardiac rhythm management devices", European Society of Cardiology, May 26, 2011, 9 pages.
Carroll, et al., "Multi-Sensor Esophageal Temperature Probe Used During Radiofrequency Ablation for Atrial Fibrillation is Associated with Increased Intraluminal Temperature Detection and Increased Risk of Esophageal Injury Compared to Single-Sensor Probe", Journal of Cardiovascular Electrophysiology vol. 24, No. 9, Sep. 2013, 8 pages.
Singh, et al., "Esophageal Injury and Temperature Monitoring During Atrial Fibrillation Ablation", American Heart Association, Circulation: Arrhythmia and Electrophysiology, vol. 1, issue 3, Aug. 1, 2008, 7 pages.
Nair, et al., "Atrioesophageal Fistula: A Review", Journal of Atrial Fibrillation vol. 8, Issue 3, October Nov. 2015, 6 pages.
Drewry, et al., "Body temperature patterns as a predictor of hospital-acquired sepsis in afebrile adult intensive care unit patients: a case-control study", Critical Care 2013, 11 pages.
Diduch, et al., "Synchronization of Data Streams in Distributed Realtime Multimodal Signal Processing Environments Using Commodity Hardware", 4 pages.
Kwon, et al., "Electrocardiogram Sampling Frequency Range Acceptable for Heart Rate Variability Analysis", The Korean Society of Medical Informatics, 2018, 9 pages.
Pouchard, et al., "Open Standards for Sensor Information Processing", Oak Ridge National Laboratory, Jul. 2009, 49 pages.
Appelboom et al., "The Promise of Wearable Activity Sensors to Define Patient Recovery", Journal of Clinical Neuroscience, vol. 21, Jul. 1, 2014, pp. 1089-1093.
Chen et al., "Type of Pelvic Disease as a Risk Factor for Surgical Site Infection in Women Undergoing Hysterectomy", Journal of Minimally Invasive Gynecology, vol. 26, No. 6, Sep. 1, 2019, pp. 1149-1156.
Erowele et al., "Treatment Options for Postoperative Ileus", US Pharmacist, vol. 35, 2010.
Sugino et al., "Surgical Task Analysis of Simulated Laparoscopic Cholecystectomy with a Navigation System", International Journal of Computer Assisted Radiology and Surgery, vol. 9, Jan. 14, 2014, pp. 825-836.
Fang et al., "Review of Colonic Anastomotic Leakage and Prevention Methods", Journal of Clinical Medicine, vol. 9, No. 4061, Dec. 16, 2020, 17 pages.
Jinbin, "Feedback Loops—Friend or Foe?", Available at <https://medium.com/unpackai/feedback-loops-friend-or-foe-81a552203228>, Oct. 19, 2020, pp. 1-3.
Li et al., "Attention-Aware Robotic Laparoscope for Human-Robot Cooperative Surgery", IEEE International Conference on Robotics and Biomimetics (ROBIO), 2013, 6 pages.
Machado, Lovina S. M., Emergency Peripartum Hysterectomy: Incidence, Indications, Risk Factors and Outcome, North American Journal of Medical Sciences, vol. 3, No. 8, Aug. 2011, doi: 10.4297/najms.2011.358, pp. 358-361.
International Search Report and Written Opinion received for PCT Application No. PCT/IB2022/050530, mailed on Apr. 25, 2022, 15 pages.
International Search Report and Written Opinion received for PCT Application No. PCT/IB2022/050540, mailed on Jul. 26, 2022, 13 pages.

(56) References Cited

OTHER PUBLICATIONS

International Search Report and Written Opinion received for PCT Application No. PCT/IB2022/050541, mailed on Jun. 7, 2022, 15 pages.

Invitation to Pay Additional Fees received for PCT Application No. PCT/IB2022/050540, mailed on Apr. 11, 2022, 9 pages.

Davies, et al., "Preoperative Optimization of the High-Risk Surgical Patient", British Journal of Anaesthesia, vol. 93, Advance Access publication, Apr. 30, 2004, pp. 121-128.

Foroutan, et al., "An Increase in Heart Rate Variability Can Be An Index For End Point of Resuscitation in Trauma Patients", Chinese Journal of Traumatology 22, vol. 22, No. 3, Apr. 16, 2019, pp. 134-137.

Gehrich, et al., "Risk of Postoperative Urinary Tract Infections Following Midurethral Sling Operations in Women Undergoing Hysterectomy", International Urogynecology Journal, vol. 27, No. 3, Oct. 14, 2015, pp. 483-490.

Kirchhoff, et al., "Complications in Colorectal Surgery: Risk Factors and Preventive Strategies", Patient Safety in vol. 04, Mar. 25, 2010, 13 pages.

Levine, et al., "Computer Automated Total Periopertative Situational Awareness and Safety System", Computer Assisted Radiology and Surgery, International Series, vol. 1281, Jun. 2005, 6 pages.

Macefield, et al., "Development of a Single, Practical Measure of Surgical Site Infection (SSI) for Patient Report or Completion", Journal of Infection Prevention, vol. 18, No. 4, 2017, pp. 170-179.

Petrella, et al., "Predicting Prolonged Air Leak After Standard Pulmonary Lobectomy: Computed Tomography And Risk Factors Stratification", The Surgeon, vol. 9, 2011, pp. 72-77.

Schug, et al., "Postoperative Pain Management of the Obese Patient", Best Practice & Research Clinical vol. 25, No. 1, 2011, pp. 73-81.

Stoppelkamp, et al., "Identification of Predictive Early Biomarkers for Sterile-SIRS after Cardiovascular Surgery", PLOS vol. 10, No. 8, Aug. 11, 2015, 20 pages.

Veliković, V. Jelena, "The Predictive Performance of the Possum Scoring System and Early Indicators of Peripheral Perfusion for Complications After Major Abdominal Surgery", University of Belgrade, School of Medicine, 2019, pp. 1-163.

Clarke-Pearson et al., "Complications of Hysterectomy", Clinical Expert Series, vol. 121, No. 3, Mar. 2013, pp. 654-673.

Derbyshire et al., "Lactate in Human Sweat: A Critical Review of Research to the Present Day", Journal of Physiotherapy, vol. 62, Jun. 8, 2012, pp. 429-440.

Ewenighi, Chinwe O. et al., "Electrolyte changes and urinalysis pattern in patients with vesicovaginal fistula compared to their healthy controls", Journal of Experimental and Integrative Medicine; Oct-Dec. 2014; vol. 4., Issue 4, 2014, 5 pages.

Gill et al., "Urinary Leakage following hysterectomy", Cambridge University Press, 2014, pp. 261-262.

Johnston et al., "Postoperative Hypoglycemia Is Associated With Worse Outcomes After Cardiac Surgery", The Annals of Thoracic Surgery, vol. 103, No. 2, Feb. 2017, pp. 1-14.

McGillion et al., "Postoperative Remote Automated Monitoring and Virtual Hospital-to-Home Care System Following Cardiac and Major Vascular Surgery: User Testing Study", Journal of Medical Internet Research, vol. 22, No. 03, Mar. 18, 2020, pp. 1-18.

Mišić et al., "Real-Time Monitoring of Bone Fracture Recovery by Using Aware, Sensing, Smart, and Active Orthopedic Devices", IEEE Internet of things Journal, vol. 5, No. 6, Dec. 2018, pp. 4466-4473.

Szarka et al., "Methods for Measurement of Gastric Motility", American Journal of Physiology-Gastrointestinal and Liver Physiology, vol. 296, No. 3, Jan. 15, 2009, pp. 461-475.

* cited by examiner

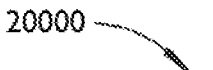
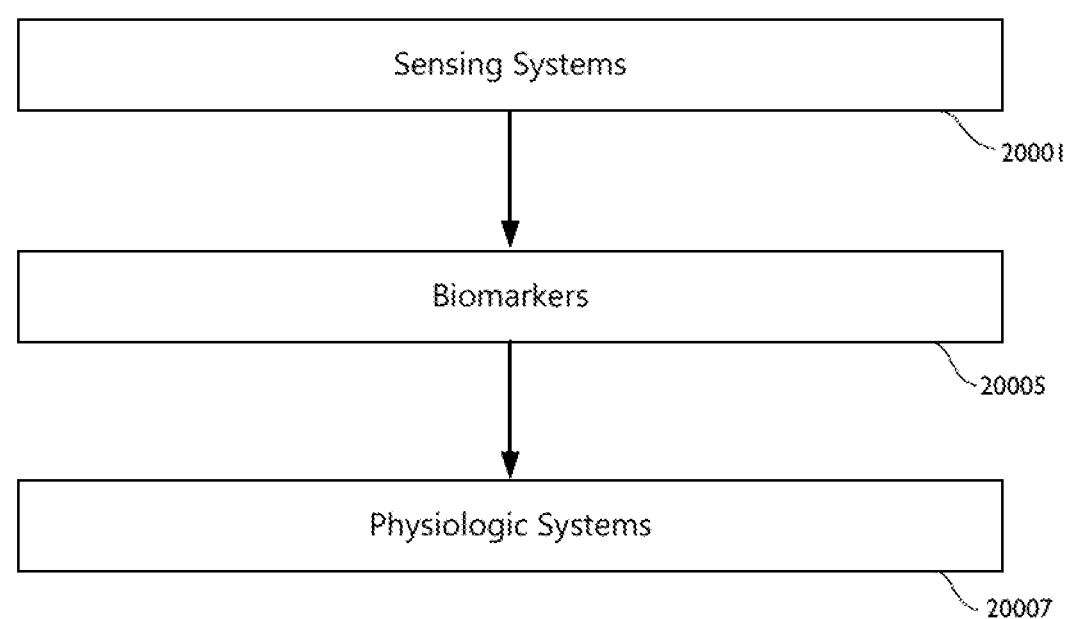
FIG. 1B

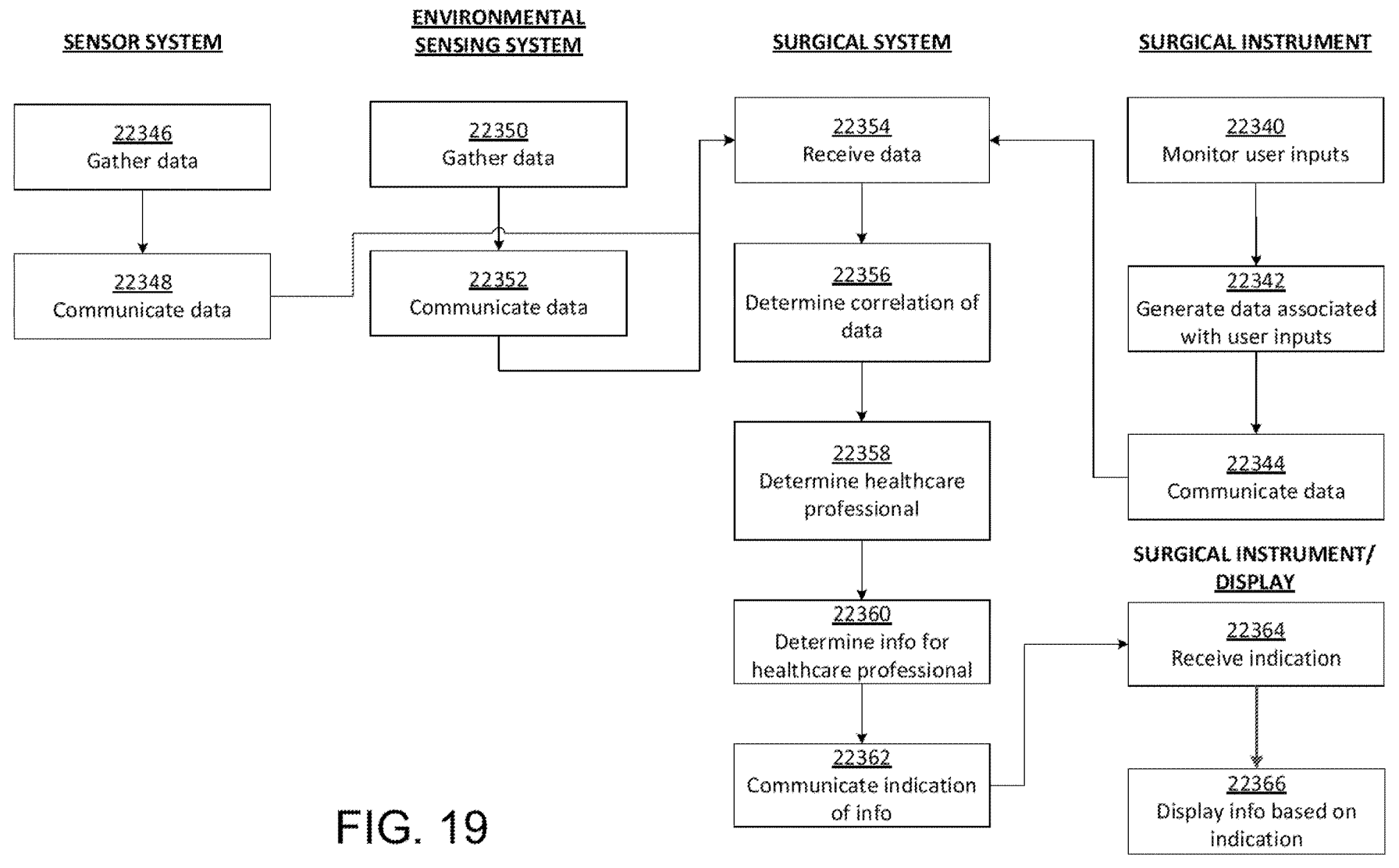

SURGICAL INSTRUMENT

22340
Monitor user inputs

22342
Generate data associated with user inputs

22344
Communicate data

SURGICAL INSTRUMENT/ DISPLAY

22364
Receive indication

22366
Display info based on indication

SURGICAL SYSTEM

22354
Receive data

22356
Determine correlation of data

22358
Determine healthcare professional

22360
Determine info for healthcare professional

22362
Communicate indication of info

ENVIRONMENTAL SENSING SYSTEM

22350
Gather data

22352
Communicate data

SENSOR SYSTEM

22346
Gather data

22348
Communicate data

FIG. 19

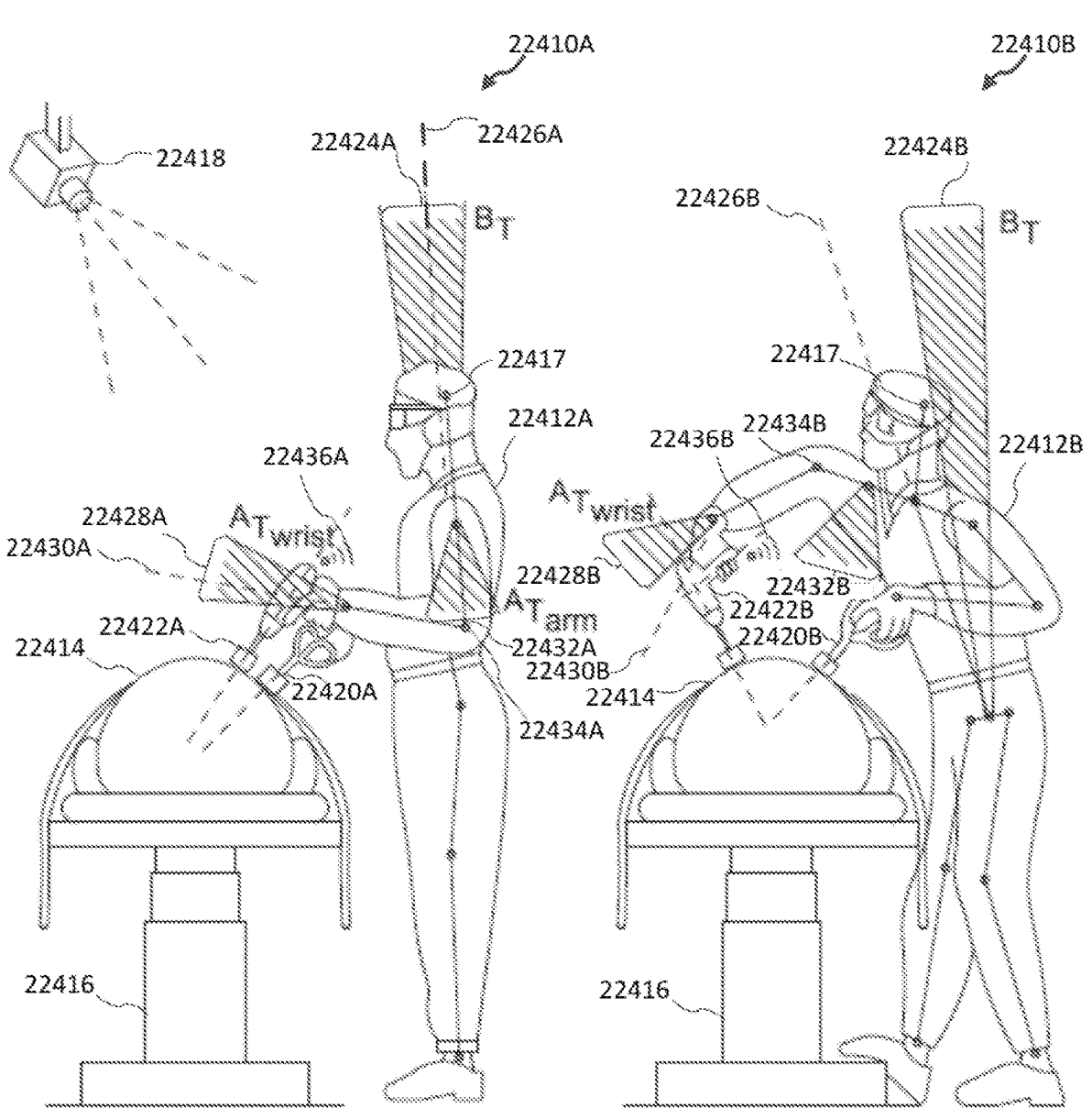
FIG. 22A                    FIG. 22B

SITUATION ADAPTABLE SURGICAL INSTRUMENT CONTROL

CROSS-REFERENCE TO RELATED APPLICATIONS

This application is related to the following, filed contemporaneously, the contents of each of which are incorporated by reference herein:

U.S. patent application Ser. No. 17/156,287, filed Jan. 22, 2021A, titled METHOD OF ADJUSTING A SURGICAL PARAMETER BASED ON BIOMARKER MEASUREMENTS.

U.S. patent application Ser. No. 17/156,296, filed Jan. 22, 2021, titled ADAPTABLE SURGICAL INSTRUMENT CONTROL.

U.S. patent application Ser. No. 17/156,304, filed Jan. 22, 2021, titled SURGICAL PROCEDURE MONITORING.

BACKGROUND

Healthcare professionals handle surgical instruments such as, for example, surgical staplers and surgical cutters while performing surgical procedures. A healthcare professional may handle an endocutter surgical instrument to position the endocutter surgical instrument at the appropriate location and orientation to engage particular tissue of a patient. The healthcare professional may interact with a surgical instrument's control components such as, for example, handles, triggers, and displays to position a surgical instrument and perform surgical operations.

SUMMARY

Systems, methods and instrumentalities are disclosed for adaptively adjusting operation and/or control of a surgical instrument and/or adaptively communicating information to a healthcare professional. Adaptation of operation, control and/or communication may be based on, for example, situational awareness of a surgical procedure. Situational awareness may include, for example, an importance level as indicated by a detected stress level and/or focus of attention of a health care provider, possession of a controllable surgical instrument by a health care provider, and/or body positioning of a health care provider. Situational awareness may be determined, for example, based on information provided by one or more personnel (e.g., wearable) sensing systems, environmental sensing systems, and/or surgical instruments. The information may comprise, for example, one or more of healthcare provider data (e.g., position, posture, balance, motion, attention, physiologic states), environmental data (e.g., operating room noise level, patient data, healthcare provider data), and/or surgical instrument data (e.g., position, possession, motion, and/or usage). A surgical computing system and/or a surgical instrument may receive information, determine situational awareness and adapt instrument operation, control and/or information communication based on situational awareness.

Situational awareness may be monitored, for example, to assess the criticality of an operation in a surgical procedure. A surgical operation may be modified based on criticality. A surgical computing system may receive biomarker data from one or more sensing systems and/or environmental data from one or more environmental sensing systems. The biomarker data may be associated with a healthcare professional operating a surgical instrument. Biomarker data may include, for example, one or more of heart rate, blood pressure, sweat, physical activity, body movement, or eye movement. Environmental data may include, for example, one or more of noise level, healthcare professional attention (e.g., based on eye tracking, such as location and/or time of view), and/or patient biomarkers. The surgical computing system may determine an importance level, for example, based on one or more of biomarker data, environmental data, and/or data associated with a surgical procedure. The surgical computing system may determine, based on the importance level, one or more operational parameters for the surgical instrument. A surgical computing system may determine whether to modify one or more operational parameters based on a determination whether data such as, for example, biomarker data, is within an expected range for a step in a surgical procedure. The surgical computing system may communicate the one or more operational parameters to the surgical instrument.

Instrument motions and operator motions may be assessed to determine the operator of a surgical instrument. A surgical computing system may receive biomarker data which may include movement data from a plurality of sensing systems associated with one of a plurality of healthcare professionals. The surgical computing system may receive usage data which may include movement data from a surgical instrument. The surgical computing system may determine which one of the plurality of healthcare providers has possession of the surgical instrument based at least on the biomarker data and usage data. For example, a surgical computing system may determine whether a healthcare provider's biomarker data including movement data corresponds to usage data including movement data from the surgical instrument. The surgical computing system may determine information for communication to a healthcare provider, for example, based on possession of the surgical instrument. Information communicated to an assistant in possession of an instrument may include, for example, information associated with preparing the surgical instrument for operation. Information communicated to a physician in possession of an instrument may include, for example, information associated with previous use of the surgical instrument. Inconsistencies between data may be detected. The surgical computing system may determine the surgical instrument is not located in an area identified for performing a surgical procedure, for example, based at least on an inconsistency between the biomarker data and usage data. The surgical computing system may determine whether there is a correlation error based on an inconsistency.

Surgical instrument operation may be adjusted, for example, based on an assessment of the posture of a health care professional. A surgical computing system may receive biomarker data from one or more sensing systems associated with a healthcare professional operating a surgical instrument. The surgical computing system may receive usage data associated with user inputs from the surgical instrument. The surgical computing system may receive environmental data from one or more environmental sensing systems. The surgical computing system may determine an evaluation of body positioning of the healthcare professional based at least in part on the biomarker data, usage data, and/or environmental data. An evaluation of body positioning may include an evaluation of posture (e.g., body posture, arm posture, or wrist posture), balance, range of motion, and/or range of reach. The surgical computing system may determine one or more operational parameters for the surgical instrument based on the evaluation of body positioning of the healthcare professional. The surgical computing system may communicate the one or more operational parameters to the surgical instrument. Operational parameters may include, for example, parameters associated with one or more of the following: controls of the surgical instrument, stoke trigger points, an activation limit or a deactivation limit, and/or activating secondary controls. The surgical computing system may receive an indication to override one or more operational parameters from the surgical instrument.

BRIEF DESCRIPTION OF THE DRAWINGS

FIG. 1B is a block diagram of an example relationship among sensing systems, biomarkers, and physiologic systems.

FIG. 19 illustrates example processing associated with determining possession of a surgical instrument and communication of information based on a correlation of instrument and healthcare professional motion.

FIGS. 22A and 22B illustrate example body positioning of a health care professional in ergonomic range and out of ergonomic range, respectively, while performing surgical tasks.

DETAILED DESCRIPTION

Applicant of the present application owns the following U.S. patent applications, patent publications, and patents, each of which is herein incorporated by reference in its entirety:

U.S. Patent Application Publication No. US 20190200844 A1 (U.S. patent application Ser. No. 16/209,385, filed Dec. 4, 2018), titled "METHOD OF HUB COMMUNICATION, PROCESSING, STORAGE AND DISPLAY," published Jul. 4, 2019;

U.S. Patent Application Publication No. US 20190201137 A1 (U.S. patent application Ser. No. 16/209,407, filed Dec. 28, 2017), titled "METHOD OF ROBOTIC HUB COMMUNICATION, DETECTION, AND CONTROL," published Jul. 4, 2019;

U.S. Patent Application Publication No. US 20190206569 A1 (U.S. patent application Ser. No. 16/209,403 filed Dec. 4, 2018), titled "METHOD OF CLOUD BASED DATA ANALYTICS FOR USE WITH THE HUB," published Jul. 4, 2019;

U.S. Provisional Patent Application Ser. No. 62/611,341, titled "INTERACTIVE SURGICAL PLATFORM," filed Dec. 28, 2017;

U.S. Patent Application Publication No. US 20170296213 A1 (U.S. patent application Ser. No. 15/130,590 filed Apr. 15, 2016), titled "SYSTEMS AND METHODS FOR CONTROLLING A SURGICAL STAPLING AND CUTTING INSTRUMENT," published Oct. 19, 2017;

U.S. Pat. No. 9,345,481, titled "STAPLE CARTRIDGE TISSUE THICKNESS SENSOR SYSTEM," issued May 24, 2016;

U.S. Patent Application Publication No. US 20140263552 (U.S. patent application Ser. No. 13/800,067 filed Mar. 13, 2013), titled "STAPLE CARTRIDGE TISSUE THICKNESS SENSOR SYSTEM," published Sep. 18, 2014;

U.S. Patent Application Publication No. US 20180360452 (U.S. patent application Ser. No. 15/628,175, filed Jun. 20, 2017), titled "TECHNIQUES FOR ADAPTIVE CONTROL OF MOTOR VELOCITY OF A SURGICAL STAPLING AND CUTTING INSTRUMENT," published Dec. 20, 2018;

U.S. Patent Application Publication No. US 20190200981 (U.S. application Ser. No. 16/209,423, filed Dec. 4, 2018), titled "METHOD OF COMPRESSING TISSUE WITHIN A STAPLING DEVICE AND SIMULTANEOUSLY DISPLAYING THE LOCATION OF THE TISSUE WITHIN THE JAWS," published Jul. 4, 2019;

U.S. Pat. No. 9,072,535, titled "SURGICAL STAPLING INSTRUMENTS WITH ROTATABLE STAPLE DEPLOYMENT ARRANGEMENTS," issued Jul. 5, 2015;

U.S. Patent Application Publication No. US 20140263541 (U.S. application Ser. No. 13/803,086, filed Mar. 14, 2013), titled "ARTICULATABLE SURGICAL INSTRUMENT COMPRISING AN ARTICULATION LOCK," published Sep. 18, 2014; and U.S. Patent Application Publication No. US 20140263551 (U.S. application Ser. No. 13/800,025, filed Mar. 13, 2013), titled "STAPLE CARTRIDGE TISSUE THICKNESS SENSOR SYSTEM," published Sep. 18, 2014.

Figure 1A:
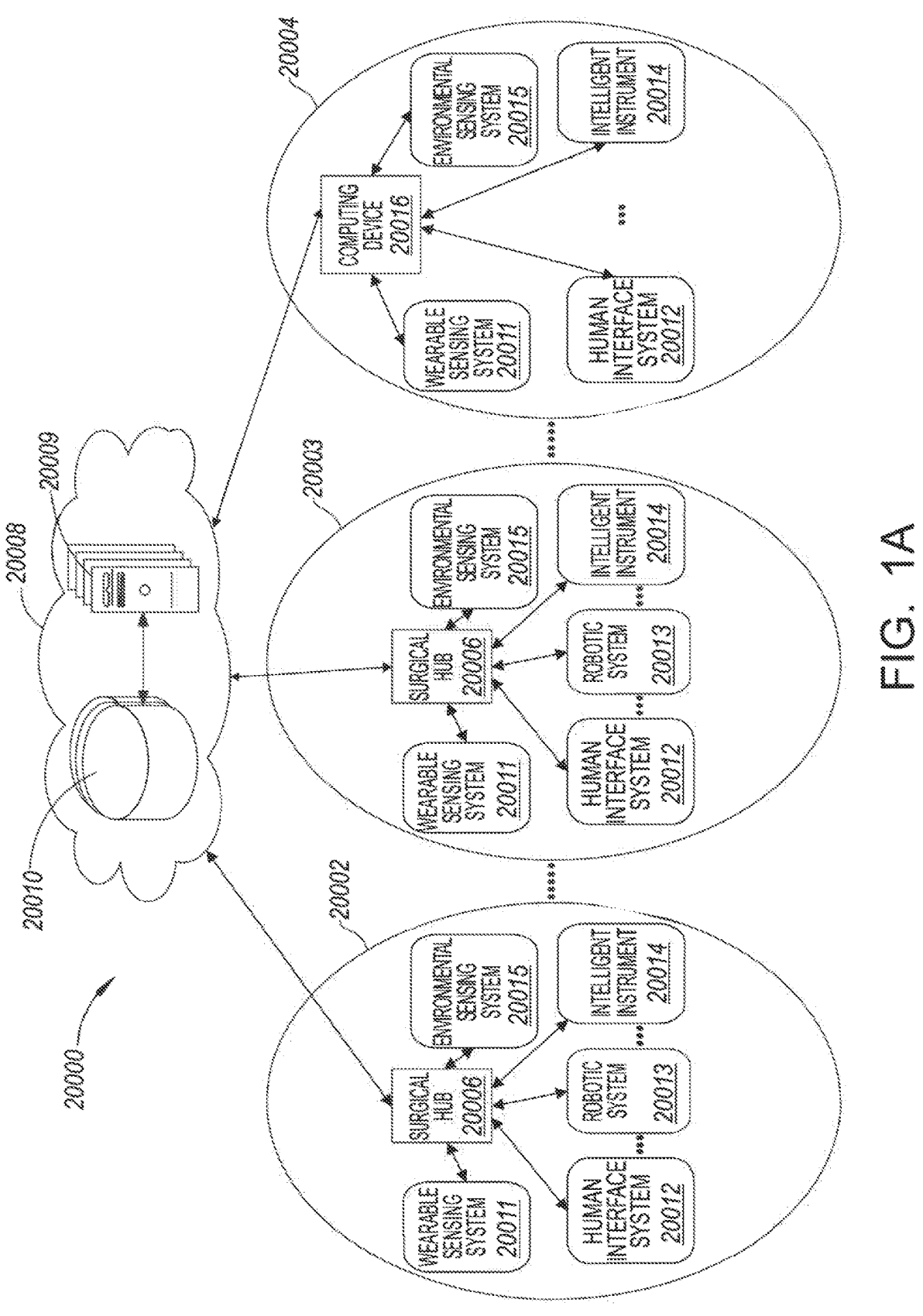
FIG. 1A is a block diagram of a computer-implemented patient and surgeon monitoring system.

FIG. 1A is a block diagram of a computer-implemented patient and surgeon monitoring system 20000. The patient and surgeon monitoring system 20000 may include one or more surgeon monitoring systems 20002 and a one or more patient monitoring systems (e.g., one or more controlled patient monitoring systems 20003 and one or more uncontrolled patient monitoring systems 20004). Each surgeon monitoring system 20002 may include a computer-implemented interactive surgical system. Each surgeon monitoring system 20002 may include at least one of the following a surgical hub 20006 in communication with a cloud computing system 20008, for example, as described in FIG. 2A. Each of the patient monitoring systems may include at least one of the following a surgical hub 20006 or a computing device 20016 in communication with a could computing system 20008, for example, as further described in FIG. 2B and FIG. 2C. The cloud computing system 20008 may include at least one remote cloud server 20009 and at least one remote cloud storage unit 20010. Each of the surgeon monitoring systems 20002, the controlled patient monitoring systems 20003, or the uncontrolled patient monitoring systems 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more surgeon sensing systems, and/or one or more patient sensing systems. The environmental sensing system 20015 may include one or more devices, for example, used for measuring one or more environmental attributes, for example, as further described in FIG. 2A. The robotic system 20013 (same as 20034 in FIG. 2A) may include a plurality of devices used for performing a surgical procedure, for example, as further described in FIG. 2A.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

FIG. 1B is a block diagram of an example relationship among sensing systems 20001, biomarkers 20005, and physiologic systems 20007. The relationship may be employed in the computer-implemented patient and surgeon monitoring system 20000 and in the systems, devices, and methods disclosed herein. For example, the sensing systems 20001 may include the wearable sensing system 20011 (which may include one or more surgeon sensing systems and one or more patient sensing systems) and the environmental sensing system 20015 as discussed in FIG. 1A. The one or more sensing systems 20001 may measure data relating to various biomarkers 20005. The one or more sensing systems 20001 may measure the biomarkers 20005 using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers 20005 as described herein using one of more of the following sensing technologies: photoplethysmography, electrocardiography, electroencephalography, colorimetry, impedimentary, potentiometry, amperometry, etc.

The biomarkers 20005 measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers 20005 may relate to physiologic systems 20007, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and surgeon monitoring system 20000, for example. The information from the biomarkers may be determined and/or used by the computer-implemented patient and surgeon monitoring system 20000 to improve said systems and/or to improve patient outcomes, for example.

The one or more sensing systems 20001, biomarkers 20005, and physiological systems 20007 are described in more detail below.

A sleep sensing system may measure sleep data, including heart rate, respiration rate, body temperature, movement, and/or brain signals. The sleep sensing system may measure sleep data using a photoplethysmogram (PPG), electrocardiogram (ECG), microphone, thermometer, accelerometer, electroencephalogram (EEG), and/or the like. The sleep sensing system may include a wearable device such as a wristband.

Based on the measured sleep data, the sleep sensing system may detect sleep biomarkers, including but not limited to, deep sleep quantifier, REM sleep quantifier, disrupted sleep quantifier, and/or sleep duration. The sleep sensing system may transmit the measured sleep data to a processing unit. The sleep sensing system and/or the processing unit may detect deep sleep when the sensing system senses sleep data, including reduced heart rate, reduced respiration rate, reduced body temperature, and/or reduced movement. The sleep sensing system may generate a sleep quality score based on the detected sleep physiology.

In an example, the sleep sensing system may send the sleep quality score to a computing system, such as a surgical hub. In an example, the sleep sensing system may send the detected sleep biomarkers to a computing system, such as a surgical hub. In an example, the sleep sensing system may send the measured sleep data to a computing system, such as a surgical hub. The computing system may derive sleep physiology based on the received measured data and generate one or more sleep biomarkers such as deep sleep quantifiers. The computing system may generate a treatment plan, including a pain management strategy, based on the sleep biomarkers. The surgical hub may detect potential risk factors or conditions, including systemic inflammation and/or reduced immune function, based on the sleep biomarkers.

A core body temperature sensing system may measure body temperature data including temperature, emitted frequency spectra, and/or the like. The core body temperature sensing system may measure body temperature data using some combination of thermometers and/or radio telemetry. The core body temperature sensing system may include an ingestible thermometer that measures the temperature of the digestive tract. The ingestible thermometer may wirelessly transmit measured temperature data. The core body temperature sensing system may include a wearable antenna that measures body emission spectra. The core body temperature sensing system may include a wearable patch that measures body temperature data.

The core body temperature sensing system may calculate body temperature using the body temperature data. The core body temperature sensing system may transmit the calculated body temperature to a monitoring device. The monitoring device may track the core body temperature data over time and display it to a user.

The core body temperature sensing system may process the core body temperature data locally or send the data to a processing unit and/or a computing system. Based on the measured temperature data, the core body temperature sensing system may detect body temperature-related biomarkers, complications and/or contextual information that may include abnormal temperature, characteristic fluctuations, infection, menstrual cycle, climate, physical activity, and/or sleep.

For example, the core body temperature sensing system may detect abnormal temperature based on temperature being outside the range of 36.5° C. and 37.5° C. For example, the core body temperature sensing system may detect post-operation infection or sepsis based on certain temperature fluctuations and/or when core body temperature reaches abnormal levels. For example, the core body temperature sensing system may detect physical activities using measured fluctuations in core body temperature.

For example, the body temperature sensing system may detect core body temperature data and trigger the sensing system to emit a cooling or heating element to raise or lower the body temperature in line with the measured ambient temperature.

In an example, the body temperature sensing system may send the body temperature-related biomarkers to a computing system, such as a surgical hub. In an example, the body temperature sensing system may send the measured body temperature data to the computing system. The computer system may derive the body temperature-related biomarkers based on the received body temperature data.

A maximal oxygen consumption (VO2 max) sensing system may measure VO2 max data, including oxygen uptake, heart rate, and/or movement speed. The VO2 max sensing system may measure VO2 max data during physical activities, including running and/or walking. The VO2 max sensing system may include a wearable device. The VO2 max sensing system may process the VO2 max data locally or transmit the data to a processing unit and/or a computing system.

Based on the measured VO2 max data, the sensing system and/or the computing system may derive, detect, and/or calculate biomarkers, including a VO2 max quantifier, VO2 max score, physical activity, and/or physical activity intensity. The VO2 max sensing system may select correct VO2 max data measurements during correct time segments to calculate accurate VO2 max information. Based on the VO2 max information, the sensing system may detect dominating cardio, vascular, and/or respiratory limiting factors. Based on the VO2 max information, risks may be predicted including adverse cardiovascular events in surgery and/or increased risk of in-hospital morbidity. For example, increased risk of in-hospital morbidity may be detected when the calculated VO2 max quantifier falls below a specific threshold, such as 18.2 ml kg−1 min−1.

In an example, the VO2 max sensing system may send the VO2 max-related biomarkers to a computing system, such as a surgical hub. In an example, the VO2 max sensing system may send the measured VO2 max data to the computing system. The computer system may derive the VO2 max-related biomarkers based on the received VO2 max data.

A physical activity sensing system may measure physical activity data, including heart rate, motion, location, posture, range-of-motion, movement speed, and/or cadence. The physical activity sensing system may measure physical activity data including accelerometer, magnetometer, gyroscope, global positioning system (GPS), PPG, and/or ECG. The physical activity sensing system may include a wearable device. The physical activity wearable device may include, but is not limited to, a watch, wrist band, vest, glove, belt, headband, shoe, and/or garment. The physical activity sensing system may locally process the physical activity data or transmit the data to a processing unit and/or a computing system.

Based on the measured physical activity data, the physical activity sensing system may detect physical activity-related biomarkers, including but not limited to exercise activity, physical activity intensity, physical activity frequency, and/or physical activity duration. The physical activity sensing system may generate physical activity summaries based on physical activity information.

For example, the physical activity sensing system may send physical activity information to a computing system. For example, the physical activity sensing system may send measured data to a computing system. The computing system may, based on the physical activity information, generate activity summaries, training plans, and/or recovery plans. The computing system may store the physical activity information in user profiles. The computing system may display the physical activity information graphically. The computing system may select certain physical activity information and display the information together or separately.

An alcohol consumption sensing system may measure alcohol consumption data including alcohol and/or sweat. The alcohol consumption sensing system may use a pump to measure perspiration. The pump may use a fuel cell that reacts with ethanol to detect alcohol presence in perspiration. The alcohol consumption sensing system may include a wearable device, for example, a wristband. The alcohol consumption sensing system may use microfluidic applications to measure alcohol and/or sweat. The microfluidic applications may measure alcohol consumption data using sweat stimulation and wicking with commercial ethanol sensors. The alcohol consumption sensing system may include a wearable patch that adheres to skin. The alcohol consumption sensing system may include a breathalyzer. The sensing system may process the alcohol consumption data locally or transmit the data to a processing unit and/or computing system.

Based on the measured alcohol consumption data, the sensing system may calculate a blood alcohol concentration. The sensing system may detect alcohol consumption conditions and/or risk factors. The sensing system may detect alcohol consumption-related biomarkers including reduced immune capacity, cardiac insufficiency, and/or arrhythmia. Reduced immune capacity may occur when a patient consumes three or more alcohol units per day. The sensing system may detect risk factors for postoperative complications including infection, cardiopulmonary complication, and/or bleeding episodes. Healthcare providers may use the detected risk factors for predicting or detecting post-operative or post-surgical complications, for example, to affect decisions and precautions taken during post-surgical care.

In an example, the alcohol consumption sensing system may send the alcohol consumption-related biomarkers to a computing system, such as a surgical hub. In an example, the alcohol consumption sensing system may send the measured alcohol consumption data to the computing system. The computer system may derive the alcohol consumption-related biomarkers based on the received alcohol consumption data.

A respiration sensing system may measure respiration rate data, including inhalation, exhalation, chest cavity movement, and/or airflow. The respiration sensing system may measure respiration rate data mechanically and/or acoustically. The respiration sensing system may measure respiration rate data using a ventilator. The respiration sensing system may measure respiration data mechanically by detecting chest cavity movement. Two or more applied electrodes on a chest may measure the changing distance between the electrodes to detect chest cavity expansion and contraction during a breath. The respiration sensing system may include a wearable skin patch. The respiration sensing system may measure respiration data acoustically using a microphone to record airflow sounds. The respiration sensing system may locally process the respiration data or transmit the data to a processing unit and/or computing system.

Based on measured respiration data, the respiration sensing system may generate respiration-related biomarkers including breath frequency, breath pattern, and/or breath depth. Based on the respiratory rate data, the respiration sensing system may generate a respiration quality score.

Based on the respiration rate data, the respiration sensing system may detect respiration-related biomarkers including irregular breathing, pain, air leak, collapsed lung, lung tissue and strength, and/or shock. For example, the respiration sensing system may detect irregularities based on changes in breath frequency, breath pattern, and/or breath depth. For example, the respiration sensing system may detect postoperative pain based on short, sharp breaths. For example, the respiration sensing system may detect an air leak based on a volume difference between inspiration and expiration. For example, the respiration sensing system may detect a collapsed lung based on increased breath frequency combined with a constant volume inhalation. For example, the respiration sensing system may detect lung tissue strength and shock including systemic inflammatory response syndrome (SIRS) based on an increase in respiratory rate, including more than 2 standard deviations. In an example, the detection described herein may be performed by a computing system based on measured data and/or related biomarkers generated by the respiration sensing system.

An oxygen saturation sensing system may measure oxygen saturation data, including light absorption, light transmission, and/or light reflectance. The oxygen saturation sensing system may use pulse oximetry. For example, the oxygen saturation sensing system may use pulse oximetry by measuring the absorption spectra of deoxygenated and oxygenated hemoglobin. The oxygen saturation sensing system may include one or more light-emitting diodes (LEDs) with predetermined wavelengths. The LEDs may impose light on hemoglobin. The oxygen saturation sensing system may measure the amount of imposed light absorbed by the hemoglobin. The oxygen saturation sensing system may measure the amount of transmitted light and/or reflected light from the imposed light wavelengths. The oxygen saturation sensing system may include a wearable device, including an earpiece and/or a watch. The oxygen saturation sensing system may process the measured oxygen saturation data locally or transmit the data to a processing unit and/or computing system.

Based on the oxygen saturation data, the oxygen saturation sensing system may calculate oxygen saturation-related biomarkers including peripheral blood oxygen saturation (SpO2), hemoglobin oxygen concentration, and/or changes in oxygen saturation rates. For example, the oxygen saturation sensing system may calculate SpO2 using the ratio of measured light absorbances of each imposed light wavelength.

Based on the oxygen saturation data, the oxygen saturation sensing system may predict oxygen saturation-related biomarkers, complications, and/or contextual information including cardiothoracic performance, delirium, collapsed lung, and/or recovery rates. For example, the oxygen saturation sensing system may detect post-operation delirium when the sensing system measures pre-operation SpO2 values below 59.5%. For example, an oxygen saturation sensing system may help monitor post-operation patient recovery. Low SpO2 may reduce the repair capacity of tissues because low oxygen may reduce the amount of energy a cell can produce. For example, the oxygen saturation sensing system may detect a collapsed lung based on low post-operation oxygen saturation. In an example, the detection described herein may be performed by a computing system based on measured data and/or related biomarkers generated by the oxygen saturation sensing system.

A blood pressure sensing system may measure blood pressure data including blood vessel diameter, tissue volume, and/or pulse transit time. The blood pressure sensing system may measure blood pressure data using oscillometric measurements, ultrasound patches, photoplethysmography, and/or arterial tonometry. The blood pressure sensing system using photoplethysmography may include a photodetector to sense light scattered by imposed light from an optical emitter. The blood pressure sensing system using arterial tonometry may use arterial wall applanation. The blood pressure sensing system may include an inflatable cuff, wristband, watch and/or ultrasound patch.

Based on the measured blood pressure data, a blood pressure sensing system may quantify blood pressure-related biomarkers including systolic blood pressure, diastolic blood pressure, and/or pulse transit time. The blood pressure sensing system may use the blood pressure-related biomarkers to detect blood pressure-related conditions such as abnormal blood pressure. The blood pressure sensing system may detect abnormal blood pressure when the measured systolic and diastolic blood pressures fall outside the range of 90/60 to 120-90 (systolic/diastolic). For example, the blood pressure sensing system may detect post-operation septic or hypovolemic shock based on measured low blood pressure. For example, the blood pressure sensing system may detect a risk of edema based on detected high blood pressure. The blood pressure sensing system may predict the required seal strength of a harmonic seal based on measured blood pressure data. Higher blood pressure may require a stronger seal to overcome bursting. The blood pressure sensing system may display blood pressure information locally or transmit the data to a system. The sensing system may display blood pressure information graphically over a period of time.

A blood pressure sensing system may process the blood pressure data locally or transmit the data to a processing unit and/or a computing system. In an example, the detection, prediction and/or determination described herein may be performed by a computing system based on measured data and/or related biomarkers generated by the blood pressure sensing system.

A blood sugar sensing system may measure blood sugar data including blood glucose level and/or tissue glucose level. The blood sugar sensing system may measure blood sugar data non-invasively. The blood sugar sensing system may use an earlobe clip. The blood sugar sensing system may display the blood sugar data.

Based on the measured blood sugar data, the blood sugar sensing system may infer blood sugar irregularity. Blood sugar irregularity may include blood sugar values falling outside a certain threshold of normally occurring values. A normal blood sugar value may include the range between 70 and 120 mg/dL while fasting. A normal blood sugar value may include the range between 90 and 160 mg/dL while not-fasting.

For example, the blood sugar sensing system may detect a low fasting blood sugar level when blood sugar values fall below 50 mg/dL. For example, the blood sugar sensing system may detect a high fasting blood sugar level when blood sugar values exceed 315 mg/dL. Based on the measured blood sugar levels, the blood sugar sensing system may detect blood sugar-related biomarkers, complications, and/or contextual information including diabetes-associated peripheral arterial disease, stress, agitation, reduced blood flow, risk of infection, and/or reduced recovery times.

The blood sugar sensing system may process blood sugar data locally or transmit the data to a processing unit and/or computing system. In an example, the detection, prediction and/or determination described herein may be performed by a computing system based on measured data and/or related biomarkers generated by the blood sugar sensing system.

A heart rate variability (HRV) sensing system may measure HRV data including heartbeats and/or duration between consecutive heartbeats. The HRV sensing system may measure HRV data electrically or optically. The HRV sensing system may measure heart rate variability data electrically using ECG traces. The HRV sensing system may use ECG traces to measure the time period variation between R peaks in a QRS complex. An HRV sensing system may measure heart rate variability optically using PPG traces. The HRV sensing system may use PPG traces to measure the time period variation of inter-beat intervals. The HRV sensing system may measure HRV data over a set time interval. The HRV sensing system may include a wearable device, including a ring, watch, wristband, and/or patch.

Based on the HRV data, an HRV sensing system may detect HRV-related biomarkers, complications, and/or contextual information including cardiovascular health, changes in HRV, menstrual cycle, meal monitoring, anxiety levels, and/or physical activity. For example, an HRV sensing system may detect high cardiovascular health based on high HRV. For example, an HRV sensing system may predict pre-operative stress, and use pre-operative stress to predict post-operative pain. For example, an HRV sensing system may indicate post-operative infection or sepsis based on a decrease in HRV.

The HRV sensing system may locally process HRV data or transmit the data to a processing unit and/or a computing system. In an example, the detection, prediction, and/or determination described herein may be performed by a computing system based on measured data and/or related biomarkers generated by the HRV sensing system.

A potential of hydrogen (pH) sensing system may measure pH data including blood pH and/or sweat pH. The pH sensing system may measure pH data invasively and/or non-invasively. The pH sensing system may measure pH data non-invasively using a colorimetric approach and pH sensitive dyes in a microfluidic circuit. In a colorimetric approach, pH sensitive dyes may change color in response to sweat pH. The pH sensing system may measure pH using optical spectroscopy to match color change in pH sensitive dyes to a pH value. The pH sensing system may include a wearable patch. The pH sensing system may measure pH data during physical activity.

Based on the measured pH data, the pH sensing system may detect pH-related biomarkers, including normal blood pH, abnormal blood pH, and/or acidic blood pH. The pH sensing system may detect pH-related biomarkers, complications, and/or contextual information by comparing measured pH data to a standard pH scale. A standard pH scale may identify a healthy pH range to include values between 7.35 and 7.45.

The pH sensing system may use the pH-related biomarkers to indicate pH conditions including post-operative internal bleeding, acidosis, sepsis, lung collapse, and/or hemorrhage. For example, the pH sensing system may predict post-operative internal bleeding based on pre-operation acidic blood pH. Acidic blood may reduce blood clotting capacity by inhibiting thrombin generation. For example, the pH sensing system may predict sepsis and/or hemorrhage based on acidic pH. Lactic acidosis may cause acidic pH. The pH sensing system may continuously monitor blood pH data as acidosis may only occur during exercise.

The pH sensing system may locally process pH data or transmit pH data to a processing unit and/or computing system. In an example, the detection, prediction and/or determination described herein may be performed by a computing system based on measured data and/or related biomarkers generated by the pH sensing system.

A hydration state sensing system may measure hydration data including water light absorption, water light reflection, and/or sweat levels. The hydration state sensing system may use optical spectroscopy or sweat-based colorimetry. The hydration state sensing system may use optical spectroscopy by imposing emitted light onto skin and measuring the reflected light. Optical spectroscopy may measure water content by measuring amplitudes of the reflected light from certain wavelengths, including 1720 nm, 1750 nm, and/or 1770 nm. The hydration state sensing system may include a wearable device that may impose light onto skin. The wearable device may include a watch. The hydration state sensing system may use sweat-based colorimetry to measure sweat levels. Sweat-based colorimetry may be processed in conjunction with user activity data and/or user water intake data.

Based on the hydration data, the hydration state sensing system may detect water content. Based on the water content, a hydration state sensing system may identify hydration-related biomarkers, complications, and/or contextual information including dehydration, risk of kidney injury, reduced blood flow, risk of hypovolemic shock during or after surgery, and/or decreased blood volume.

For example, the hydration state sensing system, based on identified hydration, may detect health risks. Dehydration may negatively impact overall health. For example, the hydration state sensing system may predict risk of post-operation acute kidney injury when it detects reduced blood flow resulting from low hydration levels. For example, the hydration state sensing system may calculate the risk of hypovolemic shock during or after surgery when the sensing system detects dehydration or decreased blood volume. The hydration state sensing system may use the hydration level information to provide context for other received biomarker data, which may include heart rate. The hydration state sensing system may measure hydration state data continuously. Continuous measurement may consider various factors, including exercise, fluid intake, and/or temperature, which may influence the hydration state data.

The hydration state sensing system may locally process hydration data or transmit the data to a processing unit and/or computing system. In an example, the detection, prediction, and/or determination described herein may be performed by a computing system based on measured data and/or related biomarkers generated by the hydration state sensing system.

A heart rate sensing system may measure heart rate data including heart chamber expansion, heart chamber contraction, and/or reflected light. The heart rate sensing system may use ECG and/or PPG to measure heart rate data. For example, the heart rate sensing system using ECG may include a radio transmitter, receiver, and one or more electrodes. The radio transmitter and receiver may record voltages across electrodes positioned on the skin resulting from expansion and contraction of heart chambers. The heart rate sensing system may calculate heart rate using measured voltage. For example, the heart rate sensing system using PPG may impose green light on skin and record the reflected light in a photodetector. The heart rate sensing system may calculate heart rate using the measured light absorbed by the blood over a period of time. The heart rate sensing system may include a watch, a wearable elastic band, a skin patch, a bracelet, garments, a wrist strap, an earphone, and/or a headband. For example, the heart rate sensing system may include a wearable chest patch. The wearable chest patch may measure heart rate data and other vital signs or critical data including respiratory rate, skin temperature, body posture, fall detection, single-lead ECG, R-R intervals, and step counts. The wearable chest patch may locally process heart rate data or transmit the data to a processing unit. The processing unit may include a display.

Based on the measured heart rate data, the heart rate sensing system may calculate heart rate-related biomarkers including heart rate, heart rate variability, and/or average heart rate. Based on the heart rate data, the heart rate sensing system may detect biomarkers, complications, and/or contextual information including stress, pain, infection, and/or sepsis. The heart rate sensing system may detect heart rate conditions when heart rate exceeds a normal threshold. A normal threshold for heartrate may include the range of 60 to 100 heartbeats per minute. The heart rate sensing system may diagnose post-operation infection, sepsis, or hypovolemic shock based on increased heart rate, including heart rate in excess of 90 beats per minute.

The heart rate sensing system may process heart rate data locally or transmit the data to a processing unit and/or computing system. In an example, the detection, prediction, and/or determination described herein may be performed by a computing system based on measured data and/or related biomarkers generated by the heart rate sensing system. A heart rate sensing system may transmit the heart rate information to a computing system, such as a surgical hub. The computing system may collect and display cardiovascular parameter information including heart rate, respiration, temperature, blood pressure, arrhythmia, and/or atrial fibrillation. Based on the cardiovascular parameter information, the computing system may generate a cardiovascular health score.

A skin conductance sensing system may measure skin conductance data including electrical conductivity. The skin conductance sensing system may include one or more electrodes. The skin conductance sensing system may measure electrical conductivity by applying a voltage across the electrodes. The electrodes may include silver or silver chloride. The skin conductance sensing system may be placed on one or more fingers. For example, the skin conductance sensing system may include a wearable device. The wearable device may include one or more sensors. The wearable device may attach to one or more fingers. Skin conductance data may vary based on sweat levels.

The skin conductance sensing system may locally process skin conductance data or transmit the data to a computing system. Based on the skin conductance data, a skin conductance sensing system may calculate skin conductance-related biomarkers including sympathetic activity levels. For example, a skin conductance sensing system may detect high sympathetic activity levels based on high skin conductance.

A peripheral temperature sensing system may measure peripheral temperature data including extremity temperature. The peripheral temperature sensing system may include a thermistor, thermoelectric effect, or infrared thermometer to measure peripheral temperature data. For example, the peripheral temperature sensing system using a thermistor may measure the resistance of the thermistor. The resistance may vary as a function of temperature. For example, the peripheral temperature sensing system using the thermoelectric effect may measure an output voltage. The output voltage may increase as a function of temperature. For example, the peripheral temperature sensing system using an infrared thermometer may measure the intensity of radiation emitted from a body's blackbody radiation. The intensity of radiation may increase as a function of temperature.

Based on peripheral temperature data, the peripheral temperature sensing system may determine peripheral temperature-related biomarkers including basal body temperature, extremity skin temperature, and/or patterns in peripheral temperature. Based on the peripheral temperature data, the peripheral temperature sensing system may detect conditions including diabetes.

The peripheral temperature sensing system may locally process peripheral temperature data and/or biomarkers or transmit the data to a processing unit. For example, the peripheral temperature sensing system may send peripheral temperature data and/or biomarkers to a computing system, such as a surgical hub. The computing system may analyze the peripheral temperature information with other biomarkers, including core body temperature, sleep, and menstrual cycle. For example, the detection, prediction, and/or determination described herein may be performed by a computing system based on measured data and/or related biomarkers generated by the peripheral temperature sensing system.

A tissue perfusion pressure sensing system may measure tissue perfusion pressure data including skin perfusion pressure. The tissue perfusion sensing system may use optical methods to measure tissue perfusion pressure data. For example, the tissue perfusion sensing system may illuminate skin and measure the light transmitted and reflected to detect changes in blood flow. The tissue perfusion sensing system may apply occlusion. For example, the tissue perfusion sensing system may determine skin perfusion pressure based on the measured pressure used to restore blood flow after occlusion. The tissue perfusion sensing system may measure the pressure to restore blood flow after occlusion using a strain gauge or laser doppler flowmetry. The measured change in frequency of light caused by movement of blood may directly correlate with the number and velocity of red blood cells, which the tissue perfusion pressure sensing system may use to calculate pressure. The tissue perfusion pressure sensing system may monitor tissue flaps during surgery to measure tissue perfusion pressure data.

Based on the measured tissue perfusion pressure data, the tissue perfusion pressure sensing system may detect tissue perfusion pressure-related biomarkers, complications, and/or contextual information including hypovolemia, internal bleeding, and/or tissue mechanical properties. For example, the tissue perfusion pressure sensing system may detect hypovolemia and/or internal bleeding based on a drop in perfusion pressure. Based on the measured tissue perfusion pressure data, the tissue perfusion pressure sensing system may inform surgical tool parameters and/or medical procedures. For example, the tissue perfusion pressure sensing system may determine tissue mechanical properties using the tissue perfusion pressure data. Based on the determined mechanical properties, the sensing system may generate stapling procedure and/or stapling tool parameter adjustment(s). Based on the determined mechanical properties, the sensing system may inform dissecting procedures. Based on the measured tissue perfusion pressure data, the tissue perfusion pressure sensing system may generate a score for overall adequacy of perfusion.

The tissue perfusion pressure sensing system may locally process tissue perfusion pressure data or transmit the data to a processing unit and/or computing system. In an example, the detection, prediction, determination, and/or generation described herein may be performed by a computing system based on measured data and/or related biomarkers generated by the tissue perfusion pressure sensing system.

A coughing and sneezing sensing system may measure coughing and sneezing data including coughing, sneezing, movement, and sound. The coughing and sneezing sensing system may track hand or body movement that may result from a user covering her mouth while coughing or sneezing. The sensing system may include an accelerometer and/or a microphone. The sensing system may include a wearable device. The wearable device may include a watch.

Based on the coughing and sneezing data, the sensing system may detect coughing and sneezing-related biomarkers, including but not limited to, coughing frequency, sneezing frequency, coughing severity, and/or sneezing severity. The sensing system may establish a coughing and sneezing baseline using the coughing and sneezing information. The coughing and sneezing sensing system may locally process coughing and sneezing data or transmit the data to a computing system.

Based on the coughing and sneezing data, the sensing system may detect coughing and sneezing-related biomarkers, complications, and/or contextual information including respiratory tract infection, infection, collapsed lung, pulmonary edema, gastroesophaegeal reflux disease, allergic rhinitis, and/or systemic inflammation. For example, the coughing and sneezing sensing system may indicate gastroesophageal reflux disease when the sensing system measures chronic coughing. Chronic coughing may lead to inflammation of the lower esophagus. Lower esophagus inflammation may affect the properties of stomach tissue for sleeve gastrectomy. For example, the coughing and sneezing sensing system may detect allergic rhinitis based on sneezing. Sneezing may link to systemic inflammation. Systemic inflammation may affect the mechanical properties of the lungs and/or other tissues. In an example, the detection, prediction, and/or determination described herein may be performed by a computing system based on measured data and/or related biomarkers generated by the coughing and sneezing sensing system.

A gastrointestinal (GI) motility sensing system may measure GI motility data including pH, temperature, pressure, and/or stomach contractions. The GI motility sensing system may use electrogastrography, electrogastroenterography, stethoscopes, and/or ultrasounds. The GI motility sensing system may include a non-digestible capsule. For example, the ingestible sensing system may adhere to the stomach lining. The ingestible sensing system may measure contractions using a piezoelectric device which generates a voltage when deformed.

Based on the GI data, the sensing system may calculate GI motility-related biomarkers including gastric, small bowel, and/or colonic transit times. Based on the gastrointestinal motility information, the sensing system may detect GI motility-related conditions including ileus. The GI motility sensing system may detect ileus based on a reduction in small bowel motility. The GI motility sensing system may notify healthcare professionals when it detects GI motility conditions. The GI motility sensing system may locally process GI motility data or transmit the data to a processing unit. In an example, the detection, prediction, and/or determination described herein may be performed by a computing system based on measured data and/or related biomarkers generated by the GI motility sensing system.

A GI tract imaging/sensing system may collect images of a patient's colon. The GI tract imaging/sensing system may include an ingestible wireless camera and a receiver. The GI tract imaging/sensing system may include one or more white LEDs, a battery, radio transmitter, and antenna. The ingestible camera may include a pill. The ingestible camera may travel through the digestive tract and take pictures of the colon. The ingestible camera may take pictures up to 35 frames per second during motion. The ingestible camera may transmit the pictures to a receiver. The receiver may include a wearable device. The GI tract imaging/sensing system may process the images locally or transmit them to a processing unit. Doctors may look at the raw images to make a diagnosis.

Based on the GI tract images, the GI tract imaging sensing system may identify GI tract-related biomarkers including stomach tissue mechanical properties or colonic tissue mechanical properties. Based on the collected images, the GI tract imaging sensing system may detect GI tract-related biomarkers, complications, and/or contextual information including mucosal inflammation, Crohn's disease, anastomotic leak, esophagus inflammation, and/or stomach inflammation. The GI tract imaging/sensing system may replicate a physician diagnosis using image analysis software. The GI tract imaging/sensing system may locally process images or transmit the data to a processing unit. In an example, the detection, prediction, and/or determination described herein may be performed by a computing system based on measured data and/or related biomarkers generated by the GI tract imaging/sensing system.

A respiratory tract bacteria sensing system may measure bacteria data including foreign DNA or bacteria. The respiratory tract bacteria sensing system may use a radio frequency identification (RFID) tag and/or electronic nose (e-nose). The sensing system using an RFID tag may include one or more gold electrodes, graphene sensors, and/or layers of peptides. The RFID tag may bind to bacteria. When bacteria bind to the RFID tag, the graphene sensor may detect a change in signal-to-signal presence of bacteria. The RFID tag may include an implant. The implant may adhere to a tooth. The implant may transmit bacteria data. The sensing system may use a portable e-nose to measure bacteria data.

Based on measured bacteria data, the respiratory tract bacteria sensing system may detect bacteria-related biomarkers including bacteria levels. Based on the bacteria data, the respiratory tract bacteria sensing system may generate an oral health score. Based on the detected bacteria data, the respiratory tract bacteria sensing system may identify bacteria-related biomarkers, complications, and/or contextual information, including pneumonia, lung infection, and/or lung inflammation. The respiratory tract bacteria sensing system may locally process bacteria information or transmit the data to a processing unit. In an example, the detection, prediction, and/or determination described herein may be performed by a computing system based on measured data and/or related biomarkers generated by the respiratory tract bacteria sensing system.

An edema sensing system may measure edema data including lower leg circumference, leg volume, and/or leg water content level. The edema sensing system may include a force sensitive resistor, strain gauge, accelerometer, gyroscope, magnetometer, and/or ultrasound. The edema sensing system may include a wearable device. For example, the edema sensing system may include socks, stockings, and/or ankle bands.

Based on the measured edema data, the edema sensing system may detect edema-related biomarkers, complications, and/or contextual information, including inflammation, rate of change in inflammation, poor healing, infection, leak, colorectal anastomotic leak, and/or water build-up.

For example, the edema sensing system may detect a risk of colorectal anastomotic leak based on fluid build-up. Based on the detected edema physiological conditions, the edema sensing system may generate a score for healing quality. For example, the edema sensing system may generate the healing quality score by comparing edema information to a certain threshold lower leg circumference. Based on the detected edema information, the edema sensing system may generate edema tool parameters including responsiveness to stapler compression. The edema sensing system may provide context for measured edema data by using measurements from the accelerometer, gyroscope, and/or magnetometer. For example, the edema sensing system may detect whether the user is sitting, standing, or lying down.

The edema sensing system may process measured edema data locally or transmit the edema data to a processing unit. In an example, the detection, prediction, and/or determination described herein may be performed by a computing system based on measured data and/or related biomarkers generated by the edema sensing system.

A mental aspect sensing system may measure mental aspect data, including heart rate, heart rate variability, brain activity, skin conductance, skin temperature, galvanic skin response, movement, and/or sweat rate. The mental aspect sensing system may measure mental aspect data over a set duration to detect changes in mental aspect data. The mental aspect sensing system may include a wearable device. The wearable device may include a wristband.

Based on the mental aspect data, the sensing system may detect mental aspect-related biomarkers, including emotional patterns, positivity levels, and/or optimism levels. Based on the detected mental aspect information, the mental aspect sensing system may identify mental aspect-related biomarkers, complications, and/or contextual information including cognitive impairment, stress, anxiety, and/or pain. Based on the mental aspect information, the mental aspect sensing system may generate mental aspect scores, including a positivity score, optimism score, confusion or delirium score, mental acuity score, stress score, anxiety score, depression score, and/or pain score.

Mental aspect data, related biomarkers, complications, contextual information, and/or mental aspect scores may be used to determine treatment courses, including pain relief therapies. For example, post-operative pain may be predicted when it detects pre-operative anxiety and/or depression. For example, based on detected positivity and optimism levels, the mental aspect sensing system may determine mood quality and mental state. Based on mood quality and mental state, the mental aspect sensing system may indicate additional care procedures that would benefit a patient, including paint treatments and/or psychological assistance. For example, based on detected cognitive impairment, confusion, and/or mental acuity, the mental aspects sensing system may indicate conditions including delirium, encephalopathy, and/or sepsis. Delirium may be hyperactive or hypoactive. For example, based on detected stress and anxiety, the mental aspect sensing system may indicate conditions including hospital anxiety and/or depression. Based on detected hospital anxiety and/or depression, the mental aspect sensing system may generate a treatment plan, including pain relief therapy and/or pre-operative support.

In an example, the detection, prediction, and/or determination described herein may be performed by a computing system based on measured data and/or related biomarkers generated by the mental aspect sensing system. The mental aspect sensing system may process mental aspect data locally or transmit the data to a processing unit.

A sweat sensing system may measure sweat data including sweat, sweat rate, cortisol, adrenaline, and/or lactate. The sweat sensing system may measure sweat data using microfluidic capture, saliva testing, nanoporous electrode systems, e-noses, reverse iontophoresis, blood tests, amperometric thin film biosensors, textile organic electrochemical transistor devices, and/or electrochemical biosensors. The sensing system may measure sweat data with microfluidic capture using a colorimetric or impedimetric method. The microfluidic capture may include a flexible patch placed in contact with skin. The sweat sensing system may measure cortisol using saliva tests. The saliva tests may use electrochemical methods and/or molecularly selective organic electrochemical transistor devices. The sweat sensing system may measure ion build-up that bind to cortisol in sweat to calculate cortisol levels. The sweat sensing system may use enzyme reactions to measure lactate. Lactate may be measured using lactate oxidase and/or lactate dehydrogenase methods.

Based on the measured sweat data, the sweat sensing system or processing unit may detect sweat-related biomarkers, complications, and/or contextual information including cortisol levels, adrenaline levels, and/or lactate levels. Based on the detected sweat data and/or related biomarkers, the sweat sensing system may indicate sweat physiological conditions including sympathetic nervous system activity, psychological stress, cellular immunity, circadian rhythm, blood pressure, tissue oxygenation, and/or post-operation pain. For example, based on sweat rate data, the sweat sensing system may detect psychological stress. Based on the detected psychological stress, the sweat sensing system may indicate heightened sympathetic activity. Heightened sympathetic activity may indicate post-operation pain.

Based on the detected sweat information, the sweat sensing system may detect sweat-related biomarkers, complications, and/or contextual information including post-operation infection, metastasis, chronic elevation, ventricular failure, sepsis, hemorrhage, hyperlactemia, and/or septic shock. For example, the sensing system may detect septic shock when serum lactate concentration exceeds a certain level, such as 2 mmol/L. For example, based on detected patterns of adrenaline surges, the sweat sensing system may indicate a risk of heart attack and/or stroke. For example, surgical tool parameter adjustments may be determined based on detected adrenaline levels. The surgical tool parameter adjustments may include settings for surgical sealing tools. For example, the sweat sensing system may predict infection risk and/or metastasis based on detected cortisol levels. The sweat sensing system may notify healthcare professionals about the condition.

In an example, the detection, prediction, and/or determination described herein may be performed by a computing system based on measured data and/or related biomarkers generated by the sweat sensing system. The sweat sensing system may locally process sweat data or transmit the sweat data to a processing unit.

A circulating tumor cell sensing system may detect circulating tumor cells. The circulating tumor cell sensing system may detect circulating tumor cells using an imaging agent. The imaging agent may use microbubbles attached with antibodies which target circulating tumor cells. The imaging agent may be injected into the bloodstream. The imaging agent may attach to circulating tumor cells. The circulating tumor cell sensing system may include an ultrasonic transmitter and receiver. The ultrasonic transmitter and receiver may detect the imaging agent attached to circulating tumor cells. The circulating tumor cell sensing system may receive circulating tumor cell data.

Based on the detected circulating tumor cells data, the circulating tumor cell sensing system may calculate metastatic risk. The presence of circulating cancerous cells may indicate metastatic risk. Circulating cancerous cells per milliliter of blood exceeding a threshold amount may indicate a metastatic risk. Cancerous cells may circulate the bloodstream when tumors metastasize. Based on the calculated metastatic risk, the circulating tumor cell sensing system may generate a surgical risk score. Based on the generated surgical risk score, the circulating tumor cell sensing system may indicate surgery viability and/or suggested surgical precautions.

In an example, the detection, prediction and/or determination described herein may be performed by a computing system based on measured data and/or related biomarkers generated by the circulating tumor cells sensing system. The circulating tumor cell sensing system may process the circulating tumor cell data locally or transmit the circulating tumor cells data to a processing unit.

An autonomic tone sensing system may measure autonomic tone data including skin conductance, heart rate variability, activity, and/or peripheral body temperature. The autonomic tone sensing system may include one or more electrodes, PPG trace, ECG trace, accelerometer, GPS, and/or thermometer. The autonomic tone sensing system may include a wearable device that may include a wristband and/or finger band.

Based on the autonomic tone data, the autonomic tone sensing system may detect autonomic tone-related biomarkers, complications, and/or contextual information, including sympathetic nervous system activity level and/or parasympathetic nervous system activity level. The autonomic tone may describe the basal balance between the sympathetic and parasympathetic nervous system. Based on the measured autonomic tone data, the autonomic tone sensing system may indicate risk for post-operative conditions including inflammation and/or infection. High sympathetic activity may associate with increase in inflammatory mediators, suppressed immune function, postoperative ileus, increased heart rate, increased skin conductance, increased sweat rate, and/or anxiety.

In an example, the detection, prediction, and/or determination described herein may be performed by a computing system based on measured data and/or related biomarkers generated by the autonomic tone sensing system. The autonomic tone sensing system may process the autonomic tone data locally or transmit the data to a processing unit.

A circadian rhythm sensing system may measure circadian rhythm data including light exposure, heart rate, core body temperature, cortisol levels, activity, and/or sleep. Based on the circadian rhythm data the circadian rhythm sensing system may detect circadian rhythm-related biomarkers, complications, and/or contextual information including sleep cycle, wake cycle, circadian patterns, disruption in circadian rhythm, and/or hormonal activity.

For example, based on the measured circadian rhythm data, the circadian rhythm sensing system may calculate the start and end of the circadian cycle. The circadian rhythm sensing system may indicate the beginning of the circadian day based on measured cortisol. Cortisol levels may peak at the start of a circadian day. The circadian rhythm sensing system may indicate the end of the circadian day based on measured heart rate and/or core body temperature. Heart rate and/or core body temperature may drop at the end of a circadian day. Based on the circadian rhythm-related biomarkers, the sensing system or processing unit may detect conditions including risk of infection and/or pain. For example, disrupted circadian rhythm may indicate pain and discomfort.

In an example, the detection, prediction, and/or determination described herein may be performed by a computing system based on measured data and/or related biomarkers generated by the circadian rhythm sensing system. The circadian rhythm sensing system may process the circadian rhythm data locally or transmit the data to a processing unit.

A menstrual cycle sensing system may measure menstrual cycle data including heart rate, heart rate variability, respiration rate, body temperature, and/or skin perfusion. Based on the menstrual cycle data, the menstrual cycle unit may indicate menstrual cycle-related biomarkers, complications, and/or contextual information, including menstrual cycle phase. For example, the menstrual cycle sensing system may detect the periovulatory phase in the menstrual cycle based on measured heart rate variability. Changes in heart rate variability may indicate the periovulatory phase. For example, the menstrual cycle sensing system may detect the luteal phase in the menstrual cycle based on measured wrist skin temperature and/or skin perfusion. Increased wrist skin temperature may indicate the luteal phase. Changes in skin perfusion may indicate the luteal phase. For example, the menstrual cycle sensing system may detect the ovulatory phase based on measured respiration rate. Low respiration rate may indicate the ovulatory phase.

Based on menstrual cycle-related biomarkers, the menstrual cycle sensing system may determine conditions including hormonal changes, surgical bleeding, scarring, bleeding risk, and/or sensitivity levels. For example, the menstrual cycle phase may affect surgical bleeding in rhinoplasty. For example, the menstrual cycle phase may affect healing and scarring in breast surgery. For example, bleeding risk may decrease during the periovulatory phase in the menstrual cycle.

In an example, the detection, prediction, and/or determination described herein may be performed by a computing system based on measured data and/or related biomarkers generated by the menstrual cycle sensing system. The menstrual cycle sensing system may locally process menstrual cycle data or transmit the data to a processing unit.

An environmental sensing system may measure environmental data including environmental temperature, humidity, mycotoxin spore count, and airborne chemical data. The environmental sensing system may include a digital thermometer, air sampling, and/or chemical sensors. The sensing system may include a wearable device. The environmental sensing system may use a digital thermometer to measure environmental temperature and/or humidity. The digital thermometer may include a metal strip with a determined resistance. The resistance of the metal strip may vary with environmental temperature. The digital thermometer may apply the varied resistance to a calibration curve to determine temperature. The digital thermometer may include a wet bulb and a dry bulb. The wet bulb and dry bulb may determine a difference in temperature, which then may be used to calculate humidity.

The environmental sensing system may use air sampling to measure mycotoxin spore count. The environmental sensing system may include a sampling plate with adhesive media connected to a pump. The pump may draw air over the plate over set time at a specific flow rate. The set time may last up to 10 minutes. The environmental sensing system may analyze the sample using a microscope to count the number of spores. The environmental sensing system may use different air sampling techniques including high-performance liquid chromatography (HPLC), liquid chromatography-tandem mass spectrometry (LC-MS/MS), and/or immunoassays and nanobodies.

The environmental sensing system may include chemical sensors to measure airborne chemical data. Airborne chemical data may include different identified airborne chemicals, including nicotine and/or formaldehyde. The chemical sensors may include an active layer and a transducer layer. The active layer may allow chemicals to diffuse into a matrix and alter some physical or chemical property. The changing physical property may include refractive index and/or H-bond formation. The transducer layer may convert the physical and/or chemical variation into a measurable signal, including an optical or electrical signal. The environmental sensing system may include a handheld instrument. The handheld instrument may detect and identify complex chemical mixtures that constitute aromas, odors, fragrances, formulations, spills, and/or leaks. The handheld instrument may include an array of nanocomposite sensors. The handheld instrument may detect and identify substances based on chemical profile.

Based on the environmental data, the sensing system may determine environmental information including climate, mycotoxin spore count, mycotoxin identification, airborne chemical identification, airborne chemical levels, and/or inflammatory chemical inhalation. For example, the environmental sensing system may approximate the mycotoxin spore count in the air based on the measured spore count from a collected sample. The sensing system may identify the mycotoxin spores which may include molds, pollens, insect parts, skin cell fragments, fibers, and/or inorganic particulate. For example, the sensing system may detect inflammatory chemical inhalation, including cigarette smoke. The sensing system may detect second-hand or third-hand smoke.

Based on the environmental information, the sensing system may generate environmental aspects conditions including inflammation, reduced lung function, airway hyper-reactivity, fibrosis, and/or reduce immune functions. For example, the environmental aspects sensing system may detect inflammation and fibrosis based on the measured environmental aspects information. The sensing system may generate instructions for a surgical tool, including a staple and sealing tool used in lung segmentectomy, based on the inflammation and/or fibrosis. Inflammation and fibrosis may affect the surgical tool usage. For example, cigarette smoke may cause higher pain scores in various surgeries.

The environmental sensing system may generate an air quality score based on the measured mycotoxins and/or airborne chemicals. For example, the environmental sensing system may notify about hazardous air quality if it detects a poor air quality score. The environmental sensing system may send a notification when the generated air quality score falls below a certain threshold. The threshold may include exposure exceeding 105 spores of mycotoxins per cubic meter. The environmental sensing system may display a readout of the environment condition exposure over time.

The environmental sensing system may locally process environmental data or transmit the data to a processing unit. In an example, the detection, prediction, and/or determination described herein may be performed by a computing system based on measured data generated by the environmental sensing system.

A light exposure sensing system may measure light exposure data. The light exposure sensing system may include one or more photodiode light sensors. For example, the light exposure sensing system using photodiode light sensors may include a semiconductor device in which the device current may vary as a function of light intensity. Incident photons may create electron-hole pairs that flow across the semiconductor junction, which may create current. The rate of electron-hole pair generation may increase as a function of the intensity of the incident light. The light exposure sensing system may include one or more photoresistor light sensors. For example, the light exposure sensing system using photoresistor light sensors may include a light-dependent resistor in which the resistance decreases as a function of light intensity. The photoresistor light sensor may include passive devices without a PN-junction. The photoresistor light sensors may be less sensitive than photodiode light sensors. The light exposure sensing system may include a wearable, including a necklace and/or clip-on button.

Based on the measured light exposure data, the light exposure sensing system may detect light exposure information including exposure duration, exposure intensity, and/or light type. For example, the sensing system may determine whether light exposure consists of natural light or artificial light. Based on the detected light exposure information, the light exposure sensing system may detect light exposure-related biomarker(s) including circadian rhythm. Light exposure may entrain the circadian cycle.

The light exposure sensing system may locally process the light exposure data or transmit the data to a processing unit. In an example, the detection, prediction, and/or determination described herein may be performed by a computing system based on measured data and/or related biomarkers generated by the light exposure sensing system.

The various sensing systems described herein may measure data, derive related biomarkers, and send the biomarkers to a computing system, such as a surgical hub as described herein with reference to FIGS. 1-12. The various sensing systems described herein may send the measured data to the computing system. The computing system may derive the related biomarkers based on the received measurement data.

The biomarker sensing systems may include a wearable device. In an example, the biomarker sensing system may include eyeglasses. The eyeglasses may include a nose pad sensor. The eyeglasses may measure biomarkers, including lactate, glucose, and/or the like. In an example, the biomarker sensing system may include a mouthguard. The mouthguard may include a sensor to measure biomarkers including uric acid and/or the like. In an example, the biomarker sensing system may include a contact lens. The contact lens may include a sensor to measure biomarkers including glucose and/or the like. In an example, the biomarker sensing system may include a tooth sensor. The tooth sensor may be graphene-based. The tooth sensor may measure biomarkers including bacteria and/or the like. In an example, the biomarker sensing system may include a patch. The patch may be wearable on the chest skin or arm skin. For example, the patch may include a chem-phys hybrid sensor. The chem-phys hybrid sensor may measure biomarkers including lactate, ECG, and/or the like. For example, the patch may include nanomaterials. The nanomaterials patch may measure biomarkers including glucose and/or the like. For example, the patch may include an iontophoretic biosensor. The iontophoretic biosensor may measure biomarkers including glucose and/or the like. In an example, the biomarker sensing system may include a microfluidic sensor. The microfluidic sensor may measure biomarkers including lactate, glucose, and/or the like. In an example, the biomarker sensing system may include an integrated sensor array. The integrated sensory array may include a wearable wristband. The integrated sensory array may measure biomarkers including lactate, glucose, and/or the like. In an example, the biomarker sensing system may include a wearable diagnostics device. The wearable diagnostic device may measure biomarkers including cortisol, interleukin-6, and/or the like. In an example, the biomarker sensing system may include a self-powered textile-based biosensor. The self-powered textile-based biosensor may include a sock. The self-powered textile-based biosensor may measure biomarkers including lactate and/or the like.

The various biomarkers described herein may be related to various physiologic systems, including behavior and psychology, cardiovascular system, renal system, skin system, nervous system, GI system, respiratory system, endocrine system, immune system, tumor, musculoskeletal system, and/or reproductive system.

Behavior and psychology may include social interactions, diet, sleep, activity, and/or psychological status. Behavior and psychology-related biomarkers, complications, contextual information, and/or conditions may be determined and/or predicted based on analyzed biomarker sensing systems data. A computing system, as described herein, may select one or more biomarkers (e.g., data from biomarker sensing systems) from behavior and psychology-related biomarkers, including sleep, circadian rhythm, physical activity, and/or mental aspects for analysis. Behavior and psychology scores may be generated based on the analyzed biomarkers, complications, contextual information, and/or conditions. Behavior and psychology scores may include scores for social interaction, diet, sleep, activity, and/or psychological status.

For example, based on the selected biomarker sensing systems data, sleep-related biomarkers, complications, and/or contextual information may be determined, including sleep quality, sleep duration, sleep timing, immune function, and/or post-operation pain. Based on the selected biomarker sensing systems data, sleep-related conditions may be predicted, including inflammation. In an example, inflammation may be predicted based on analyzed pre-operation sleep. Elevated inflammation may be determined and/or predicted based on disrupted pre-operation sleep. In an example, immune function may be determined based on analyzed pre-operation sleep. Reduced immune function may be predicted based on disrupted pre-operation sleep. In an example, post-operation pain may be determined based on analyzed sleep. Post-operation pain may be determined and/or predicted based on disrupted sleep. In an example, pain and discomfort may be determined based on analyzed circadian rhythm. A compromised immune system may be determined based on analyzed circadian rhythm cycle disruptions.

For example, based on the selected biomarker sensing systems data, activity-related biomarkers, complications, and/or contextual information may be determined, including activity duration, activity intensity, activity type, activity pattern, recovery time, mental health, physical recovery, immune function, and/or inflammatory function. Based on the selected biomarker sensing systems data, activity-related conditions may be predicted. In an example, improved physiology may be determined based on analyzed activity intensity. Moderate intensity exercise may indicate shorter hospital stays, better mental health, better physical recovery, improved immune function, and/or improved inflammatory function. Physical activity type may include aerobic activity and/or non-aerobic activity. Aerobic physical activity may be determined based on analyzed physical activity, including running, cycling, and/or weight training. Non-aerobic physical activity may be determined based on analyzed physical activity, including walking and/or stretching.

For example, based on the selected biomarker sensing systems data, psychological status-related biomarkers, complications, and/or contextual information may be determined, including stress, anxiety, pain, positive emotions, abnormal states, and/or post-operative pain. Based on the selected biomarker sensing systems data, psychological status-related conditions may be predicted, including physical symptoms of disease. Higher post-operative pain may be determined and/or predicted based on analyzed high levels of pre-operative stress, anxiety, and/or pain. Physical symptoms of disease may be predicted based on determined high optimism.

The detection, prediction, determination, and/or generation described herein may be performed by a computing system described herein, such as a surgical hub, a computing device, and/or a smart device based on measured data and/or related biomarkers generated by the biomarker sensing systems.

The cardiovascular system may include the lymphatic system, blood vessels, blood, and/or heart. Cardiovascular system-related biomarkers, complications, contextual information, and/or conditions may be determined and/or predicted based on analyzed biomarker sensing systems data. Systemic circulation conditions may include conditions for the lymphatic system, blood vessels, and/or blood. A computing system may select one or more biomarkers (e.g., data from biomarker sensing systems) from cardiovascular system-related biomarkers, including blood pressure, VO2 max, hydration state, oxygen saturation, blood pH, sweat, core body temperature, peripheral temperature, edema, heart rate, and/or heart rate variability for analysis.

For example, based on the selected biomarker sensing systems data, lymphatic system-related biomarkers, complications, and/or contextual information may be determined, including swelling, lymph composition, and/or collagen deposition. Based on the selected biomarker sensing systems data, lymphatic system-related conditions may be predicted, including fibrosis, inflammation, and/or post-operation infection. Inflammation may be predicted based on determined swelling. Post-operation infection may be predicted based on determined swelling. Collagen deposition may be determined based on predicted fibrosis. Increased collagen deposition may be predicted based on fibrosis. Harmonic tool parameter adjustments may be generated based on determined collagen deposition increases. Inflammatory conditions may be predicted based on analyzed lymph composition. Different inflammatory conditions may be determined and/or predicted based on changes in lymph peptidome composition. Metastatic cell spread may be predicted based on predicted inflammatory conditions. Harmonic tool parameter adjustments and margin decisions may be generated based on predicted inflammatory conditions.

For example, based on the selected biomarker sensing systems data, blood vessel-related biomarkers, complications, and/or contextual information may be determined, including permeability, vasomotion, pressure, structure, healing ability, harmonic sealing performance, and/or cardiothoracic health fitness. Surgical tool usage recommendations and/or parameter adjustments may be generated based on the determined blood vessel-related biomarkers. Based on the selected biomarker sensing systems data, blood vessel-related conditions may be predicted, including infection, anastomotic leak, septic shock and/or hypovolemic shock. In an example, increased vascular permeability may be determined based on analyzed edema, bradykinin, histamine, and/or endothelial adhesion molecules. Endothelial adhesion molecules may be measured using cell samples to measure transmembrane proteins. In an example, vasomotion may be determined based on selected biomarker sensing systems data. Vasomotion may include vasodilators and/or vasoconstrictors. In an example, shock may be predicted based on the determined blood pressure-related biomarkers, including vessel information and/or vessel distribution. Individual vessel structure may include arterial stiffness, collagen content, and/or vessel diameter. Cardiothoracic health fitness may be determined based on VO2 max. Higher risk of complications may be determined and/or predicted based on poor VO2 max.

For example, based on the selected biomarker sensing systems data, blood-related biomarkers, complications, and/or contextual information may be determined, including volume, oxygen, pH, waste products, temperature, hormones, proteins, and/or nutrients. Based on the selected biomarker sensing systems data, blood-related complications and/or contextual information may be determined, including cardiothoracic health fitness, lung function, recovery capacity, anaerobic threshold, oxygen intake, carbon dioxide ($CO_2$) production, fitness, tissue oxygenation, colloid osmotic pressure, and/or blood clotting ability. Based on derived blood-related biomarkers, blood-related conditions may be predicted, including post-operative acute kidney injury, hypovolemic shock, acidosis, sepsis, lung collapse, hemorrhage, bleeding risk, infection, and/or anastomotic leak.

For example, post-operative acute kidney injury and/or hypovolemic shock may be predicted based on the hydration state. For example, lung function, lung recovery capacity, cardiothoracic health fitness, anaerobic threshold, oxygen uptake, and/or $CO_2$ product may be predicted based on the blood-related biomarkers, including red blood cell count and/or oxygen saturation. For example, cardiovascular complications may be predicted based on the blood-related biomarkers, including red blood cell count and/or oxygen saturation. For example, acidosis may be predicted based on the pH. Based on acidosis, blood-related conditions may be indicated, including sepsis, lung collapse, hemorrhage, and/or increased bleeding risk. For example, based on sweat, blood-related biomarkers may be derived, including tissue oxygenation. Insufficient tissue oxygenation may be predicted based on high lactate concentration. Based on insufficient tissue oxygenation, blood-related conditions may be predicted, including hypovolemic shock, septic shock, and/ or left ventricular failure. For example, based on the temperature, blood temperature-related biomarkers may be derived, including menstrual cycle and/or basal temperature. Based on the blood temperature-related biomarkers, blood temperature-related conditions may be predicted, including sepsis and/or infection. For example, based on proteins, including albumin content, colloid osmotic pressure may be determined. Based on the colloid osmotic pressure, blood protein-related conditions may be predicted, including edema risk and/or anastomotic leak. Increased edema risk and/or anastomotic leak may be predicted based on low colloid osmotic pressure. Bleeding risk may be predicted based on blood clotting ability. Blood clotting ability may be determined based on fibrinogen content. Reduced blood clotting ability may be determined based on low fibrinogen content.

For example, based on the selected biomarker sensing systems data, the computing system may derive heart-related biomarkers, complications, and/or contextual information, including heart activity, heart anatomy, recovery rates, cardiothoracic health fitness, and/or risk of complications. Heart activity biomarkers may include electrical activity and/or stroke volume. Recovery rate may be determined based on heart rate biomarkers. Reduced blood supply to the body may be determined and/or predicted based on irregular heart rate. Slower recovery may be determined and/or predicted based on reduced blood supply to the body. Cardiothoracic health fitness may be determined based on analyzed VO2 max values. VO2 max values below a certain threshold may indicate poor cardiothoracic health fitness. VO2 max values below a certain threshold may indicate a higher risk of heart-related complications.

The detection, prediction, determination, and/or generation described herein may be performed by a computing system described herein, such as a surgical hub, a computing device, and/or a smart device, based on measured data and/or related biomarkers generated by the biomarker sensing systems.

Renal system-related biomarkers, complications, contextual information, and/or conditions may be determined and/or predicted based on analyzed biomarker sensing systems data. A computing system, as described herein, may select one or more biomarkers (e.g., data from biomarker sensing systems) from renal system-related biomarkers for analysis. Based on the selected biomarker sensing systems data, renal system-related biomarkers, complications, and/or contextual information may be determined including ureter, urethra, bladder, kidney, general urinary tract, and/or ureter fragility. Based on the selected biomarker sensing systems data, renal system-related conditions may be predicted, including acute kidney injury, infection, and/or kidney stones. In an example, ureter fragility may be determined based on urine inflammatory parameters. In an example, acute kidney injury may be predicted based on analyzed Kidney Injury Molecule-1 (KIM-1) in urine.

The detection, prediction, determination, and/or generation described herein may be performed by a computing system described herein, such as a surgical hub, a computing device, and/or a smart device based on measured data and/or related biomarkers generated by the biomarker sensing systems.

The skin system may include biomarkers relating to microbiome, skin, nails, hair, sweat, and/or sebum. Skin-related biomarkers may include epidermis biomarkers and/or dermis biomarkers. Sweat-related biomarkers may include activity biomarkers and/or composition biomarkers. Skin system-related biomarkers, complications, contextual information, and/or conditions may be determined and/or predicted based on analyzed biomarker sensing systems data. A computing system, as described herein, may select one or more biomarkers (e.g., data from biomarker sensing systems) from skin-related biomarkers, including skin conductance, skin perfusion pressure, sweat, autonomic tone, and/or pH for analysis.

For example, based on selected biomarker sensing systems data, skin-related biomarkers, complications, and/or contextual information may be determined, including color, lesions, trans-epidermal water loss, sympathetic nervous system activity, elasticity, tissue perfusion, and/or mechanical properties. Stress may be predicted based on determined skin conductance. Skin conductance may act as a proxy for sympathetic nervous system activity. Sympathetic nervous system activity may correlate with stress. Tissue mechanical properties may be determined based on skin perfusion pressure. Skin perfusion pressure may indicate deep tissue perfusion. Deep tissue perfusion may determine tissue mechanical properties. Surgical tool parameter adjustments may be generated based on determined tissue mechanical properties.

Based on selected biomarker sensing systems data, skin-related conditions may be predicted.

For example, based on selected biomarker sensing systems data, sweat-related biomarkers, complications, and/or contextual information may be determined, including activity, composition, autonomic tone, stress response, inflammatory response, blood pH, blood vessel health, immune function, circadian rhythm, and/or blood lactate concentration. Based on selected biomarker sensing systems data, sweat-related conditions may be predicted, including ileus, cystic fibrosis, diabetes, metastasis, cardiac issues, and/or infections.

For example, sweat composition-related biomarkers may be determined based on selected biomarker data. Sweat composition biomarkers may include proteins, electrolytes, and/or small molecules. Based on the sweat composition biomarkers, skin system complications, conditions, and/or contextual information may be predicted, including ileus, cystic fibrosis, acidosis, sepsis, lung collapse, hemorrhage, bleeding risk, diabetes, metastasis, and/or infection. For example, based on protein biomarkers, including sweat neuropeptide Y and/or sweat antimicrobials, stress response may be predicted. Higher sweat neuropeptide Y levels may indicate greater stress response. Cystic fibrosis and/or acidosis may be predicted based on electrolyte biomarkers, including chloride ions, pH, and other electrolytes. High lactate concentrations may be determined based on blood pH. Acidosis may be predicted based on high lactate concentrations. Sepsis, lung collapse, hemorrhage, and/or bleeding risk may be predicted based on predicted acidosis. Diabetes, metastasis, and/or infection may be predicted based on small molecule biomarkers. Small molecule biomarkers may include blood sugar and/or hormones. Hormone biomarkers may include adrenaline and/or cortisol. Based on predicted metastasis, blood vessel health may be determined. Infection due to lower immune function may be predicted based on detected cortisol. Lower immune function may be determined and/or predicted based on high cortisol. For example, sweat-related conditions, including stress response, inflammatory response, and/or ileus, may be predicted based on determined autonomic tone. Greater stress response, greater inflammatory response, and/or ileus may be determined and/or predicted based on high sympathetic tone.

The detection, prediction, determination, and/or generation described herein may be performed by a computing system described herein, such as a surgical hub, a computing device, and/or a smart device based on measured data and/or related biomarkers generated by the biomarker sensing systems.

Nervous system-related biomarkers, complications, contextual information, and/or conditions may be determined and/or predicted based on analyzed biomarker sensing systems data. A computing system, as described herein, may select one or more biomarkers (e.g., data from biomarker sensing systems) from nervous system-related biomarkers, including circadian rhythm, oxygen saturation, autonomic tone, sleep, activity, and/or mental aspects for. The nervous system may include the central nervous system (CNS) and/or the peripheral nervous system. The CNS may include brain and/or spinal cord. The peripheral nervous system may include the autonomic nervous system, motor system, enteric system, and/or sensory system.

For example, based on the selected biomarker sensing systems data, CNS-related biomarkers, complications, and/ or contextual information may be determined, including post-operative pain, immune function, mental health, and/or recovery rate. Based on the selected biomarker sensing systems data, CNS-related conditions may be predicted, including inflammation, delirium, sepsis, hyperactivity, hypoactivity, and/or physical symptoms of disease. In an example, a compromised immune system and/or high pain score may be predicted based on disrupted sleep. In an example, post-operation delirium may be predicted based on oxygen saturation. Cerebral oxygenation may indicate post-operation delirium.

For example, based on the selected biomarker sensing systems data, peripheral nervous system-related biomarkers, complications, and/or contextual information may be determined. Based on the selected biomarker sensing systems data, peripheral nervous system-related conditions may be predicted, including inflammation and/or ileus. In an example, high sympathetic tone may be predicted based on autonomic tone. Greater stress response may be predicted based on high sympathetic tone. Inflammation and/or ileus may be predicted based on high sympathetic tone.

The detection, prediction, determination, and/or generation described herein may be performed by a computing system described herein, such as a surgical hub, a computing device, and/or a smart device based on measured data and/or related biomarkers generated by the biomarker sensing systems.

The GI system may include the upper GI tract, lower GI tract, ancillary organs, peritoneal space, nutritional states, and microbiomes. The upper GI may include the mouth, esophagus, and/or stomach. The lower GI may include the small intestine, colon, and/or rectum. Ancillary organs may include pancreas, liver, spleen, and/or gallbladder. Peritoneal space may include mesentry and/or adipose blood vessels. Nutritional states may include short-term, long-term, and/or systemic. GI-related biomarkers, complications, contextual information, and/or conditions may be determined and/or predicted based on analyzed biomarker sensing systems data. A computing system, as described herein, may select one or more biomarkers (e.g., data from biomarker sensing systems) from GI-related biomarkers, including coughing and sneezing, respiratory bacteria, GI tract imaging/sensing, GI motility, pH, tissue perfusion pressure, environmental, and/or alcohol consumption for analysis.

The upper GI may include the mouth, esophagus, and/or stomach. For example, based on the selected biomarker sensing systems data, mouth and esophagus-related biomarkers, complications, and/or contextual information, may be determined, including stomach tissue properties, esophageal motility, colonic tissue change, bacteria presence, tumor size, tumor location, and/or tumor tension. Based on the selected biomarker sensing systems data, mouth and esophagus-related conditions may be predicted, including inflammation, surgical site infection (SSI), and/or gastro-esophageal disease. The mouth and esophagus may include mucosa, muscularis, lumen, and/or mechanical properties. Lumen biomarkers may include lumen contents, lumen microbial flora, and/or lumen size. In an example, inflammation may be predicted based on analyzed coughing biomarkers. Gastro-esophageal reflux disease may be predicted based on inflammation. Stomach tissue properties may be predicted based on gastro-esophageal disease. In an example, esophageal motility may be determined based on collagen content and/or muscularis function. In an example, changes to colonic tissue may be indicated based on salivary cytokines. Inflammatory bowel disease (IBD) may be predicted based on changes to colonic tissue. Salivary cytokines may increase in IBD. SSI may be predicted based on analyzed bacteria. Based on the analyzed bacteria, the bacteria may be identified. Respiratory pathogens in the mouth may indicate likelihood of SSI. Based on lumen size and/or location, surgical tool parameter adjustments may be generated. Surgical tool parameter adjustments may include staple sizing, surgical tool fixation, and/or surgical tool approach. In an example, based on mechanical properties, including elasticity, a surgical tool parameter adjustment to use adjunct material may be generated to minimize tissue tension. Additional mobilization parameter adjustments may be generated to minimize tissue tension based on analyzed mechanical properties.

For example, based on the selected biomarker sensing systems data, stomach-related biomarkers, complications, and/or contextual information, may be determined including tissue strength, tissue thickness, recovery rate, lumen location, lumen shape, pancreas function, stomach food presence, stomach water content, stomach tissue thickness, stomach tissue shear strength, and/or stomach tissue elasticity. Based on the selected biomarker sensing systems data, stomach-related conditions may be predicted, including ulcer, inflammation, and/or gastro-esophageal reflux disease. The stomach may include mucosa, muscularis, serosa, lumen, and mechanical properties. Stomach-related conditions, including ulcers, inflammation, and/or gastro-esophageal disease may be predicted based on analyzed coughing and/or GI tract imaging. Stomach tissue properties may be determined based on gastro-esophageal reflux disease. Ulcers may be predicted based on analyzed *H. pylori*. Stomach tissue mechanical properties may be determined based on GI tract images. Surgical tool parameter adjustments may be generated based on the determined stomach tissue mechanical properties. Risk of post-operative leak may be predicted based on determined stomach tissue mechanical properties. In an example, key components for tissue strength and/or thickness may be determined based on analyzed collagen content. Key components of tissue strength and thickness may affect recovery. In an example, blood supply and/or blood location may be determined based on serosa biomarkers. In an example, biomarkers, including pouch size, pouch volume, pouch location, pancreas function, and/or food presence may be determined based on analyzed lumen biomarkers. Lumen biomarkers may include lumen location, lumen shape, gastric emptying speed, and/or lumen contents. Pouch size may be determined based on start and end locations of the pouch. Gastric emptying speed may be determined based on GI motility. Pancreas function may be determined based on gastric emptying speed. Lumen content may be determined based on analyzed gastric pH. Lumen content may include stomach food presence. For example, solid food presence may be determined based on gastric pH variation. Low gastric pH may be predicted based on an empty stomach. Basic gastric pH may be determined based on eating. Buffering by food may lead to basic gastric pH. Gastric pH may increase based on stomach acid secretion. Gastric pH may return to low value when the buffering capacity of food is exceeded. Intraluminal pH sensors may detect eating. For example, stomach water content, tissue thickness, tissue shear strength, and/or tissue elasticity may be determined based on tissue perfusion pressure. Stomach mechanical properties may be determined based on stomach water content. Surgical tool parameter adjustments may be generated based on the stomach mechanical properties. Surgical tool parameter adjustments may be generated based on key components of tissue strength and/or friability. Post-surgery leakage may be predicted based on key components of tissue strength and/or friability.

The lower GI may include the small intestine, colon, and/or rectum. For example, based on the selected biomarker sensing systems data, small intestine-related biomarkers, complications, contextual information, and/or conditions may be determined, including caloric absorption rate, nutrient absorption rate, bacteria presence, and/or recovery rate. Based on the selected biomarker sensing systems data, small intestine-related conditions may be predicted, including ileus and/or inflammation. The small intestine biomarkers may include muscularis, serosa, lumen, mucosa, and/or mechanical properties. For example, post-operation small bowel motility changes may be determined based on GI motility. Ileus may be predicted based on post-operation small bowel motility changes. GI motility may determine caloric and/or nutrient absorption rates. Future weight loss may be predicted based on accelerated absorption rates. Absorption rates may be determined based on fecal rates, composition, and/or pH. Inflammation may be predicted based on lumen content biomarkers. Lumen content biomarkers may include pH, bacteria presence, and/or bacteria amount. Mechanical properties may be determined based on predicted inflammation. Mucosa inflammation may be predicted based on stool inflammatory markers. Stool inflammatory markers may include calprotectin. Tissue property changes may be determined based on mucosa inflammation. Recovery rate changes may be determined based on mucosa inflammation.

For example, based on the selected biomarker sensing systems data, colon and rectum-related biomarkers, complications, and/or contextual information may be determined, including small intestine tissue strength, small intestine tissue thickness, contraction ability, water content, colon and rectum tissue perfusion pressure, colon and rectum tissue thickness, colon and rectum tissue strength, and/or colon and rectum tissue friability. Based on the selected biomarker sensing systems data, colon and rectum-related conditions may be predicted, including inflammation, anastomotic leak, ulcerative colitis, Crohn's disease, and/or infection. Colon and rectum may include mucosa, muscularis, serosa, lumen, function, and/or mechanical properties. In an example, mucosa inflammation may be predicted based on stool inflammatory markers. Stool inflammatory markers may include calprotectin. An increase in anastomotic leak risk may be determined based on inflammation.

Surgical tool parameter adjustments may be generated based on the determined increased risk of anastomotic leak. Inflammatory conditions may be predicted based on GI tract imaging. Inflammatory conditions may include ulcerative colitis and/or Crohn's disease. Inflammation may increase the risk of anastomotic leak. Surgical tool parameter adjustments may be generated based on inflammation. In an example, the key components of tissue strength and/or thickness may be determined based on collagen content. In an example, colon contraction ability may be determined based on smooth muscle alpha-actin expression. In an example, the inability of colon areas to contract may be determined based on abnormal expression. Colon contraction inability may be determined and/or predicted based on pseudo-obstruction and/or ileus. In an example, adhesions, fistula, and/or scar tissue may be predicted based on serosa biomarkers. Colon infection may be predicted based on bacterial presence in stool. The stool bacteria may be identified. The bacteria may include commensals and/or pathogens. In an example, inflammatory conditions may be predicted based on pH. Mechanical properties may be determined based on inflammatory conditions. Gut inflammation may be predicted based on ingested allergens. Constant exposure to ingested allergens may increase gut inflammation. Gut inflammation may change mechanical properties. In an example, mechanical properties may be determined based on tissue perfusion pressure. Water content may be determined based on tissue perfusion pressure. Surgical tool parameter adjustments may be generated based on determined mechanical properties.

Ancillary organs may include the pancreas, liver, spleen, and/or gallbladder. Based on the selected biomarker sensing systems data, ancillary organ-related biomarkers, complications, and/or contextual information may be determined including gastric emptying speed, liver size, liver shape, liver location, tissue health, and/or blood loss response. Based on the selected biomarker sensing systems data, ancillary organ-related conditions may be predicted, including gastroparesis. For example, gastric emptying speed may be determined based on enzyme load and/or titratable base biomarkers. Gastroparesis may be predicted based on gastric emptying speed. Lymphatic tissue health may be determined based on lymphocyte storage status. A patient's ability to respond to an SSI may be determined based on lymphatic tissue health. Venous sinuses tissue health may be determined based on red blood cell storage status. A patient's response to blood loss in surgery may be predicted based on venous sinuses tissue health.

Nutritional states may include short-term nutrition, long-term nutrition, and/or systemic nutrition. Based on the selected biomarker sensing systems data, nutritional state-related biomarkers, complications, and/or contextual information may be determined, including immune function. Based on the selected biomarker sensing systems data, nutritional state-related conditions may be predicted, including cardiac issues. Reduced immune function may be determined based on nutrient biomarkers. Cardiac issues may be predicted based on nutrient biomarkers. Nutrient biomarkers may include macronutrients, micronutrients, alcohol consumption, and/or feeding patterns.

Patients who have had gastric bypass may have an altered gut microbiome that may be measured in the feces.

The detection, prediction, determination, and/or generation described herein may be performed by a computing system described herein, such as a surgical hub, a computing device, and/or a smart device based on measured data and/or related biomarkers generated by the biomarker sensing systems.

The respiratory system may include the upper respiratory tract, lower respiratory tract, respiratory muscles, and/or system contents. The upper respiratory tract may include the pharynx, larynx, mouth and oral cavity, and/or nose. The lower respiratory tract may include the trachea, bronchi, aveoli, and/or lungs. The respiratory muscles may include the diaphragm and/or intercostal muscles. Respiratory system-related biomarkers, complications, contextual information, and/or conditions may be determined and/or predicted based on analyzed biomarker sensing systems data. A computing system, as described herein, may select one or more biomarkers (e.g., data from biomarker sensing systems) from respiratory system-related biomarkers, including bacteria, coughing and sneezing, respiration rate, VO2 max, and/or activity for analysis.

The upper respiratory tract may include the pharynx, larynx, mouth and oral cavity, and/or nose. For example, based on the selected biomarker sensing systems data, upper respiratory tract-related biomarkers, complications, and/or contextual information may be determined. Based on the selected biomarker sensing systems data, upper respiratory tract-related conditions may be predicted, including SSI, inflammation, and/or allergic rhinitis. In an example, SSI may be predicted based on bacteria and/or tissue biomarkers. Bacteria biomarkers may include commensals and/or pathogens. Inflammation may be indicated based on tissue biomarkers. Mucosa inflammation may be predicted based on nose biomarkers, including coughing and sneezing. General inflammation and/or allergic rhinitis may be predicted based on mucosa biomarkers. Mechanical properties of various tissues may be determined based on systemic inflammation.

The lower respiratory tract may include the trachea, bronchi, aveoli, and/or lungs. For example, based on the selected biomarker sensing systems data, lower respiratory tract-related biomarkers, complications, and/or contextual information may be determined, including bronchopulmonary segments. Based on the selected biomarker sensing systems data, lower respiratory tract-related conditions may be predicted. Surgical tool parameter adjustments may be generated based on the determined biomarkers, complications, and/or contextual information. Surgical tool parameter adjustments may be generated based on the predicted conditions.

Based on the selected biomarker sensing systems data, lung-related biomarkers, complications, and/or contextual information may be determined, including poor surgical tolerance. Lung-related biomarkers may include lung respiratory mechanics, lung disease, lung surgery, lung mechanical properties, and/or lung function. Lung respiratory mechanics may include total lung capacity (TLC), tidal volume (TV), residual volume (RV), expiratory reserve volume (ERV), inspiratory reserve volume (IRV), inspiratory capacity (IC), inspiratory vital capacity (IVC), vital capacity (VC), functional residual capacity (FRC), residual volume expressed as a percent of total lung capacity (RV/TLC %), alveolar gas volume (VA), lung volume (VL), forced vital capacity (FVC), forced expiratory volume over time (FEVt), difference between inspired and expired carbon monoxide (DLco), volume exhaled after first second of forced expiration (FEV1), forced expiratory flow related to portion of functional residual capacity curve (FEFx), maximum instantaneous flow during functional residual capacity (FEFmax), forced inspiratory flow (FIF), highest forced expiratory flow measured by peak flow meter (PEF), and maximal voluntary ventilation (MVV).

TLC may be determined based on lung volume at maximal inflation. TV may be determined based on volume of air moved into or out of the lungs during quiet breathing. RV may be determined based on air volume remaining in lungs after a maximal exhalation. ERV may be determined based on maximal volume inhaled from the end-inspiratory level. IC may be determined based on aggregated IRV and TV values. IVC may be determined based on maximum air volume inhaled at the point of maximum expiration. VC may be determined based on the difference between the RV value and TLC value. FRC may be determined based on the lung volume at the end-expiratory position. FVC may be determined based on the VC value during a maximally forced expiratory effort. Poor surgical tolerance may be determined based on the difference between inspired and expired carbon monoxide, such as when the difference falls below 60%. Poor surgical tolerance may be determined based on the volume exhaled at the end of the first second of force expiration, such as when the volume falls below 35%. MVV may be determined based on the volume of air expired in a specified period during repetitive maximal effort.

Based on the selected biomarker sensing systems data, lung-related conditions may be predicted, including emphysema, chronic obstructive pulmonary disease, chronic bronchitis, asthma, cancer, and/or tuberculosis. Lung diseases may be predicted based on analyzed spirometry, x-rays, blood gas, and/or diffusion capacity of the aveolar capillary membrane. Lung diseases may narrow airways and/or create airway resistance. Lung cancer and/or tuberculosis may be detected based on lung-related biomarkers, including persistent coughing, coughing blood, shortness of breath, chest pain, hoarseness, unintentional weight loss, bone pain, and/or headaches. Tuberculosis may be predicted based on lung symptoms including coughing for 3 to 5 weeks, coughing blood, chest pain, pain while breathing or coughing, unintentional weight loss, fatigue, fever, night sweats, chills, and/or loss of appetite.

Surgical tool parameter adjustments and surgical procedure adjustments may be generated based on lung-related biomarkers, complications, contextual information, and/or conditions. Surgical procedure adjustments may include pneumonectomy, lobectomy, and/or sub-local resections. In an example, a surgical procedure adjustment may be generated based on a cost-benefit analysis between adequate resection and the physiologic impact on a patient's ability to recover functional status. Surgical tool parameter adjustments may be generated based on determined surgical tolerance. Surgical tolerance may be determined based on the FEC1 value. Surgical tolerance may be considered adequate when FEV1 exceeds a certain threshold, which may include values above 35%. Post-operation surgical procedure adjustments, including oxygenation and/or physical therapy, may be generated based on determined pain scores. Post-operation surgical procedure adjustments may be generated based on air leak. Air leak may increase cost associated with the post-surgical recovery and morbidity following lung surgery.

Lung mechanical property-related biomarkers may include perfusion, tissue integrity, and/or collagen content. Plura perfusion pressure may be determined based on lung water content levels. Mechanical properties of tissue may be determined based on plura perfusion pressure. Surgical tool parameter adjustments may be generated based on plura perfusion pressure. Lung tissue integrity may be determined based on elasticity, hydrogen peroxide (H2O2) in exhaled breath, lung tissue thickness, and/or lung tissue shear strength. Tissue friability may be determined based on elasticity. Surgical tool parameter adjustments may be generated based on post-surgery leakage. Post-surgery leakage may be predicted based on elasticity. In an example, fibrosis may be predicted based on H2O2 in exhaled breath. Fibrosis may be determined and/or predicted based on increased H2O2 concentration. Surgical tool parameter adjustments may be generated based on predicted fibrosis. Increased scarring in lung tissue may be determined based on predicted fibrosis. Surgical tool parameter adjustments may be generated based on determined lung tissue strength. Lung tissue strength may be determined based on lung thickness and/or lung tissue shear strength. Post-surgery leakage may be predicted based on lung tissue strength.

Respiratory muscles may include the diaphragm and/or intercostal muscles. Based on the selected biomarker sensing systems data, respiratory muscle-related biomarkers, complications, and/or contextual information may be determined. Based on the selected biomarker sensing systems data, respiratory muscle-related conditions may be predicted, including respiratory tract infections, collapsed lung, pulmonary edema, post-operation pain, air leak, and/or serious lung inflammation. Respiratory muscle-related conditions, including respiratory tract infections, collapsed lung, and/or pulmonary edema, may be predicted based on diaphragm-related biomarkers, including coughing and/or sneezing. Respiratory muscle-related conditions, including post-operation pain, air leak, collapsed lung, and/or serious lung inflammation may be predicted based on intercostal muscle biomarkers, including respiratory rate.

Based on the selected biomarker sensing systems data, respiratory system content-related biomarkers, complications, and/or contextual information may be determined, including post-operation pain, healing ability, and/or response to surgical injury. Based on the selected biomarker sensing systems data, respiratory system content-related conditions may be predicted, including inflammation and/or fibrosis. The selected biomarker sensing systems data may include environmental data, including mycotoxins and/or airborne chemicals. Respiratory system content-related conditions may be predicted based on airborne chemicals. Inflammation and/or fibrosis may be predicted based on irritants in the environment. Mechanical properties of tissue may be determined based on inflammation and/or fibrosis. Post-operation pain may be determined based on irritants in the environment. Airway inflammation may be predicted based on analyzed mycotoxins and/or arsenic. Surgical tool parameter adjustments may be generated based on airway inflammation. Altered tissue properties may be determined based on analyzed arsenic.

The detection, prediction, determination, and/or generation described herein may be performed by a computing system described herein, such as a surgical hub, a computing system, and/or a smart device based on measured data and/or related biomarkers generated by the biomarker sensing systems.

The endocrine system may include the hypothalamus, pituitary gland, thymus, adrenal gland, pancreas, testes, intestines, ovaries, thyroid gland, parathyroid, and/or stomach. Endocrine system-related biomarkers, complications, and/or contextual information may be determined based on analyzed biomarker sensing systems data, including immune system function, metastasis, infection risk, insulin secretion, collagen production, menstrual phase, and/or high blood pressure. Endocrine system-related conditions may be predicted based on analyzed biomarker sensing systems data. A computing system, as described herein, may select one or more biomarkers (e.g., data from biomarker sensing systems) from endocrine system-related biomarkers, including hormones, blood pressure, adrenaline, cortisol, blood glucose, and/or menstrual cycle for analysis. Surgical tool parameter adjustments and/or surgical procedure adjustments may be generated based on the endocrine system-related biomarkers, complications, contextual information, and/or conditions.

For example, based on the selected biomarker sensing systems data, hypothalamus-related biomarkers, complications, and/or contextual information may be determined, including blood pressure regulation, kidney function, osmotic balance, pituitary gland control, and/or pain tolerance. Based on the selected biomarker sensing systems data, hypothalamus-related conditions may be predicted, including edema. The hormone biomarkers may include anti-diuretic hormone (ADH) and/or oxytocin. ADH may affect blood pressure regulation, kidney function, osmotic balance, and/or pituitary gland control. Pain tolerance may be determined based on analyzed oxytocin. Oxytocin may have an analgesic effect. Surgical tool parameter adjustments may be generated based on predicted edema.

For example, based on the selected biomarker sensing systems data, pituitary gland-related biomarkers, complications, and/or contextual information may be determined, including circadian rhythm entrainment, menstrual phase, and/or healing speed. Based on the selected biomarker sensing systems data, pituitary gland-related conditions may be predicted. Circadian entrainment may be determined based on adrenocorticotropic hormones (ACTH). Circadian rhythm entrainment may provide context for various surgical outcomes. Menstrual phase may be determined based on reproduction function hormone biomarkers. Reproduction function hormone biomarkers may include luteinizing hormone and/or follicle stimulating hormone. Menstrual phase may provide context for various surgical outcomes. The menstrual cycle may provide context for biomarkers, complications, and/or conditions, including those related to the reproductive system. Wound healing speed may be determined based on thyroid regulation hormones, including thyrotropic releasing hormone (TRH).

For example, based on the selected biomarker sensing systems data, thymus-related biomarkers, complications, and/or contextual information may be determined, including immune system function. Based on the selected biomarker sensing systems data, thymus-related conditions may be predicted. Immune system function may be determined based on thymosins. Thymosins may affect adaptive immunity development.

For example, based on the selected biomarker sensing systems data, adrenal gland-related biomarkers, complications, and/or contextual information may be determined, including metastasis, blood vessel health, immunity level, and/or infection risk. Based on the selected biomarker sensing system data, adrenal gland-related conditions may be predicted, including edema. Metastasis may be determined based on analyzed adrenaline and/or nonadrenaline. Blood vessel health may be determined based on analyzed adrenaline and/or nonadrenaline. A blood vessel health score may be generated based on the determined blood vessel health. Immunity capability may be determined based on analyzed cortisol. Infection risk may be determined based on analyzed cortisol. Metastasis may be predicted based on analyzed cortisol. Circadian rhythm may be determined based on measured cortisol. High cortisol may lower immunity, increase infection risk, and/or lead to metastasis. High cortisol may affect circadian rhythm. Edema may be predicted based on analyzed aldosterone. Aldosterone may promote fluid retention. Fluid retention may relate to blood pressure and/or edema.

For example, based on the selected biomarker sensing systems data, pancreas-related biomarkers, complications, and/or contextual information may be determined, including blood sugar, hormones, polypeptides, and/or blood glucose control. Based on the selected biomarker sensing systems data, pancreas-related conditions may be predicted. The pancreas-related biomarkers may provide contextual information for various surgical outcomes. Blood sugar biomarkers may include insulin. Hormone biomarkers may include somatostatin. Polypeptide biomarkers may include pancreatic polypeptide. Blood glucose control may be determined based on insulin, somatostatin, and/or pancreatic polypeptide. Blood glucose control may provide contextual information for various surgical outcomes.

For example, based on the selected biomarker sensing systems data, testes-related biomarkers, complications, and/or contextual information may be determined, including reproductive development, sexual arousal, and/or immune system regulation. Based on the selected biomarker sensing systems data, testes-related conditions may be predicted. Testes-related biomarkers may include testosterone. Testosterone may provide contextual information for biomarkers, complications, and/or conditions, including those relating to the reproductive system. High levels of testosterone may suppress immunity.

For example, based on the selected biomarker sensing systems data, stomach/testes-related biomarkers, complications, and/or contextual information may be determined, including glucose handling, satiety, insulin secretion, digestion speed, and/or sleeve gastrectomy outcomes. Glucose handling and satiety biomarkers may include glucagon-like peptide-1 (GLP-1), cholecystokinin (CCK), and/or peptide YY. Appetite and/or insulin secretion may be determined based on analyzed GLP-1. Increased GLP-1 may be determined based on enhanced appetite and insulin secretion. Sleeve gastrectomy outcomes may be determined based on analyzed GLP-1. Satiety and/or sleeve gastrectomy outcomes may be determined based on analyzed CCK. Enhanced CCK levels may be predicted based on previous sleeve gastrectomy. Appetite and digestion speeds may be determined based on analyzed peptide YY. Increased peptide YY may reduce appetite and/or increase digestion speeds.

For example, based on the selected biomarker sensing systems data, hormone-related biomarkers, complications, and/or contextual information may be determined, including estrogen, progesterone, collagen product, fluid retention, and/or menstrual phase. Collagen production may be determined based on estrogen. Fluid retention may be determined based on estrogen. Surgical tool parameter adjustments may be generated based on determined collagen production and/or fluid retention.

For example, based on the selected biomarker sensing systems data, thyroid gland and parathyroid-related biomarkers, complications, and/or contextual information may be determined, including calcium handling, phosphate handling, metabolism, blood pressure, and/or surgical complications. Metabolism biomarkers may include triiodothyronine (T3) and/or thyroxine (T4). Blood pressure may be determined based on analyzed T3 and T4. High blood pressure may be determined based on increased T3 and/or increased T4. Surgical complications may be determined based on analyzed T3 and/or T4.

For example, based on the selected biomarker sensing systems data, stomach-related biomarkers, complications, and/or contextual information may be determined, including appetite. Stomach-related biomarkers may include ghrelin. Ghrelin may induce appetite.

The detection, prediction, determination, and/or generation described herein may be performed by a computing system described herein, such as a surgical hub, a computing system, and/or a smart device based on measured data and/or related biomarkers generated by the biomarker sensing systems.

Immune system-related biomarkers may relate to antigens and irritants, antimicrobial enzymes, the complement system, chemokines and cytokines, the lymphatic system, bone marrow, pathogens, damage-associated molecular patterns (DAMPs), and/or cells. Immune system-related biomarkers, complications, and/or contextual information may be determined based on analyzed biomarker sensing systems data. A computing system, as described herein, may select one or more biomarkers (e.g., data from biomarker sensing systems) from immune system-related biomarkers, including alcohol consumption, pH, respiratory rate, edema, sweat, and/or environment for analysis. Antigens/irritants For example, based on the selected biomarker sensing systems data, antigen and irritant-related biomarkers, complications, and/or contextual information may be determined, including healing ability, immune function, and/or cardiac issues. Based on the selected biomarker sensing systems data, antigen and irritant-related conditions may be predicted, including inflammation. Antigen and irritant-related biomarkers may include inhaled chemicals, inhaled irritants, ingested chemicals, and/or ingested irritants. Inhaled chemicals or irritants may be determined based on analyzed environmental data, including airborne chemicals, mycotoxins, and/or arsenic. Airborne chemicals may include cigarette smoke, asbestos, crystalline silica, alloy particles, and/or carbon nanotubes. Lung inflammation may be predicted based on analyzed airborne chemicals. Surgical tool parameter adjustments may be generated based on determined lung inflammation. Airway inflammation may be predicted based on analyzed mycotoxin and/or arsenic. Surgical tool parameter adjustments may be generated based on determined airway inflammation. Arsenic exposure may be determined based on urine, saliva, and/or ambient air sample analyses.

For example, based on the selected biomarker sensing systems data, antimicrobial enzyme-related biomarkers, complications, and/or contextual information may be determined, including colon state. Based on the selected biomarker sensing systems data, antimicrobial enzyme-related conditions may be predicted, including GI inflammation, acute kidney injury, *E. faecalis* infection, and/or *S. aureus* infection. Antimicrobial enzyme biomarkers may include lysozyme, lipocalin-2 (NGAL), and/or orosomuccoid. GI inflammation may be predicted based on analyzed lysozyme. Increased levels in lysozyme may be determined and/or predicted based on GI inflammation. Colon state may be determined based on analyzed lysozyme. Surgical tool parameter adjustments may be generated based on analyzed lysozyme levels. Acute kidney injury may be predicted based on analyzed NGAL. NGAL may be detected from serum and/or urine.

For example, based on the selected biomarker sensing systems data, complement system-related biomarkers, complications, and/or contextual information may be determined, including bacterial infection susceptibility. Bacterial infection susceptibility may be determined based on ana-lyzed complement system deficiencies.

For example, based on the selected biomarker sensing systems data, chemokine and cytokine-related biomarkers, complications, and/or contextual information may be deter-mined, including infection burden, inflammation burden, vascular permeability regulation, omentin, colonic tissue properties, and/or post-operation recovery. Based on the selected biomarker sensing systems data, chemokine and cytokine-related conditions may be predicted, including inflammatory bowel diseases, post-operation infection, lung fibrosis, lung scarring, pulmonary fibrosis, gastroesophageal reflux disease, cardiovascular disease, edema, and/or hyper-plasia. Infection and/or inflammation burden biomarkers may include oral, salivary, exhaled, and/or C-reactive pro-tein (CRP) data. Salivary cytokines may include inter-leukin-1 beta (IL-1β), interleukin-6 (IL-6), tumor necrosis factor alpha (TNF-α) and/or interleukin-8 (IL-8).

In an example, inflammatory bowel diseases may be predicted based on analyzed salivary cytokines. Increased salivary cytokines may be determined based on inflamma-tory bowel diseases. Colonic tissue properties may be deter-mined based on predicted inflammatory bowel diseases. Colonic tissue properties may include scarring, edema, and/or ulcering. Post-operation recovery and/or infection may be determined based on predicted inflammatory bowel diseases. Tumor size and/or lung scarring may be deter-mined based on analyzed exhaled biomarkers. Lung fibrosis, pulmonary fibrosis, and/or gastroesophageal reflux disease may be predicted based on analyzed exhaled biomarkers. Exhaled biomarkers may include exhaled cytokines, pH, hydrogen peroxide ($H_2O_2$), and/or nitric oxide. Exhaled cytokines may include IL-6, TNF-α, and/or interleukin-17 (IL-17). Lung fibrosis may be predicted based on measured pH and/or $H_2O_2$ from exhaled breath. Fibrosis may be predicted based on increased $H_2O_2$ concentration. Increased lung tissue scarring may be predicted based on fibrosis. Surgical tool parameter adjustments may be generated based on predicted lung fibrosis. In an example, pulmonary fibrosis and/or gastroesophageal reflux disease may be predicted based on analyzed exhaled nitric oxide. Pulmonary fibrosis may be predicted based on determined increased nitrates and/or nitrites. Gastroesophageal disease may be predicted based on determined reduced nitrates and/or nitrites. Surgi-cal tool parameter adjustments may be generated based on predicted pulmonary fibrosis and/or gastroesophageal reflux disease. Cardiovascular disease, inflammatory bowel dis-eases, and/or infection may be predicted based on analyzed CRP biomarkers. Risk of serious cardiovascular disease may increase with high CRP concentration. Inflammatory bowel disease may be predicted based on elevated CRP concen-tration. Infection may be predicted based on elevated CRP concentration. In an example, edema may be predicted based on analyzed vascular permeability regulation biomarkers. Increased vascular permeability during inflammation may be determined based on analyzed bradykinin and/or hista-mine. Edema may be predicted based on increased vascular permeability during inflammation. Vascular permeability may be determined based on endothelial adhesion mol-ecules. Endothelial adhesion molecules may be determined based on cell samples. Endothelial adhesion molecules may affect vascular permeability, immune cell recruitment, and/or fluid build-up in edema. Surgical tool parameter adjust-ments may be generated based on analyzed vascular perme-ability regulation biomarkers. In an example, hyperplasia may be predicted based on analyzed omentin. Hyperplasia may alter tissue properties. Surgical tool parameter adjust-ments may be generated based on predicted hyperplasia.

For example, based on the selected biomarker sensing systems data, lymphatic system-related biomarkers, compli-cations, and/or contextual information may be determined, including lymph nodes, lymph composition, lymph location, and/or lymph swelling. Based on the selected biomarker sensing systems data, lymphatic system-related conditions may be predicted, including post-operation inflammation, post-operation infection, and/or fibrosis. Post-operation inflammation and/or infection may be predicted based on determined lymph node swelling. Surgical tool parameter adjustments may be generated based on the analyzed lymph node swelling. Surgical tool parameter adjustments, includ-ing harmonic tool parameter adjustments, may be generated based on the determined collagen deposition. Collagen deposition may increase with lymph node fibrosis. Inflam-matory conditions may be predicted based on lymph com-position. Metastatic cell spread may be determined based on lymph composition. Surgical tool parameter adjustments may be generated based on lymph peptidome. Lymph pep-tidome may change based on inflammatory conditions.

For example, based on the selected biomarker sensing systems data, pathogen-related biomarkers, complications, and/or contextual information may be determined, including pathogen-associated molecular patterns (PAMPs), pathogen burden, *H. pylori*, and/or stomach tissue properties. Based on the selected biomarker sensing systems data, pathogen-related conditions may be predicted, including infection, stomach inflammation, and/or ulcering. PAMPs biomarkers may include pathogen antigens. Pathogen antigens may impact pathogen burden. Stomach inflammation and/or potential ulcering may be predicted based on predicted infection. Stomach tissue property alterations may be deter-mined based on predicted infection.

For example, based on the selected biomarker sensing systems data, DAMPs-related biomarkers, complications, and/or contextual information may be determined, including stress (e.g., cardiovascular, metabolic, glycemic, and/or cel-lular) and/or necrosis. Based on the selected biomarker sensing systems data, DAMPs-related conditions may be predicted, including acute myocardial infarction, intestinal inflammation, and/or infection. Cellular stress biomarkers may include creatine kinase MB, pyruvate kinase isoenzyme type M2 (M2-PK), irisin, and/or microRNA. In an example, acute myocardial infarction may be predicted based on analyzed creatine kinase MB biomarkers. Intestinal inflam-mation may be predicted based on analyzed M2-PK bio-markers. Stress may be determined based on analyzed irisin biomarkers. Inflammatory diseases and/or infection may be predicted based on analyzed microRNA biomarkers. Surgi-cal tool parameter adjustments may be generated based on predicted inflammation and/or infection. Inflammation and/or infection may be predicted based on analyzed necrosis biomarkers. Necrosis biomarkers may include reactive oxy-gen species (ROS). Inflammation and/or infection may be predicted based on increased ROS. Post-operation recovery may be determined based on analyzed ROS.

For example, based on the selected biomarker sensing systems, cell-related biomarkers, complications, and/or con-textual information may be determined, including granulo-cytes, natural killer cells (NK cells), macrophages, lympho-cytes, and/or colonic tissue properties. Based on the selected biomarker sensing systems, cell-related conditions may be predicted, including post-operation infection, ulceratic coli-tis, inflammation, and/or inflammatory bowel disease. Granulocyte biomarkers may include eosinophilia and/or neutrophils. Eosinophilia biomarkers may include sputum cell count, eosinophilic cationic protein, and/or fractional exhaled nitric oxide. Neutrophil biomarkers may include S100 proteins, myeloperoxidase, and/or human neutrophil lipocalin. Lymphocyte biomarkers may include antibodies, adaptive response, and/or immune memory. The antibodies may include immunoglobulin A (IgA) and/or immunoglobulin M (IgM). In an example, post-operational infection and/or pre-operation inflammation may be predicted based on analyzed sputum cell count. Ulcerative colitis may be predicted based on analyzed eosinophilic cationic protein. Altered colonic tissue properties may be determined based on the predicted ulcerative colitis. Eosinophils may produce eosinophilic cationic protein which may be determined based on ulcerative colitis. Inflammation may be predicted based on analyzed fractional exhaled nitric oxide. The inflammation may include type 1 asthma-like inflammation. Surgical tool parameter adjustments may be generated based on the predicted inflammation. In an example, inflammatory bowel diseases may be predicted based on S100 proteins. The S100 proteins may include calprotectin. Colonic tissue properties may be determined based on the predicted inflammatory bowel diseases. Ulcerative colitis may be predicted based on analyzed myeloperoxidase and/or human neutrophil lipocalin. Altered colonic tissue properties may be determined based on predicted ulcerative colitis. In an example, inflammation may be predicted based on antibody biomarkers. Bowel inflammation may be predicted based on IgA. Cardiovascular inflammation may be predicted based on IgM.

The detection, prediction, determination, and/or generation described herein may be performed by a computing system described herein, such as a surgical hub, a computing device, and/or a smart device based on measured data and/or related biomarkers generated by the biomarker sensing systems.

Tumors may include benign and/or malignant tumors. Tumor-related biomarkers, complications, contextual information, and/or conditions may be determined and/or predicted based on analyzed biomarker sensing systems data. A computing system, as described herein, may select one or more biomarkers (e.g., data from biomarker sensing systems) from tumor-related biomarkers, including circulating tumor cells for analysis.

For example, based on the selected biomarker sensing systems data, benign tumor-related biomarkers, conditions, and/or contextual information may be determined, including benign tumor replication, benign tumor metabolism, and/or benign tumor synthesis. Benign tumor replication may include rate of mitotic activity, mitotic metabolism, and/or synthesis biomarkers. Benign tumor metabolism may include metabolic demand and/or metabolic product biomarkers. Benign tumor synthesis may include protein expression and/or gene expression biomarkers.

For example, based on the selected biomarker sensing systems data, malignant tumor-related biomarkers, complications, and/or contextual information may be determined, including malignant tumor synthesis, malignant tumor metabolism, malignant tumor replication, microsatellite stability, metastatic risk, metastatic tumors, tumor growth, tumor recession, and/or metastatic activity. Based on the selected biomarker sensing systems data, malignant tumor-related conditions may be predicted, including cancer. Malignant tumor synthesis may include gene expression and/or protein expression biomarkers. Gene expression may be determined based on tumor biopsy and/or genome analysis. Protein expression biomarkers may include cancer antigen 125 (CA-125) and/or carcinoembryonic antigen (CEA). CEA may be measured based on urine and/or saliva. Malignant tumor replication data may include rate of mitotic activity, mitotic encapsulation, tumor mass, and/or microRNA 200c.

In an example, microsatellite stability may be determined based on analyzed gene expression. Metastatic risk may be determined based on determined microsatellite stability. Higher metastatic risk may be determined and/or predicted based on low microsatellite instability. In an example, metastatic tumors, tumor growth, tumor metastasis, and/or tumor recession may be determined based on analyzed protein expression. Metastatic tumors may be determined and/or predicted based on elevated CA-125. Cancer may be predicted based on CA-125. Cancer may be predicted based on certain levels of CEA. Tumor growth, metastasis, and/or recession may be monitored based on detected changes in CEA. Metastatic activity may be determined based on malignant tumor replication. Cancer may be predicted based on malignant tumor replication. MicroRNA 200c may be released into blood by certain cancers. Metastatic activity may be determined and/or predicted based on presence of circulating tumor cells.

The detection, prediction, determination, and/or generation described herein may be performed by a computing system described herein, such as a surgical hub, a computing device, and/or a smart device based on measured data and/or related biomarkers generated by the biomarker sensing systems.

The musculoskeletal system may include muscles, bones, marrow, and/or cartilage. The muscles may include smooth muscle, cardiac muscle, and/or skeletal muscle. The smooth muscle may include calmodulin, connective tissue, structural features, hyperplasia, actin, and/or myosin. The bones may include calcified bone, osteoblasts, and/or osteoclasts. The marrow may include red marrow and/or yellow marrow. The cartilage may include cartilaginous tissue and/or chondrocytes. Musculoskeletal system-related biomarkers, complications, contextual information, and/or conditions may be determined and/or predicted based on analyzed biomarker sensing systems data. A computing system, as described herein, may select one or more biomarkers (e.g., data from biomarker sensing systems) from musculoskeletal-related biomarkers for analysis.

For example, based on the selected biomarker sensing systems data, muscle-related biomarkers, complications, and/or contextual information may be determined, including serum calmodulin levels, mechanical strength, muscle body, hyperplasia, muscle contraction ability, and/or muscle damage. Based on the selected biomarker sensing systems data, muscle-related conditions may be predicted. In an example, neurological conditions may be predicted based on analyzed serum calmodulin levels. Mechanical strength may be determined based on analyzed smooth muscle collagen levels. Collagen may affect mechanical strength as collagen may bind smooth muscle filament together. Muscle body may be determined based on analyzed structural features. The muscle body may include an intermediate body and/or a dense body. Hyperplasia may be determined based on analyzed omentin levels. Omentin may indicate hyperplasia. Hyperplasia may be determined and/or predicted based on thick areas of smooth muscles. Muscle contraction ability may be determined based on analyzed smooth muscle alpha-actin expression. Muscle contraction inability may result from an abnormal expression of actin in smooth muscle. In an example, muscle damage may be determined based on analyzed circulating smooth muscle myosin and/or skeletal muscle myosin. Muscle strength may be determined based on analyzed circulating smooth muscle myosin. Muscle damage and/or weak, friable smooth muscle may be determined and/or predicted based on circulating smooth muscle myosin and/or skeletal muscle myosin. Smooth muscle myosin may be measured from urine. In an example, muscle damage may be determined based on cardiac and/or skeletal muscle biomarkers. Cardiac and/or skeletal muscle biomarkers may include circulating troponin. Muscle damage may be determined and/or predicted based on circulating troponin alongside myosin.

For example, based on the selected biomarker sensing systems data, bone-related biomarkers, complications, and/or contextual information may be determined, including calcified bone properties, calcified bone functions, osteoblasts number, osteoid secretion, osteoclasts number, and/or secreted osteoclasts.

For example, based on the selected biomarker sensing systems data, marrow-related biomarkers, complications, and/or contextual information may be determined, including tissue breakdown and/or collagen secretion. Arthritic breakdown of cartilaginous tissue may be determined based on analyzed cartilaginous tissue biomarkers. Collage secretion by muscle cells may be determined based on analyzed chondrocyte biomarkers.

The detection, prediction, determination, and/or generation described herein may be performed by a computing system described herein, such as a surgical hub, a computing device, and/or a smart device based on measured data and/or related biomarkers generated by the biomarker sensing systems.

Reproductive system-related biomarkers, complications, contextual information, and/or conditions may be determined and/or predicted based on analyzed biomarker sensing systems data. A computing system, as described herein, may select one or more biomarkers (e.g., data from biomarker sensing systems) from reproductive system-related biomarkers for analysis. Reproductive system-related biomarkers, complications, and/or contextual information may be determined based on analyzed biomarker sensing systems data, including female anatomy, female function, menstrual cycle, pH, bleeding, wound healing, and/or scarring. Female anatomy biomarkers may include the ovaries, vagina, cervix, fallopian tubes, and/or uterus. Female function biomarkers may include reproductive hormones, pregnancy, menopause, and/or menstrual cycle. Reproductive system-related conditions may be predicted based on analyzed biomarker sensing systems data, including endometriosis, adhesions, vaginosis, bacterial infection, SSI, and/or pelvic abscesses.

In an example, endometriosis may be predicted based on female anatomy biomarkers. Adhesions may be predicted based on female anatomy biomarkers. The adhesions may include sigmoid colon adhesions. Endometriosis may be predicted based on menstrual blood. Menstrual blood may include molecular signals from endometriosis. Sigmoid colon adhesions may be predicted based on predicted endometriosis. In an example, menstrual phase and/or menstrual cycle length may be determined based on the menstrual cycle. Bleeding, wound healing, and/or scarring may be determined based on the analyzed menstrual phase. Risk of endometriosis may be predicted based on the analyzed menstrual cycle. Higher risk of endometriosis may be predicted based on shorter menstrual cycle lengths. Molecular signals may be determined based on analyzed menstrual blood and/or discharge pH. Endometriosis may be predicted based on the determined molecular signals. Vaginal pH may be determined based on analyzed discharge pH. Vaginosis and/or bacterial infections may be predicted based on the analyzed vaginal pH. Vaginosis and/or bacterial infections may be predicted based on changes in vaginal pH. Risk of SSI and/or pelvic abscesses during gynecologic procedures may be predicted based on predicted vaginosis.

The detection, prediction, determination, and/or generation described herein may be performed by any of the computing systems within any of the computer-implemented patient and surgeon monitoring systems described herein, such as a surgical hub, a computing device, and/or a smart device based on measured data and/or related biomarkers generated by the one or more sensing systems.

Figure 2A:
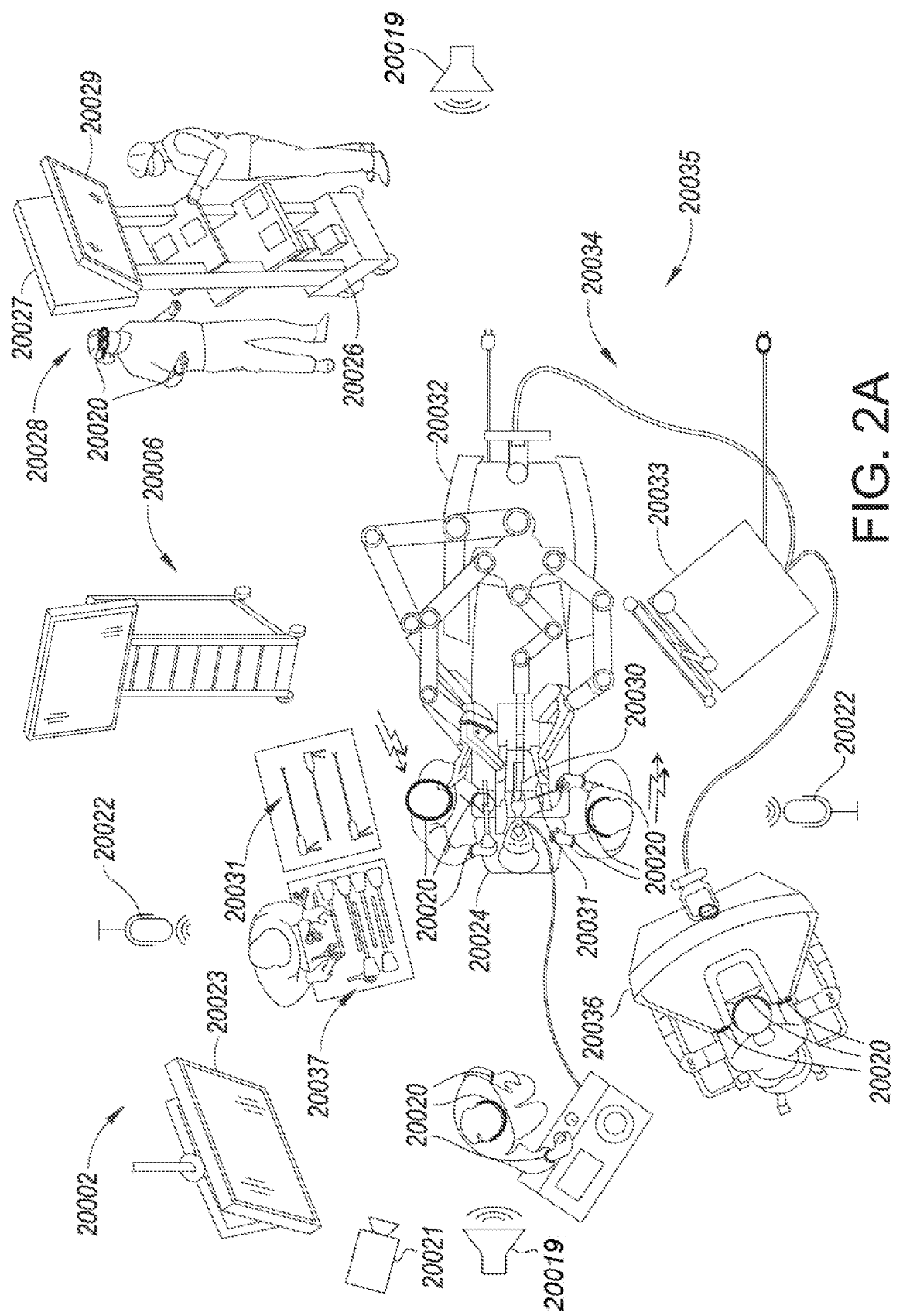
FIG. 2A shows an example of a surgeon monitoring system in a surgical operating room.

FIG. 2A shows an example of a surgeon monitoring system 20002 in a surgical operating room. As illustrated in FIG. 2A, a patient is being operated on by one or more health care professionals (HCPs). The HCPs are being monitored by one or more surgeon sensing systems 20020 worn by the HCPs. The HCPs and the environment surrounding the HCPs may also be monitored by one or more environmental sensing systems including, for example, a set of cameras 20021, a set of microphones 20022, and other sensors, etc. that may be deployed in the operating room. The surgeon sensing systems 20020 and the environmental sensing systems may be in communication with a surgical hub 20006, which in turn may be in communication with one or more cloud servers 20009 of the cloud computing system 20008, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2A, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2A, a surgical instrument 20031 is being used in the surgical procedure as part of the surgeon monitoring system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2A illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of micro-organisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1 may include one or more sensing systems, for example, surgeon sensing systems 20020 as shown in FIG. 2A. The surgeon sensing systems 20020 may include sensing systems to monitor and detect a set of physical states and/or a set of physiological states of a healthcare provider (HCP). An HCP may be a surgeon or one or more healthcare personnel assisting the surgeon or other healthcare service providers in general. In an example, a sensing system 20020 may measure a set of biomarkers to monitor the heart rate of an HCP. In another example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the surgeon sensing systems 20020 may measure one or more surgeon biomarkers associated with an HCP and send the measurement data associated with the surgeon biomarkers to the surgical hub 20006. The surgeon sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following-stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 2B:
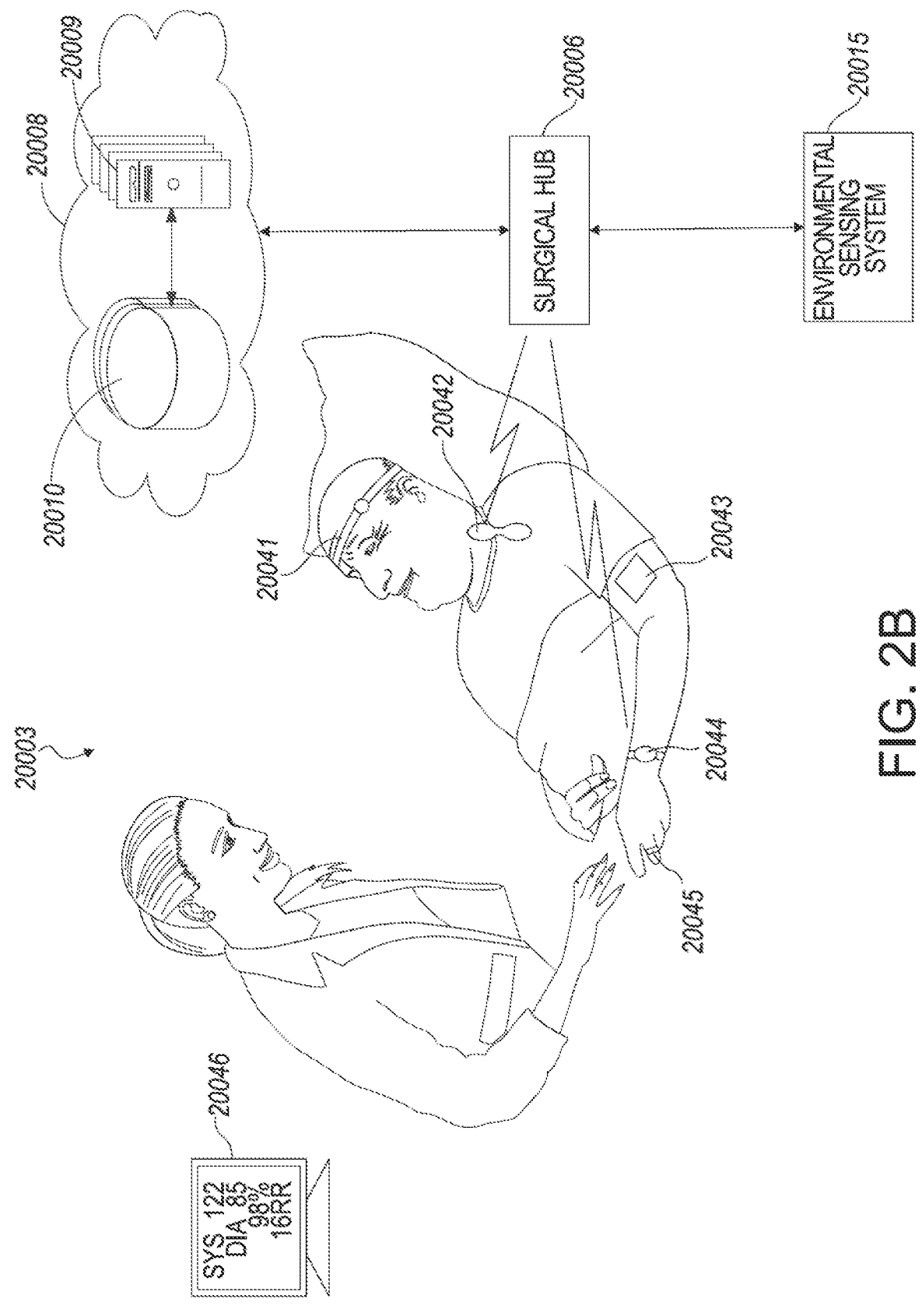
FIG. 2B shows an example of a patient monitoring system (e.g., a controlled patient monitoring system).

FIG. 2B shows an example of a patient monitoring system 20003 (e.g., a controlled patient monitoring system). As illustrated in FIG. 2B, a patient in a controlled environment (e.g., in a hospital recovery room) may be monitored by a plurality of sensing systems (e.g., patient sensing systems 20041). A patient sensing system 20041 (e.g., a head band) may be used to measure an electroencephalogram (EEG) to measure electrical activity of the brain of a patient. A patient sensing system 20042 may be used to measure various biomarkers of the patient including, for example, heart rate, VO2 level, etc. A patient sensing system 20043 (e.g., flexible patch attached to the patient's skin) may be used to measure sweat lactate and/or potassium levels by analyzing small amounts of sweat that is captured from the surface of the skin using microfluidic channels. A patient sensing system 20044 (e.g., a wristband or a watch) may be used to measure blood pressure, heart rate, heart rate variability, VO2 levels, etc. using various techniques, as described herein. A patient sensing system 20045 (e.g., a ring on finger) may be used to measure peripheral temperature, heart rate, heart rate variability, VO2 levels, etc. using various techniques, as described herein. The patient sensing systems 20041-20045 may use a radio frequency (RF) link to be in communication with the surgical hub 20006. The patient sensing systems 20041-20045 may use one or more of the following RF protocols for communication with the surgical hub 20006: Bluetooth, Bluetooth Low-Energy (BLE), Bluetooth Smart, Zigbee, Z-wave, IPv6 Low-power wireless Personal Area Network (6LoWPAN), Thread, Wi-Fi, etc.

The sensing systems 20041-20045 may be in communication with a surgical hub 20006, which in turn may be in communication with a remote server 20009 of the remote cloud computing system 20008. The surgical hub 20006 is also in communication with an HID 20046. The HID 20046 may display measured data associated with one or more patient biomarkers. For example, the HID 20046 may display blood pressure, Oxygen saturation level, respiratory rate, etc. The HID 20046 may display notifications for the patient or an HCP providing information about the patient, for example, information about a recovery milestone or a complication. In an example, the information about a recovery milestone or a complication may be associated with a surgical procedure the patient may have undergone. In an example, the HID 20046 may display instructions for the patient to perform an activity. For example, the HID 20046 may display inhaling and exhaling instructions. In an example the HID 20046 may be part of a sensing system.

As illustrated in FIG. 2B, the patient and the environment surrounding the patient may be monitored by one or more environmental sensing systems 20015 including, for example, a microphone (e.g., for detecting ambient noise associated with or around a patient), a temperature/humidity sensor, a camera for detecting breathing patterns of the patient, etc. The environmental sensing systems 20015 may be in communication with the surgical hub 20006, which in turn is in communication with a remote server 20009 of the remote cloud computing system 20008.

In an example, a patient sensing system 20044 may receive a notification information from the surgical hub 20006 for displaying on a display unit or an HID of the patient sensing system 20044. The notification information may include a notification about a recovery milestone or a notification about a complication, for example, in case of post-surgical recovery. In an example, the notification information may include an actionable severity level associated with the notification. The patient sensing system 20044 may display the notification and the actionable severity level to the patient. The patient sensing system may alert the patient using a haptic feedback. The visual notification and/or the haptic notification may be accompanied by an audible notification prompting the patient to pay attention to the visual notification provided on the display unit of the sensing system.

Figure 2C:
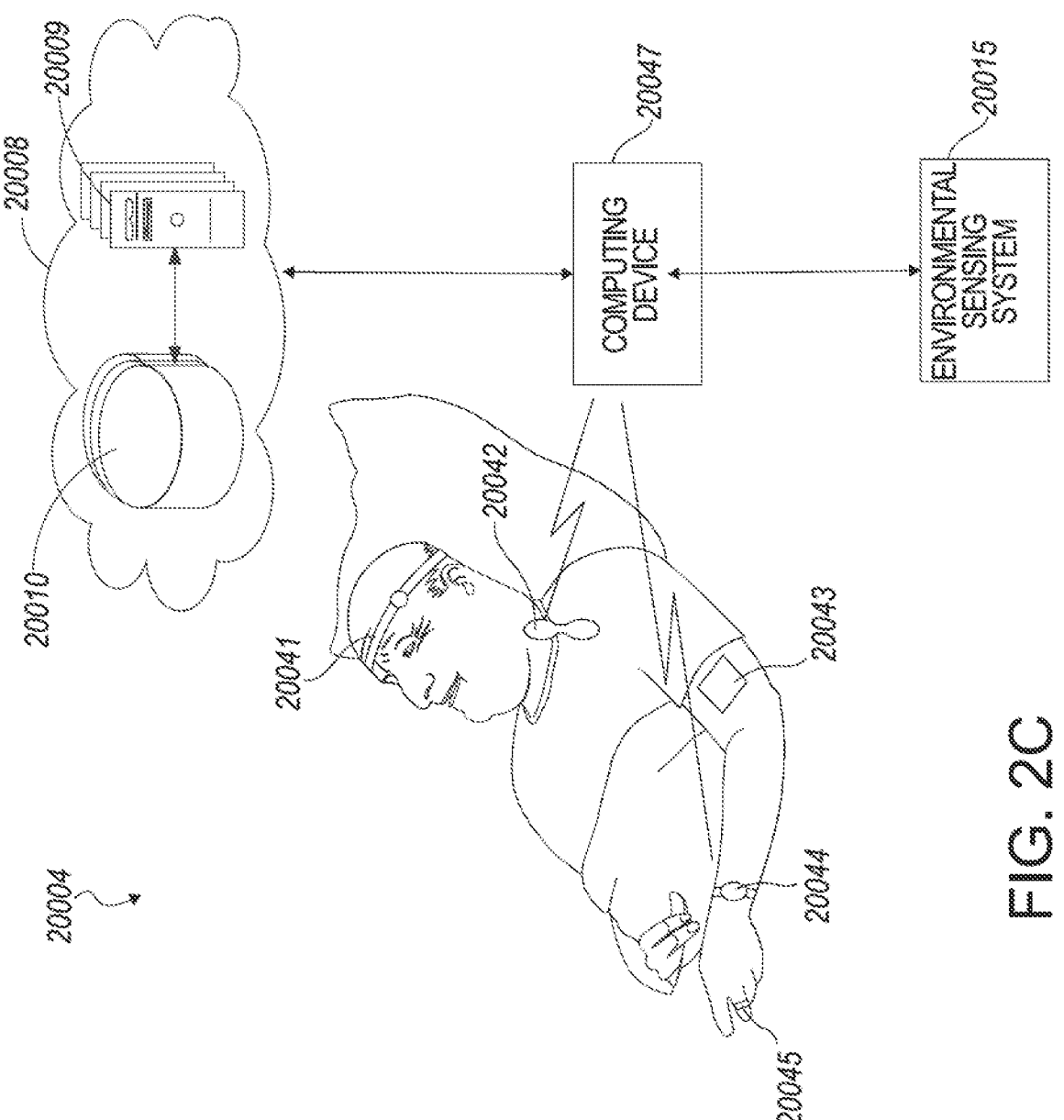
FIG. 2C shows an example of a patient monitoring system (e.g., an uncontrolled patient monitoring system).

FIG. 2C shows an example of a patient monitoring system (e.g., an uncontrolled patient monitoring system 20004). As illustrated in FIG. 2C, a patient in an uncontrolled environment (e.g., a patient's residence) is being monitored by a plurality of patient sensing systems 20041-20045. The patient sensing systems 20041-20045 may measure and/or monitor measurement data associated with one or more patient biomarkers. For example, a patient sensing system 20041, a head band, may be used to measure an electroencephalogram (EEG). Other patient sensing systems 20042, 20043, 20044, and 20045 are examples where various patient biomarkers are monitored, measured, and/or reported, as described in FIG. 2B. One or more of the patient sensing systems 20041-20045 may be send the measured data associated with the patient biomarkers being monitored to the computing device 20047, which in turn may be in communication with a remote server 20009 of the remote cloud computing system 20008. The patient sensing systems 20041-20045 may use a radio frequency (RF) link to be in communication with a computing device 20047 (e.g., a smart phone, a tablet, etc.). The patient sensing systems 20041-20045 may use one or more of the following RF protocols for communication with the computing device 20047: Bluetooth, Bluetooth Low-Energy (BLE), Bluetooth Smart, Zigbee, Z-wave, IPv6 Low-power wireless Personal Area Network (6LoWPAN), Thread, Wi-Fi, etc. In an example, the patient sensing systems 20041-20045 may be connected to the computing device 20047 via a wireless router, a wireless hub, or a wireless bridge.

The computing device 20047 may be in communication with a remote server 20009 that is part of a cloud computing system 20008. In an example, the computing device 20047 may be in communication with a remote server 20009 via an internet service provider's cable/FIOS networking node. In an example, a patient sensing system may be in direct communication with a remote server 20009. The computing device 20047 or the sensing system may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

In an example, a computing device 20047 may display information associated with a patient biomarker. For example, a computing device 20047 may display blood pressure, Oxygen saturation level, respiratory rate, etc. A computing device 20047 may display notifications for the patient or an HCP providing information about the patient, for example, information about a recovery milestone or a complication.

In an example, the computing device 20047 and/or the patient sensing system 20044 may receive a notification information from the surgical hub 20006 for displaying on a display unit of the computing device 20047 and/or the patient sensing system 20044. The notification information may include a notification about a recovery milestone or a notification about a complication, for example, in case of post-surgical recovery. The notification information may also include an actionable severity level associated with the notification. The computing device 20047 and/or the sensing system 20044 may display the notification and the actionable severity level to the patient. The patient sensing system may also alert the patient using a haptic feedback. The visual notification and/or the haptic notification may be accompanied by an audible notification prompting the patient to pay attention to the visual notification provided on the display unit of the sensing system.

Figure 3:
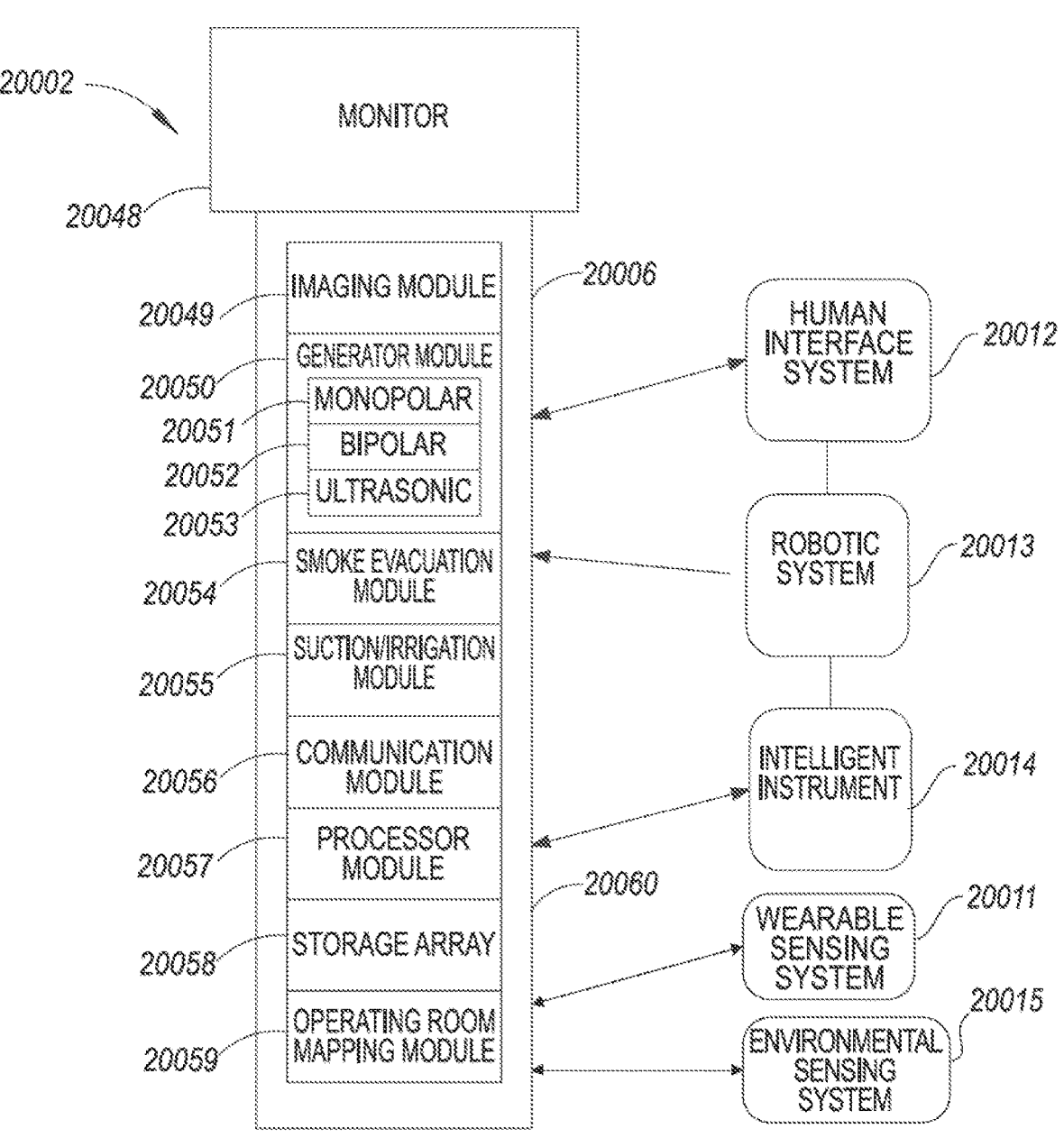
FIG. 3 illustrates an example surgical hub paired with various systems.

FIG. 3 shows an example surgeon monitoring system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be a generator module 20050 with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
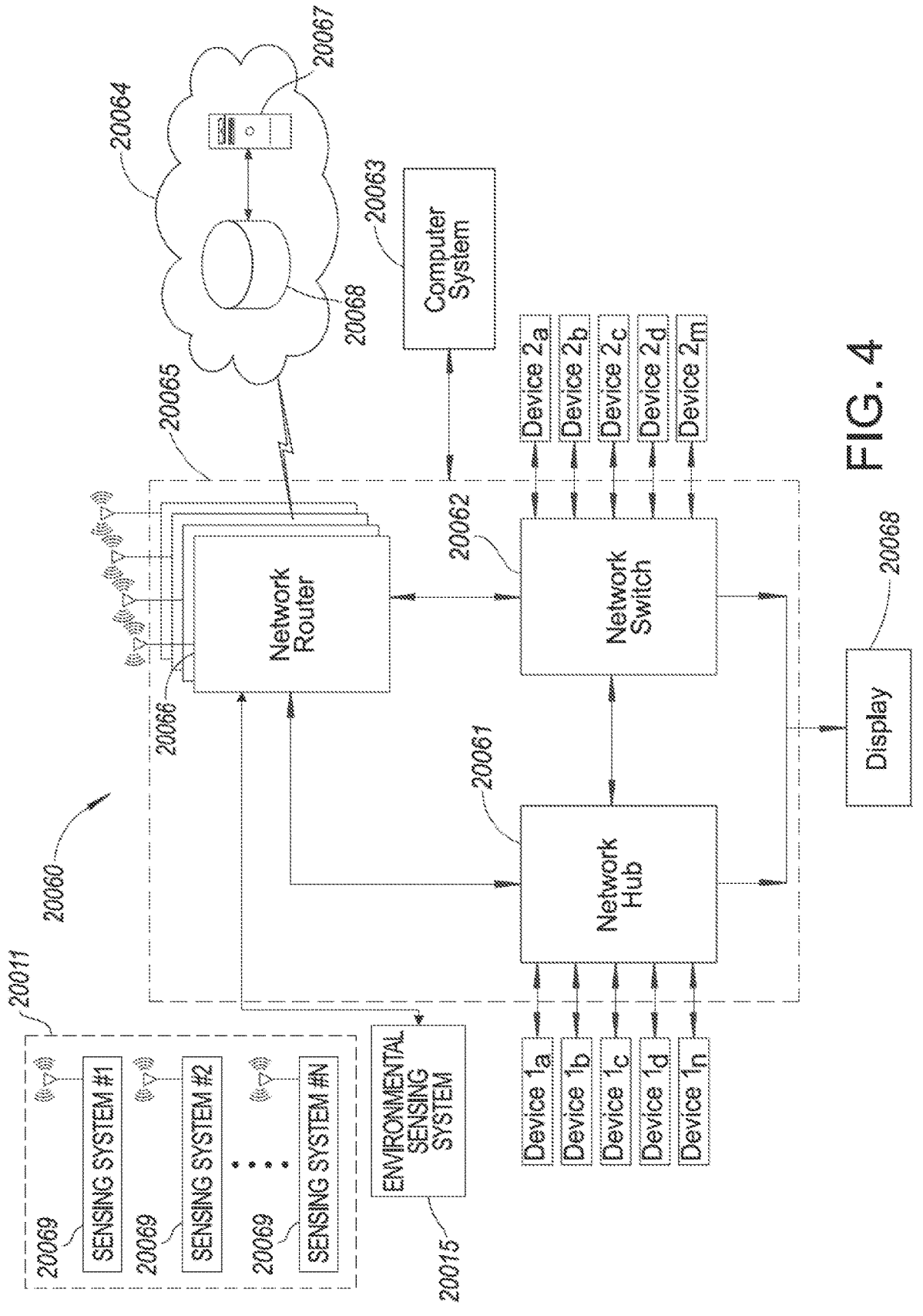
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, an environment sensing system, and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation. Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20063. Data associated with the devices 1a-1n may be transferred to cloud-based computers via the router for remote data processing and manipulation. Data associated with the devices 1a-1n may also be transferred to the local computer system 20063 for local data processing and manipulation. Modular devices 2a-2m located in the same operating theater also may be coupled to a network switch 20062. The network switch 20062 may be coupled to the network hub 20061 and/or the network router 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include a surgeon sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1*a*-1*n*/2*a*-2*m* or the sensing systems 20069 to the cloud-base system 20064. One or more of the devices 1*a*-1*n*/2*a*-2*m* or the sensing systems 20069 coupled to the network hub 20061 or network switch 20062 may collect data or measurement data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different ser-vices—such as servers, storage, and applications—are deliv-ered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1*a*-1*n*/2*a*-2*m* located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1*a*-1*n*/2*a*-2*m*, the surgical data network can provide improved surgical outcomes, reduced costs, and improved patient satisfaction. At least some of the devices 1*a*-1*n*/2*a*-2*m* may be employed to view tissue states to assess leaks or perfusion of sealed tissue after a tissue sealing and cutting procedure. At least some of the devices 1*a*-1*n*/2*a*-2*m* may be employed to identify pathol-ogy, such as the effects of diseases, using the cloud-based computing to examine data including images of samples of body tissue for diagnostic purposes. This may include local-ization and margin confirmation of tissue and phenotypes. At least some of the devices 1*a*-1*n*/2*a*-2*m* may be employed to identify anatomical structures of the body using a variety of sensors integrated with imaging devices and techniques such as overlaying images captured by multiple imaging devices. The data gathered by the devices 1*a*-1*n*/2*a*-2*m*, including image data, may be transferred to the cloud computing system 20064 or the local computer system 20063 or both for data processing and manipulation including image pro-cessing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physi-ological conditions of a surgeon operating on a patient or a patient being prepared for a surgical procedure or a patient recovering after a surgical procedure. The cloud-based com-puting system 20064 may be used to monitor biomarkers associated with a surgeon or a patient in real-time and to generate surgical plans based at least on measurement data gathered prior to a surgical procedure, provide control signals to the surgical instruments during a surgical proce-dure, notify a patient of a complication during post-surgical period.

The operating theater devices 1*a*-1*n* may be connected to the modular communication hub 20065 over a wired channel or a wireless channel depending on the configuration of the devices 1*a*-1*n* to a network hub 20061. The network hub 20061 may be implemented, in one aspect, as a local network broadcast device that works on the physical layer of the Open System Interconnection (OSI) model. The network hub may provide connectivity to the devices 1*a*-1*n* located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1*a*-1*n* can send data at a time through the network hub 20061. The network hub 20061 may not have routing tables or intelligence regarding where to send infor-mation and broadcasts all network data across each connec-tion and to a remote server 20067 of the cloud computing system 20064. The network hub 20061 can detect basic network errors such as collisions but having all information broadcast to multiple ports can be a security risk and cause bottlenecks.

The operating theater devices 2*a*-2*m* may be connected to a network switch 20062 over a wired channel or a wireless channel. The network switch 20062 works in the data link layer of the OSI model. The network switch 20062 may be a multicast device for connecting the devices 2*a*-2*m* located in the same operating theater to the network. The network switch 20062 may send data in the form of frames to the network router 20066 and may work in full duplex mode. Multiple devices 2*a*-2*m* can send data at the same time through the network switch 20062. The network switch 20062 stores and uses MAC addresses of the devices 2*a*-2*m* to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or net-work switch 20062 to cloud-based computer resources for further processing and manipulation of the data collected by any one of or all the devices 1*a*-1*n*/2*a*-2*m* and wearable sensing system 20011. The network router 20066 may be employed to connect two or more different networks located in different locations, such as, for example, different oper-ating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be imple-mented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1*a*-1*n* and devices 2*a*-2*m* located in the operating theater.

In examples, the operating theater devices 1*a*-1*n*/2*a*-2*m* and/or the sensing systems 20069 may communicate to the modular communication hub 20065 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1*a*-1*n*/2*a*-2*m* and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1*a*-1*n*/2*a*-2*m* and/or the sensing systems 20069 and may handle a data type known as frames. Frames may carry the data generated by the devices 1*a*-1*n*/2*a*-2*m* and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1*a*-1*n*/2*a*-2*m*.

Figure 5:
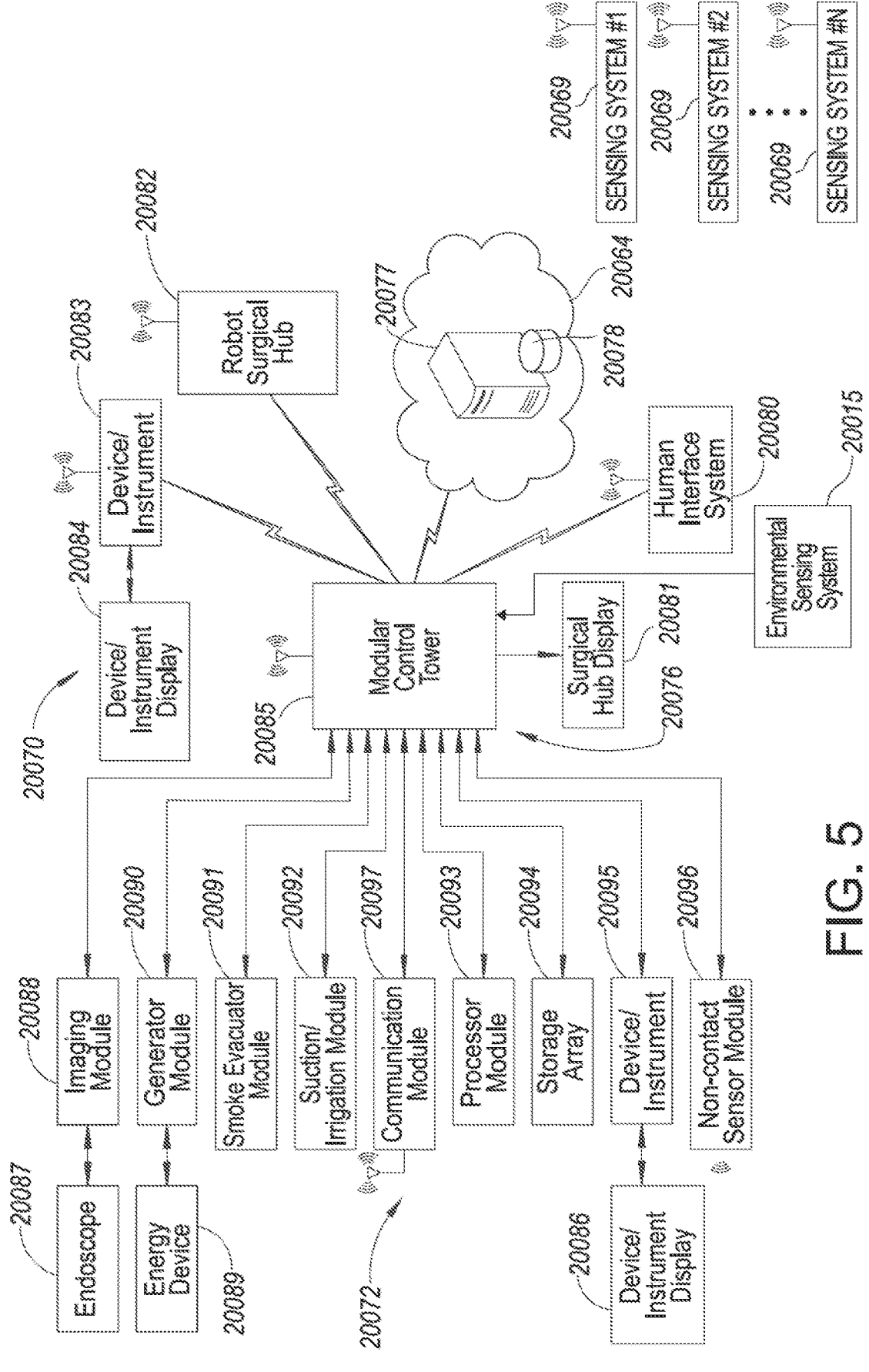
FIG. 5 illustrates an example computer-implemented interactive surgical system that may be part of a surgeon monitoring system.
Figure 6A:
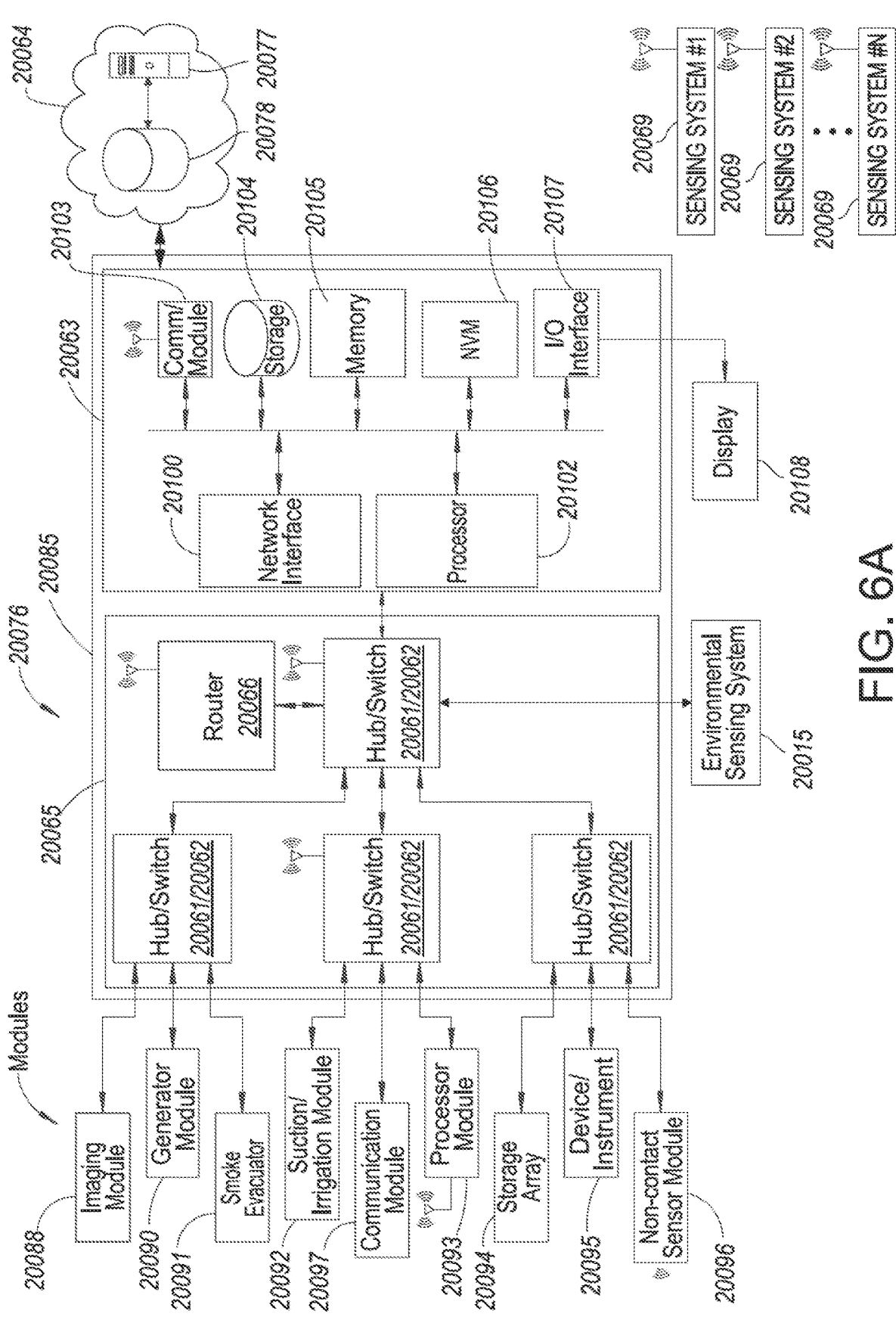
FIG. 6A illustrates a surgical hub comprising a plurality of modules coupled to a modular control tower.

FIG. 5 illustrates a computer-implemented interactive surgical system 20070 that may be a part of the surgeon monitoring system 20002. The computer-implemented interactive surgical system 20070 is similar in many respects to the surgeon sensing system 20002. For example, the computer-implemented interactive surgical system 20070 may include one or more surgical sub-systems 20072, which are similar in many respects to the surgeon monitoring systems 20002. Each sub-surgical system 20072 includes at least one surgical hub 20076 in communication with a cloud computing system 20064 that may include a remote server 20077 and a remote storage 20078. In one aspect, the computer-implemented interactive surgical system 20070 may include a modular control tower 20085 connected to multiple operating theater devices such as sensing systems (e.g., surgeon sensing systems 20002 and/or patient sensing system 20003), intelligent surgical instruments, robots, and other computerized devices located in the operating theater. As shown in FIG. 6A, the modular control tower 20085 may include a modular communication hub 20065 coupled to a local computing system 20063.

As illustrated in the example of FIG. 5, the modular control tower 20085 may be coupled to an imaging module 20088 that may be coupled to an endoscope 20087, a generator module 20090 that may be coupled to an energy device 20089, a smoke evacuator module 20091, a suction/irrigation module 20092, a communication module 20097, a processor module 20093, a storage array 20094, a smart device/instrument 20095 optionally coupled to a display 20086 and 20084 respectively, and a non-contact sensor module 20096. The modular control tower 20085 may also be in communication with one or more sensing systems 20069 and an environmental sensing system 20015. The sensing systems 20069 may be connected to the modular control tower 20085 either directly via a router or via the communication module 20097. The operating theater devices may be coupled to cloud computing resources and data storage via the modular control tower 20085. A robot surgical hub 20082 also may be connected to the modular control tower 20085 and to the cloud computing resources. The devices/instruments 20095 or 20084, human interface system 20080, among others, may be coupled to the modular control tower 20085 via wired or wireless communication standards or protocols, as described herein. The human interface system 20080 may include a display sub-system and a notification sub-system. The modular control tower 20085 may be coupled to a hub display 20081 (e.g., monitor, screen) to display and overlay images received from the imaging module 20088, device/instrument display 20086, and/or other human interface systems 20080. The hub display 20081 also may display data received from devices connected to the modular control tower 20085 in conjunction with images and overlaid images.

FIG. 6A illustrates a surgical hub 20076 comprising a plurality of modules coupled to the modular control tower 20085. As shown in FIG. 6A, the surgical hub 20076 may be connected to a generator module 20090, the smoke evacuator module 20091, suction/irrigation module 20092, and the communication module 20097. The modular control tower 20085 may comprise a modular communication hub 20065, e.g., a network connectivity device, and a computer system 20063 to provide local wireless connectivity with the sensing systems, local processing, complication monitoring, visualization, and imaging, for example. As shown in FIG. 6A, the modular communication hub 20065 may be connected in a configuration (e.g., a tiered configuration) to expand a number of modules (e.g., devices) and a number of sensing systems 20069 that may be connected to the modular communication hub 20065 and transfer data associated with the modules and/or measurement data associated with the sensing systems 20069 to the computer system 20063, cloud computing resources, or both. As shown in FIG. 6A, each of the network hubs/switches 20061/20062 in the modular communication hub 20065 may include three downstream ports and one upstream port. The upstream network hub/switch may be connected to a processor 20102 to provide a communication connection to the cloud computing resources and a local display 20108. At least one of the network/hub switches 20061/20062 in the modular communication hub 20065 may have at least one wireless interface to provided communication connection between the sensing systems 20069 and/or the devices 20095 and the cloud computing system 20064. Communication to the cloud computing system 20064 may be made either through a wired or a wireless communication channel.

The surgical hub 20076 may employ a non-contact sensor module 20096 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 20063 may comprise a processor 20102 and a network interface 20100. The processor 20102 may be coupled to a communication module 20103, storage 20104, memory 20105, non-volatile memory 20106, and input/output (I/O) interface 20107 via a system bus. The system bus can be any of several types of bus structure(s) including the memory bus or memory controller, a peripheral bus or external bus, and or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 20102 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with Stellar-isWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor 20102 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 20063 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface 20107. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

Figure 6B:
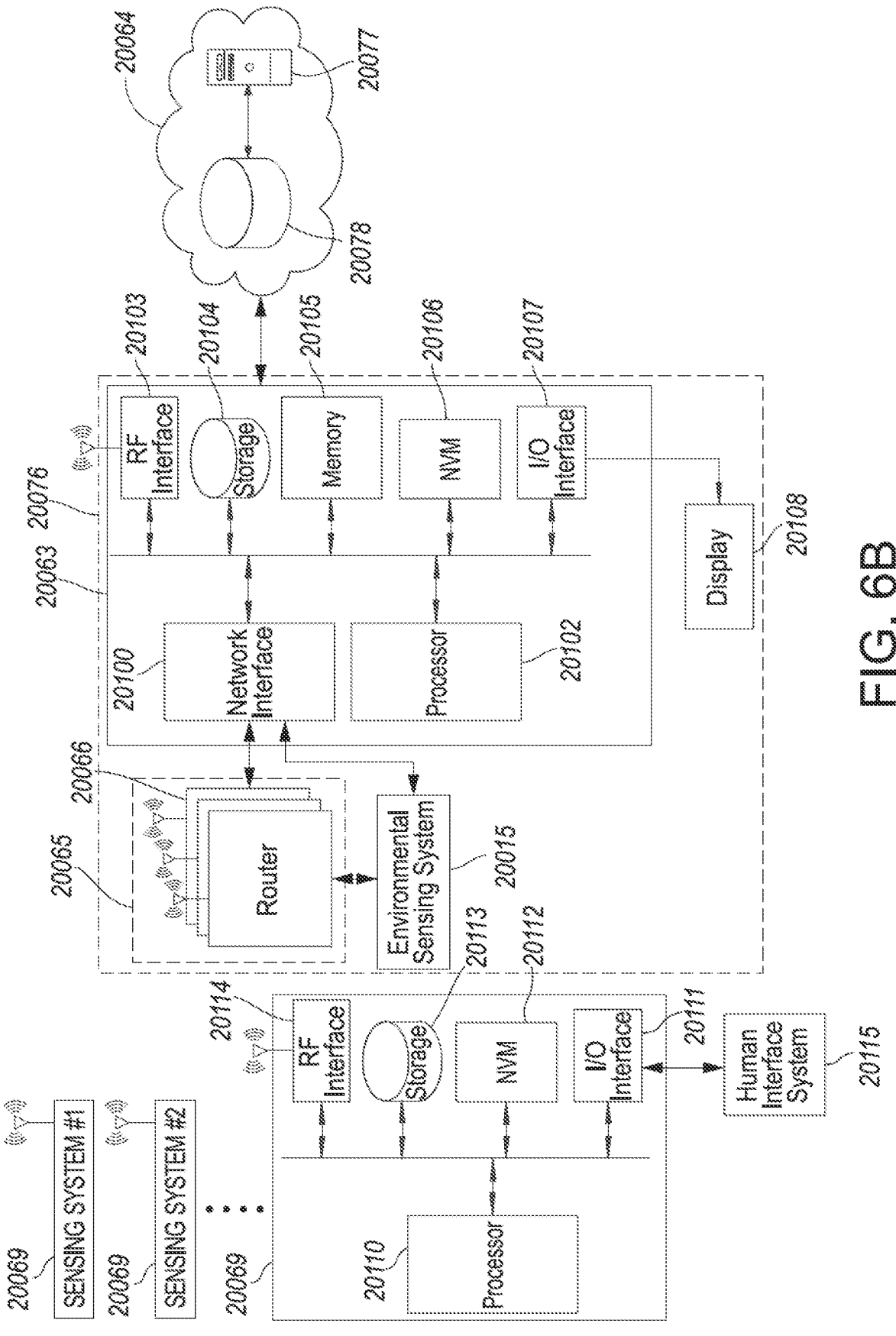
FIG. 6B illustrates an example of a controlled patient monitoring system.

In various examples, the computer system 20063 of FIG. 4, FIG. 6A and FIG. 6B, the imaging module 20088 and/or human interface system 20080, and/or the processor module 20093 of FIG. 5 and FIG. 6A may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

FIG. 6B illustrates an example of a wearable monitoring system, e.g., a controlled patient monitoring system. A controlled patient monitoring system may be the sensing system used to monitor a set of patient biomarkers when the patient is at a healthcare facility. The controlled patient monitoring system may be deployed for pre-surgical patient monitoring when a patient is being prepared for a surgical procedure, in-surgical monitoring when a patient is being operated on, or in post-surgical monitoring, for example, when a patient is recovering, etc. As illustrated in FIG. 6B, a controlled patient monitoring system may include a surgical hub system 20076, which may include one or more routers 20066 of the modular communication hub 20065 and a computer system 20063. The routers 20065 may include wireless routers, wired switches, wired routers, wired or wireless networking hubs, etc. In an example, the routers 20065 may be part of the infrastructure. The computing system 20063 may provide local processing for monitoring various biomarkers associated with a patient or a surgeon, and a notification mechanism to indicate to the patient and/or a healthcare provided (HCP) that a milestone (e.g., a recovery milestone) is met or a complication is detected. The computing system 20063 of the surgical hub system 20076 may also be used to generate a severity level associated with the notification, for example, a notification that a complication has been detected.

Figure 6C:
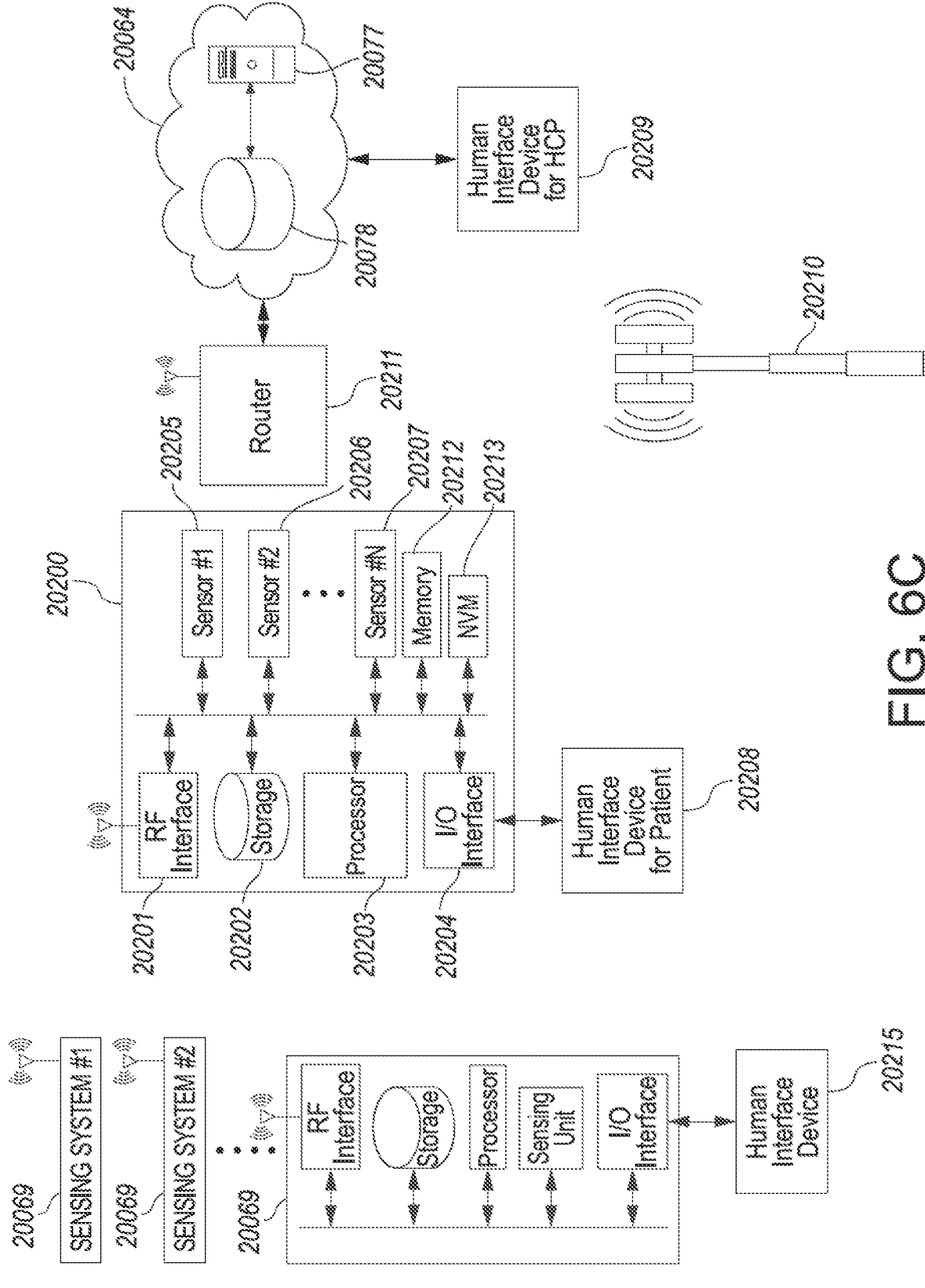
FIG. 6C illustrates an example of an uncontrolled patient monitoring system.
Figure 7A:
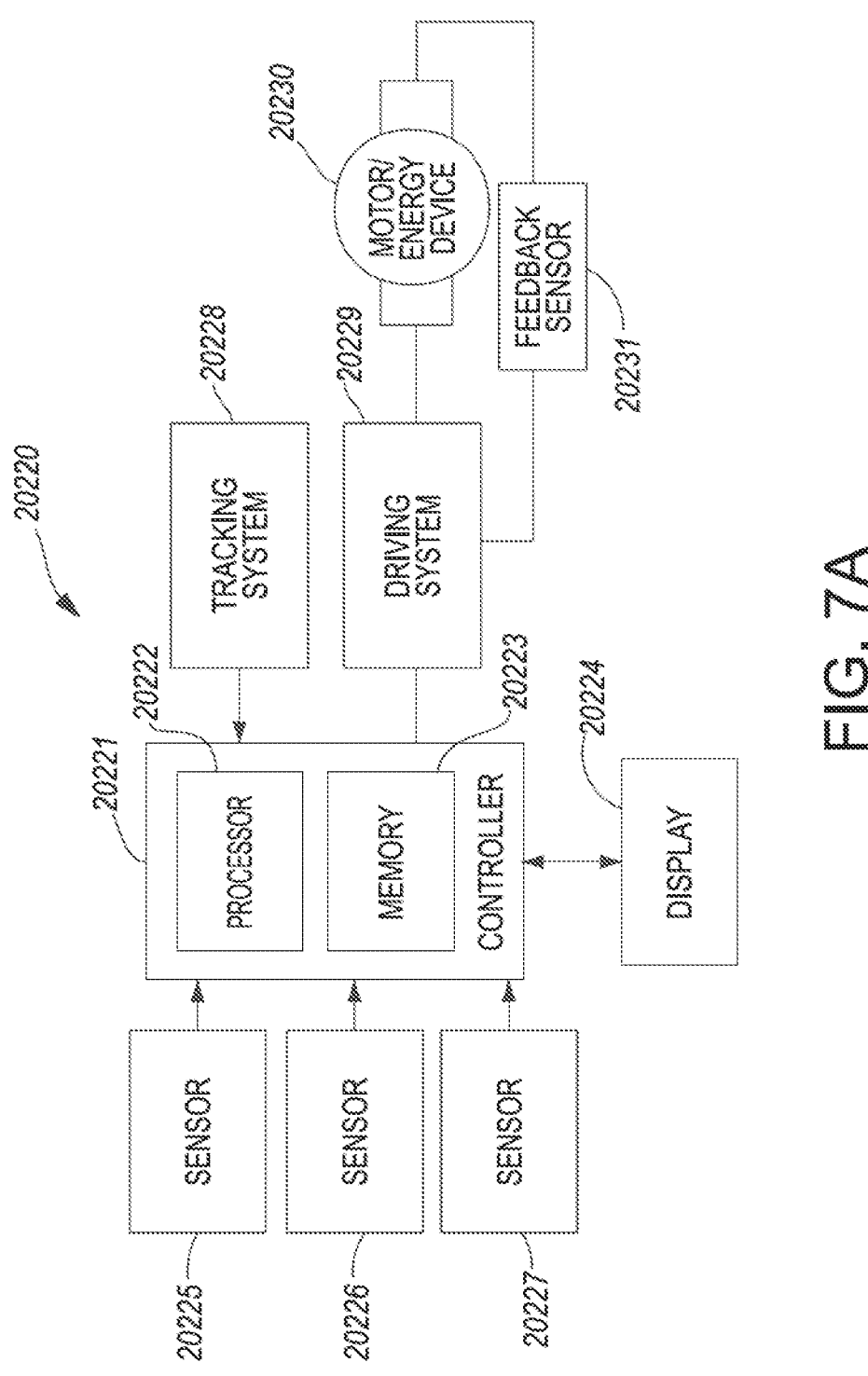
FIG. 7A illustrates a logic diagram of a control system of a surgical instrument or a tool.
Figure 7B:
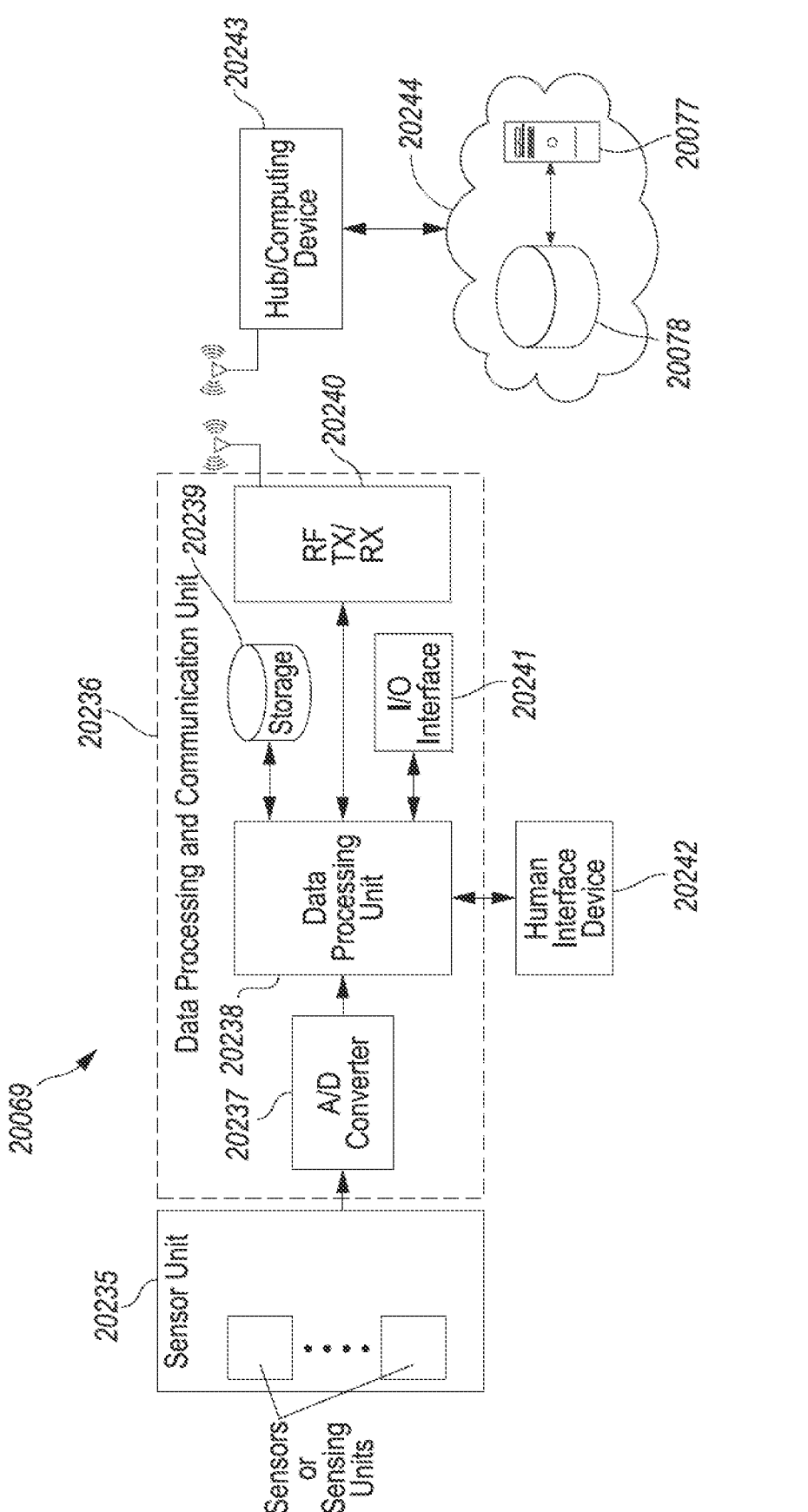
FIG. 7B shows an exemplary sensing system with a sensor unit and a data processing and communication unit.
Figure 7C:
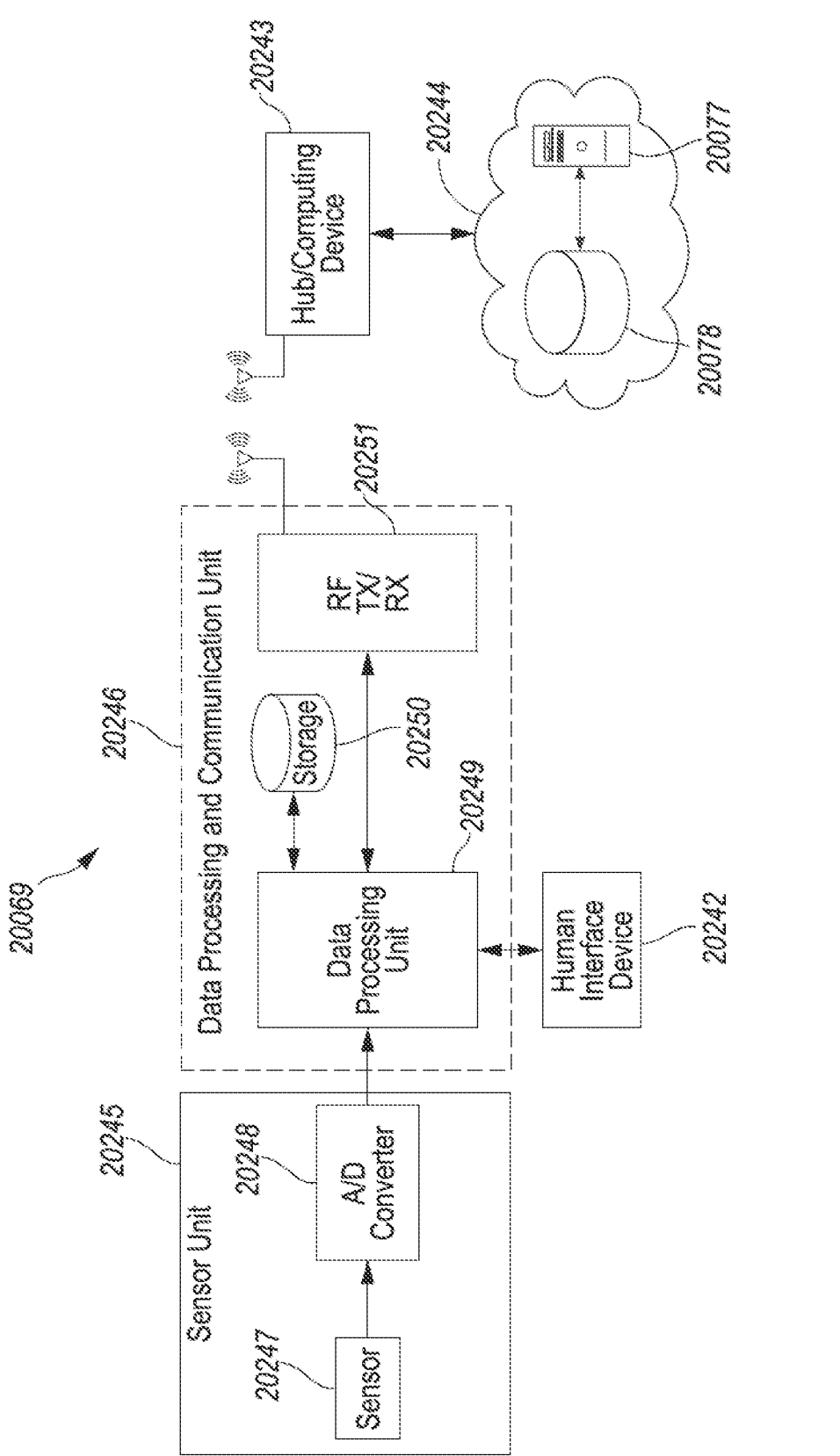
FIG. 7C shows an exemplary sensing system with a sensor unit and a data processing and communication unit.
Figure 7D:
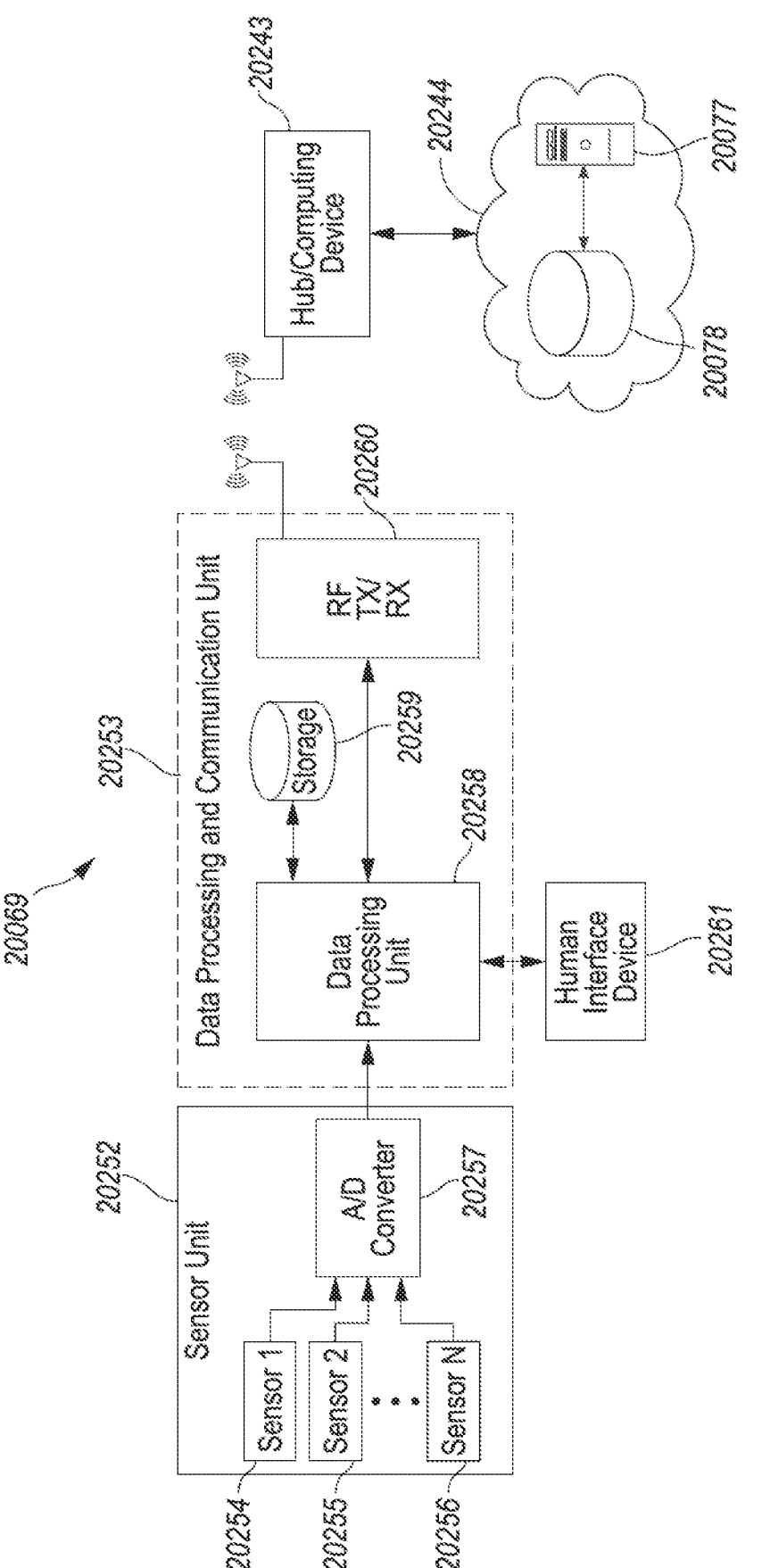
FIG. 7D shows an exemplary sensing system with a sensor unit and a data processing and communication unit.

The computing system 20063 of FIG. 4, FIG. 6B, the computing device 20200 of FIG. 6C, the hub/computing device 20243 of FIG. 7B, FIG. 7C, or FIG. 7D may be a surgical computing system or a hub device, a laptop, a tablet, a smart phone, etc.

As shown in FIG. 6B, a set of sensing systems 20069 and/or an environmental sensing system 20015 (as described in FIG. 2A) may be connected to the surgical hub system 20076 via the routers 20065. The routers 20065 may also provide a direct communication connection between the sensing systems 20069 and the cloud computing system 20064, for example, without involving the local computer system 20063 of the surgical hub system 20076. Communication from the surgical hub system 20076 to the cloud 20064 may be made either through a wired or a wireless communication channel.

As shown in FIG. 6B, the computer system 20063 may include a processor 20102 and a network interface 20100. The processor 20102 may be coupled to a radio frequency (RF) interface or a communication module 20103, storage 20104, memory 20105, non-volatile memory 20106, and input/output interface 20107 via a system bus, as described in FIG. 6A. The computer system 20063 may be connected with a local display unit 20108. In some examples, the display unit 20108 may be replaced by a HID. Details about the hardware and software components of the computer system are provided in FIG. 6A.

As shown in FIG. 6B, a sensing system 20069 may include a processor 20110. The processor 20110 may be coupled to a radio frequency (RF) interface 20114, storage 20113, memory (e.g., a non-volatile memory) 20112, and I/O interface 20111 via a system bus. The system bus can be any of several types of bus structure(s) including the memory bus or memory controller, a peripheral bus or external bus, and/or a local bus, as described herein. The processor 20110 may be any single-core or multicore processor as described herein.

It is to be appreciated that the sensing system 20069 may include software that acts as an intermediary between sensing system users and the computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

The sensing system 20069 may be connected to a human interface system 20115. The human interface system 20115 may be a touch screen display. The human interface system 20115 may include a human interface display for displaying information associated with a surgeon biomarker and/or a patient biomarker, display a prompt for a user action by a patient or a surgeon, or display a notification to a patient or a surgeon indicating information about a recovery millstone or a complication. The human interface system 20115 may be used to receive input from a patient or a surgeon. Other human interface systems may be connected to the sensing system 20069 via the I/O interface 20111. For example, the human interface device 20115 may include devices for providing a haptic feedback as a mechanism for prompting a user to pay attention to a notification that may be displayed on a display unit.

The sensing system 20069 may operate in a networked environment using logical connections to one or more remote computers, such as cloud computer(s), or local computers. The remote cloud computer(s) can be a personal computer, server, router, network PC, workstation, micro-processor-based appliance, peer device, or other common network node, and the like, and typically includes many or all of the elements described relative to the computer system. The remote computer(s) may be logically connected to the computer system through a network interface. The network interface may encompass communication networks such as local area networks (LANs), wide area networks (WANs), and/or mobile networks. LAN technologies may include Fiber Distributed Data Interface (FDDI), Copper Distributed Data Interface (CDDI), Ethernet/IEEE 802.3, Token Ring/IEEE 802.5, Wi-Fi/IEEE 802.11, and the like. WAN technologies may include, but are not limited to, point-to-point links, circuit-switching networks like Inte-grated Services Digital Networks (ISDN) and variations thereon, packet-switching networks, and Digital Subscriber Lines (DSL). The mobile networks may include communi-cation links based on one or more of the following mobile communication protocols: GSM/GPRS/EDGE (2G), UMTS/HSPA (3G), long term evolution (LTE) or 4G, LTE-Advanced (LTE-A), new radio (NR) or 5G, etc.

FIG. 6C illustrates an exemplary uncontrolled patient monitoring system, for example, when the patient is away from a healthcare facility. The uncontrolled patient moni-toring system may be used for pre-surgical patient monitor-ing when a patient is being prepared for a surgical procedure but is away from a healthcare facility, or in post-surgical monitoring, for example, when a patient is recovering away from a healthcare facility.

As illustrated in FIG. 6C, one or more sensing systems 20069 are in communication with a computing device 20200, for example, a personal computer, a laptop, a tablet, or a smart phone. The computing system 20200 may provide processing for monitoring of various biomarkers associated with a patient, a notification mechanism to indicate that a milestone (e.g., a recovery milestone) is met or a compli-cation is detected. The computing system 20200 may also provide instructions for the user of the sensing system to follow. The communication between the sensing systems 20069 and the computing device 20200 may be established directly using a wireless protocol as described herein or via the wireless router/hub 20211.

As shown in FIG. 6C, the sensing systems 20069 may be connected to the computing device 20200 via router 20211. The router 20211 may include wireless routers, wired switches, wired routers, wired or wireless networking hubs, etc. The router 20211 may provide a direct communication connection between the sensing systems 20069 and the cloud servers 20064, for example, without involving the local computing device 20200. The computing device 20200 may be in communication with the cloud server 20064. For example, the computing device 20200 may be in commu-nication with the cloud 20064 through a wired or a wireless communication channel. In an example, a sensing system

20069 may be in communication with the cloud directly over a cellular network, for example, via a cellular base station 20210.

As shown in FIG. 6C, the computing device 20200 may include a processor 20203 and a network or an RF interface 20201. The processor 20203 may be coupled to a storage 20202, memory 20212, non-volatile memory 20213, and input/output interface 20204 via a system bus, as described in FIG. 6A and FIG. 6B. Details about the hardware and software components of the computer system are provided in FIG. 6A. The computing device 20200 may include a set of sensors, for example, sensor #1 20205, sensor #2 20206 up to sensor #n 20207. These sensors may be a part of the computing device 20200 and may be used to measure one or more attributes associated with the patient. The attributes may provide a context about a biomarker measurement performed by one of the sensing systems 20069. For example, sensor #1 may be an accelerometer that may be used to measure acceleration forces in order to sense move-ment or vibrations associated with the patient. In an example, the sensors 20205 to 20207 may include one or more of: a pressure sensor, an altimeter, a thermometer, a lidar, or the like.

As shown in FIG. 6B, a sensing system 20069 may include a processor, a radio frequency interface, a storage, a memory or non-volatile memory, and input/output interface via a system bus, as described in FIG. 6A. The sensing system may include a sensor unit and a processing and communication unit, as described in FIG. 7B through 7D. The system bus can be any of several types of bus structure(s) including the memory bus or memory controller, a peripheral bus or external bus, and/or a local bus, as described herein. The processor may be any single-core or multicore processor, as described herein.

The sensing system 20069 may be in communication with a human interface system 20215. The human interface system 20215 may be a touch screen display. The human interface system 20215 may be used to display information associated with a patient biomarker, display a prompt for a user action by a patient, or display a notification to a patient indicating information about a recovery millstone or a complication. The human interface system 20215 may be used to receive input from a patient. Other human interface systems may be connected to the sensing system 20069 via the I/O interface. For example, the human interface system may include devices for providing a haptic feedback as a mechanism for prompting a user to pay attention to a notification that may be displayed on a display unit. The sensing system 20069 may operate in a networked environ-ment using logical connections to one or more remote computers, such as cloud computer(s), or local computers, as described in FIG. 6B.

FIG. 7A illustrates a logical diagram of a control system 20220 of a surgical instrument or a surgical tool in accor-dance with one or more aspects of the present disclosure. The surgical instrument or the surgical tool may be config-urable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

In one aspect, the microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement $d1$ of the of the displacement member, where $d1$ is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement $d1+d2+ . . . dn$ of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiberoptic, magneto-optic, and microelectromechanical systemsbased magnetic sensors, among others.

In one aspect, the position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

In one form, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5 and FIG. 6A.

FIG. 7B shows an example sensing system 20069. The sensing system may be a surgeon sensing system or a patient sensing system. The sensing system 20069 may include a sensor unit 20235 and a human interface system 20242 that are in communication with a data processing and communication unit 20236. The data processing and communication unit 20236 may include an analog-to-digital converted 20237, a data processing unit 20238, a storage unit 20239, and an input/output interface 20241, a transceiver 20240. The sensing system 20069 may be in communication with a surgical hub or a computing device 20243, which in turn is in communication with a cloud computing system 20244. The cloud computing system 20244 may include a cloud storage system 20078 and one or more cloud servers 20077.

The sensor unit 20235 may include one or more ex vivo or in vivo sensors for measuring one or more biomarkers. The biomarkers may include, for example, Blood pH, hydration state, oxygen saturation, core body temperature, heart rate, Heart rate variability, Sweat rate, Skin conductance, Blood pressure, Light exposure, Environmental temperature, Respiratory rate, Coughing and sneezing, Gastrointestinal motility, Gastrointestinal tract imaging, Tissue perfusion pressure, Bacteria in respiratory tract, Alcohol consumption, Lactate (sweat), Peripheral temperature, Positivity and optimism, Adrenaline (sweat), Cortisol (sweat), Edema, Mycotoxins, VO2 max, Pre-operative pain, chemicals in the air, Circulating tumor cells, Stress and anxiety, Confusion and delirium, Physical activity, Autonomic tone, Circadian rhythm, Menstrual cycle, Sleep, etc. These biomarkers may be measured using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The sensors may measure the biomarkers as described herein using one of more of the following sensing technologies: photoplethysmography, electrocardiography, electroencephalography, colorimetry, impedimentary, potentiometry, amperometry, etc.

As illustrated in FIG. 7B, a sensor in the sensor unit 20235 may measure a physiological signal (e.g., a voltage, a current, a PPG signal, etc.) associated with a biomarker to be measured. The physiological signal to be measured may depend on the sensing technology used, as described herein. The sensor unit 20235 of the sensing system 20069 may be in communication with the data processing and communication unit 20236. In an example, the sensor unit 20235 may communicate with the data processing and communication unit 20236 using a wireless interface. The data processing and communication unit 20236 may include an analog-to-digital converter (ADC) 20237, a data processing unit 20238, a storage 20239, an I/O interface 20241, and an RF transceiver 20240. The data processing unit 20238 may include a processor and a memory unit.

The sensor unit 20235 may transmit the measured physiological signal to the ADC 20237 of the data processing and communication unit 20236. In an example, the measured physiological signal may be passed through one or more filters (e.g., an RC low-pass filter) before being sent to the ADC. The ADC may convert the measured physiological signal into measurement data associated with the biomarker. The ADC may pass measurement data to the data processing unit 20238 for processing. In an example, the data processing unit 20238 may send the measurement data associated with the biomarker to a surgical hub or a computing device 20243, which in turn may send the measurement data to a cloud computing system 20244 for further processing. The data processing unit may send the measurement data to the surgical hub or the computing device 20243 using one of the wireless protocols, as described herein. In an example, the data processing unit 20238 may first process the raw measurement data received from the sensor unit and send the processed measurement data to the surgical hub or a computing device 20243.

In an example, the data processing and communication unit 20236 of the sensing system 20069 may receive a threshold value associated with a biomarker for monitoring from a surgical hub, a computing device 20243, or directly from a cloud server 20077 of the cloud computing system 20244. The data processing unit 20236 may compare the measurement data associated with the biomarker to be monitored with the corresponding threshold value received from the surgical hub, the computing device 20243, or the cloud server 20077. The data processing and communication unit 20236 may send a notification message to the HID 20242 indicating that a measurement data value has crossed the threshold value. The notification message may include the measurement data associated with the monitored biomarker. The data processing and computing unit 20236 may send a notification via a transmission to a surgical hub or a computing device 20243 using one of the following RF protocols: Bluetooth, Bluetooth Low-Energy (BLE), Bluetooth Smart, Zigbee, Z-wave, IPv6 Low-power wireless Personal Area Network (6LoWPAN), Wi-Fi. The data processing unit 20238 may send a notification (e.g., a notification for an HCP) directly to a cloud server via a transmission to a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G. In an example, the sensing unit may be in communication with the hub/computing device via a router, as described in FIG. 6A through FIG. 6C.

FIG. 7C shows an example sensing system 20069 (e.g., a surgeon sensing system or a patient sensing system). The sensing system 20069 may include a sensor unit 20245, a data processing and communication unit 20246, and a human interface device 20242. The sensor unit 20245 may include a sensor 20247 and an analog-to-digital converted (ADC) 20248. The ADC 20248 in the sensor unit 20245 may convert a physiological signal measured by the sensor 20247 into measurement data associated with a biomarker. The sensor unit 20245 may send the measurement data to the data processing and communication unit 20246 for further processing. In an example, the sensor unit 20245 may send the measurement data to the data processing and communication unit 20246 using an inter-integrated circuit (I2C) interface.

The data processing and communication unit 20246 includes a data processing unit 20249, a storage unit 20250, and an RF transceiver 20251. The sensing system may be in communication with a surgical hub or a computing device 20243, which in turn may be in communication with a cloud computing system 20244. The cloud computing system 20244 may include a remote server 20077 and an associated remote storage 20078. The sensor unit 20245 may include one or more ex vivo or in vivo sensors for measuring one or more biomarkers, as described herein.

The data processing and communication unit 20246 after processing the measurement data received from the sensor unit 20245 may further process the measurement data and/or send the measurement data to the smart hub or the computing device 20243, as described in FIG. 7B. In an example, the data processing and communication unit 20246 may send the measurement data received from the sensor unit 20245 to the remote server 20077 of the cloud computing system 20244 for further processing and/or monitoring.

FIG. 7D shows an example sensing system 20069 (e.g., a surgeon sensing system or a patient sensing system). The sensing system 20069 may include a sensor unit 20252, a data processing and communication unit 20253, and a human interface system 20261. The sensor unit 20252 may include a plurality of sensors 20254, 20255 up to 20256 to measure one or more physiological signals associated with a patient or surgeon's biomarkers and/or one or more physical state signals associated with physical state of a patient or a surgeon. The sensor unit 20252 may also include one or more analog-to-digital converter(s) (ADCs) 20257. A list of biomarkers may include biomarkers such as those biomarkers disclosed herein. The ADC(s) 20257 in the sensor unit 20252 may convert each of the physiological signals and/or physical state signals measured by the sensors 20254-20256 into respective measurement data. The sensor unit 20252 may send the measurement data associated with one or more biomarkers as well as with the physical state of a patient or a surgeon to the data processing and communication unit 20253 for further processing. The sensor unit 20252 may send the measurement data to the data processing and communication unit 20253 individually for each of the sensors Sensor 1 20254 to Sensor N 20256 or combined for all the sensors. In an example, the sensor unit 20252 may send the measurement data to the data processing and communication unit 20253 via an I2C interface.

The data processing and communication unit 20253 may include a data processing unit 20258, a storage unit 20259, and an RF transceiver 20260. The sensing system 20069 may be in communication with a surgical hub or a computing device 20243, which in turn is in communication with a cloud computing system 20244 comprising at least one remote server 20077 and at least one storage unit 20078. The sensor units 20252 may include one or more ex vivo or in vivo sensors for measuring one or more biomarkers, as described herein.

Figure 8:
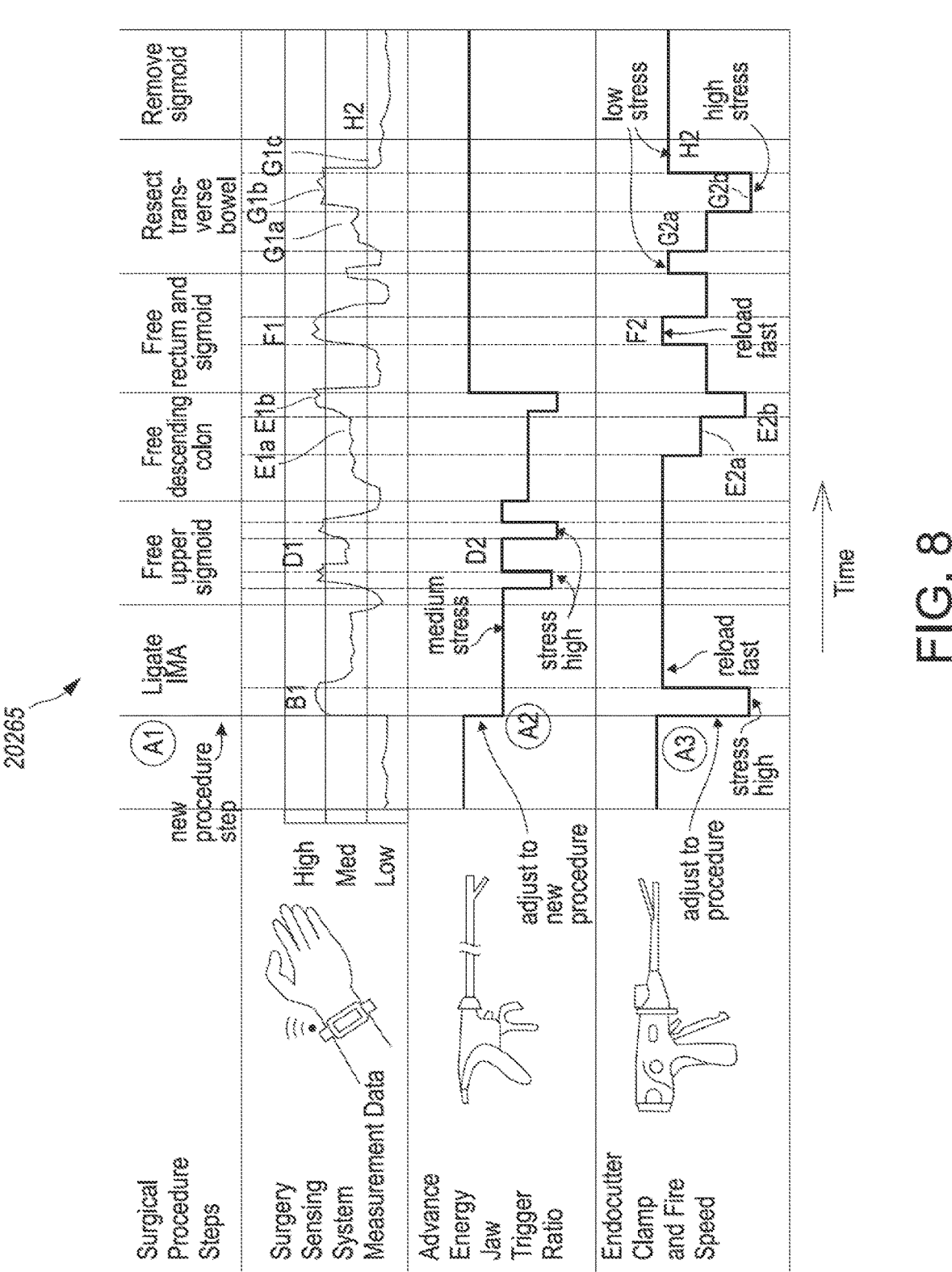
FIG. 8 illustrates an exemplary timeline of an illustrative surgical procedure indicating adjusting operational parameters of a surgical device based on a surgeon biomarker level.

FIG. 8 is an example of using a surgical task situational awareness and measurement data from one or more surgeon sensing systems to adjust surgical instrument controls. FIG. 8 illustrates a timeline 20265 of an illustrative surgical procedure and the contextual information that a surgical hub can derive from data received from one or more surgical devices, one or more surgeon sensing systems, and/or one or more environmental sensing systems at each step in the surgical procedure. The devices that could be controlled by a surgical hub may include advanced energy devices, endocutter clamps, etc. The surgeon sensing systems may include sensing systems for measuring one or more biomarkers associated with the surgeon, for example, heart rate, sweat composition, respiratory rate, etc. The environmental sensing system may include systems for measuring one or more of the environmental attributes, for example, cameras for detecting a surgeon's position/movements/breathing pattern, spatial microphones, for example to measure ambient noise in the surgical theater and/or the tone of voice of a healthcare provider, temperature/humidity of the surroundings, etc.

In the following description of the timeline 20265 illustrated in FIG. 8, reference should also be made to FIG. 5. FIG. 5 provides various components used in a surgical procedure. The timeline 20265 depicts the steps that may be taken individually and/or collectively by the nurses, surgeons, and other medical personnel during the course of an exemplary colorectal surgical procedure. In a colorectal surgical procedure, a situationally aware surgical hub 20076 may receive data from various data sources throughout the course of the surgical procedure, including data generated each time a healthcare provider (HCP) utilizes a modular device/instrument 20095 that is paired with the surgical hub 20076. The surgical hub 20076 may receive this data from the paired modular devices 20095. The surgical hub may receive measurement data from sensing systems 20069. The surgical hub may use the data from the modular device/instruments 20095 and/or measurement data from the sensing systems 20069 to continually derive inferences (i.e., contextual information) about an HCP's stress level and the ongoing procedure as new data is received, such that the stress level of the surgeon relative to the step of the procedure that is being performed is obtained. The situational awareness system of the surgical hub 20076 may perform one or more of the following: record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the FOV of the medical imaging device, change the energy level of an ultrasonic surgical instrument or RF electrosurgical instrument), or take any other such action described herein. In an example, these steps may be performed by a remote server 20077 of a cloud system 20064 and communicated with the surgical hub 20076.

As a first step (not shown in FIG. 8 for brevity), the hospital staff members may retrieve the patient's EMR from the hospital's EMR database. Based on select patient data in the EMR, the surgical hub 20076 may determine that the procedure to be performed is a colorectal procedure. The staff members may scan the incoming medical supplies for the procedure. The surgical hub 20076 may cross-reference the scanned supplies with a list of supplies that can be utilized in various types of procedures and confirms that the mix of supplies corresponds to a colorectal procedure. The surgical hub 20076 may pair each of the sensing systems 20069 worn by different HCPs.

Once each of the devices is ready and pre-surgical preparation is complete, the surgical team may begin by making incisions and place trocars. The surgical team may perform access and prep by dissecting adhesions, if any, and identifying inferior mesenteric artery (IMA) branches. The surgical hub 20076 can infer that the surgeon is in the process of dissecting adhesions, at least based on the data it may receive from the RF or ultrasonic generator indicating that an energy instrument is being fired. The surgical hub 20076 may cross-reference the received data with the retrieved steps of the surgical procedure to determine that an energy instrument being fired at this point in the process (e.g., after the completion of the previously discussed steps of the procedure) corresponds to the dissection step.

After dissection, the HCP may proceed to the ligation step (e.g., indicated by A1) of the procedure. As illustrated in FIG. 8, the HCP may begin by ligating the IMA. The surgical hub 20076 may infer that the surgeon is ligating arteries and veins because it may receive data from the advanced energy jaw device and/or the endocutter indicating that the instrument is being fired. The surgical hub may also receive measurement data from one of the HCP's sensing systems indicating higher stress level of the HCP (e.g., indicated by B1 mark on the time axis). For example, higher stress level may be indicated by change in the HCP's heart rate from a base value. The surgical hub 20076, like the prior step, may derive this inference by cross-referencing the receipt of data from the surgical stapling and cutting instrument with the retrieved steps in the process (e.g., as indicated by A2 and A3). The surgical hub 20076 may monitor the advance energy jaw trigger ratio and/or the endocutter clamp and firing speed during the high stress time periods. In an example, the surgical hub 20076 may send an assistance control signal to the advanced energy jaw device and/or the endocutter device to control the device in operation. The surgical hub may send the assistance signal based on the stress level of the HCP that is operating the surgical device and/or situational awareness known to the surgical hub. For example, the surgical hub 20076 may send control assistance signals to an advanced energy device or an endocutter clamp, as indicated in FIG. 8 by A2 and A3.

The HCP may proceed to the next step of freeing the upper sigmoid followed by freeing descending colon, rectum, and sigmoid. The surgical hub 20076 may continue to monitor the high stress markers of the HCP (e.g., as indicated by D1, E1a, E1b, F1). The surgical hub 20076 may send assistance signals to the advanced energy jaw device and/or the endocutter device during the high stress time periods, as illustrated in FIG. 8.

After mobilizing the colon, the HCP may proceed with the segmentectomy portion of the procedure. For example, the surgical hub 20076 may infer that the HCP is transecting the bowel and sigmoid removal based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. It should be noted that surgeons regularly switch back and forth between surgical stapling/cutting instruments and surgical energy (e.g., RF or ultrasonic) instruments depending upon the step in the procedure because different instruments are better adapted for particular tasks. Therefore, the sequence in which the stapling/cutting instruments and surgical energy instruments are used can indicate what step of the procedure the surgeon is performing.

The surgical hub may determine and send a control signal to surgical device based on the stress level of the HCP. For example, during time period G1b, a control signal G2b may be sent to an endocutter clamp. Upon removal of the sigmoid, the incisions are closed, and the post-operative portion of the procedure may begin. The patient's anesthesia can be reversed. The surgical hub 20076 may infer that the patient is emerging from the anesthesia based on one or more sensing systems attached to the patient.

Figure 9:
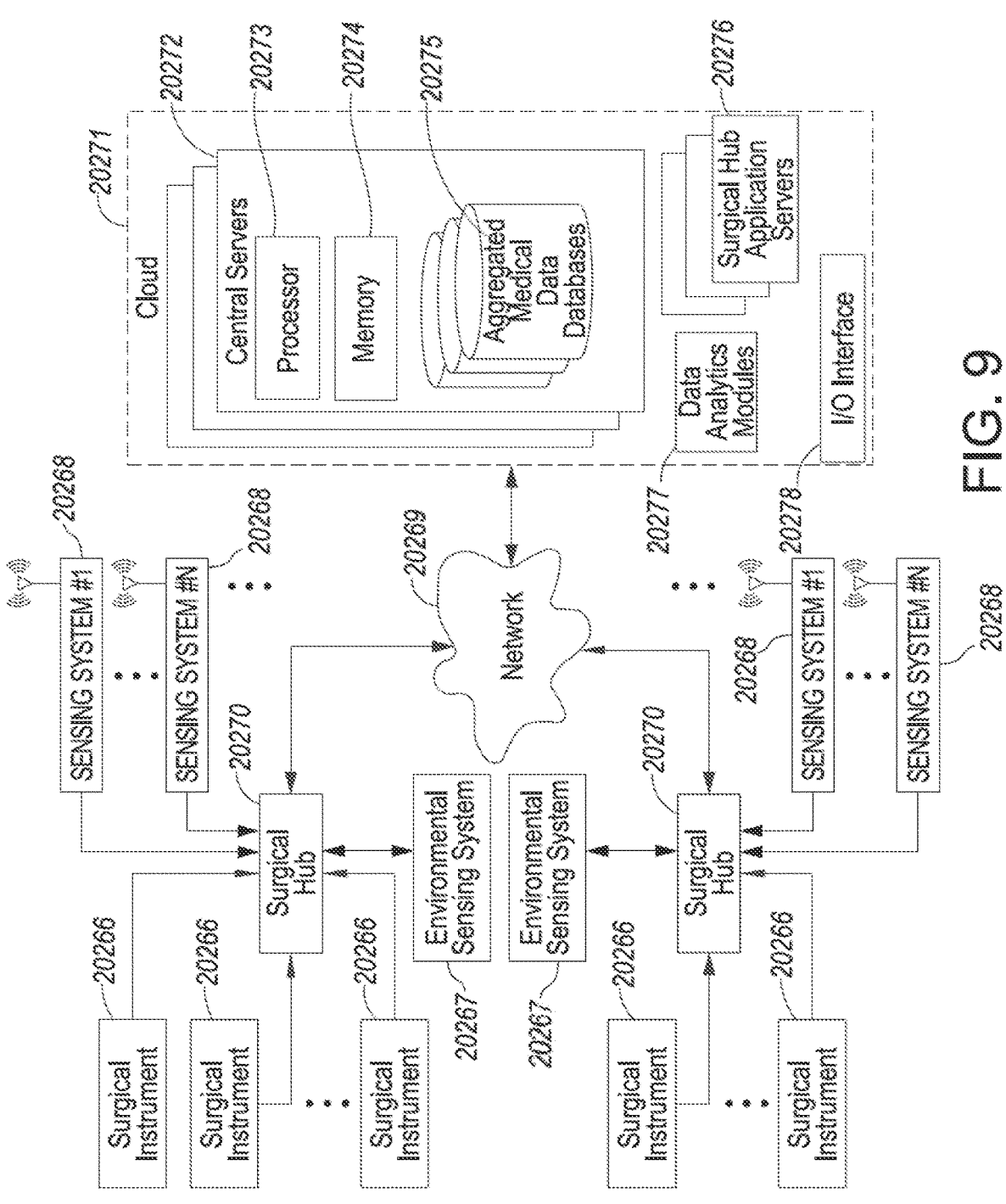
FIG. 9 is a block diagram of the computer-implemented interactive surgeon/patient monitoring system.

FIG. 9 is a block diagram of the computer-implemented interactive surgical system with surgeon/patient monitoring, in accordance with at least one aspect of the present disclosure. In one aspect, the computer-implemented interactive surgical system may be configured to monitor surgeon biomarkers and/or patient biomarkers using one or more sensing systems 20069. The surgeon biomarkers and/or the patient biomarkers may be measured before, after, and/or during a surgical procedure. In one aspect, the computer-implemented interactive surgical system may be configured to monitor and analyze data related to the operation of various surgical systems 20069 that include surgical hubs, surgical instruments, robotic devices and operating theaters or healthcare facilities. The computer-implemented interactive surgical system may include a cloud-based analytics system. The cloud-based analytics system may include one or more analytics servers.

As illustrated in FIG. 9, the cloud-based monitoring and analytics system may comprise a plurality of sensing systems 20268 (may be the same or similar to the sensing systems 20069), surgical instruments 20266 (may be the same or similar to instruments 20031), a plurality of surgical hubs 20270 (may be the same or similar to hubs 20006), and a surgical data network 20269 (may be the same or similar to the surgical data network described in FIG. 4) to couple the surgical hubs 20270 to the cloud 20271 (may be the same or similar to cloud computing system 20064). Each of the plurality of surgical hubs 20270 may be communicatively coupled to one or more surgical instruments 20266. Each of the plurality of surgical hubs 20270 may also be communicatively coupled to the one or more sensing systems 20268, and the cloud 20271 of the computer-implemented interactive surgical system via the network 20269. The surgical hubs 20270 and the sensing systems 20268 may be communicatively coupled using wireless protocols as described herein. The cloud system 20271 may be a remote centralized source of hardware and software for storing, processing, manipulating, and communicating measurement data from the sensing systems 20268 and data generated based on the operation of various surgical systems 20268.

As shown in FIG. 9, access to the cloud system 20271 may be achieved via the network 20269, which may be the Internet or some other suitable computer network. Surgical hubs 20270 that may be coupled to the cloud system 20271 can be considered the client side of the cloud computing system (e.g., cloud-based analytics system). Surgical instruments 20266 may be paired with the surgical hubs 20270 for control and implementation of various surgical procedures and/or operations, as described herein. Sensing systems 20268 may be paired with surgical hubs 20270 for in-surgical surgeon monitoring of surgeon related biomarkers, pre-surgical patient monitoring, in-surgical patient monitoring, or post-surgical monitoring of patient biomarkers to track and/or measure various milestones and/or detect various complications. Environmental sensing systems 20267 may be paired with surgical hubs 20270 measuring environmental attributes associated with a surgeon or a patient for surgeon monitoring, pre-surgical patient monitoring, in-surgical patient monitoring, or post-surgical monitoring of patient.

Surgical instruments 20266, environmental sensing systems 20267, and sensing systems 20268 may comprise wired or wireless transceivers for data transmission to and from their corresponding surgical hubs 20270 (which may also comprise transceivers). Combinations of one or more of surgical instruments 20266, sensing systems 20268, or surgical hubs 20270 may indicate particular locations, such as operating theaters, intensive care unit (ICU) rooms, or recovery rooms in healthcare facilities (e.g., hospitals), for providing medical operations, pre-surgical preparation, and/or post-surgical recovery. For example, the memory of a surgical hub 20270 may store location data.

As shown in FIG. 9, the cloud system 20271 may include one or more central servers 20272 (may be same or similar to remote server 20067), surgical hub application servers

20276, data analytics modules 20277, and an input/output ("I/O") interface 20278. The central servers 20272 of the cloud system 20271 may collectively administer the cloud computing system, which includes monitoring requests by client surgical hubs 20270 and managing the processing capacity of the cloud system 20271 for executing the requests. Each of the central servers 20272 may comprise one or more processors 20273 coupled to suitable memory devices 20274 which can include volatile memory such as random-access memory (RAM) and non-volatile memory such as magnetic storage devices. The memory devices 20274 may comprise machine executable instructions that when executed cause the processors 20273 to execute the data analytics modules 20277 for the cloud-based data analysis, real-time monitoring of measurement data received from the sensing systems 20268, operations, recommendations, and other operations as described herein. The processors 20273 can execute the data analytics modules 20277 independently or in conjunction with hub applications independently executed by the hubs 20270. The central servers 20272 also may comprise aggregated medical data databases 20275, which can reside in the memory 20274.

Based on connections to various surgical hubs 20270 via the network 20269, the cloud 20271 can aggregate data from specific data generated by various surgical instruments 20266 and/or monitor real-time data from sensing systems 20268 and the surgical hubs 20270 associated with the surgical instruments 20266 and/or the sensing systems 20268. Such aggregated data from the surgical instruments 20266 and/or measurement data from the sensing systems 20268 may be stored within the aggregated medical databases 20275 of the cloud 20271. In particular, the cloud 20271 may advantageously track real-time measurement data from the sensing systems 20268 and/or perform data analysis and operations on the measurement data and/or the aggregated data to yield insights and/or perform functions that individual hubs 20270 could not achieve on their own. To this end, as shown in FIG. 9, the cloud 20271 and the surgical hubs 20270 are communicatively coupled to transmit and receive information. The I/O interface 20278 is connected to the plurality of surgical hubs 20270 via the network 20269. In this way, the I/O interface 20278 can be configured to transfer information between the surgical hubs 20270 and the aggregated medical data databases 20275. Accordingly, the I/O interface 20278 may facilitate read/write operations of the cloud-based analytics system. Such read/write operations may be executed in response to requests from hubs 20270. These requests could be transmitted to the surgical hubs 20270 through the hub applications. The I/O interface 20278 may include one or more high speed data ports, which may include universal serial bus (USB) ports, IEEE 1394 ports, as well as Wi-Fi and Bluetooth I/O interfaces for connecting the cloud 20271 to surgical hubs 20270. The hub application servers 20276 of the cloud 20271 may be configured to host and supply shared capabilities to software applications (e.g., hub applications) executed by surgical hubs 20270. For example, the hub application servers 20276 may manage requests made by the hub applications through the hubs 20270, control access to the aggregated medical data databases 20275, and perform load balancing.

The cloud computing system configuration described in the present disclosure may be designed to address various issues arising in the context of medical operations (e.g., pre-surgical monitoring, in-surgical monitoring, and post-surgical monitoring) and procedures performed using medical devices, such as the surgical instruments 20266, 20031.

In particular, the surgical instruments 20266 may be digital surgical devices configured to interact with the cloud 20271 for implementing techniques to improve the performance of surgical operations. The sensing systems 20268 may be systems with one or more sensors that are configured to measure one or more biomarkers associated with a surgeon perfuming a medical operation and/or a patient on whom a medical operation is planned to be performed, is being performed or has been performed. Various surgical instruments 20266, sensing systems 20268, and/or surgical hubs 20270 may include human interface systems (e.g., having a touch-controlled user interfaces) such that clinicians and/or patients may control aspects of interaction between the surgical instruments 20266 or the sensing system 20268 and the cloud 20271. Other suitable user interfaces for control such as auditory controlled user interfaces may also be used.

The cloud computing system configuration described in the present disclosure may be designed to address various issues arising in the context of monitoring one or more biomarkers associated with a healthcare professional (HCP) or a patient in pre-surgical, in-surgical, and post-surgical procedures using sensing systems 20268. Sensing systems 20268 may be surgeon sensing systems or patient sensing systems configured to interact with the surgical hub 20270 and/or with the cloud system 20271 for implementing techniques to monitor surgeon biomarkers and/or patient biomarkers. Various sensing systems 20268 and/or surgical hubs 20270 may comprise touch-controlled human interface systems such that the HCPs or the patients may control aspects of interaction between the sensing systems 20268 and the surgical hub 20270 and/or the cloud systems 20271. Other suitable user interfaces for control such as auditory controlled user interfaces may also be used.

Figure 10:
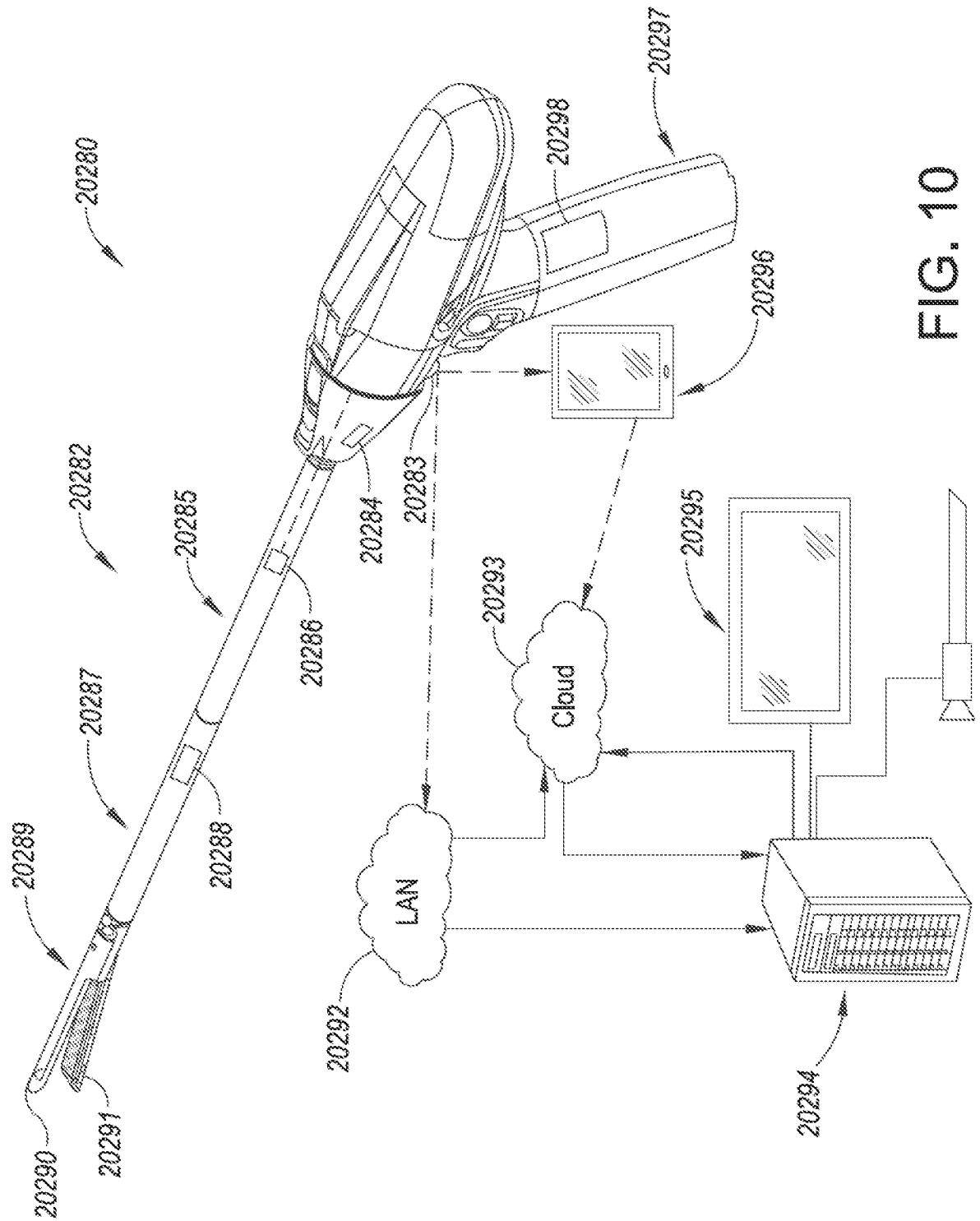
FIG. 10 shows an example surgical system that includes a handle having a controller and a motor, an adapter releasably coupled to the handle, and a loading unit releasably coupled to the adapter.

FIG. 10 illustrates an example surgical system 20280 in accordance with the present disclosure and may include a surgical instrument 20282 that can be in communication with a console 20294 or a portable device 20296 through a local area network 20292 or a cloud network 20293 via a wired or wireless connection. In various aspects, the console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub 20270, as illustrated in FIG. 9. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figures 11A, 11B, 11C, 11D:
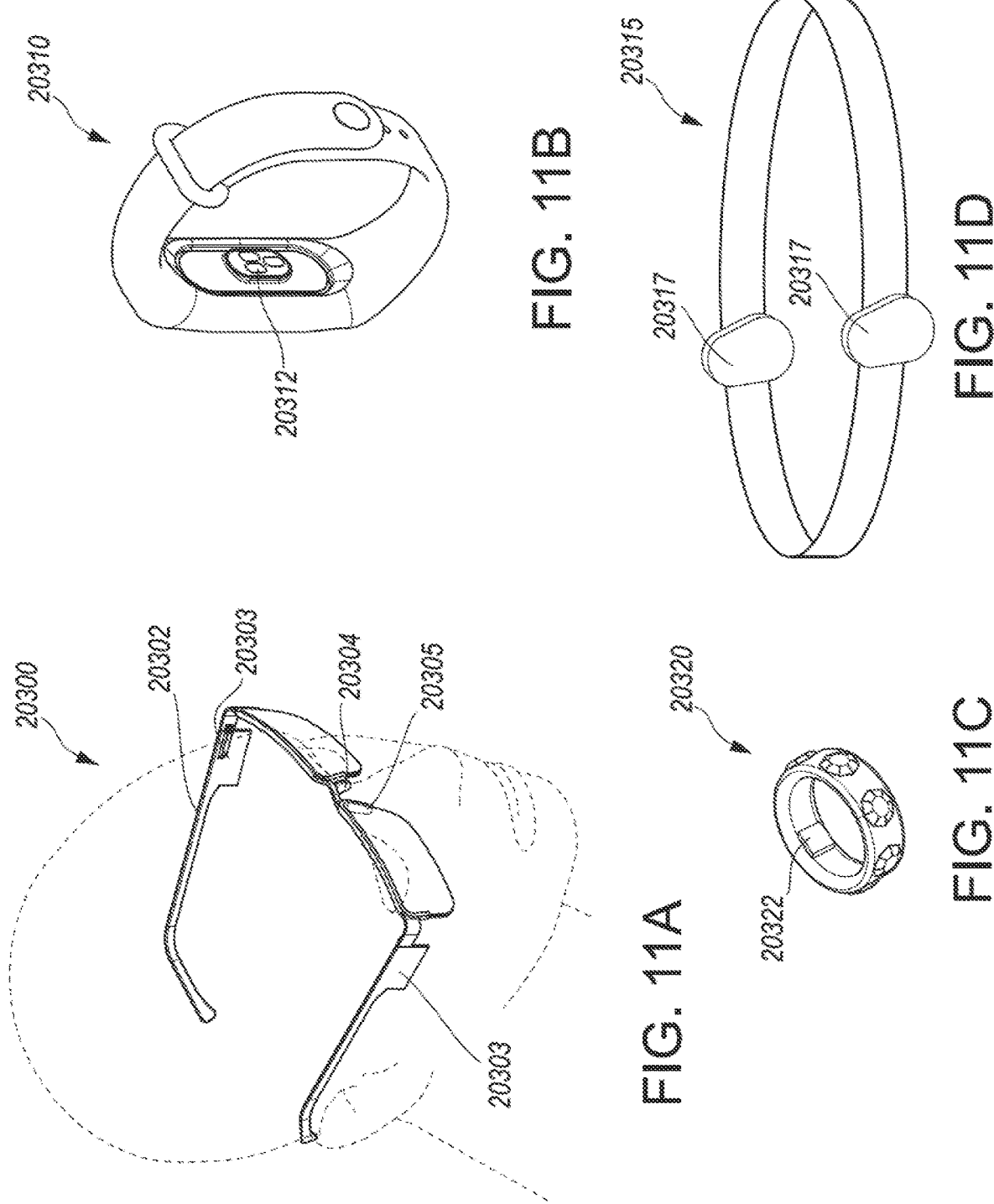
FIGS. 11A-11D illustrate examples of sensing systems that may be used for monitoring surgeon biomarkers or patient biomarkers.

FIG. 11A to FIG. 11D illustrates examples of wearable sensing systems, e.g., surgeon sensing systems or patient sensing systems. FIG. 11A is an example of eyeglasses-based sensing system 20300 that may be based on an electrochemical sensing platform. The sensing system 20300 may be capable of monitoring (e.g., real-time monitoring) of sweat electrolytes and/or metabolites using multiple sensors 20304 and 20305 that are in contact with the surgeon's or patient's skin. For example, the sensing system 20300 may use an amperometry based biosensor 20304 and/or a potentiometry based biosensor 20305 integrated with the nose bridge pads of the eyeglasses 20302 to measure current and/or the voltage.

The amperometric biosensor 20304 may be used to measure sweat lactate levels (e.g., in mmol/L). Lactate that is a product of lactic acidosis that may occur due to decreased tissue oxygenation, which may be caused by sepsis or hemorrhage. A patient's lactate levels (e.g., >2 mmol/L) may be used to monitor the onset of sepsis, for example, during post-surgical monitoring. The potentiometric biosensor 20305 may be used to measure potassium levels in the patient's sweat. A voltage follower circuit with an operational amplifier may be used for measuring the potential signal between the reference and the working electrodes. The output of the voltage follower circuit may be filtered and converted into a digital value using an ADC.

The amperometric sensor 20304 and the potentiometric sensor 20305 may be connected to circuitries 20303 placed on each of the arms of the eyeglasses. The electrochemical sensors may be used for simultaneous real-time monitoring of sweat lactate and potassium levels. The electrochemical sensors may be screen printed on stickers and placed on each side of the glasses nose pads to monitor sweat metabolites and electrolytes. The electronic circuitries 20303 placed on the arms of the glasses frame may include a wireless data transceiver (e.g., a low energy Bluetooth transceiver) that may be used to transmit the lactate and/or potassium measurement data to a surgical hub or an intermediary device that may then forward the measurement data to the surgical hub. The eyeglasses-based sensing system 20300 may use signal conditioning unit to filter and amplify the electrical signal generated from the electrochemical sensors 20305 or 20304, a microcontroller to digitize the analog signal, and a wireless (e.g., a low energy Bluetooth) module to transfer the data to a surgical hub or a computing device, for example, as described in FIGS. 7B through 7D.

FIG. 11B is an example of a wristband-type sensing system 20310 comprising a sensor assembly 20312 (e.g., Photoplethysmography (PPG)-based sensor assembly or Electrocardiogram (ECG) based-sensor assembly). For example, in the sensing system 20310, the sensor assembly 20312 may collect and analyze arterial pulse in the wrist. The sensor assembly 20312 may be used to measure one or more biomarkers (e.g., heart rate, heart rate variability (HRV), etc.). In case of a sensing system with a PPG-based sensor assembly 20312, light (e.g., green light) may be passed through the skin. A percentage of the green light may be absorbed by the blood vessels and some of the green light may be reflected and detected by a photodetector. These differences or reflections are associated with the variations in the blood perfusion of the tissue and the variations may be used in detecting the heart-related information of the cardiovascular system (e.g., heart rate). For example, the amount of absorption may vary depending on the blood volume. The sensing system 20310 may determine the heart rate by measuring light reflectance as a function of time. HRV may be determined as the time period variation (e.g., standard deviation) between the steepest signal gradient prior to a peak, known as inter-beat intervals (IBIs).

In the case of a sensing system with an ECG-based sensor assembly 20312, a set of electrodes may be placed in contact with skin. The sensing system 20310 may measure voltages across the set of electrodes placed on the skin to determine heart rate. HRV in this case may be measured as the time period variation (e.g., standard deviation) between R peaks in the QRS complex, known as R-R intervals.

The sensing system 20310 may use a signal conditioning unit to filter and amplify the analog PPG signal, a microcontroller to digitize the analog PPG signal, and a wireless (e.g., a Bluetooth) module to transfer the data to a surgical hub or a computing device, for example, as described in FIGS. 7B through 7D.

FIG. 11C is an example ring sensing system 20320. The ring sensing system 20320 may include a sensor assembly (e.g., a heart rate sensor assembly) 20322. The sensor assembly 20322 may include a light source (e.g., red or green light emitting diodes (LEDs)), and photodiodes to detect reflected and/or absorbed light. The LEDs in the sensor assembly 20322 may shine light through a finger and the photodiode in the sensor assembly 20322 may measure heart rate and/or oxygen level in the blood by detecting blood volume change. The ring sensing system 20320 may include other sensor assemblies to measure other biomarkers, for example, a thermistor or an infrared thermometer to measure the surface body temperature. The ring sensing system 20320 may use a signal conditioning unit to filter and amplify the analog PPG signal, a microcontroller to digitize the analog PPG signal, and a wireless (e.g., a low energy Bluetooth) module to transfer the data to a surgical hub or a computing device, for example, as described in FIGS. 7B through 7D.

FIG. 11D is an example of an electroencephalogram (EEG) sensing system 20315. As illustrated in FIG. 11D, the sensing system 20315 may include one or more EEG sensor units 20317. The EEG sensor units 20317 may include a plurality of conductive electrodes placed in contact with the scalp. The conductive electrodes may be used to measure small electrical potentials that may arise outside of the head due to neuronal action within the brain. The EEG sensing system 20315 may measure a biomarker, for example, delirium by identifying certain brain patterns, for example, a slowing or dropout of the posterior dominant rhythm and loss of reactivity to eyes opening and closing. The ring sensing system 20315 may have a signal conditioning unit for filtering and amplifying the electrical potentials, a micro-controller to digitize the electrical signals, and a wireless (e.g., a low energy Bluetooth) module to transfer the data to a smart device, for example, as described in FIGS. 7B through 7D.

Figure 12:
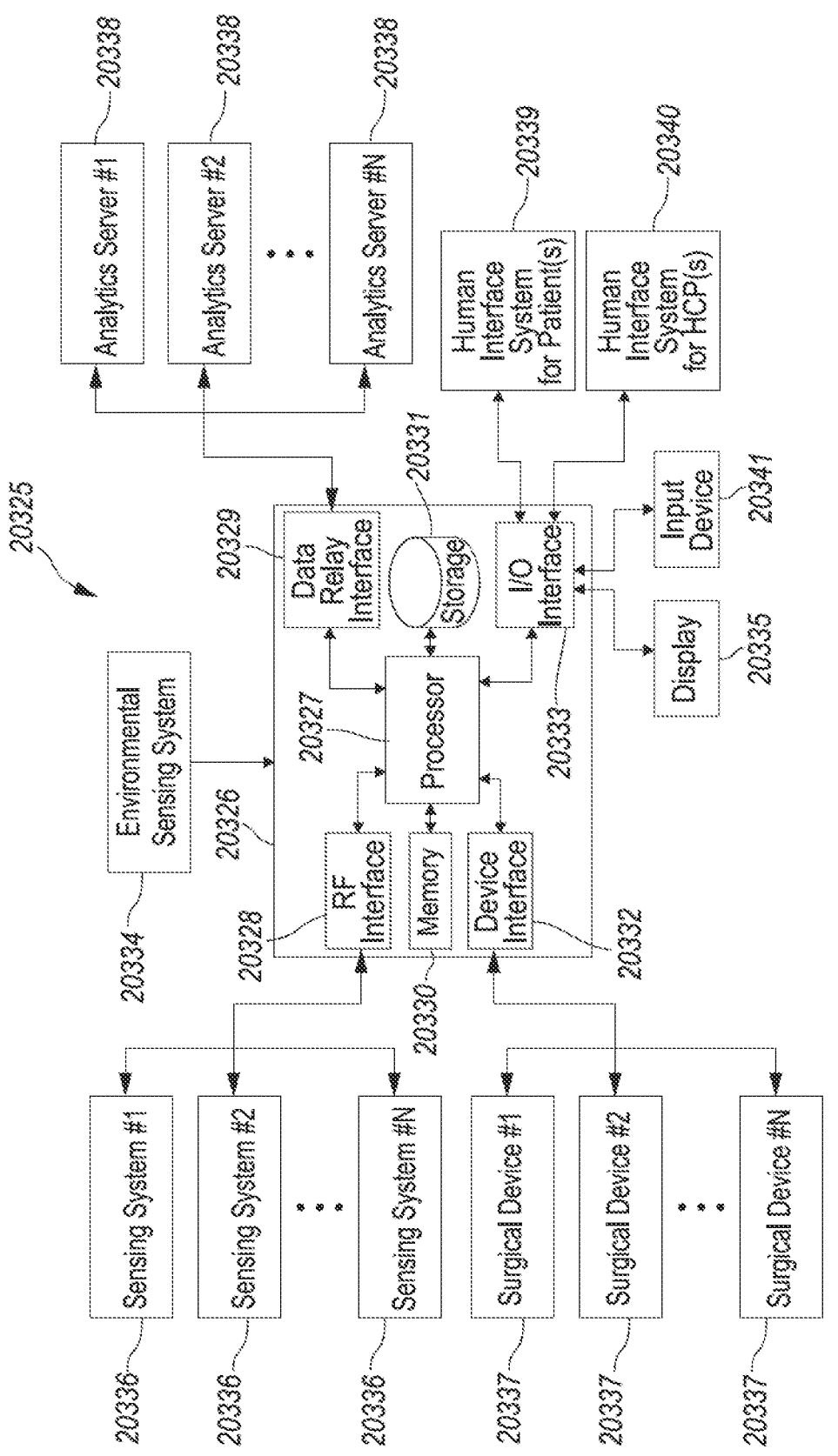
FIG. 12 is a block diagram of a patient monitoring system or a surgeon monitoring system.

FIG. 12 illustrates a block diagram of a computer-implemented patient/surgeon monitoring system 20325 for monitoring one or more patient or surgeon biomarkers prior to, during, and/or after a surgical procedure. As illustrated in FIG. 12, one or more sensing systems 20336 may be used to measure and monitor the patient biomarkers, for example, to facilitate patient preparedness before a surgical procedure, and recovery after a surgical procedure. Sensing systems 20336 may be used to measure and monitor the surgeon biomarkers in real-time, for example, to assist surgical tasks by communicating relevant biomarkers (e.g., surgeon biomarkers) to a surgical hub 20326 and/or the surgical devices 20337 to adjust their function. The surgical device functions that may be adjusted may include power levels, advancement speeds, closure speed, loads, wait times, or other tissue dependent operational parameters. The sensing systems 20336 may also measure one or more physical attributes associated with a surgeon or a patient. The patient biomarkers and/or the physical attributes may be measured in real time.

The computer-implemented wearable patient/surgeon wearable sensing system 20325 may include a surgical hub 20326, one or more sensing systems 20336, and one or more surgical devices 20337. The sensing systems and the surgical devices may be communicably coupled to the surgical hub 20326. One or more analytics servers 20338, for example part of an analytics system, may also be communicably coupled to the surgical hub 20326. Although a single surgical hub 20326 is depicted, it should be noted that the wearable patient/surgeon wearable sensing system 20325 may include any number of surgical hubs 20326, which can be connected to form a network of surgical hubs 20326 that are communicably coupled to one or more analytics servers 20338, as described herein.

In an example, the surgical hub 20326 may be a computing device. The computing device may be a personal computer, a laptop, a tablet, a smart mobile device, etc. In an example, the computing device may be a client computing device of a cloud-based computing system. The client computing device may be a thin client.

In an example, the surgical hub 20326 may include a processor 20327 coupled to a memory 20330 for executing instructions stored thereon, a storage 20331 to store one or more databases such as an EMR database, and a data relay interface 20329 through which data is transmitted to the analytics servers 20338. In an example, the surgical hub 20326 further may include an I/O interface 20333 having an input device 20341 (e.g., a capacitive touchscreen or a keyboard) for receiving inputs from a user and an output device 20335 (e.g., a display screen) for providing outputs to a user. In an example, the input device and the output device may be a single device. Outputs may include data from a query input by the user, suggestions for products or a combination of products to use in a given procedure, and/or instructions for actions to be carried out before, during, and/or after a surgical procedure. The surgical hub 20326 may include a device interface 20332 for communicably coupling the surgical devices 20337 to the surgical hub 20326. In one aspect, the device interface 20332 may include a transceiver that may enable one or more surgical devices 20337 to connect with the surgical hub 20326 via a wired interface or a wireless interface using one of the wired or wireless communication protocols described herein. The surgical devices 20337 may include, for example, powered staplers, energy devices or their generators, imaging systems, or other linked systems, for example, smoke evacuators, suction-irrigation devices, insufflation systems, etc.

In an example, the surgical hub 20326 may be communicably coupled to one or more surgeon and/or patient sensing systems 20336. The sensing systems 20336 may be used to measure and/or monitor, in real-time, various biomarkers associated with a surgeon performing a surgical procedure or a patient on whom a surgical procedure is being performed. A list of the patient/surgeon biomarkers measured by the sensing systems 20336 is provided herein. In an example, the surgical hub 20326 may be communicably coupled to an environmental sensing system 20334. The environmental sensing systems 20334 may be used to measure and/or monitor, in real-time, environmental attributes, for example, temperature/humidity in the surgical theater, surgeon movements, ambient noise in the surgical theater caused by the surgeon's and/or the patient's breathing pattern, etc.

When sensing systems 20336 and the surgical devices 20337 are connected to the surgical hub 20326, the surgical hub 20326 may receive measurement data associated with one or more patient biomarkers, physical state associated with a patient, measurement data associated with surgeon biomarkers, and/or physical state associated with the surgeon from the sensing systems 20336, for example, as illustrated in FIG. 7B through 7D. The surgical hub 20326 may associate the measurement data, e.g., related to a surgeon, with other relevant pre-surgical data and/or data from situational awareness system to generate control signals for controlling the surgical devices 20337, for example, as illustrated in FIG. 8.

In an example, the surgical hub 20326 may compare the measurement data from the sensing systems 20336 with one or more thresholds defined based on baseline values, pre-surgical measurement data, and/or in surgical measurement data. The surgical hub 20326 may compare the measurement data from the sensing systems 20336 with one or more thresholds in real-time. The surgical hub 20326 may generate a notification for displaying. The surgical hub 20326 may send the notification for delivery to a human interface system for patient 20339 and/or the human interface system for a surgeon or an HCP 20340, for example, if the measurement data crosses (e.g., is greater than or lower than) the defined threshold value. The determination whether the notification would be sent to one or more of the to the human interface system for patient 20339 and/or the human interface system for an HCP 2340 may be based on a severity level associated with the notification. The surgical hub 20326 may also generate a severity level associated with the notification for displaying. The severity level generated may be displayed to the patient and/or the surgeon or the HCP. In an example, the patient biomarkers to be measured and/or monitored (e.g., measured and/or monitored in real-time) may be associated with a surgical procedural step. For example, the biomarkers to be measured and monitored for transection of veins and arteries step of a thoracic surgical procedure may include blood pressure, tissue perfusion pressure, edema, arterial stiffness, collagen content, thickness of connective tissue, etc., whereas the biomarkers to be measured and monitored for lymph node dissection step of the surgical procedure may include monitoring blood pressure of the patient. In an example, data regarding postoperative complications could be retrieved from an EMR database in the storage 20331 and data regarding staple or incision line leakages could be directly detected or inferred by a situational awareness system. The surgical procedural outcome data can be inferred by a situational awareness system from data received from a variety of data sources, including the surgical devices 20337, the sensing systems 20336, and the databases in the storage 20331 to which the surgical hub 20326 is connected.

The surgical hub 20326 may transmit the measurement data and physical state data it received from the sensing systems 20336 and/or data associated with the surgical devices 20337 to analytics servers 20338 for processing thereon. Each of the analytics servers 20338 may include a memory and a processor coupled to the memory that may execute instructions stored thereon to analyze the received data. The analytics servers 20338 may be connected in a distributed computing architecture and/or utilize a cloud computing architecture. Based on this paired data, the analytics system 20338 may determine optimal and/or preferred operating parameters for the various types of modular devices, generate adjustments to the control programs for the surgical devices 20337, and transmit (or "push") the updates or control programs to the one or more surgical devices 20337. For example, an analytics system 20338 may correlate the perioperative data it received from the surgical hub 20236 with the measurement data associated with a physiological state of a surgeon or an HCP and/or a physiological state of the patient. The analytics system 20338 may determine when the surgical devices 20337 should be controlled and send an update to the surgical hub 20326. The surgical hub 20326 may then forward the control program to the relevant surgical device 20337.

Additional detail regarding the computer-implemented wearable patient/surgeon wearable sensing system 20325, including the surgical hub 30326, one or more sensing systems 20336 and various surgical devices 20337 connectable thereto, are described in connection with FIG. 5 through FIG. 7D.

FIGS. 13 to 16 depict a motor-driven surgical instrument 150010 for cutting and fastening that may or may not be reused. Additional information regarding a motor-driven surgical instrument 150010 may be found in U.S. Patent Publication No. 20190200981 (from U.S. application Ser. No. 16/209,423, filed Dec. 4, 2018), titled "METHOD OF COMPRESSING TISSUE WITHIN A STAPLING DEVICE AND SIMULTANEOUSLY DISPLAYING THE LOCATION OF THE TISSUE WITHIN THE JAWS," published Jul. 4, 2019, the contents of which are hereby incorporated herein in their entirety. In the illustrated examples, the surgical instrument 150010 includes a housing 150012 that comprises a handle assembly 150014 that is configured to be grasped, manipulated, and actuated by the clinician. The housing 150012 is configured for operable attachment to an interchangeable shaft assembly 150200 that has an end effector 150300 operably coupled thereto that is configured to perform one or more surgical tasks or procedures. In accordance with the present disclosure, various forms of interchangeable shaft assemblies may be effectively employed in connection with robotically controlled surgical systems. The term "housing" may encompass a housing or similar portion of a robotic system that houses or otherwise operably supports at least one drive system configured to generate and apply at least one control motion that could be used to actuate interchangeable shaft assemblies. The term "frame" may refer to a portion of a handheld surgical instrument. The term "frame" also may represent a portion of a robotically controlled surgical instrument and/or a portion of the robotic system that may be used to operably control a surgical instrument. Interchangeable shaft assemblies may be employed with various robotic systems, instruments, components, and methods disclosed in U.S. Pat. No. 9,072,535, titled SURGICAL STAPLING INSTRUMENTS WITH ROTATABLE STAPLE DEPLOYMENT ARRANGEMENTS, which is herein incorporated by reference in its entirety.

Figure 13:
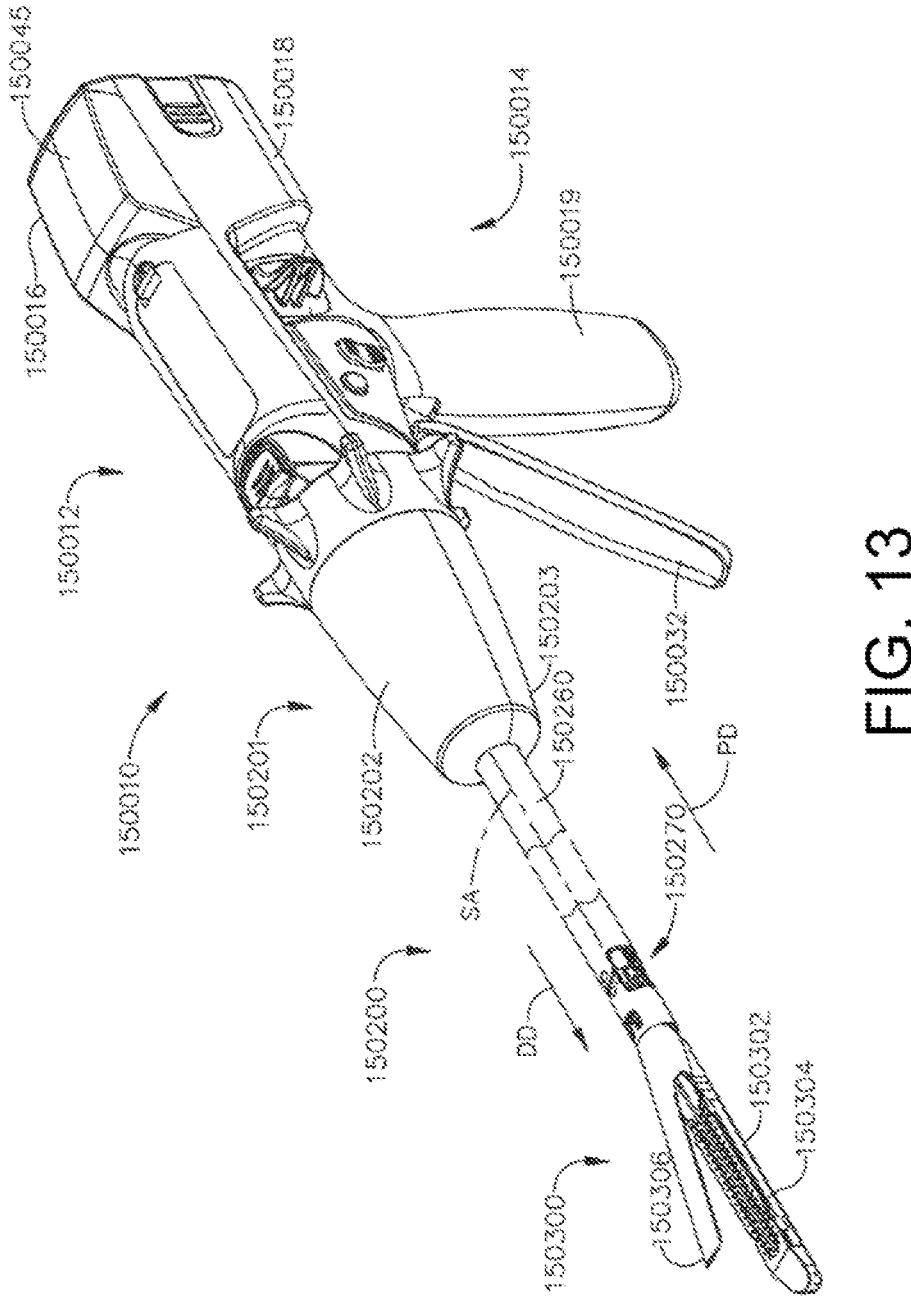
FIG. 13 illustrates a perspective view of an example surgical instrument that has an example interchangeable shaft assembly operably coupled thereto.

FIG. 13 is a perspective view of a surgical instrument 150010 that has an interchangeable shaft assembly 150200 operably coupled thereto, in accordance with at least one aspect of this disclosure. The housing 150012 includes an end effector 150300 that comprises a surgical cutting and fastening device configured to operably support a surgical staple cartridge 150304 therein. The housing 150012 may be configured for use in connection with interchangeable shaft assemblies that include end effectors that are adapted to support different sizes and types of staple cartridges, have different shaft lengths, sizes, and types. The housing 150012 may be employed with a variety of interchangeable shaft assemblies, including assemblies configured to apply other motions and forms of energy such as, radio frequency (RF) energy, ultrasonic energy, and/or motion to end effector arrangements adapted for use in connection with various surgical applications and procedures. The end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

The handle assembly 150014 may comprise a pair of interconnectable handle housing segments 150016, 150018 interconnected by screws, snap features, adhesive, etc. The handle housing segments 150016, 150018 cooperate to form a pistol grip portion 150019 that can be gripped and manipulated by the clinician. The handle assembly 150014 operably supports a plurality of drive systems configured to generate and apply control motions to corresponding portions of the interchangeable shaft assembly that is operably attached thereto. A display may be provided below a cover 150045.

Figure 14:
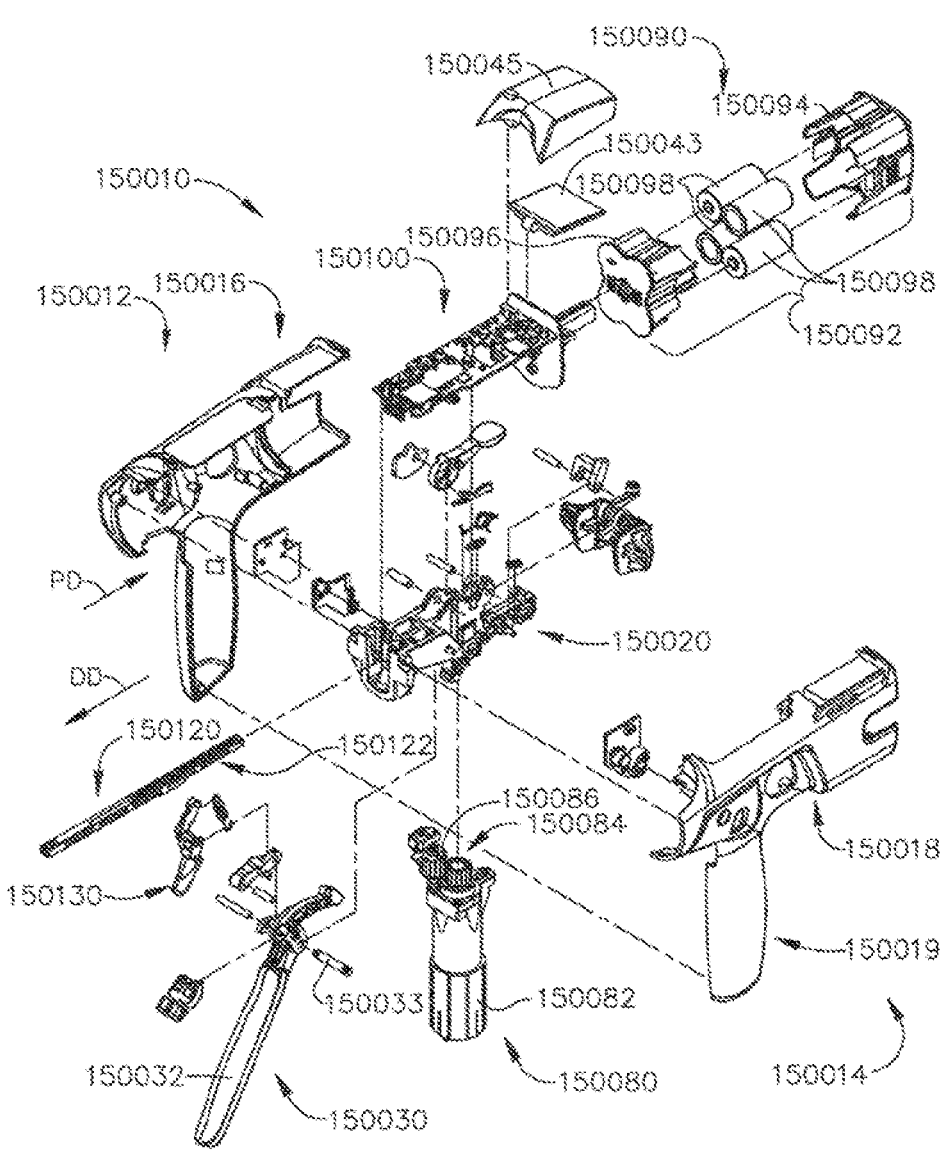
FIG. 14 illustrates an exploded assembly view of a portion of the example surgical instrument of FIG. 13.

FIG. 14 is an exploded assembly view of a portion of the surgical instrument 150010 of FIG. 13, in accordance with at least one aspect of this disclosure. The handle assembly 150014 may include a frame 150020 that operably supports a plurality of drive systems. The frame 150020 can operably support a "first" or closure drive system 150030, which can apply closing and opening motions to the interchangeable shaft assembly 150200. The closure drive system 150030 may include an actuator such as a closure trigger 150032 pivotally supported by the frame 150020. The closure trigger 150032 is pivotally coupled to the handle assembly 150014 by a pivot pin 150033 to enable the closure trigger 150032 to be manipulated by a clinician. When the clinician grips the pistol grip portion 150019 of the handle assembly 150014, the closure trigger 150032 can pivot from a starting or "unactuated" position to an "actuated" position and more particularly to a fully compressed or fully actuated position.

The handle assembly 150014 and the frame 150020 may operably support a firing drive system 150080 configured to apply firing motions to corresponding portions of the interchangeable shaft assembly attached thereto. The firing drive system 150080 may employ an electric motor 150082 located in the pistol grip portion 150019 of the handle assembly 150014. The electric motor 150082 may be a DC brushed motor having a maximum rotational speed of approximately 25,000 RPM, for example. In other arrangements, the motor may include a brushless motor, a cordless motor, a synchronous motor, a stepper motor, or any other suitable electric motor. The electric motor 150082 may be powered by a power source 150090 that may comprise a removable power pack 150092. The removable power pack 150092 may comprise a proximal housing portion 150094 configured to attach to a distal housing portion 150096. The proximal housing portion 150094 and the distal housing portion 150096 are configured to operably support a plurality of batteries 150098 therein. Batteries 150098 may each comprise, for example, a Lithium Ion (LI) or other suitable battery. The distal housing portion 150096 is configured for removable operable attachment to a control circuit board 150100, which is operably coupled to the electric motor 150082. Several batteries 150098 connected in series may power the surgical instrument 150010. The power source 150090 may be replaceable and/or rechargeable. A display 150043, which is located below the cover 150045, is electrically coupled to the control circuit board 150100. The cover 150045 may be removed to expose the display 150043.

The electric motor 150082 can include a rotatable shaft (not shown) that operably interfaces with a gear reducer assembly 150084 mounted in meshing engagement with a set, or rack, of drive teeth 150122 on a longitudinally movable drive member 150120. The longitudinally movable drive member 150120 has a rack of drive teeth 150122 formed thereon for meshing engagement with a corresponding drive gear 150086 of the gear reducer assembly 150084.

In use, a voltage polarity provided by the power source 150090 can operate the electric motor 150082 in a clockwise direction wherein the voltage polarity applied to the electric motor by the battery can be reversed in order to operate the electric motor 150082 in a counter-clockwise direction. When the electric motor 150082 is rotated in one direction, the longitudinally movable drive member 150120 will be axially driven in the distal direction "DD." When the electric motor 150082 is driven in the opposite rotary direction, the longitudinally movable drive member 150120 will be axially driven in a proximal direction "PD." The handle assembly 150014 can include a switch that can be configured to reverse the polarity applied to the electric motor 150082 by the power source 150090. The handle assembly 150014 may include a sensor configured to detect the position of the longitudinally movable drive member 150120 and/or the direction in which the longitudinally movable drive member 150120 is being moved.

Actuation of the electric motor 150082 can be controlled by a firing trigger 150130 that is pivotally supported on the handle assembly 150014. The firing trigger 150130 may be pivoted between an unactuated position and an actuated position.

Turning back to FIG. 13, the interchangeable shaft assembly 150200 includes an end effector 150300 comprising an elongated channel 150302 configured to operably support a surgical staple cartridge 150304 therein. The end effector 150300 may include an anvil 150306 that is pivotally supported relative to the elongated channel 150302. The interchangeable shaft assembly 150200 may include an articulation joint 150270. Construction and operation of the end effector 150300 and the articulation joint 150270 are set forth in U.S. Patent Application Publication No. 2014/0263541, titled ARTICULATABLE SURGICAL INSTRUMENT COMPRISING AN ARTICULATION LOCK, which is herein incorporated by reference in its entirety. The interchangeable shaft assembly 150200 may include a proximal housing or nozzle 150201 comprised of nozzle portions 150202, 150203. The interchangeable shaft assembly 150200 may include a closure tube 150260 extending along a shaft axis SA that can be utilized to close and/or open the anvil 150306 of the end effector 150300.

Turning back to FIG. 13, the closure tube 150260 is translated distally (direction "DD") to close the anvil 150306, for example, in response to the actuation of the closure trigger 150032 in the manner described in U.S. Patent Application Publication No. 2014/0263541. The anvil 150306 is opened by proximally translating the closure tube 150260. In the anvil-open position, the closure tube 150260 is moved to its proximal position.

Figure 15:
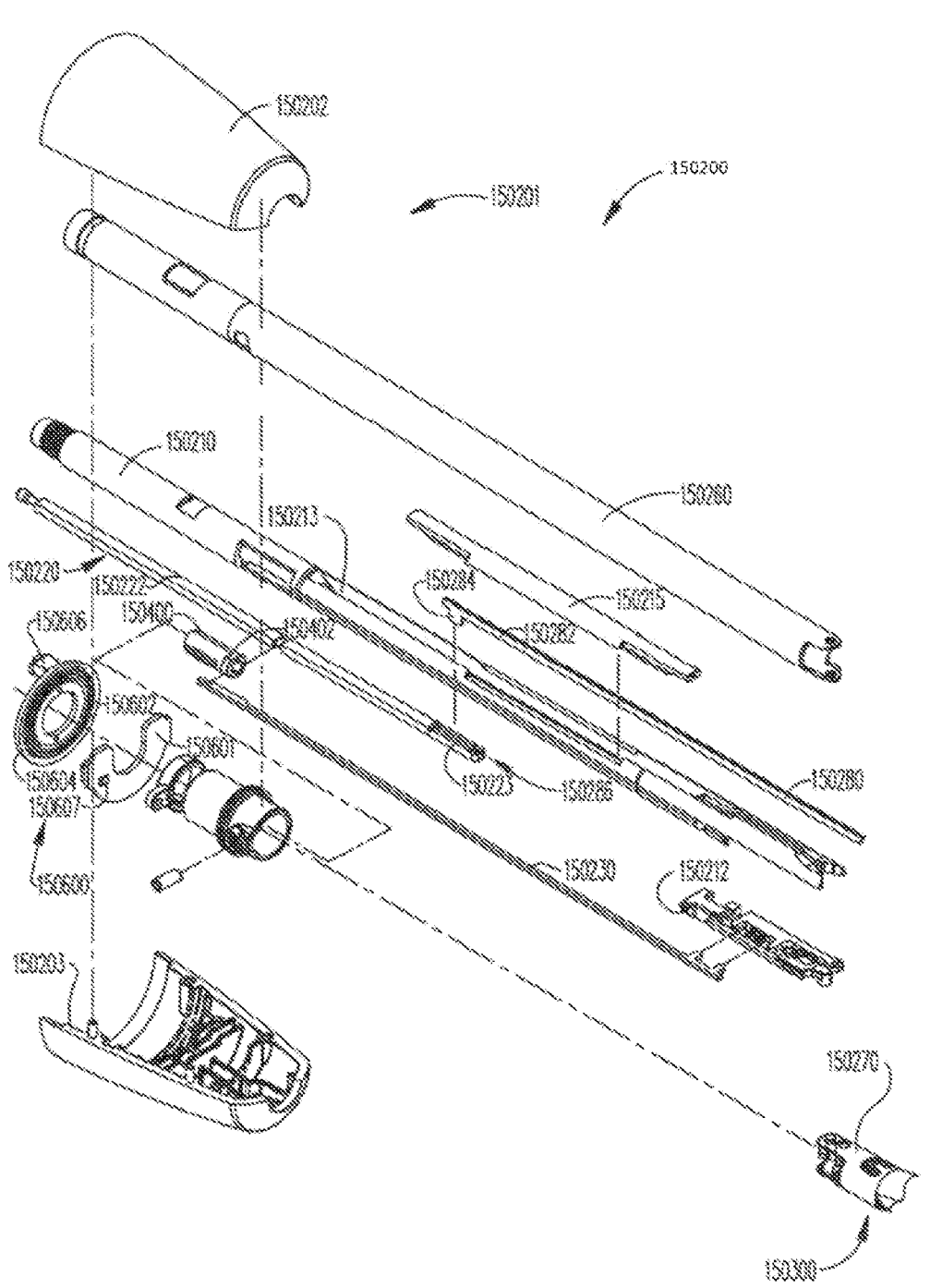
FIG. 15 illustrates an exploded assembly view of portions of the example interchangeable shaft assembly.

FIG. 15 is another exploded assembly view of portions of the interchangeable shaft assembly 150200, in accordance with at least one aspect of this disclosure. The interchangeable shaft assembly 150200 may include a firing member 150220 supported for axial travel within the spine 150210. The firing member 150220 includes an intermediate shaft 150222 configured to attach to a distal cutting portion or knife bar 150280. The firing member 150220 may be referred to as a "second shaft" or a "second shaft assembly". The intermediate firing shaft 150222 may include a longitudinal slot 150223 in a distal end configured to receive a tab 150284 on the proximal end 150282 of the knife bar 150280. The longitudinal slot 150223 and the proximal end 150282 may be configured to permit relative movement there between and can comprise a slip joint 150286. The slip joint 150286 can permit the intermediate firing shaft 150222 of the firing member 150220 to articulate the end effector 150300 about the articulation joint 150270 without moving, or at least substantially moving, the knife bar 150280. Once the end effector 150300 has been suitably oriented, the intermediate firing shaft 150222 can be advanced distally until a proximal sidewall of the longitudinal slot 150223 contacts the tab 150284 to advance the knife bar 150280 and fire the staple cartridge positioned within the channel 150302. The spine 150210 has an elongated opening or window 150213 therein to facilitate assembly and insertion of the intermediate firing shaft 150222 into the spine 150210. Once the intermediate firing shaft 150222 has been inserted therein, a top frame segment 150215 may be engaged with the shaft frame 150212 to enclose the intermediate firing shaft 150222 and knife bar 150280 therein. Operation of the firing member 150220 may be found in U.S. Patent Application Publication No. 2014/0263541. A spine 150210 can be configured to slidably support a firing member 150220 and the closure tube 150260 that extends around the spine 150210. The spine 150210 may slidably support an articulation driver 150230.

The interchangeable shaft assembly 150200 can include a clutch assembly 150400 configured to selectively and releasably couple the articulation driver 150230 to the firing member 150220. The clutch assembly 150400 includes a lock collar, or lock sleeve 150402, positioned around the firing member 150220 wherein the lock sleeve 150402 can be rotated between an engaged position in which the lock sleeve 150402 couples the articulation driver 150230 to the firing member 150220 and a disengaged position in which the articulation driver 150230 is not operably coupled to the firing member 150220. When the lock sleeve 150402 is in the engaged position, distal movement of the firing member 150220 can move the articulation driver 150230 distally and, correspondingly, proximal movement of the firing member 150220 can move the articulation driver 150230 proximally. When the lock sleeve 150402 is in the disengaged position, movement of the firing member 150220 is not transmitted to the articulation driver 150230 and, as a result, the firing member 150220 can move independently of the articulation driver 150230. The nozzle 150201 may be employed to operably engage and disengage the articulation drive system with the firing drive system in the various manners described in U.S. Patent Application Publication No. 2014/0263541.

The interchangeable shaft assembly 150200 can comprise a slip ring assembly 150600 which can be configured to conduct electrical power to and/or from the end effector 150300 and/or communicate signals to and/or from the end effector 150300, for example. The slip ring assembly 150600 can comprise a proximal connector flange 150604 and a distal connector flange 150601 positioned within a slot defined in the nozzle portions 150202, 150203. The proximal connector flange 150604 can comprise a first face and the distal connector flange 150601 can comprise a second face positioned adjacent to and movable relative to the first face. The distal connector flange 150601 can rotate relative to the proximal connector flange 150604 about the shaft axis SA-SA (FIG. 13). The proximal connector flange 150604 can comprise a plurality of concentric, or at least substantially concentric, conductors 150602 defined in the first face thereof. A connector 150607 can be mounted on the proximal side of the distal connector flange 150601 and may have a plurality of contacts wherein each contact corresponds to and is in electrical contact with one of the conductors 150602. Such an arrangement permits relative rotation between the proximal connector flange 150604 and the distal connector flange 150601 while maintaining electrical contact there between. The proximal connector flange 150604 can include an electrical connector 150606 that can place the conductors 150602 in signal communication with a shaft circuit board, for example. In at least one instance, a wiring harness comprising a plurality of conductors can extend between the electrical connector 150606 and the shaft circuit board. The electrical connector 150606 may extend proximally through a connector opening defined in the chassis mounting flange. U.S. Patent Application Publication No. 2014/0263551, titled STAPLE CARTRIDGE TISSUE THICKNESS SENSOR SYSTEM, is incorporated herein by reference in its entirety. U.S. Patent Application Publication No. 2014/0263552, titled STAPLE CARTRIDGE TISSUE THICKNESS SENSOR SYSTEM, is incorporated by reference in its entirety. Further details regarding slip ring assembly 150600 may be found in U.S. Patent Application Publication No. 2014/0263541.

The interchangeable shaft assembly 150200 can include a proximal portion fixably mounted to the handle assembly 150014 and a distal portion that is rotatable about a longitudinal axis. The rotatable distal shaft portion can be rotated relative to the proximal portion about the slip ring assembly 150600. The distal connector flange 150601 of the slip ring assembly 150600 can be positioned within the rotatable distal shaft portion.

Figure 16:
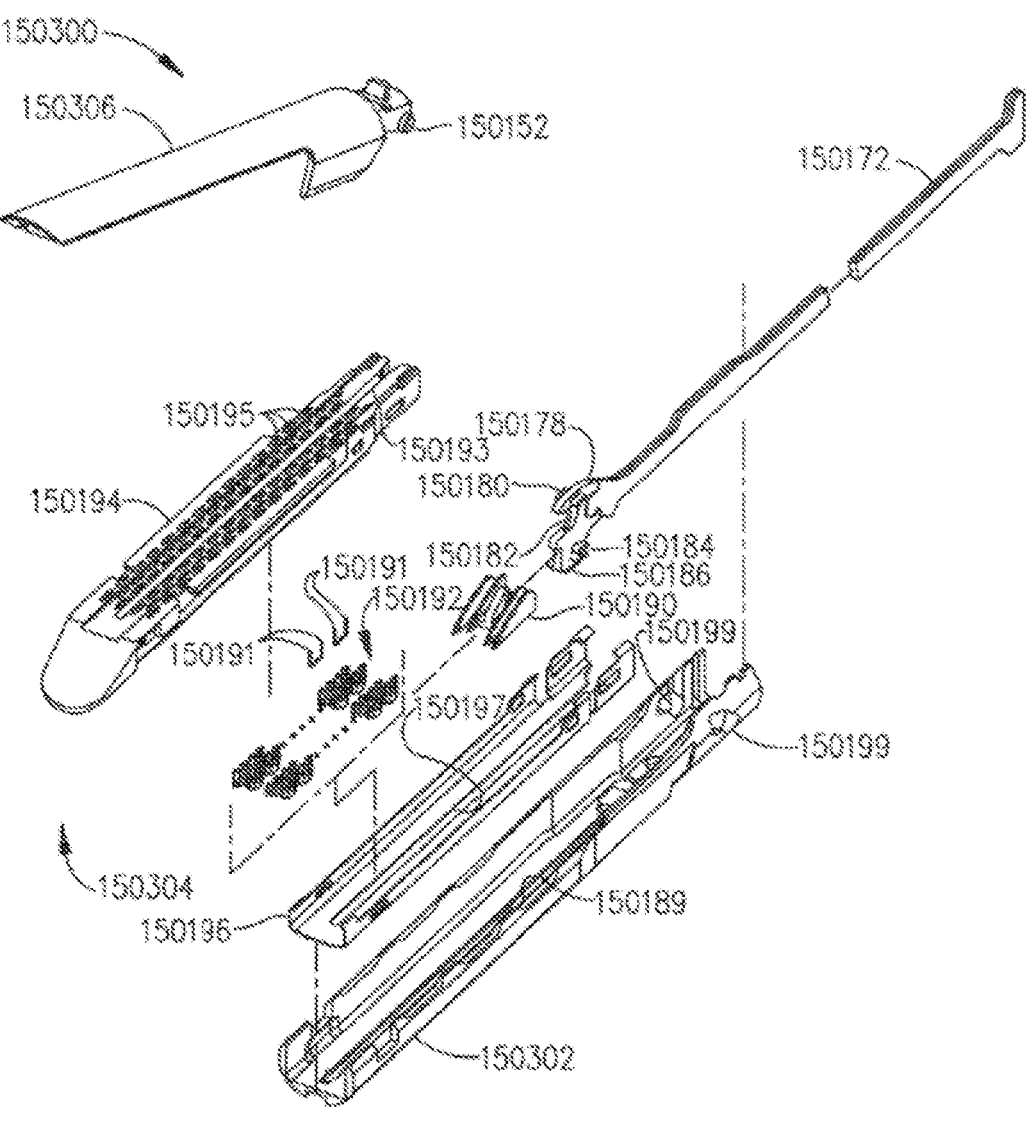
FIG. 16 illustrates an exploded view of an end effector of the example surgical instrument of FIG. 13.

FIG. 16 is an exploded view of one aspect of an end effector 150300 of the surgical instrument 150010 of FIG. 13, in accordance with at least one aspect of this disclosure. The end effector 150300 may include the anvil 150306 and the surgical staple cartridge 150304. The anvil 150306 may be coupled to an elongated channel 150302. Apertures 150199 can be defined in the elongated channel 150302 to receive pins 150152 extending from the anvil 150306 to allow the anvil 150306 to pivot from an open position to a closed position relative to the elongated channel 150302 and surgical staple cartridge 150304. A firing bar 150172 is configured to longitudinally translate into the end effector 150300. The firing bar 150172 may be constructed from one solid section, or may include a laminate material comprising a stack of steel plates. The firing bar 150172 comprises an I-beam 150178 and a cutting edge 150182 at a distal end thereof. A distally projecting end of the firing bar 150172 can be attached to the I-beam 150178 to assist in spacing the anvil 150306 from a surgical staple cartridge 150304 positioned in the elongated channel 150302 when the anvil 150306 is in a closed position. The I-beam 150178 may include a sharpened cutting edge 150182 to sever tissue as the I-beam 150178 is advanced distally by the firing bar 150172. In operation, the I-beam 150178 may, or fire, the surgical staple cartridge 150304. The surgical staple cartridge 150304 can include a molded cartridge body 150194 that holds a plurality of staples 150191 resting upon staple drivers 150192 within respective upwardly open staple cavities 150195. A wedge sled 150190 is driven distally by the I-beam 150178, sliding upon a cartridge tray 150196 of the surgical staple cartridge 150304. The wedge sled 150190 upwardly cams the staple drivers 150192 to force out the staples into deforming contact with the anvil 150306 while the cutting edge 150182 of the I-beam 150178 severs clamped tissue.

The I-beam 150178 can include upper pins 150180 that engage the anvil 150306 during firing. The I-beam 150178 may include middle pins 150184 and a bottom foot 150186 to engage portions of the cartridge body 150194, cartridge tray 150196, and elongated channel 150302. When a surgical staple cartridge 150304 is positioned within the elongated channel 150302, a slot 150193 defined in the cartridge body 150194 can be aligned with a longitudinal slot 150197 defined in the cartridge tray 150196 and a slot 150189 defined in the elongated channel 150302. In use, the I-beam 150178 can slide through the aligned longitudinal slots 150193, 150197, and 150189 wherein, as indicated in FIG. 16, the bottom foot 150186 of the I-beam 150178 can engage a groove running along the bottom surface of elongated channel 150302 along the length of slot 150189, the middle pins 150184 can engage the top surfaces of cartridge tray 150196 along the length of longitudinal slot 150197, and the upper pins 150180 can engage the anvil 150306. The I-beam 150178 can space, or limit the relative movement between, the anvil 150306 and the surgical staple cartridge 150304 as the firing bar 150172 is advanced distally to fire the staples from the surgical staple cartridge 150304 and/or incise the tissue captured between the anvil 150306 and the surgical staple cartridge 150304. The firing bar 150172 and the I-beam 150178 can be retracted proximally allowing the anvil 150306 to be opened to release the two stapled and severed tissue portions.

Figure 17A:
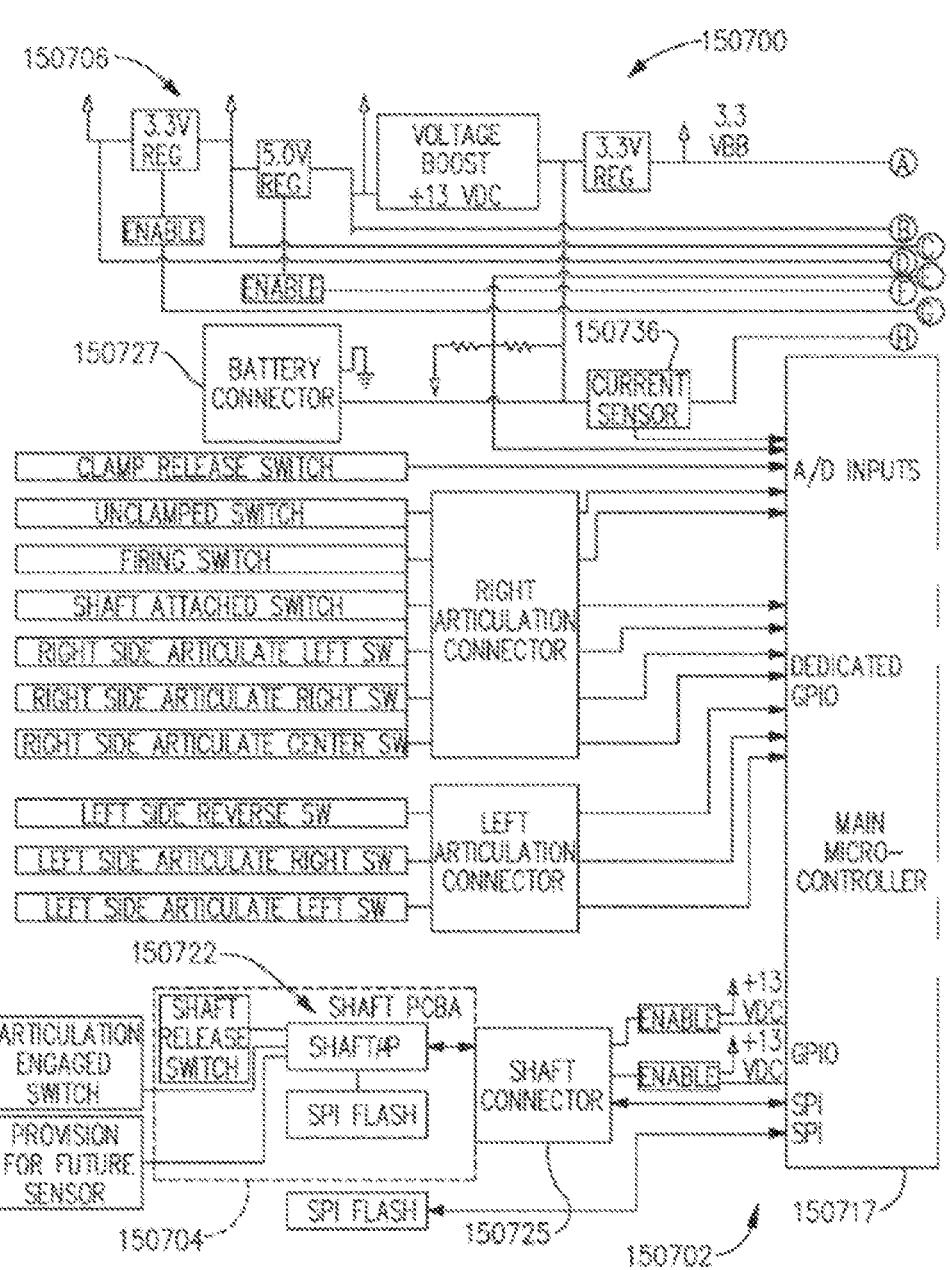
FIG. 17A illustrates a block diagram of a control circuit of the surgical instrument of FIG. 13 spanning two drawing sheets, in accordance with at least one aspect of this disclosure.
Figure 17B:
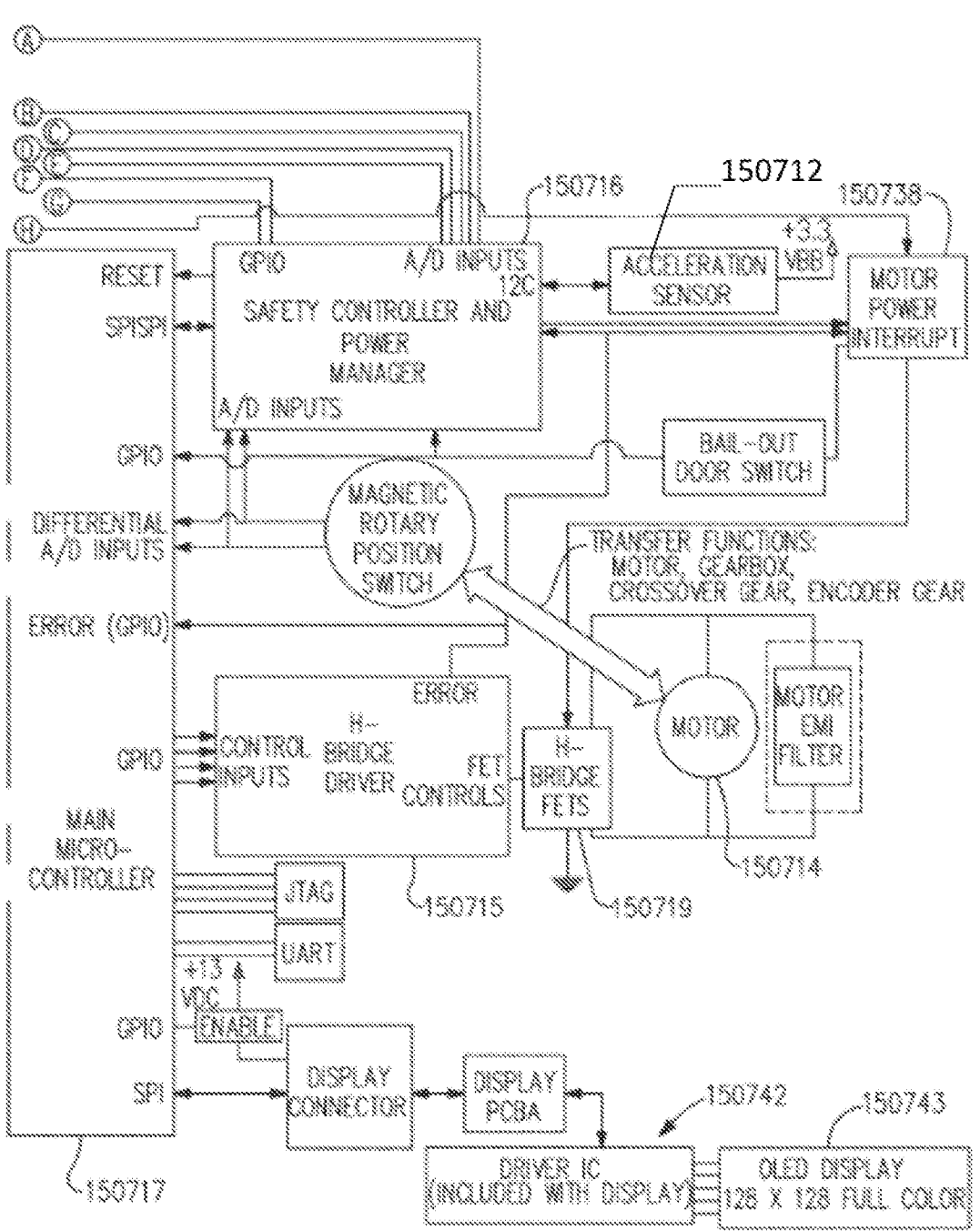
FIG. 17B illustrates a block diagram of a control circuit of the example surgical instrument of FIG. 13 spanning two drawing sheets.

FIGS. 17A and 17B is a block diagram of a control circuit 150700 of the surgical instrument 150010 of FIG. 13 spanning two drawing sheets, in accordance with at least one aspect of this disclosure. Referring primarily to FIGS. 17A and 17B, a handle assembly 150702 may include a motor 150714 which can be controlled by a motor driver 150715 and can be employed by the firing system of the surgical instrument 150010. In various forms, the motor 150714 may be a DC brushed driving motor having a maximum rotational speed of approximately 25,000 RPM. In other arrangements, the motor 150714 may include a brushless motor, a cordless motor, a synchronous motor, a stepper motor, or any other suitable electric motor. The motor driver 150715 may comprise an H-Bridge driver comprising field-effect transistors (FETs) 150719, for example. The motor 150714 can be powered by the power assembly 150706 releasably mounted to the handle assembly 150200 for supplying control power to the surgical instrument 150010. The power assembly 150706 may comprise a battery which may include a number of battery cells connected in series that can be used as the power source to power the surgical instrument 150010. In certain circumstances, the battery cells of the power assembly 150706 may be replaceable and/or rechargeable. In at least one example, the battery cells can be Lithium-Ion batteries which can be separably couplable to the power assembly 150706.

The shaft assembly 150704 may include a shaft assembly controller 150722 which can communicate with a safety controller and power management controller 150716 through an interface while the shaft assembly 150704 and the power assembly 150706 are coupled to the handle assembly 150702. For example, the interface may comprise a first interface portion 150725 which may include one or more electric connectors for coupling engagement with corresponding shaft assembly electric connectors and a second interface portion 150727 which may include one or more electric connectors for coupling engagement with corresponding power assembly electric connectors to permit electrical communication between the shaft assembly controller 150722 and the power management controller 150716 while the shaft assembly 150704 and the power assembly 150706 are coupled to the handle assembly 150702. One or more communication signals can be transmitted through the interface to communicate one or more of the power requirements of the attached interchangeable shaft assembly 150704 to the power management controller 150716. In response, the power management controller may modulate the power output of the battery of the power assembly 150706, as described below in greater detail, in accordance with the power requirements of the attached shaft assembly 150704. The connectors may comprise switches which can be activated after mechanical coupling engagement of the handle assembly 150702 to the shaft assembly 150704 and/or to the power assembly 150706 to allow electrical communication between the shaft assembly controller 150722 and the power management controller 150716.

The interface can facilitate transmission of the one or more communication signals between the power management controller 150716 and the shaft assembly controller 150722 by routing such communication signals through a main controller 150717 residing in the handle assembly 150702, for example. In other circumstances, the interface can facilitate a direct line of communication between the power management controller 150716 and the shaft assembly controller 150722 through the handle assembly 150702 while the shaft assembly 150704 and the power assembly 150706 are coupled to the handle assembly 150702.

The main controller 150717 may be any single core or multicore processor such as those known under the trade name ARM Cortex by Texas Instruments. In one aspect, the main controller 150717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 150706 may include a power management circuit which may comprise the power management controller 150716, a power modulator 150738, and a current sense circuit 150736. The power management circuit can be configured to modulate power output of the battery based on the power requirements of the shaft assembly 150704 while the shaft assembly 150704 and the power assembly 150706 are coupled to the handle assembly 150702. The power management controller 150716 can be programmed to control the power modulator 150738 of the power output of the power assembly 150706 and the current sense circuit 150736 can be employed to monitor power output of the power assembly 150706 to provide feedback to the power management controller 150716 about the power output of the battery so that the power management controller 150716 may adjust the power output of the power assembly 150706 to maintain a desired output. The power management controller 150716 and/or the shaft assembly controller 150722 each may comprise one or more processors and/or memory units which may store a number of software modules.

The surgical instrument 150010 (FIGS. 13 to 16) may comprise an output device 150742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 150742 may comprise a display 150743 which may be included in the handle assembly 150702. The shaft assembly controller 150722 and/or the power management controller 150716 can provide feedback to a user of the surgical instrument 150010 through the output device 150742. The interface can be configured to connect the shaft assembly controller 150722 and/or the power management controller 150716 to the output device 150742. The output device 150742 can instead be integrated with the power assembly 150706. In such circumstances, communication between the output device 150742 and the shaft assembly controller 150722 may be accomplished through the interface while the shaft assembly 150704 is coupled to the handle assembly 150702.

The control circuit 150700 comprises circuit segments configured to control operations of the powered surgical instrument 150010. A safety controller segment (Segment 1) comprises a safety controller and the main controller 150717 segment (Segment 2). The safety controller and/or the main controller 150717 are configured to interact with one or more additional circuit segments such as an acceleration segment, a display segment, a shaft segment, an encoder segment, a motor segment, and a power segment. Each of the circuit segments may be coupled to the safety controller and/or the main controller 150717. The main controller 150717 is also coupled to a flash memory. The main controller 150717 also comprises a serial communication interface. The main controller 150717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 150010. It should be understood that the term processor as used herein includes any microprocessor, processors, controller, controllers, or other basic computing device that incorporates the functions of a computer's central processing unit (CPU) on an integrated circuit or at most a few integrated circuits. The main controller 150717 is a multipurpose, programmable device that accepts digital data as input, processes it according to instructions stored in its memory, and provides results as output. It is an example of sequential digital logic, as it has internal memory. The control circuit 150700 can be configured to implement one or more of the processes described herein.

The acceleration segment (Segment 3) may comprise an acceleration sensor 150712. The acceleration sensor 150712 may comprise, for example, an accelerometer. The acceleration sensor 150712 may be configured to detect movement or acceleration of the powered surgical instrument 150010. Data generated by the acceleration sensor 150712 may be associated with the acceleration, motion, and/or orientation of the surgical instrument 150010 or a portion of the surgical instrument. The acceleration sensor 150712 may communicate data within the surgical instrument 150010 and/or to systems external to the surgical instrument such as, for example, a surgical hub. Data generated by the acceleration sensor 150712 may be used to modify operations of the surgical instrument. Input from the accelerometer may be used, for example, to identify the location of the surgical instrument 150010, to transition to and from a an operational (e.g., sleep) mode, to identify an orientation of the powered surgical instrument 150010, and/or to identify when the surgical instrument has been dropped. The acceleration sensor 150712 may be communicatively coupled with the safety controller and/or the main controller 150717 and may communicate data to the controllers for processing and communication to outside of the surgical instrument 150010.

The acceleration sensor 150712 may be programmed to measure various forms of acceleration including, for example, coordinate acceleration as well as those that may not necessarily be coordinate acceleration (rate of change of velocity). The acceleration sensor 150712 may be programmed to determine the acceleration associated with the phenomenon of weight experienced by a test mass at rest in the frame of reference of the acceleration sensor 150712. For example, the acceleration sensor 150712 at rest on the surface of the earth may measure an acceleration g=9.8 m/s2 (gravity) straight upwards, due to its weight. The acceleration sensor 150712 may measure g-force acceleration. The acceleration sensor 150712 may comprise a single, double, or triple axis accelerometer. The acceleration sensor 150712 may comprise one or more inertial sensors to detect and measure acceleration, tilt, shock, vibration, rotation, and multiple degrees-of-freedom (DoF). A suitable inertial sensor may comprise an accelerometer (single, double, or triple axis), a magnetometer to measure a magnetic field in space such as the earth's magnetic field, and/or a gyroscope to measure angular velocity.

The display segment (Segment 4) comprises a display connector coupled to the main controller 150717. The display connector couples the main controller 150717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, a liquid-crystal display (LCD), and/or or any other suitable display. In some examples, the display segment is coupled to the safety controller.

The shaft segment (Segment 5) comprises controls for an interchangeable shaft assembly 150200 (FIGS. 13 and 15) coupled to the surgical instrument 150010 (FIGS. 13 to 16) and/or one or more controls for an end effector 150300 coupled to the interchangeable shaft assembly 150200. The shaft segment comprises a shaft connector configured to couple the main controller 150717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 150200 and/or the shaft PCBA. The shaft PCBA may be coupled to the interchangeable shaft assembly 150200 and/or integral with the surgical instrument 150010. In some examples, the shaft segment comprises a second shaft EEPROM. The second shaft EEPROM comprises a plurality of algorithms, routines, parameters, and/or other data corresponding to one or more shaft assemblies 150200 and/or end effectors 150300 that may be interfaced with the powered surgical instrument 150010.

The position encoder segment (Segment 6) comprises one or more magnetic angle rotary position encoders. The one or more magnetic angle rotary position encoders are configured to identify the rotational position of the motor 150714, an interchangeable shaft assembly 150200 (FIGS. 13 and 15), and/or an end effector 150300 of the surgical instrument 150010 (FIGS. 13 to 16). In some examples, the magnetic angle rotary position encoders may be coupled to the safety controller and/or the main controller 150717.

The motor circuit segment (Segment 7) comprises a motor 150714 configured to control movements of the powered surgical instrument 150010 (FIGS. 13 to 16). The motor 150714 is coupled to the main microcontroller processor 150717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 150717 and/or the safety controller. In some examples, the motor 150714 is coupled to a motor electro-magnetic interference (EMI) filter.

The motor controller controls a first motor flag and a second motor flag to indicate the status and position of the motor 150714 to the main controller 150717. The main controller 150717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 150717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 150717. The switches may be configured to control operations of the surgical instrument 150010 (FIGS. 13 to 16), of the segmented circuit, and/or indicate a status of the surgical instrument 150010. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly 150200 (FIGS. 13 and 15) and/or the end effector 150300 (FIGS. 13 and 16). A left side reverse switch and a right side reverse switch are coupled to the main controller 150717. The left side switches comprising the left side articulation left switch, the left side articulation right switch, the left side articulation center switch, and the left side reverse switch are coupled to the main controller 150717 by a left flex connector. The right side switches comprising the right side articulation left switch, the right side articulation right switch, the right side articulation center switch, and the right side reverse switch are coupled to the main controller 150717 by a right flex connector. A firing switch, a clamp release switch, and a shaft engaged switch are coupled to the main controller 150717.

Any suitable mechanical, electromechanical, or solid state switches may be employed to implement the plurality of switches, in any combination. For example, the switches may be limit switches operated by the motion of components associated with the surgical instrument 150010 (FIGS. 13 to 16) or the presence of an object. Such switches may be employed to control various functions associated with the surgical instrument 150010. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). Other switches may include wireless switches, ultrasonic switches, accelerometers, inertial sensors, among others.

Systems, methods and instrumentalities are disclosed for adaptively adjusting operation and/or control of a surgical instrument and/or adaptively communicating information to a healthcare professional (e.g., surgeon, assistant). Adaptation of operation, control and/or communication may be based on, for example, situational awareness (e.g., of a surgical procedure). Situational awareness may include, for example, an importance level (e.g., a stress level and/or attention) of a health care provider, possession of a controllable surgical instrument by a health care provider, and/or body positioning of a health care provider. Situational awareness may be determined, for example, based on information provided by one or more personnel (e.g., wearable) sensing systems, environmental sensing systems, and/or surgical instruments. The information may comprise one or more of healthcare provider data (e.g., position, posture, balance, motion, attention, physiologic states), environmental data (e.g., operating room noise level, patient data, healthcare provider data), and/or surgical instrument data (e.g., position, possession, motion, and/or usage). A surgical computing system (e.g., a hub) and/or a surgical instrument may receive (e.g., sensed) information, determine situational awareness and adapt instrument operation, control and/or information communication based on situational awareness.

Situational awareness may be monitored, for example, to assess the criticality of an operation (e.g., a task) in a surgical procedure. A surgical operation may be modified, for example, based on criticality. A surgical computing system may receive biomarker data from one or more sensing systems and/or environmental data from one or more environmental sensing systems. The biomarker data may be associated with a healthcare professional operating a surgical instrument. Biomarker data may include, for example, one or more of heart rate, blood pressure, sweat, physical activity, body movement, or eye movement. Environmental data may include, for example, one or more of noise level, healthcare professional attention (e.g., based on eye tracking, such as location and/or time of view), and/or patient biomarkers. The surgical computing system may determine an importance level, for example, based (e.g., wholly or partly) on one or more of biomarker data, environmental data, and/or data associated with a surgical procedure. The surgical computing system may determine (e.g., based on the importance level) one or more operational parameters for the surgical instrument. A surgical computing system may, for example, (e.g., determine whether to) modify one or more operational parameters based on a determination whether data (e.g., biomarker data) is within an expected range for a step in a surgical procedure. A surgical computing system may, for example, determine a task associated with attention of the healthcare professional and operational parameters for a surgical instrument base on the determined task. The surgical computing system may communicate the one or more operational parameters to the surgical instrument.

Figure 18:
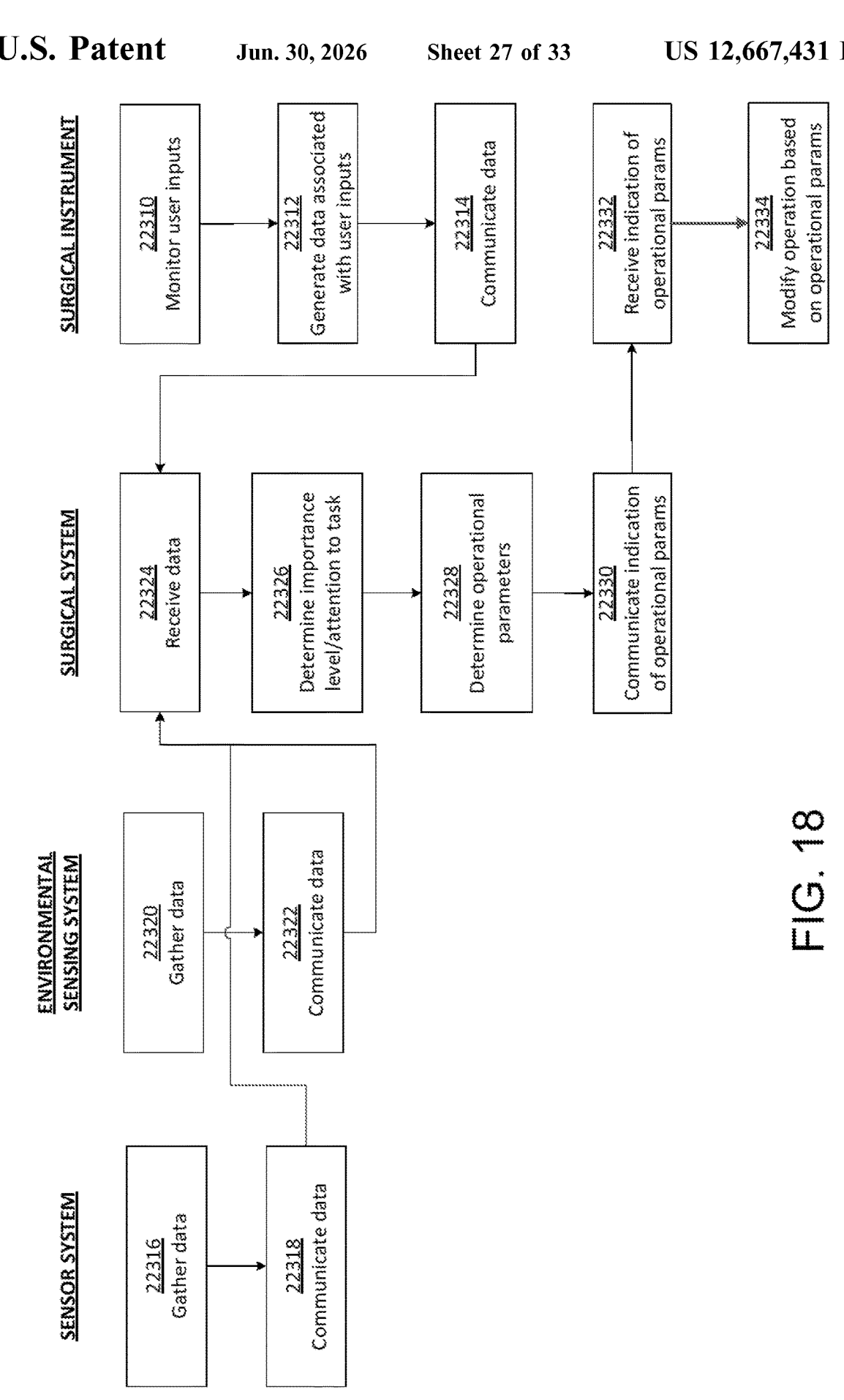
FIG. 18 illustrates example processing associated with determining operational parameters of a surgical instrument based on a determination of importance level and/or attention to a task.

FIG. 18 illustrates an example of processing associated with determining operational parameters of a surgical instrument based on a determination of criticality (e.g., importance level and/or attention to a task). Task criticality may be determined, for example, by monitoring surgeon biomarkers to develop (e.g., determine) situational awareness. Situational awareness monitoring may support (e.g., enable or provide) an understanding of a surgical task. One or more personnel and/or environmental sensors may monitor one or more biomarkers (e.g., user stress trigger biomarker levels, noise levels, physical action biomarkers, such as precision and/or minute hand motions) to determine task criticality. A determined task criticality level may be communicated to a surgical computing system and/or a surgical instrument, for example, to adjust operational parameters of a surgical instrument (e.g., to improve user control). Situational awareness may be used to adapt instrument control algorithms.

Intercommunication between a surgical instrument, a surgical computing device, at least one (e.g., wearable) sensor and/or at least one environmental sensor may provide a surgical computing system and/or a surgical instrument with situational awareness of a task and/or task objectives (e.g., speed versus precision versus outcome). A surgical computing device and/or a surgical instrument may adjust the control of one or more surgical instrument actuators based on situational awareness. One or more HCP sensing systems may monitor one or more biomarkers to generate sensor data, which may be communicated from the HCP sensing system(s) to the surgical computing system and/or surgical instrument, for example, to provide (e.g., additional and/or alternative) context about the importance or criticality of a surgical task. HCP sensor data may support dynamic adaptation of surgical instrument operation and/or controls for an HCP. HCP biomarkers may include, for example, stress, heart rate, and/or the like. Environmental data (e.g., from an OR) may include, for example, noise level, staff movements, attention level, and/or the like.

As shown in FIG. 18, at 22310, a surgical instrument, which may be a surgical instrument 20282 (e.g., as described in connection with FIG. 10), may monitor user inputs to the surgical instrument. The surgical instrument 20282 may monitor user input associated with movement and positioning of the surgical instrument 20282. The surgical instrument 20282 may employ, for example, an acceleration sensor 150712 (e.g., as shown in FIG. 17B) to monitor the movement and positioning of the surgical instrument 20282. The surgical instrument 20282 may monitor the orientation of the surgical instrument 20282 and a length of time the surgical instrument 20282 is maintained in a particular position. The surgical instrument 20282 may monitor user inputs associated with operation of controls of the surgical instrument 20282. For example, the surgical instrument 20282 may monitor inputs associated with controlling the operation of jaws for clamping patient tissue. The surgical instrument 20282 may monitor, for example, the degree that a control trigger is pressed, the speed at which the trigger is pressed, and a length of time a trigger is held in a particular control position.

At 22312, the surgical instrument 20282 may generate usage data associated with the user inputs monitored and detected by the surgical instrument 20282 at 22110. The surgical instrument 20282 may generate usage data associated with the movement and positioning of the surgical instrument 20282 and/or associated with the user inputs associated with controlling operations of the surgical instrument 20282.

At 22314, the surgical instrument 20282 may communicate the usage data to a surgical computing system which may be, for example, a surgical hub 20006.

At 22316, data associated with the one or more healthcare professionals who operate the surgical instrument 20282 may (e.g., also) be gathered. Healthcare professionals operating the surgical instruments 20282 and/or who are in the area where the surgical procedure is being performed may have one or more sensing systems applied thereto. Sensing systems 20069, such as those described herein in connection with FIG. 6B, may be applied to the healthcare professionals to collect sensor data. The sensing systems 20069 may sense and gather sensor data, which may include biometric data such as, for example, data associated with heart rate, blood pressure, respiration, temperature, sweat rate, sweat composition, frequency of blinking, etc. The sensing systems 20069 may sense and gather sensor data associated with physical activity (e.g., position, movement) and/or lack thereof (e.g., static waits) of the healthcare professional alone and/or in the aggregate with other personnel, such as, for example, positions and/or movements of the healthcare professional's arms, hands, legs, and/or torso.

At 22318, the surgical instrument 20282 may communicate the sensor data to the surgical computing system 20006.

At 22320, environmental data associated with one or more conditions or attributes in a surgical environment may be gathered (e.g., to determine the importance of phases or steps in a surgical procedure). Conditions or attributes in a surgical environment may include, for example, one or more of a (e.g., an ambient) noise level, HCP positions, HCP movements, HCP attention location (e.g., based on eye tracking, such as location and/or time of view), and/or patient biomarker data (e.g., patient biomarker notifications and/or alarms). One or more environmental sensing systems 20015 may be deployed in a surgical environment as part of a surgical monitoring system 20000 to collect environmental data. Environmental sensing systems 20015, such as those described herein in connection with FIG. 6B, may be activated to collect sensor data. The environmental sensing system(s) 20015 may be systems for measuring one more of the environmental attributes and may include, for example, cameras (e.g., for detecting a surgeon's position, movements, and/or breathing pattern), spatial microphones (e.g., to measure ambient noise in the surgical theater and/or the tone of voice of a healthcare provider), climate sensor(s) (e.g., to measure temperature and/or humidity of the surroundings), etc. The environmental sensing systems 20015 may sense and gather environmental data, which may include data associated with, for example, the surgical environment, people in the surgical environment (e.g., healthcare professionals and patient), instruments in the surgical environment, etc. The environmental sensing systems 20015 may (e.g., also) sense and gather sensor data associated with, for example, positions and/or movements of the healthcare professional (e.g., position and/or movement of the healthcare professional's arms, hands, legs, and/or torso) and/or positions and/or movements of surgical instruments.

At 22322, the environmental sensing system 20015 may communicate the environmental sensor data to the surgical computing system 20006.

At 22324, the surgical computing system 20006 may receive the sensor data from the (e.g., personnel or wearable) sensing systems 20069, usage data from the surgical instrument(s) 20282, and/or environmental data from the environmental sensing system(s) 20015.

At 22326, the surgical computing system 20006 may process the received usage data, sensor data, and/or environmental sensor data (e.g., data set(s)) and may determine an importance level and/or attention to task based on the received data. The surgical computing system 20006 may be configured to determine an importance level and/or attention to task based on the indications from the sensor data, environmental data, and/or usage data regarding the surgical procedure and the healthcare professionals performing the surgical procedure. For example, the surgical computing system 20006 (e.g., situationally aware surgical hub 20076 shown in FIG. 5) may process the sensor data from the (e.g., personnel or wearable) sensing systems 20069, usage data from the surgical instrument(s) 20282, and/or environmental data from the environmental sensing system(s) 20015 to determine an importance level and/or attention to task. For example, the surgical computing system 20006 may translate or map one or more selected data items in the received data set(s) to an importance level and/or an attention to a task. In an example, a criticality level (e.g., low, medium, high) may be inferred from a stress level (e.g., low, medium, high) of an HCP using the surgical instrument(s) 20282, and/or surgical instrument usage data indicating a phase or portion of a surgical procedure. A determination (e.g., mapping) may be based on, for example, the surgical instrument determined to be in use (e.g., and by whom based on sensor and/or environmental data) during a determined stage of a surgical operation.

At 22328, the surgical computing system 20006 may determine one or more operational parameters for one or more surgical instruments based on the importance level and/or attention to task determined at 22326. The surgical computing system 20006 may be configured to determine (e.g., translate or map) the importance level and/or attention to task determined at 22326 to one or more operational parameters for a surgical instrument in use during the determined task. For example, operational parameters for an advanced energy jaw trigger ratio or an endocutter clamp and fire speed may be selected or adjusted based on the detected importance level and/or attention to task. In some examples, operational parameters may be adjusted in proportion to detected stress levels of a surgeon using the device.

At 22330, the surgical computing system 20006 may communicate an indication of the determined operational parameters to the surgical instrument 20282. The surgical computing system 20006 may be configured to communicate an indication to a surgical instrument 20282 determined to be in use during the determined task of the surgical procedure.

At 22332, the surgical instrument 20282 may receive the indication of the determined operational parameters. For example, an endocutter may receive operational parameters for clamp and fire speed or an advanced energy device may receive operational parameters for a jaw trigger ratio.

At 22334, the surgical instrument 20282 may modify operation based upon the received indication of the determined operational parameter(s). For example, an endocutter surgical instrument 20282 may reduce clamp and fire speed if the received operational parameter(s) indicate to reduce clamp and fire speed or the received clamp and fire speed is slower than an existing clamp and fire speed.

The surgical computing system 20006 may receive instrument usage data, sensor data, and/or environmental data associated with numerous different surgical procedures and situations. The importance level, attention to task, and/or operational parameters determined by the surgical computing system 20006 may vary based on the received usage data, sensor data, and/or environmental data.

For example, with reference to the timeline 20265 for a surgical (e.g., colorectal) procedure shown in FIG. 8, the surgical computing system 20006 (e.g., situationally aware surgical hub 20076 shown in FIG. 5) may receive data from various data sources throughout the course of the surgical procedure. The surgical hub 20076 may receive instrument usage data, which may be generated each time an HCP utilizes a modular device/instrument 20095 that is paired with the surgical hub 20076 (e.g., advanced energy device and/or endocutter used in the surgical procedure). The surgical hub 20076 may receive sensor data (e.g., measurement data) from one or more surgeon sensing systems 20069 for measuring one or more biomarkers associated with the surgeon, such as one or more of heart rate, sweat composition, respiratory rate, etc. The sensor data may be processed to determine, e.g., as shown in FIG. 8, low, mid and high stress levels of a surgeon during one or more phases or steps of a surgical (e.g., colorectal) procedure. An importance level may be inferred, at least in part, from a determined stress level.

The surgical hub 20076 may derive inferences (i.e., contextual information) about an HCP's stress level and/or the importance level of an ongoing procedure, e.g., at least in part, from the usage data from the modular device/ instruments 20095 and sensed measurement data from the sensing systems 20069. The stress level of an HCP (e.g., surgeon) may be indicated or determined relative to the step of the procedure that is being performed. The surgical hub 20076 may perform one or more of the following (e.g., using a situational awareness system): provide data or prompts (e.g., via a display screen) that may be pertinent to a procedural step, adjust modular devices based on the context (e.g., activate monitors, adjust the FOV of the medical imaging device, change the energy level of an ultrasonic surgical instrument or RF electrosurgical instrument, change clamp and fire speed, change a jaw trigger ratio), etc.

FIG. 8 shows an example of an ongoing procedure from left to right, moving from dissection to ligating the inferior mesenteric artery (IMA) branches, etc. The surgical hub 20076 may infer procedural steps (e.g., start, end), at least based on usage data received from surgical instruments. The surgical hub 20076 may infer that the surgeon is ligating arteries and veins, for example, based on receiving data from the advanced energy jaw device and/or the endocutter indicating that the instrument is being fired. The surgical hub may (e.g., also) receive measurement data from one of the HCP's sensing systems, such as an indication of a higher stress level of the HCP (e.g., indicated by B1 mark on the time axis). A higher stress level may be indicated, for example, by a change in the HCP's heart rate (e.g., from a base value). The surgical hub 20076 may derive the inference of the ligate IMA step by cross-referencing the receipt of data from the surgical stapling and cutting instrument (e.g., as indicated by A2 and A3) with the retrieved steps in the known surgical process.

The surgical hub 20076 may determine one or more operational parameters for one or more surgical instruments 20282 based on the determined importance level (e.g., stress level). For example, the surgical hub 20076 may monitor (e.g., and control) the advance energy jaw trigger ratio and/or the endocutter clamp and fire speed based on stress levels, e.g., during high, medium and/or low stress time periods. In an example, the surgical hub 20076 may send an assistance control signal to the advanced energy jaw device and/or the endocutter device to control the device in operation (e.g., during high stress of the HCP). The surgical hub may send the assistance signal based on the stress level of the HCP that is operating the surgical device and/or situational awareness known to the surgical hub. For example, the surgical hub 20076 may send control assistance signals to an advanced energy device or an endocutter clamp, as indicated in FIG. 8 by Aa2 and A3. In an example (e.g., as shown in FIG. 8 at A2 and A3), the advanced energy jaw trigger ratio and the endocutter clamp and fire speed are reduced, respectively, based on detection of high stress from the surgery sensing system measurement data.

The HCP may proceed to the next step of freeing the upper sigmoid followed by freeing descending colon, rectum and sigmoid. The surgical hub 20076 may continue to receive inputs from the advanced energy jaw device and/or the endocutter device and may continue to monitor sensing system measurement data for high stress markers of the HCP (e.g., as indicated by D1, E1a, E1b, F1). The surgical hub 20076 may send assistance (e.g., adaptive control) signals to the advanced energy jaw device and/or the endocutter device, for example, during the high stress time periods, as illustrated in FIG. 8.

An HCP may mobilize the colon and resect the sigmoid, beginning with resecting the transverse bowel portion of the procedure. For example, the surgical hub 20076 may infer that the HCP is performing the transverse bowel resection and sigmoid removal based on data from the surgical stapling and cutting instrument, e.g., including data from the surgical stapling and cutting instrument cartridge. The cartridge data may correspond to the size or type of staple being fired by the instrument, for example. The cartridge data may indicate the type of tissue being stapled and/or transected, for example, as different types of staples are utilized for different types of tissues. An HCP (e.g., surgeon) may switch back and forth between surgical stapling/cutting instruments and surgical energy (e.g., RF or ultrasonic) instruments depending upon the particular step in the procedure because different instruments are better adapted for particular tasks. A sequence of use of the stapling/cutting instruments and surgical energy instruments may indicate what step of the procedure the surgeon is performing.

In some examples (e.g., as shown in FIG. 8), the surgical hub 20076 may determine and send (e.g., wirelessly communicate) a control signal to a surgical device 20282 based on the determined stress level of the HCP using the surgical instrument 20282. The stress level may be deemed or mapped to an importance level for a portion of a surgical procedure. For example, during time period G1*b*, a control signal G2*b* may be sent to an endocutter clamp to reduce endocutter clamp and fire speed in proportion to the determined high stress level (e.g., high importance level). During time period G1*c*, a control signal H2 may be sent to the endocutter clamp to increase endocutter clamp and fire speed in proportion to the determined low stress level (e.g., low importance level). The operation of the advanced energy jaw device and/or the endocutter device may be modified, for example, by implementing (e.g., executing) the control signal received from the surgical hub 20076. In various implementations, an importance level may be determined based, at least in part, on one or more biomarkers, such as one or more of heart rate, blood pressure, sweat, physical activity, body movement, or eye movement (e.g., with or without determining a stress level). In some examples, an importance level may be determined based at least in part on environmental data (e.g., with or without biomarker data). Determining criticality (e.g., stress level), receiving sensed biomarker data, environmental data, and usage data, analyzing received data, and determining instrument operational parameters, etc. (e.g., operations disclosed herein) may be performed by one or more surgical computing systems and/or surgical instruments.

Sensor data and/or environmental data may be derived from attention monitoring of one or more HCPs (e.g., using one or more surgical instruments). Attention monitoring may include, for example, one or more sensors providing data that tracks eye movements or a view (e.g., eye tracking) of an HCP to determine where an HCP attention is focused, and for how long, which may be referred to as time on target. Attention tracking may be used to determine criticality of a task and/or one or more specific portions thereof such as, for example, portions of a task or area of operation. The surgical hub 20076 may communicate more refined (e.g., more precise) information and/or parameters (e.g., feedback) to surgical instruments 20272 involved in a procedure and/or displays to improve the HCP's control of the surgical instruments 20272 (e.g., precision control of jaw actuation mechanisms), for example, by combining task criticality detection with HCP (e.g., surgeon) attention tracking and/or the time span of focus. HCP attention monitoring may be used, for example, to determine which displays and/or portions thereof an HCP may be focusing on. The hub 20076 may determine criticality (e.g., importance level) and/or change or update information displayed to an HCP on one or more monitors based (e.g., at least in part) on attention tracking. For example, sensed and/or environmental data may indicate that a surgeon's physical gestural behavior appears to show the surgeon having difficulty seeing the task/job. The hub 20076 may (e.g., in response), for example, improve the zoom and/or focus on the area of interest in a displayed image for as the surgeon and/or inquire (e.g., ask) the surgeon whether he/she would like the section magnified or overlaid with a multi-spectral feed to improve visualization.

Instrument motions and operator motions may be assessed, for example, to determine the operator of a surgical instrument. A surgical computing system 20006 may receive biomarker data (e.g., movement data) from a plurality of sensing systems. A sensing system may be associated with one of a plurality of healthcare professionals. The surgical computing system may receive usage data such as, for example, movement data, from a surgical instrument. The surgical computing system may determine which one of the plurality of healthcare providers has possession of the surgical instrument, for example, based at least on the biomarker data and usage data. For example, a surgical computing system may determine whether a healthcare provider's biomarker data (e.g., movement data) corresponds to usage data such as, for example, movement data, from the surgical instrument. The surgical computing system may determine information for communication to a healthcare provider, for example, based on possession of the surgical instrument. Information communicated to an assistant in possession of an instrument may include, for example, information associated with preparing the surgical instrument for operation. Information communicated to a physician in possession of an instrument may include, for example, information associated with previous use of the surgical instrument. Inconsistencies between data may be detected. The surgical computing system may determine the surgical instrument is not located in an area identified for performing a surgical procedure, for example, based at least on an inconsistency between the biomarker data and usage data. The surgical computing system may determine whether there is a correlation error based on an inconsistency.

Differentiation of the criticality of a task (e.g., the step at hand) in a surgical procedure (e.g., in the OR) may be implemented (e.g., used) with procedure step tracking. Procedure step tracking may be performed by the surgical computing system 20006, for example, to support (e.g., control) device operation, such as moving between "Fast and Efficient" and "Accurate and Precise" modes of operation. Fast and efficient operation may be reflected or distinguished, for example, by larger gross motions, faster clamp and release operations, accelerated articulation angle changes, higher advanced energy power levels, and/or faster firing of staplers. Accurate and precise operation may be reflected or distinguished, for example, by lower (e.g., reduced) advanced energy levels, which may result in slower operation and/or longer weld times, slower and/or finer articulation angle changes with larger delays in starting motion to minimize overshoot and/or inadvertent operation, slower stapler firing speeds, more gentle and/or slower clamp rates to improve tissue creep and/or minimize collateral tissue tension damage, etc.

Logging procedure step tracking with sensed data from the personnel (e.g., wearable) sensors and/or environmental sensors an HCP may support (e.g., allow) determination of trends and correlations. Deviations from the trends or correlations or irregularities from the trends may be highlighted to the healthcare professional, communicated to the surgical instrument, etc. In an example procedure such as, for example, a lobectomy procedure, there may be four primary jobs to perform including dissection and transection of the vessels, bronchus, parenchyma and lymph nodes. Transection of the vessels may be acritical step in the procedure. A heart rate monitor wom by the surgeon may indicate a heart rate increase as compared to a baseline heartrate around the transection of vessels portion of the procedure. The surgical computing system 20006 may determine to not react to an increased heartrate given a historical context, for example, unless the heart rate is higher than the historical average for the user. The surgical computing system 20006 may provide a communication to the healthcare provider and/or modify operation of a surgical instrument if it determines that a surgeon's heart rate for a parenchyma firing may be below the surgeon's heart rate for a vessel firing, but higher than historical heart rate data.

Speech patterns and/or a speech tone of a surgeon and/or operating room staff may be monitored by one or more sensing systems. Anxiety, stress and/or pressure may cause changes to breathing patterns, which may contribute to voice and/or speech difficulty for an HCP. An HCP's mood may change, for example, based on certain situations or agitates, which may affect an HCP's tone of speech. Anxiety, stress and/or pressure, mood changes, etc. may lead to physical behavior, such as shakiness, rapid breathing, dizziness, and/or frustration. A sensor, such as a microphone, may be used to monitor speech patterns and/or tones. The sensed data may be used by the surgical computing system 20006 to determine to adjust one or more environment variables to reduce stress and assist an HCP with maintaining focus.

The surgical computing system 20006 may determine to adjust one or more environmental characteristics or variables based on the received data. One or more operating room sounds may be changed (e.g., based on criticality), for example, to improve HCP perception and remove distractions. A monitoring system alarm and/or notification levels may be modified (e.g., reduced), for example, if an HCP is performing a critical (e.g., tense) task. Operating room lighting may be modified (e.g., based on criticality), for example, to improve contrast and/or focus while limiting distracting and/or overwhelming light intensity. One or more screens, displays, and/or content may be changed (e.g., based on criticality), for example, to alleviate pressure/stress of content displayed. For example, the surgical computing system may determine to enlarge important aspects and/or change contrast between acute elements relevant to a task or the situation at hand and/or allow secondary data to remain in a more semi-transparent state.

The surgical computing system 20006 may determine to notify an HCP regarding one or more biomarkers. The surgical computing system 20006 may determine one or more biomarkers are out of an expected range, which may indicate stress. The surgical computing system 20006 may communicate breathing instructions to the HCP to mitigate the effect. The surgical computing system 20006 may select music which may provide an audible rhythm to alter a respiratory pattern and/or other biomarker indicating HCP stress.

FIG. 19 illustrates an example of processing associated with determining possession of a surgical instrument and communication of information based on a correlation of instrument and HCP motion. As shown in FIG. 19, at 22340, a surgical instrument, which may be a surgical instrument 20282 (e.g., as described in connection with FIG. 10), may monitor user inputs to the surgical instrument. The surgical instrument 20282 may monitor user input associated with movement and positioning of the surgical instrument 20282. The surgical instrument 20282 may employ, for example, an acceleration sensor 150712 (e.g., as shown in FIG. 17B) to monitor the movement and positioning of the surgical instrument 20282. The surgical instrument 20282 may monitor the orientation of the surgical instrument 20282 and a length of time the surgical instrument 20282 is maintained in a particular position. The surgical instrument 20282 may monitor user inputs associated with operation of controls of the surgical instrument 20282. For example, the surgical instrument 20282 may monitor inputs associated with controlling the operation of jaws for clamping patient tissue. The surgical instrument 20282 may monitor, for example, the degree that a control trigger is pressed, the speed at which the trigger is pressed, and a length of time a trigger is held in a particular control position.

At 22342, the surgical instrument 20282 may generate usage data associated with the user inputs monitored and detected by the surgical instrument 20282 at 22340. The surgical instrument 20282 may generate usage data associated with the movement and positioning of the surgical instrument 20282, and/or associated with the user inputs associated with controlling operations of the surgical instrument 20282.

At 22344, the surgical instrument 20282 may communicate the usage data to a surgical computing system which may be, for example, a surgical hub 20006.

At 22346, data associated with the one or more healthcare professionals who operate the surgical instrument(s) 20282 may (e.g., also) be gathered. Healthcare professionals operating the surgical instruments 20282 and/or who are in the area where the surgical procedure is being performed may have one or more sensing systems applied thereto. Sensing systems 20069, such as those described herein in connection with FIG. 6B, may be applied to the healthcare professionals to collect sensor (e.g., HCP biomarker) data. The sensing systems 20069 may sense and gather sensor data, which may include biometric data such as, for example, data associated with heart rate, blood pressure, respiration, temperature, sweat rate, sweat composition, frequency of blinking, etc. The sensing systems 20069 may sense and gather sensor data associated with physical activity (e.g., position, movement) and/or lack thereof (e.g., static waits) of the healthcare professional alone and/or in the aggregate with other personnel, such as, for example, position and/or movement of the healthcare professional's arms, hands, legs, and/or torso.

At 22348, the surgical instrument 20282 may communicate the sensor data to the surgical computing system 20006.

At 22350, environmental data associated with one or more conditions or attributes in a surgical environment may (e.g., also) be gathered. Conditions or attributes in a surgical environment may include, for example, one or more of a (e.g., an ambient) noise level, HCP positions, HCP movements, HCP attention location (e.g., based on eye tracking, such as location and/or time of view), surgical instrument movements, and/or patient biomarker data (e.g., patient biomarker notifications and/or alarms). One or more environmental sensing systems 20015 may be deployed in a surgical environment as part of a surgical monitoring system 20000 to collect environmental data. Environmental sensing systems 20015, such as those described herein in connection with FIG. 6B, may be activated to collect sensed environmental data. The environmental sensing system(s) 20015 may measure one more of the environmental attributes and may include, for example, cameras (e.g., for detecting an HCP's position, movements, and/or breathing pattern), spatial microphones (e.g., to measure ambient noise in the surgical theater and/or the tone of voice of a healthcare provider), climate sensor(s) (e.g., to measure temperature and/or humidity of the surroundings), etc. The environmental sensing systems 20015 may sense and gather environmental data, which may include data associated with, for example, the surgical environment, people in the surgical environment (e.g., healthcare professionals and patient), instruments in the surgical environment, etc. The environmental sensing systems 20015 may sense and gather sensor data associated with, for example, positions and/or movements of the healthcare professional including, for example, position and/or movement of the healthcare professional's arms, hands, legs, and/or torso, and/or positions and/or movements of surgical instruments.

At 22352, the environmental sensing system 20015 may communicate the environmental sensor data to the surgical computing system 20006.

At 22354, the surgical computing system 20006 may receive the sensor data from the (e.g., personnel or wearable) sensing systems 20069, usage data from the surgical instrument(s) 20282, and/or environmental data from the environmental sensing system(s) 20015.

At 22356, the surgical computing system 20006 may process the received usage data, sensor data, and/or environmental sensor data (e.g., data set(s)) and may determine whether there are one or more correlations based on the received data. The surgical computing system 20006 may be configured to determine whether the data sets indicate correlation of movements between one or more HCPs and one or more surgical instruments based on the sensor data, environmental data, and/or usage data regarding the surgical procedure and the healthcare professionals performing the surgical procedure. For example, the surgical computing system 20006, which may be, for example, situationally aware surgical hub 20076 shown in FIG. 5, may process the sensor data from the personnel or wearable sensing systems 20069, usage data from the surgical instrument(s) 20282, and/or environmental data from the environmental sensing system(s) 20015 to determine one or more correlations in movement data. For example, the surgical computing system 20006 may correlate movement of a surgeon with movement of an advanced energy device and/or an endocutter during performance of a task in a surgical procedure, as shown by example in FIG. 20. A correlation of movements may be based on, for example, environmental data from one or more operating room cameras tracking surgeon movements and instrument usage data, e.g., including accelerometer data generated by one or more accelerometer sensor(s) in the surgical instrument 20282 determined to be in use during a determined stage of a surgical operation. A surgical instrument 20282 may detect motions and orientations (e.g., by using built-in accelerometers). One or more correlations may be determined, for example, by comparing position, orientation and/or motion data for one or more surgical instruments 20282 with position and/or motion data from sensed data and/or environmental data pertaining to for one or more healthcare professionals who may be, for example, one or more surgeons, back-table nurses, assistants, and/or rotation nurses. One or more correlations may determine which healthcare professional is holding and/or using which instrument.

At 22358, the surgical computing system 20006 may determine one or more healthcare professionals in possession of and/or using one or more surgical instruments, for example, based on the one or more correlations determined at 22356. The surgical computing system 20006 may be configured to determine location, possession and/or use of surgical instruments based on correlation(s) and/or lack of correlation(s). For example, detected instrument motions and operating room detected personnel physical activities may be used to determine a location of a surgical instrument 20282 (e.g., in the operating room, not in the operating room, in the possession of a healthcare professional or not in the possession of a healthcare professional.

A surgical computing system 20006 may use detection of instrument motions and operating room personnel physical activities to determine whether there is a correlation or synchronization error in the system monitoring the sensors. For example, a surgical computing system 20006 may determine an alignment issue if instrument data indicates an instrument is moving or changing orientation in the operating room while sensor data and/or environmental data do not indicate any personnel are moving in a correlated manner. The surgical computing system 2006 may perform an analysis to determine whether there is a problem and, if so, a potential solution, for example, if the detected problem occurs over a pre-determined amount of time and/or number of motions. A surgical computing system 20006 may determine that an instrument is in a nearby operating room or storage room and is not being used in the current operating room. Solutions to a misalignment problem may include, for example, re-calibration, re-correlating, etc.

The surgical computing system 20006 may flag a synchronization issue with the data and/or may attempt to re-fuse and adjust "ad hoc" time stamping of operating room datasets, for example, if the surgical computing system 20006 determines that a healthcare professional's physical monitor appears to have similarly correlated motions that are out of sequence to the instrument motion(s).

The surgical computing system 20006 may re-calibrate and/or re-align the orientation of some or all in-room sensors to the main room coordinate system, for example, if the inverse of the motions detected by the instruments are correlated to a healthcare professional's physical biomarkers.

The surgical computing system 20006 may (e.g., visually) detect whether there are one or more healthcare professionals that are not wearing one or more sensors. The surgical computing system 20006 may attempt to re-index the room personnel, for example, if multiple (e.g., repeated) motions (e.g., over time) of a surgical instrument do not correlate to any operating room staff motions. The surgical computing system 20006 may assume that a surgical device is in another room and inadvertently paired to the incorrect surgical computing system, for example, if there are no additional detected personal. The surgical computing system 20006 may communicate with one or more adjacent operating room surgical computing systems, for example, to attempt to return monitoring of the inadvertently paired instrument to the room in which the surgical instrument is located.

At 22360, the surgical computing system 20006 may determine information for communication to one or more healthcare professionals. For example, the surgical computing system 20006 may determine information pertinent to communicate to an assistant. If the surgical device 20282 motion data correlates with motion by the assistant, such as may occur when an assistant may be preparing or reloading an instrument for a surgeon, the surgical computing system 20006 may determine based on correlated motion data that a back-table nurse has possession of a surgical instrument 20282. The usage data may indicate that the surgical device was recently fired and has not been reloaded. The surgical computing system 20006 may determine or select information to be displayed. The surgical computing system 20006 may determine the information should be displayed with emphasis, such as capitalization, highlighting, flashing or blinking. The information may indicate that the surgical device 20282 has a "used" cartridge in the jaws to minimize reintroduction of the surgical device 20282 without reloading. The surgical computing system 20006 may determine or select information to be displayed as steps-for-use. For example, the surgical computing system 20006 may determine information to be displayed associated with cleaning and/or reloading the surgical instrument 20282. Operational parameters may be adjusted in proportion to detected stress levels of a surgeon using the device. A surgical computing device 20006 may determine based on correlated motion data that a surgeon has possession of a surgical instrument 20282. The usage data may also indicate that the surgical instrument was recently fired and has not been reloaded. The surgical computing device 20006 may determine or select information to be displayed to the surgeon to indicate previous firing data and/or any notifications or alerts that occurred due to recent use of the surgical instrument 20282.

At 22362, the surgical computing system 20006 may communicate an indication of the determined information for display to the surgical instrument 20282 and/or an associated display unit such as, for example, display 20023 or other suitable display in the operating room.

At 22364, the surgical instrument 20282 and/or display unit 20023 may receive the indication of the determined information (e.g., display information). For example, a surgical stapler may receive information for a surgeon in possession of the stapler indicating previous firing data and/or any notifications or alerts that occurred due to recent use of the surgical instrument 20282.

At 22366, the surgical instrument 20282 and/or display unit 20023 may display the received information. For example, a surgical stapler and/or a related display may display information for a surgeon in possession of the stapler indicating previous firing data and/or any notifications or alerts that occurred due to recent use of the surgical instrument 20282.

The surgical computing system 20006 may receive instrument usage data, sensor data, and/or environmental data associated with numerous different surgical procedures and situations. The location, orientation, and/or motion of one or more surgical instruments, the location and/or motion of one or more healthcare professionals, and/or the possession of one or more surgical instruments determined by the surgical computing system 20006 may vary based on the received usage data, sensor data, and/or environmental data.

Figure 20:
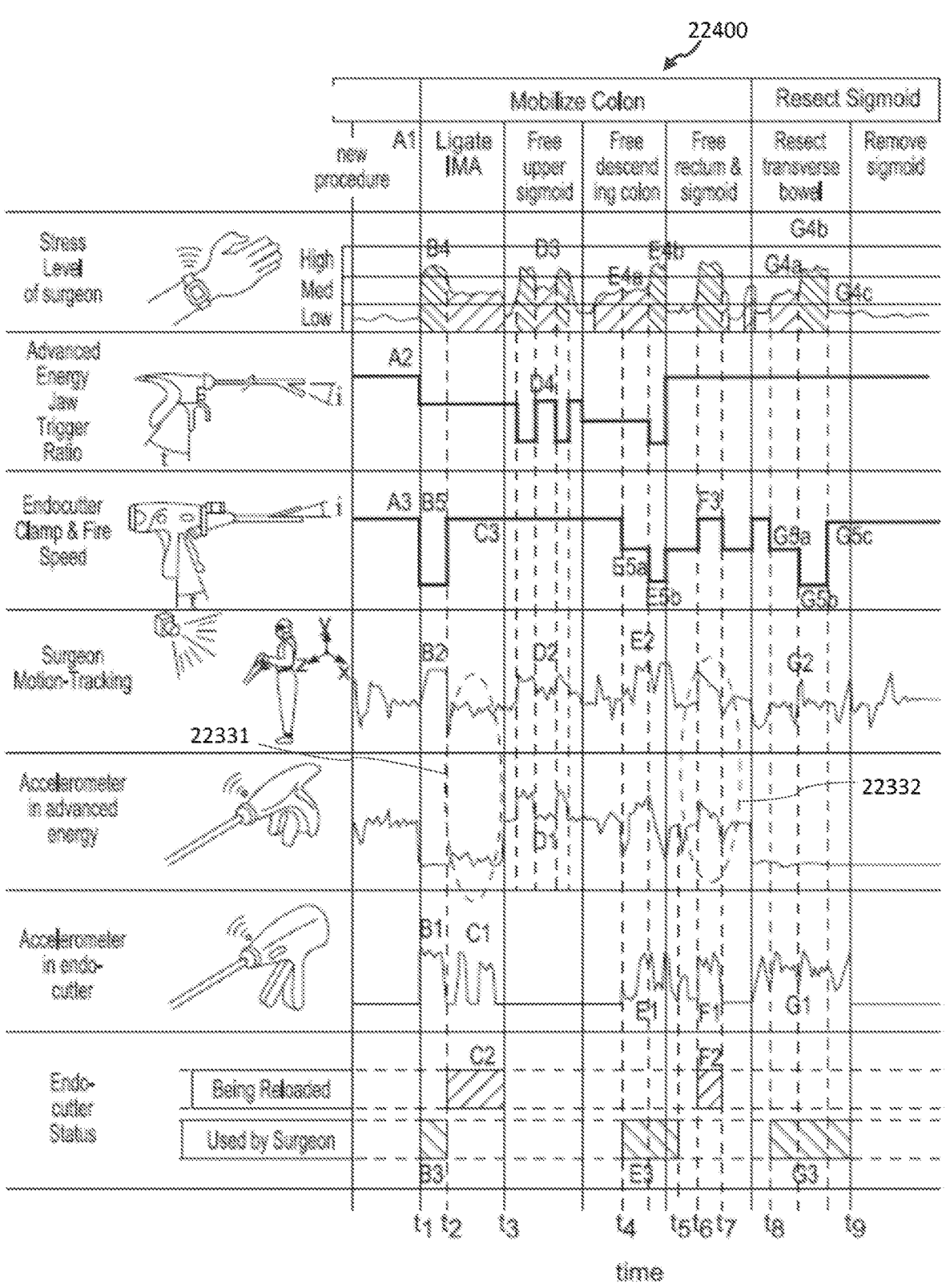
FIG. 20 illustrates an example timeline for a surgical procedure indicating possession of surgical instruments by one of multiple health care professionals based on correlation of motion data for instruments and health care professionals.

FIG. 20 depicts an example surgical procedure timeline and corresponding values associated with surgical instrument data, personnel sensor data, and/or environmental data during the surgical procedure. A surgical computing system may determine the particular healthcare professional who has possession of and is operating a surgical instrument at moments in time during the surgical procedure based upon the surgical instrument data, personnel sensor data, and/or environmental data.

A surgical computing system 20006, which may be a situationally aware surgical hub 20076 as described in connection with FIG. 5, may receive data from various data sources during the course of a surgical procedure. The surgical hub 20076 may receive instrument usage data, which may be generated by a surgical instrument such as, for example, a modular device/surgical instrument 20095, in response to a healthcare professional handling, operating, and/or utilizing the instrument. The surgical instrument may be, for example, an advanced energy device and/or endocutter. The surgical hub 20076 may receive motion data, which may be generated by accelerometer sensors within the surgical instruments. The surgical hub 20076 may receive sensor data, which may include measurement data, from one or more surgeon sensing systems 20069 for measuring one or more biomarkers associated with the surgeon, such as one or more of heart rate, sweat composition, respiratory rate, etc. The sensor data may be processed to determine, e.g., as shown in FIG. 20, low, mid and high stress (e.g., importance) levels of a surgeon during one or more phases or steps of a surgical procedure. The surgical hub 20076 may receive environmental data from one or more environmental sensing systems 20015, which may include motion data for one or more healthcare professionals and/or one or more surgical instruments 20272 from one or more motion sensing cameras 20021, which may indicate movement in multiple (e.g., three) dimensions.

The surgical hub 20076 may derive inferences, which may include contextual information, about movements in an ongoing procedure based at least in part on the usage data from the modular device/instruments 20095, motion data from the modular device/instruments 20095, sensed measurement data from the sensing systems 20069, and/or environmental data (e.g., including motion data). Motion may be indicated or determined relative to the step of the procedure that is being performed. The surgical hub 20076 may perform one or more of the following using, for example, a situational awareness system: provide data or prompts (e.g., via a display screen) that may be pertinent to a procedural step and/or the healthcare professional in possession of an instrument; adjust modular devices based on the context (e.g., activate monitors, adjust the FOV, focus and/or zoom of the medical imaging device, change the energy level of an ultrasonic surgical instrument or RF electrosurgical instrument, change clamp and fire speed, change a jaw trigger ratio); etc.

In FIG. 20, the timeline 22400 may correspond to an example colorectal surgical procedure performed using, for example, at least an advanced energy jaw device and an endocutter. Portions of the timeline that correspond to particular steps in the surgical procedure are designated using columns. As shown, columns are denoted for the following surgical procedure steps: Ligate IMA; Free upper sigmoid; Free descending colon; Free rectum & sigmoid; Resect transverse bowel; and Remove sigmoid. FIG. 20 depicts a plurality of vertically arranged rows, with each row depicting a value across time for various data items associated with the surgical procedure. Rows are designated to illustrate values for the following: stress level of the surgeon; advanced energy jaw trigger ratio; endocutter claim and fire speed; surgeon motion-tracking; accelerometer in advanced energy; accelerometer in the endocutter; and endocutter status. It will be appreciated that the top three rows, which are labelled stress level of surgeon, advanced energy jaw trigger ratio, and endocutter clamp and fire speed, generally correspond to the three rows depicted in and described in connection with FIG. 8.

Referring to FIG. 20, as shown, during the period of time before time t1, the surgical hub 20076 may derive a stress level from biomarker data received from sensing systems applied to the healthcare professional who is performing the surgical procedure. As shown, at the initial stages of the procedure prior to time t1, the surgeon's stress level is relatively low. The surgical hub 20076 may use received usage data from the advanced energy jaw device to determine an initial value for a trigger ratio as indicated in the second row. The surgical hub 20076 may rely upon received usage data from the endocutter device to determine an initial value for a clamp and fire speed for the endocutter as indicated in the third row. The surgical hub 20076 may use environment sensor data to track movements by the surgeon as depicted in a fourth row. As shown, in the period before time t1, the surgeon may be moving in preparation for the procedure. The surgical hub 20076 may use usage data including accelerometer data from the advanced energy jaw device to derive values of motion for the advanced energy jaw device as depicted in the fifth row from the top. As shown, in the period before time t1, the advanced energy jaw device may be moving, which may indicate the device may be used in the procedure. The surgical hub 20076 may use usage data including accelerometer data from the endocutter to derive values for motion associated with the endocutter as depicted in the sixth row from the top. As shown, in the period before time t1, the endocutter may not be moving indicating it is not in use or intended for imminent use. The surgical hub 20076 may use the received data to determine the status of the endocutter as indicated in a seventh row. The surgical hub 20076 may determine whether the endocutter is being reloaded or whether it is being used by the surgeon.

In FIG. 20, the steps in the surgical procedure are depicted from left to right, moving from dissection to ligating the IMA branches, etc. The surgical hub 20076 may infer procedural steps, at least based on usage data received from surgical instruments. The surgical hub 20076 may infer that the surgeon is ligating arteries and veins, for example, based on receiving data from the advanced energy jaw device and/or the endocutter indicating that the instrument is being fired. The surgical hub may receive measurement data from one of the healthcare professional's sensing systems, from which the surgical hub may derive a stress level for the healthcare provider as indicated in the top row depicted in FIG. 20. A surgical hub 20076 may determine that a healthcare professional is experiencing a higher stress level by determining the data indicates a change in the healthcare professional's heart rate from a base value. The surgical hub 20076 may derive the inference of the ligate IMA step by cross-referencing the receipt of data from the surgical stapling and cutting instrument (e.g., as indicated by A2 and A3) with the retrieved steps in the known surgical process.

The surgical hub 20076 may determine which instruments are in use and/or which HCP has possession of the instruments, for example, based on determined correlation of position and/or movement data for one or more HCPs and one or more surgical instruments 20282. For brevity, FIG. 20 shows motion tracking data for a surgeon HCP, but not an assistant HCP, who may, for example, clean and reload surgical instruments while a surgeon utilizes another surgical instrument. It will be understood that the surgical hub 20076 may receive and process data for multiple individuals in the operating room and process the information consistent with data associated with the surgeon.

As shown in FIG. 20, two phases are shown during the ligate IMA step. A phase B is depicted between times t1 and t2, and a phase C is depicted between time t2 and t3. During the phase B of the ligate IMA step of the procedure, the surgical hub 20076 may determine that the motion associated with the endocutter, as noted at B1, and which may be determined based on one or more accelerometers in the endocutter, is similar to or correlates to the motion of the surgeon, as noted at B2, which may be determined based on one or more environmental sensors. The surgical hub 20076 may determine based on the similarity or correlation, that the surgeon is using the endocutter in phase B phase of the ligate IMA step. The status of being used by the surgeon is noted at B3 in the endocutter status row.

During the period between t1 and t2, corresponding to the time that the endocutter is in use, the surgical hub 20076 may determine from biomarker data that the stress of the surgeon is elevated as noted at B4. The surgical hub 20076 may react by communicating with the endocutter to reduce the clamp and fire speed as noted at B5. While advanced energy device may not be in use, the surgical hub 20076 may anticipate per the procedure that the advanced energy device will soon be used and may adjust the jaw trigger ratio as shown in the second row. The surgical hub 20076 may determine, based on the correlation(s) of position and/or movement data, information to communicate to the surgeon via the endocutter during phase B phase of the ligate IMA step. The endocutter may display the information received from the surgical hub 20076. The information displayed may relate to the procedural steps and actions that may be taken.

Between times t1 and t2, the surgical hub 20076 may determine that advanced energy device motion shown in the fifth row is similar to or correlates with surgeon motion. The correlation is noted by the dashed oval 22331. The surgical hub 20076 may determine, based on the correlation, that the surgeon is using the advanced energy device during phase C in the ligate IMA step of the surgical procedure. The surgical hub 20076 may determine based on received biomarker data that the surgeon is experiencing medium levels of stress. The surgical hub 20076 may determine, based on the procedural step and the medium stress level, to maintain the jaw trigger ratio at its existing value. The surgical hub 20076 may determine, based on the correlation(s) of position and/or movement data, information to communicate to the surgeon via the advanced energy device during phase C of the ligate IMA step. The advanced energy device may display the information received from the surgical hub 20076.

Referring to the endocutter status row, during phase C, as indicated by C2, the surgical hub 20076 may determine that motion detected for another HCP such as, for example, a back table nurse, may correlate with endocutter motion C1. The surgical hub 20076 may determine that correlated motion alone and/or in combination with contextual information such as the endocutter usage data may indicate that the back table nurse is cleaning and reloading the endocutter while, for example, the surgeon uses the advanced energy device during phase C. The surgical hub 20076 may determine, based on the correlation(s) of position and/or movement data, information to communicate to the back table nurse via the endocutter or a related display during phase C of the ligate IMA step. The endocutter and/or related display may display the information received from the surgical hub 20076.

The HCP(s) may progress to the free upper sigmoid step of the surgical procedure which begins at time t3. During the upper sigmoid step, which may be referred to as phase D, the surgical hub 20076 may determine that the surgeon motion, indicated by D2, correlates with the motion of the advanced energy device, which is indicated by D1. The surgical hub 20076 may determine, based on the correlation, that the surgeon is using the advanced energy device during phase D. The surgical hub 20076 may determine based on received sensor data that the surgeon may be experiencing elevated stress levels during performance of the free upper sigmoid step as noted at D3. The surgical hub 20076 may communicate with the advanced energy device to adjust the advanced energy jaw trigger ratio during phase D as indicated at D4. During periods when the surgeon is experiencing high stress, the surgical hub 20076 may lower the jaw trigger ratio and may return the ratio to a second level during periods that the surgeon is experiencing medium levels of stress. The surgical hub 20076 may determine, based on the correlation(s) of position and/or movement data, information to communicate to the surgeon via the advanced energy device during phase D. The advanced energy device and/or an associated display may display the information received from the surgical hub 20076.

The healthcare professionals may progress to the free descending colon and free rectum and sigmoid steps of the procedure. During the period between time t4 and t5, which may be referred to as phase E, the surgical hub 20076 may determine that the surgeon motion, indicated at E2, correlates with the motion of the endocutter, indicated at E1. As noted at E3, the surgical hub 20076 may determine, based on the correlation, that the surgeon is using the endocutter during phase E which may span portions of the free descending colon and free rectum and sigmoid steps. The surgical hub 20076 may determine, based on the correlation(s) of position and/or movement data, information to communicate to the surgeon via the endocutter during phase E. The endocutter and/or a display may display the information received from the surgical hub 20076.

The surgical hub 20076 may determine from biomarker data that during a first portion of phase E, that the surgeon is experiencing an elevated level of stress as noted at E4a. The surgical hub 20076 may address the elevated stress level by communicating with the endocutter to reduce the clamping and firing speed configuration as noted at E5a. During a second portion of phase E, the surgical hub 20076 may determine from received biomarker data that the surgeon stress level as further increased as noted at E4b. The surgical hub may address the elevated stress level by communicating with the endocutter to further reduce the clamping and firing speed as noted at E5b.

During phase F of the free rectum and sigmoid steps of the procedure, between time t6 and t7, the surgical hub 20076 may determine that endocutter motion F1 is not similar to surgeon motion, indicating the surgeon is not using the endocutter as noted in endocutter status row of FIG. 20. The surgical hub 20076 may determine that advanced energy device motion is similar to surgeon motion, as noted in FIG. 20 by dashed oval 22332, indicating the surgeon is using the advanced energy device in performing the free rectum and sigmoid steps of the procedure. For brevity, the advanced energy status is not shown in FIG. 20. The surgical hub 20076 may determine, based on the correlation(s) of position and/or movement data, information to communicate to the surgeon via the advanced energy device.

During phase F, as indicated by F2 in FIG. 20, the surgical hub 20076 may determine that motion detected for another HCP (e.g., a back table nurse) may correlate with endocutter motion F1. The surgical hub 20076 may determine that correlated motion alone and/or in combination with contextual information (e.g., endocutter usage data) indicate the back table nurse is cleaning and reloading the endocutter while the surgeon uses the advanced energy device. While the endocutter is being reloaded, the surgical hub 20076 may communicate with the endocutter to have the clamping and firing speed reset to an initial value as indicated at F3. The surgical hub 20076 may determine, based on the correlation(s) of position and/or movement data, information to communicate to the back table nurse via the endocutter during the F phase of the free rectum and sigmoid steps of the procedure. The endocutter may display the information received from the surgical hub 20076.

An HCP may progress to the resect transverse bowel step of the procedure, where the surgical hub 20076 may determine that the surgeon motion G2 between time t8 and t9 correlates with the motion of the endocutter G1, indicating the surgeon is using the endocutter as noted at G3. The surgical hub 20076 may (e.g., based on the correlation(s) of position and/or movement data) determine information to communicate to the surgeon via the endocutter and/or related display. The endocutter and/or display may display the information received from the surgical hub 20076. The surgical hub 20076 may determine, based on received biomarker data, stress levels for the surgeon during the process of resecting the transverse bowel. The surgical hub 20076 may determine that during the procedure the stress level of the surgeon may increase as noted at G4a and G4b. The surgical hub 20076 may communicate with the endocutter to adjust down the clamping and firing speed as noted at G5a and G5b. When the surgical hub 20076 determines the stress has returned to a low level, as shown at G4c, the speed of the endocutter returns to its initial values as shown at G5c.

As illustrated in FIG. 20, the surgical hub 20076 may determine and send (e.g., wirelessly communicate) information to a surgical device 20282 based on the determined correlation of position and/or motion of an HCP (e.g., based on biomarker and/or environmental data) and the surgical instrument 20282 (e.g., based on usage and/or motion data). Information determined (e.g., selected) for communication may be device-dependent, HCP-dependent, procedure-dependent, and/or procedural step-dependent. One or more surgical computing systems and/or surgical instruments may: determine instrument location, orientation, movement, and/or possession; receive sensed biomarker data, environmental data, and/or usage data; analyze received data; determine instrument information to communicate; communicate information, etc.

Instrument operation may be adjusted, for example, based on an assessment of the posture of a health care professional. A surgical computing system may receive biomarker data (e.g., from one or more sensing systems) associated with a healthcare professional operating a surgical instrument. The surgical computing system may receive usage data associated with user inputs from the surgical instrument. The surgical computing system may receive environmental data from one or more environmental sensing systems. The surgical computing system may determine an evaluation of body positioning of the healthcare professional, for example, based at least in part on the biomarker data, usage data, and/or environmental data. An evaluation of body positioning may include an evaluation of posture (e.g., body posture, arm posture, or wrist posture), balance, range of motion, and/or range of reach. The surgical computing system may determine one or more operational parameters for the surgical instrument based, for example, on the evaluation of body positioning of the healthcare professional. The surgical computing system may communicate the one or more operational parameters to the surgical instrument. Operational parameters may include, for example, parameters associated with one or more of the following: controls of the surgical instrument, stoke trigger points, an activation limit or a deactivation limit, and/or activating secondary controls. The surgical computing system may receive (e.g., from the surgical instrument) an indication to override one or more operational parameters.

Figure 21:
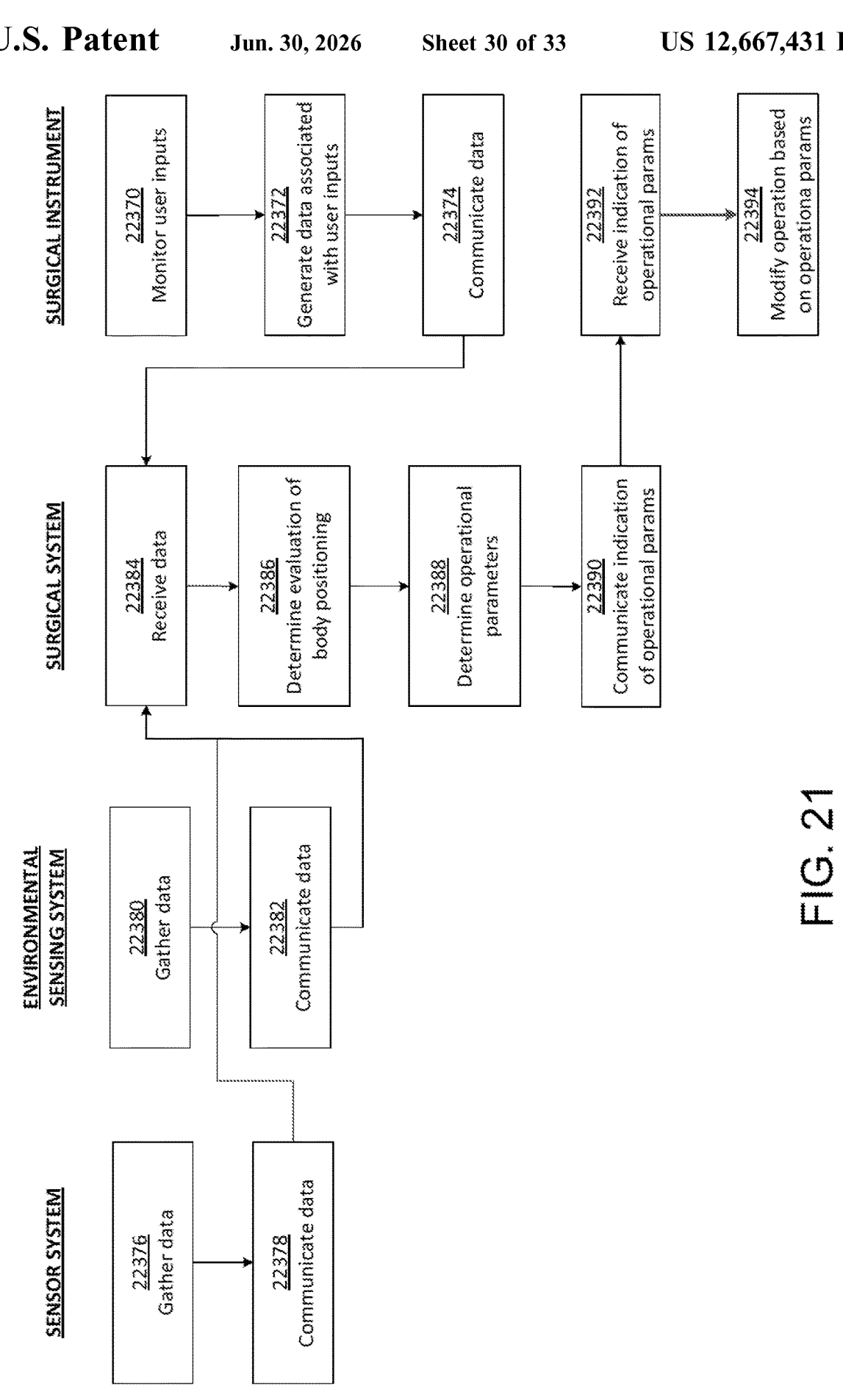
FIG. 21 illustrates example processing associated with determining operational parameters of a surgical instrument based on a determination of the positioning of a health care provider for a surgical task.

FIG. 21 illustrates example processing associated with determining operational parameters of a surgical instrument based on a determination of the positioning of a health care provider for a surgical task. FIGS. 21-24 illustrate examples of determining adjustment(s) to the operation and/or control of surgical instruments if/when an HCP using the surgical instruments exceeds one or more thresholds based on, for example, situational awareness data indicating the HCP's posture, reach, lift capacity, grip force capability, and/or other body mechanics and ergonomic limits, the position, motion and/or orientation of the surgical instruments. An HCP may be allocated a range of positions (e.g., for body, arm, wrist) between thresholds. Sensor data, environmental data, and/or instrument data, which may indicate HCP and/or instrument positioning, may be evaluated against one or more thresholds. Operational parameters of instruments may be determined, for example, based on exceeding and/or the magnitude of exceeding one or more thresholds.

Referring to FIG. 21, at 22370, a surgical instrument, which may be a surgical instrument 20282 (e.g., as described in connection with FIG. 10), may monitor user inputs to the surgical instrument. The surgical instrument 20282 may monitor user input associated with movement and positioning of the surgical instrument 20282. The surgical instrument 20282 may employ, for example, an acceleration sensor 150712 (e.g., as shown in FIG. 17B) to monitor the movement and positioning of the surgical instrument 20282. The surgical instrument 20282 may monitor the orientation of the surgical instrument 20282 and a length of time the surgical instrument 20282 is maintained in a particular position. The surgical instrument 20282 may monitor user inputs associated with operation of controls of the surgical instrument 20282. For example, the surgical instrument 20282 may monitor inputs associated with controlling the operation of jaws for clamping patient tissue. The surgical instrument 20282 may monitor, for example, the degree that a control trigger is pressed, the speed at which the trigger is pressed, and a length of time a trigger is held in a particular control position.

At 22372, the surgical instrument 20282 may generate usage data associated with the user inputs monitored and detected by the surgical instrument 20282 at 22110. The surgical instrument 20282 may generate usage data associated with the movement and positioning of the surgical instrument 20282 and/or associated with the user inputs associated with controlling operations of the surgical instrument 20282.

At 22374, the surgical instrument 20282 may communicate the usage data to a surgical computing system which may be, for example, a surgical hub 20006.

At 22376, data associated with the one or more healthcare professionals who operate the surgical instrument 20282 may (e.g., also) be gathered. Healthcare professionals operating the surgical instruments 20282 and/or who are in the area where the surgical procedure is being performed may have one or more sensing systems applied thereto. Sensing systems 20069, such as those described herein in connection with FIG. 6B, may be applied to the healthcare professionals to collect sensor data. The sensing systems 20069 may sense and gather sensor data, which may include biometric data such as, for example, data associated with heart rate, blood pressure, respiration, temperature, sweat rate, sweat composition, frequency of blinking, etc. The sensing systems 20069 may sense and gather sensor data associated with physical activity (e.g., movement) and/or lack thereof (e.g., static waits) of the healthcare professional alone and/or in the aggregate with other personnel, such as, for example, movement of the healthcare professional's arms (e.g., shoulders, elbows, wrists), hands, legs, feet, and/or torso.

At 22378, the surgical instrument 20282 may communicate the sensor data to the surgical computing system 20006.

At 22380, environmental data associated with one or more conditions or attributes in a surgical environment may be gathered and may be used to determine the importance of phases or steps in a surgical procedure. Conditions or attributes in a surgical environment may include, for example, one or more of a noise (e.g., ambient noise) level, HCP positions, HCP movements, HCP attention location, which may be based on eye tracking, such as location and/or time of view, and/or patient biomarker data, which may comprise patient biomarker notifications and/or alarms. One or more environmental sensing systems 20015 may be deployed in a surgical environment as part of a surgical monitoring system 20000 to collect environmental data. Environmental sensing systems 20015, such as those described herein in connection with FIG. 6B, may be activated to collect sensor data. The environmental sensing system(s) 20015 may include systems for measuring one more of the environmental attributes and may include, for example: cameras which may be configured to detect a surgeon's position, movements, and/or breathing pattern; spatial microphones which may be configured to measure ambient noise in the surgical theater and/or the tone of voice of a healthcare provider; and climate sensor(s) which may be configured to measure temperature and/or humidity of the surroundings. The environmental sensing systems 20015 may sense and gather environmental data, which may include data associated with, for example, the surgical environment, people in the surgical environment (e.g., healthcare professionals and patient), instruments in the surgical environment, etc. The environmental sensing systems 20015 may sense and gather sensor data associated with, for example, positions and/or movements of the healthcare professional (e.g., position and/or movement of the healthcare professional's arms, hands, legs, and/or torso) and/or movement of surgical instruments.

At 22382, the environmental sensing system 20015 may communicate the environmental sensor data to the surgical computing system 20006.

At 22384, the surgical computing system 20006 may receive the sensor data from the (e.g., personnel or wearable) sensing systems 20069, usage data from the surgical instrument(s) 20282, and/or environmental data from the environmental sensing system(s) 20015. For example, an HCP's wearable sensing system and/or an environmental sensing system may inform a surgical instrument 20082 and/or a surgical hub 20076 with sensor data and/or environmental data that may indicate the healthcare provider is exceeding one or more threshold limits of awkwardness, lack of balance, and/or over-extended reach. User body positioning (e.g., posture and balance precariousness) may be monitored, for example, to enable the surgical hub 20006 to compensate with operation and/or control adjustments for a surgical instrument 20282 to reduce or minimize the impact of awkward body positioning on the user.

At 22386, the surgical computing system 20006 may process the received usage data, sensor data, and/or environmental sensor data (e.g., data set(s)) and may evaluate the body positions of one or more HCPs based on the received data. The surgical computing system 20006 may be configured to determine body positions based on the indications from the sensor data, environmental data, and/or usage data regarding the surgical procedure and the healthcare professionals performing the surgical procedure. For example, the surgical computing system 20006, which may be, for example, a situationally aware surgical hub 20076 described in connection with FIG. 5, may process the sensor data from the personnel or wearable sensing systems 20069, usage data from the surgical instrument(s) 20282, and/or environmental data from the environmental sensing system(s) 20015 to determine HCP body positions which may comprise body positions relative to one or more surgical instruments. The surgical computing system 20006 may determine the position of one or more body parts for one or more HCPs, such as one or more of the following: head, face, body, chest, arms (e.g., shoulder, elbow, wrist), hands, legs (e.g., hips, knees, ankles), feet, etc. The surgical computing system 20006 may evaluate the determined positions of one or more body parts (e.g., alone or in combination) in comparison to one or more body thresholds Br and/or to other information, such as the time period one or more positions are held and/or out of range, the location, position, orientation, motion pertaining to one or more surgical instruments, the location, position, and/or motion of one or more HCPs, and/or the portion, step or phase of the surgical procedure. For example, an evaluation may assess body position relative to a body position range $B_{Trange}$ between body position thresholds Br. The surgical computing system 20006 may determine to make adjustments if/when a body (or a portion thereof) is out of a body position range $B_{Trange}$ in excess of a body position threshold Br. The center of a body position range $B_{Trange}$ may be a body position balance. An evaluation may assess arm (e.g., shoulder, elbow, wrist) position relative to an arm position range $A_{Trange}$ between arm position thresholds $A_T$. The surgical computing system 20006 may determine to make adjustments if/when an arm (e.g., or a portion thereof) is out of an arm position range $A_{Trange}$ in excess of an arm position threshold $A_T$. The center of an arm position range $A_{Trange}$ may be an arm position balance. An evaluation may be based on, for example, the surgical instrument determined to be in use (e.g., and by whom based on sensor and/or environmental data) during a determined stage of a surgical operation.

At 22388, the surgical computing system 20006 may determine one or more operational parameters for one or more surgical instruments based on the body position evaluation determined at 22386. The surgical computing system 20006 may be configured to determine (e.g., translate or map) the determined body position(s) (e.g., alone or relative to one or more surgical instruments) determined at 22386 to one or more operational parameters for one or more surgical instrument in use during the determined task. Surgical instrument operation and control may be adapted, for example, because body position and/or instrument position (e.g., momentary and over time) may impact fatigue, stress, balance, strength, range of motion, hand/arm reach and/or other capabilities of an HCP. Surgical hub 20006 and/or surgical instrument 20282 may determine (e.g., select and/or adjust) operational parameters, for example, to minimize inadvertent or unintentional actuation (e.g., activation, deactivation), incomplete strokes, bumping secondary controls, confusion due to inverted controls, and/or the like. In some examples, actuation (e.g., activation, deactivation) forces of a surgical instrument may be tracked and adjusted if/when a user (e.g., an HCP, such as a surgeon) is determined to be in an awkward position/orientation that may limit the user's capabilities. In some examples, the limits to activate and/or deactivate (e.g., engage and/or disengage) physical and/or virtual controls may be changed based on received position data. For example, surgical computing system 20006 and/or surgical instrument 20282 may complete control actuations that near the limits of the actuators range, and may implement wait times before activating opposing motions or deactivation trigger actuations to minimize the possibility of inadvertent micro-release causing unintended actions. A hub 20006 and/or surgical instrument 20282 may adjust instrument operation and/or control based on HCP body positioning, such as posture (e.g., body posture, arm posture, or wrist posture), balance, range of motion, range of reach (e.g., hand and/or arm reach), etc. Adjustment(s) may be applied to any suitable aspect of a surgical instrument including, for example: actuators, activation/deactivation positions, ranges, forces and/or stokes, and which controls are active/inactive including, for example, additional or alternative actuators such as a remote actuator.

The surgical hub 20006 and/or instrument 20282 may adjust operation parameters (e.g., stoke trigger points, an activation limit, a deactivation limit), activate/deactivate secondary controls, and/or adjust other operation and/or controls of the surgical instrument 20282 based, for example, on the HCP's compromised orientation/posture. Actuation controls in a surgical instrument 20282 such as, for example, a powered surgical stapler, may have hall effect sensors for monitoring a range (e.g., a full range) of actuator motion. Activation controls may have an "activation" stoke location and a "deactivation" stoke location on the actuator release action. Activation and deactivation stoke locations may be separate from each other, for example, to calibrate tolerance of the instrument control (e.g., to start and stop the motor uniformly/repeatably from one instrument to the next). Stokes trigger points may be adjusted to minimize stress on the user, for example, if the user is in awkward orientations with respect to the instrument control.

In some examples, the surgical hub 20006 and/or instrument 20282 may adjust the activation and deactivation limits of the controls for the surgical instrument 20282 independently, e.g., depending on the detected range-of-motion limits of the user being exceeded. For example, the hub 20006 and/or the surgical instrument 20282 may determine that the surgical instrument 20282 is at the limit of an HCP's arm reach. The hub 20006 and/or instrument 20282 may adjust (e.g., increase) the activation limit, for example, to minimize a false positive activation as may occur if the user inadvertently squeezed the trigger while extending reach to the control. The hub 20006 and/or the surgical instrument 20282 may (e.g., by contrast) adjust the "deactivation" limit to or near zero, for example, so that once the user has the actuator in motion, the actuator may continue to move until the user releases (e.g., fully releases) the trigger. The independent control of activation and deactivation may be based on one or more assumptions, which may be conditionally based on determined body positioning. For example, the hub 20006 and/or instrument 20282 may determine control of instrument 20282 based on an assumption that a user in one or more awkward body positions may inadvertently reduce pressure on the control over time and/or stop/pause, for example, due to fatigue of the spring load of the trigger during use.

The hub 20006 and/or instrument 20282 may control devices differently for similar body positioning. The control may be device specific. In some examples, the controls of a powered surgical instrument 20282 may be spring biased into the disengaged state and/or the stoke limit triggers for activation and deactivation may be adjustable. The amount of control displacement may be adjustable. The force to activate and/or deactivate the control may be adjustable. A user may be holding an endocutter in an inverted position relative to the user in order to get the correct angle of the end-effector to the transection site given the articulation and shaft rotation limitations. The endocutter may also be vertical to the patient due to the patient positioning on the table to get appropriate surgical site access. One or more sensing systems 20011 and/or environmental sensing systems 20015 that sense physical activity may indicate to the surgical hub 20006 and/or the endocutter that the HCP (e.g., surgeon) is at full arm reach with his/her hand upside down to the handle of the endocutter while leaning over the table and in a poorly balanced posture. The sensing systems 20011 and/or environmental sensing systems 20015 may communicate the ergonomic threshold limits to the hub 20006, which may communicate updated control algorithms to the endocutter. The updated control algorithms may reduce the force threshold on the actuators of the endocutter controls so that the HCP may pull the triggers with less force while at the limits of hand and/or arm reach. The updated control algorithms may create a larger delay between control actuation and actuator energizing, for example, to minimize inadvertent control actuation while the HCP may be in an extended or unbalanced state.

Operation and/or control adjustments for one or more actuator control algorithms for one or more surgical instruments may be based on general adjustments applicable to multiple HCPs and/or specific adjustments applicable to a specific HCP. Operation and control of surgical instruments 20282 may be situation-specific, device-specific and/or user-specific. For example, a surgical hub 20006 and/or surgical instrument 20282 may determine adjustments to instrument operation and/or controls (e.g., forces and strokes) based on the frame size or body type of the detected user. Adjustments for surgical instruments (e.g., based on position-based parameters) may be determined (e.g., selected) from user-specific categories based on one or more physical characteristics of HCPs, such as one or more of sex, age, height, weight, arm length, torso length, etc. Adjustment (e.g., of control loop) operation and/or controls of surgical instruments 20282 may be based on the situation-specific and/or user-specific unique needs of the user in the sensed situation.

A surgical computing system or hub 20006 and/or a surgical instrument 20282 may, in connection with determining operational parameters and based on body position data for a user, enable pairing or utilization of an additional and/or alternative actuator (e.g., a remote actuator) to operate the device in addition to or in place of the (e.g., built-in) actuator. A user may be unable, due to, for example, orientation and/or posture, to access one or more configured actuation controls, which may mean that adjusting the inaccessible controls may not assist the user. Additional and/or alternative controls may be (e.g., selectively) activated for a user, for example, based on user positional data. Additional and/or alternative controls may be on a surgical device 20282 and/or remote from the surgical device 20282. Additional and/or alternative controls may be dedicated and/or multipurpose controls, which may be selectable and/or pairable with one or more operations of a surgical device 20282.

At 22390, the surgical computing system 20006 may communicate an indication of the determined operational parameters to the surgical instrument 20282. The surgical computing system 20006 may be configured to communicate an indication to a surgical instrument 20282 determined to be in use during the determined task of the surgical procedure.

At 22392, the surgical instrument 20282 may receive the indication of the determined operational parameters. For example, an endocutter may receive operational parameters that reduce the force threshold on the actuators of the endocutter controls so that the HCP may pull the triggers with less force.

One or more operational parameters and/or adjustments thereto may be overridden via, for example, a surgical instrument 20282 and/or a surgical hub 20006. A healthcare professional may reject one or more operational parameters such as, for example, adjusted operational parameters, and the surgical instrument 20282 may indicate the user's override to the surgical hub 20076. A user may reject/override operational parameters generally and/or specifically. An override indication provided by a user to a surgical hub 20006 and/or surgical instrument 20282 may be, for example, verbal, gestural, manual, etc.

At 22394, the surgical instrument 20282 may, if the operational parameters are not overridden, modify operation based upon the received indication of the determined operational parameter(s). For example, an endocutter surgical instrument 20282 may reduce the force threshold on the actuators of the endocutter controls so the HCP may pull the triggers with less force.

The surgical computing system 20006 may receive instrument usage data, sensor data, and/or environmental data associated with numerous different surgical procedures and situations. The importance level, attention to task, and/or operational parameters determined by the surgical computing system 20006 may vary based on the received usage data, sensor data, and/or environmental data.

For example, with reference to the timeline 20265 for a surgical colorectal procedure shown in FIG. 2A, the surgical computing system 20006, which may be, for example, situationally aware surgical hub 20076 described in connection with FIG. 5, may receive data from various data sources throughout the course of the surgical procedure. The surgical hub 20076 may receive instrument usage data indicating instrument location, positioning and/or orientation, which may be generated each time an HCP utilizes a modular device/instrument 20095 that is paired with the surgical hub 20076. A modular device/instrument 20095 may be, for example, an advanced energy device and/or endocutter. The surgical hub 20076 may receive sensor data, which may be measurement data, from one or more surgeon sensing systems 20069 indicating body positioning associated with the surgeon. The surgical hub 20076 may receive environmental sensor data from one or more environmental sensing systems 20015 indicating body positioning associated with the surgeon. The body positioning data may be processed by the surgical hub 20076 to determine one or more operational and/or control adjustments for one or more surgical instruments 20095 during one or more phases or steps of a surgical procedure to compensate for determined body positioning of an HCP.

FIGS. 22A and 22B illustrate example body positioning of a health care provider in ergonomic range (FIG. 22A) and out of ergonomic range (FIG. 22B), respectively, while performing surgical tasks. FIGS. 22A and 22B show examples of a surgeon 25412 in a first operating room (OR) scene 22410A and a second OR scene 22410B. In the first OR scene 22410A, the surgeon 25412A is shown with body, arm, and wrist positions within ergonomic ranges. In the second OR scene 22410B, the surgeon 25412B is shown with body, arm, and wrist positions outside ergonomic ranges. One or more monitored body parts may be in or outside respective ergonomic ranges.

Referring to FIG. 22A, a surgeon 25412A, a first instrument 22420A, and a second instrument 22422A are shown in first positions, which are designated by A, which may indicate the surgeon 22412A is performing a first portion of a surgical procedure on the patient 22414 positioned on operating table 22416. The first body positions/orientations of the surgeon 22412A may be tracked, for example, by one or more wearable sensors 22417 on the body of the surgeon 22412A and/or one or more environmental sensors (e.g., cameras) 22418 in the OR. The first positions of the first surgical instrument 22420A and the second surgical instrument 22422A may be tracked, for example, by one or more sensors (e.g., accelerometers) on or in the first and second surgical instruments 22420A, 22422A and/or by one or more environmental sensors (e.g., cameras) 22418 in the OR. The first surgical instrument 22420A may comprise a passive surgical instrument without positioning/orientation sensors, such as a clamp, and the second surgical instrument 22422A may comprise a powered instrument with positioning/orientation sensors such as, for example, an endocutter. The second instrument 22422A may wirelessly communicate 22436A usage, position, and/or orientation data, for example, with a surgical computing system.

As shown in scene 22410A, the surgeon's body (e.g., torso) position (e.g., body angle or balance) 22426A, which may be tracked by one or more sensors, is within an ergonomic body position range 22424A. The ergonomic body position range 22424A is indicated as the area between ergonomic body positioning thresholds B-r. A surgical computing system 20006, which may be a situationally aware surgical hub 20076, may not adjust the operating parameters of the second surgical device 22422A based on a determination that the surgeon's body position 22426A is within the ergonomic body position range 22424A, which may be predefined (e.g., as a default and/or custom range).

The surgeon's arm position (e.g., arm angle) 22434A, which may be tracked by one or more sensors, is within an ergonomic arm position range 22432A. The ergonomic arm position range 22432A is indicated as the area between ergonomic arm positioning thresholds $A_{Tarm}$. A surgical computing system 20006, which may be a situationally aware surgical hub 20076, may not adjust the operating parameters of the second surgical device 22422A based on a determination that the surgeon's arm position 22434A is within the ergonomic arm position range 22432A, which may be predefined (e.g., as a default and/or custom range).

The surgeon's wrist position (e.g., wrist angle) 22430A, which may be tracked by one or more sensors, is within an ergonomic wrist position range 22428A. The ergonomic wrist position range 22428A is indicated as the area between ergonomic wrist positioning thresholds $A_{Twrist}$. A surgical computing system 20006 may not adjust the operating parameters of the second surgical device 22422A based on a determination that the surgeon's wrist position 22430A is within the ergonomic wrist position range 22428A, which may be predefined (e.g., as a default and/or custom range).

FIG. 22B shows an example of a second OR scene 22410B, where the surgeon 25412B, the first instrument 22420B, and the second instrument 22422B are in second positions designated B, which may indicate the surgeon 22412B is performing a second portion of a surgical procedure on the patient 22414 positioned on operating table 22416. The second body positions/orientations of the surgeon 22412B may be tracked, for example, by one or more wearable sensors 22417 on the body of the surgeon 22412B and/or one or more environmental sensors (e.g., cameras) 22418 in the OR. The second positions of the first surgical instrument 22420B and the second surgical instrument 22422B may be tracked, for example, by one or more sensors (e.g., accelerometers) on or in the first and second surgical instruments 22420B, 22422B and/or by one or more environmental sensors (e.g., cameras) 22418 in the OR. In an example, the first surgical instrument 22420B may comprise a passive surgical instrument without positioning/orientation sensors, such as a clamp, and the second surgical instrument 22422B may comprise a powered instrument with positioning/orientation sensors (e.g., an endocutter). The second instrument 22422B may wirelessly communicate 22436B usage, position, and/or orientation data, for example, with a surgical computing system (not shown).

As shown in the second OR scene 22410B, the surgeon's body (e.g., torso) position (e.g., body angle or balance) 22426B, which may be tracked by one or more sensors, may be outside an ergonomic body position range 22424B. The ergonomic body position range 22424B is indicated as the area between ergonomic body positioning thresholds Br. A surgical computing system 20006, which may be a situationally aware surgical hub 20076, may adjust the operating parameters of the second surgical device 22422B based on a determination that the surgeon's body position 22426B is outside the ergonomic body position range 22424B, which may be predefined (e.g., as a default and/or custom range).

As shown in the second OR scene 22410B, the surgeon's arm position (e.g., arm angle) 22434B, which may be tracked by one or more sensors, is outside an ergonomic arm position range 22432B. The ergonomic arm position range 22432B is indicated as the area between ergonomic arm positioning thresholds $A_{Tarm}$. A surgical computing system 20006, which may be a situationally aware surgical hub 20076, may adjust the operating parameters of the second surgical device 22422B based on a determination that the surgeon's arm position 22434B is outside the ergonomic arm position range 22432B, which may be predefined (e.g., as a default and/or custom range).

As shown in the second OR scene 22410B, the surgeon's wrist position (e.g., wrist angle) 22430B (e.g., as tracked by one or more sensors) is outside an ergonomic wrist position range 22428B. The ergonomic wrist position range 22428B is indicated as the area between ergonomic wrist positioning thresholds $A_{Twrist}$. A surgical computing system 20006 (e.g., a situationally aware surgical hub 20076) may (e.g., as described herein) adjust the operating parameters of the second surgical device 22422B based on a determination that the surgeon's wrist position 22430B is outside the ergonomic wrist position range 22428B, which may be predefined (e.g., as a default and/or custom range).

Figures 23A, 23B:
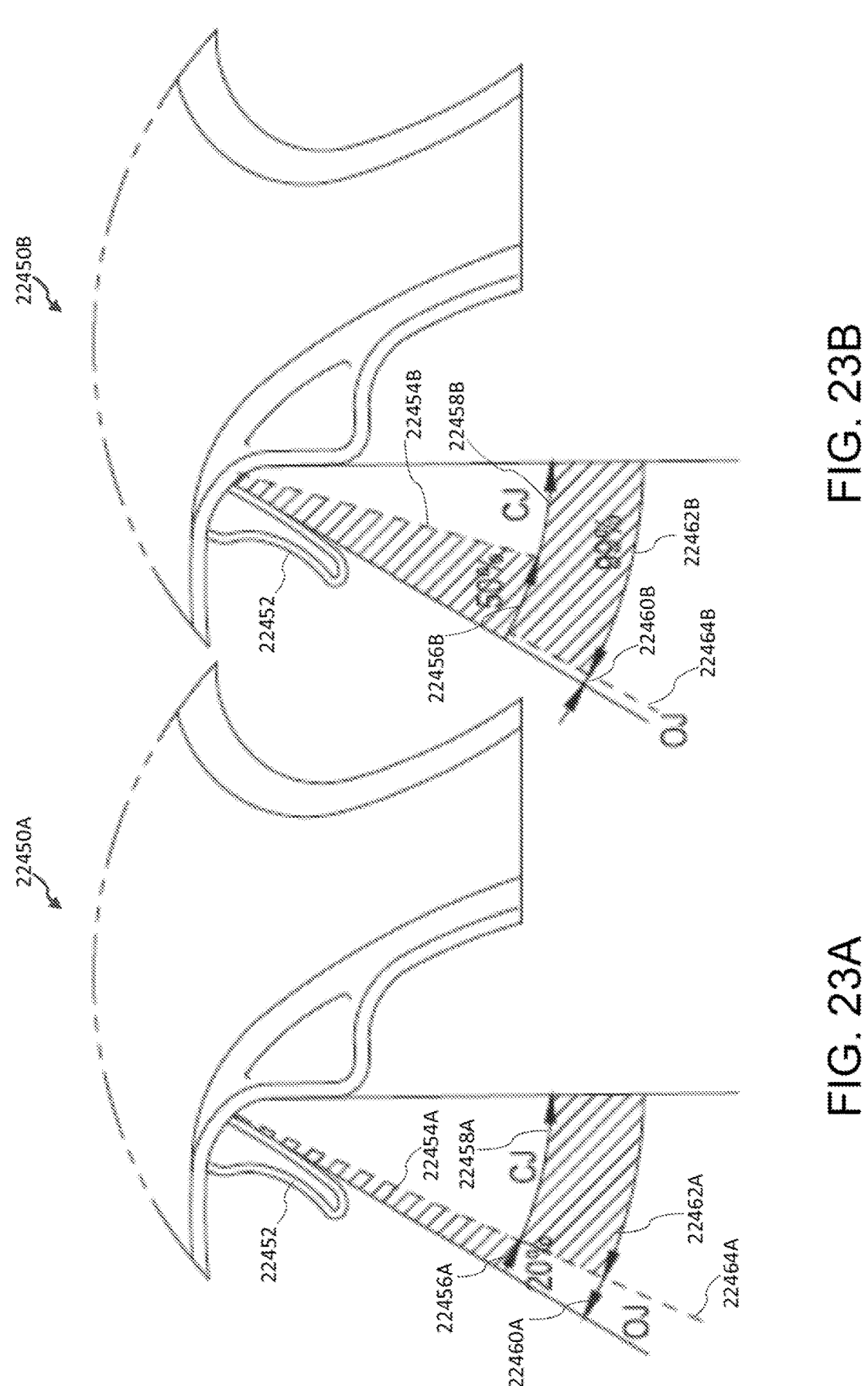
FIGS. 23A and 23B illustrate example adjustments to controls of a surgical instrument based on body positioning of a health care provider determined to be in ergonomic range and out of ergonomic range, respectively, while performing surgical tasks.

FIGS. 23A and 23B illustrate examples of determining adjustments to controls of a surgical instrument based on body positioning of a health care provider determined to be in ergonomic range and out of ergonomic range, respectively, while performing surgical tasks. FIG. 23A shows an example of an unadjusted (e.g., default or original) control parameter configuration of a surgical instrument and FIG. 23B shows an example of an adjusted (e.g., adapted) control parameter configuration of the surgical instrument. In the examples shown in FIGS. 23A and 23B, trigger activation and deactivation are independently controlled by automated adjustment based on determined body position/orientation and/or surgical device position/orientation. Trigger activation and deactivation may be dependently controlled by automated adjustment based on determined body position/orientation and/or surgical device position/orientation).

FIG. 23A shows an example of an unadjusted (e.g., default or original) trigger control parameter configuration 22450A of the second surgical instrument 22422A in the first OR scene 22410A shown in FIG. 22A, where the body position 22426A, arm position 22434A and wrist position 22430A of the surgeon 22412A are, respectively, within the ergonomic body position range 22424A, the ergonomic arm position range 22432A, and the ergonomic wrist position range 22428A.

As shown by example in the unadjusted control parameter configuration 22450A, a trigger 22452 for a surgical device, which may be, for example, an endocutter, may be configured (e.g., by control algorithm operating parameters) to close jaws (e.g., end effector 20289 jaws, such as a first jaw 20291 and a second jaw 20290) at a first jaw closure activation limit 22454A. As shown in FIG. 23A, the first jaw closure activation limit 22454A may be a 20% trigger stroke, where the jaws remain open during a first range 22456A (e.g., from 0% to 20% trigger stroke) and close in a second (close jaw (CJ) range 22458A (e.g., from 20% to 100% trigger stroke).

As shown by example in the unadjusted control parameter configuration 22450A, the trigger 22452 for the surgical device (e.g., an endocutter) may be configured (e.g., by control algorithm operating parameters) to open already closed jaws (e.g., end effector 20289 jaws, such as a first jaw 20291 and a second jaw 20290) at a first jaw closure deactivation limit 22464A. In an example (e.g., as shown in FIG. 23A), the first jaw closure deactivation limit 22464A may be a 20% trigger stroke, where the jaws remain closed during a first range 22462A (e.g., from 100% to 20% trigger stroke) and open in a second (open jaw (OJ) range 22460A (e.g., from 20% to 0% trigger stroke).

FIG. 23B shows an example of an adjusted (e.g., adapted) trigger control parameter configuration 22450B of the second surgical instrument 22422B in the second OR scene 22410B shown in FIG. 22B, where the body position 22426B, arm position 22434B and/or wrist position 22430B of the surgeon 22412B may be, respectively, outside the ergonomic body position range 22424B, the ergonomic arm position range 22432B, and the ergonomic wrist position range 22428B. A surgical computing system 20006, which may be a situationally aware surgical hub 20076, may adjust the operating parameters of the first surgical device 22422A (e.g., with the unadjusted trigger control parameter configuration 22450A) to the second surgical device 22422B (e.g., with the adjusted trigger control parameter configuration 22450B) based on a determination that the surgeon's body position 22426B, arm position 22434B, and/or wrist position 22430B is, respectively, outside the ergonomic body position range 22424B, the ergonomic arm position range 22432B, and/or the ergonomic wrist position range 22428B. The closure activation and/or closure deactivation limits may be adjusted, for example, to alleviate or compensate for limited capabilities of the surgeon 22412B in one or more awkward positions/orientations.

In the adjusted control parameter configuration 22450B, the trigger 22452 for the surgical device (e.g., an endocutter) may be configured (e.g., adjusted by control algorithm operating parameters) to close jaws (e.g., end effector 20289 jaws, such as a first jaw 20291 and a second jaw 20290) at a first jaw closure activation limit 22454B. In an example (e.g., as shown in FIG. 23B), the first adapted jaw closure activation limit 22454B may be a 50% trigger stroke, where the jaws remain open during a first adjusted range 22456B

(e.g., from 0% to 50% trigger stroke) and close in a second adjusted (close jaw (CJ)) range 22458B (e.g., from 50% to 100% trigger stroke). The closure activation limit may be adjusted (e.g., increased from 20% to 50%), for example, to minimize unintended/false positive activation when the surgeon's hand and/or arm position is/are extended out of range.

In the adjusted control parameter configuration 22450B, the trigger 22452 for the surgical device (e.g., an endocutter) may be configured (e.g., by control algorithm operating parameters) to open already closed jaws (e.g., end effector 20289 jaws, such as a first jaw 20291 and a second jaw 20290) at a first jaw closure deactivation limit 22464B. In an example (e.g., as shown in FIG. 23B), the first jaw closure deactivation limit 22464B may be a 1% trigger stroke, where the jaws remain closed during a first adjusted range 22462B (e.g., from 100% to 1% trigger stroke) and open in a second adjusted (open jaw (OJ) range 22460B (e.g., from 1% to 0% trigger stroke). The closure deactivation limit may be adjusted (e.g., decreased from 20% to 1%), for example, to account for the surgeon inadvertently releasing the trigger 22452 over time due to fatigue (e.g., in the surgeon's finger squeezing the trigger 22452).

Figure 24:
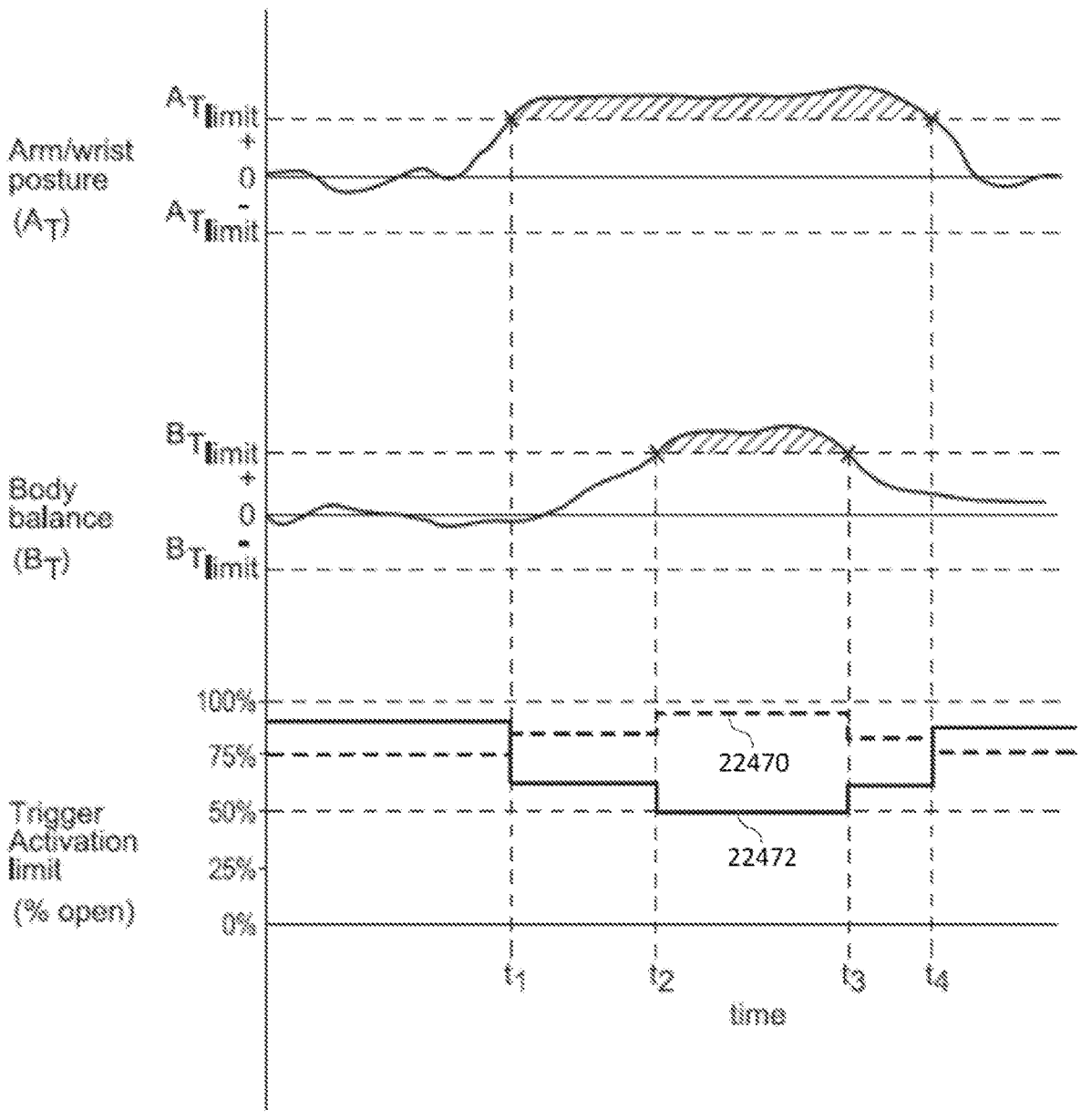
FIG. 24 illustrates example monitoring the body positioning of a health care provider performing surgical tasks with a surgical instrument and determining adjustments to operation or controls of the surgical instrument based on whether the body positioning is determined to be in ergonomic body positioning range.

FIG. 24 illustrates processing to modify operation controls of surgical instrument based on monitoring of body position and arm/wrist posture of a healthcare profession who is handling a surgical instrument. In the top portion of FIG. 24, a value representing arm/wrist posture of a healthcare professional is graphed across time. The healthcare professional may be handling a surgical instrument such as, for example, a surgical instrument 22422 as described in connection with FIGS. 22A, 22B, 23A, and 23B. Two thresholds are shown, a positive $A_{Tlimit}$ and a negative $A_{Tlimit}$, which together define an acceptable range for arm/wrist posture during a surgical procedure. The values representing the arm/wrist posture may be sensed by sensing systems and environment systems and communicated to a surgical computing system 20006.

A graph of a value representing the healthcare professional's body balance or posture across time is depicted below the arm/wrist posture data. Two thresholds are depicted, a positive $B_{Tlimit}$ and a negative $B_{Tlimit}$, which together define an acceptable range for the healthcare professional's body position while performing the surgical procedure. The values representing the body posture may be sensed by sensing systems and environment systems and communicated to a surgical computing system 20006.

Below the graph of the body balance is a graph of a trigger activation limit for jaw clamping and jaw unclamping across time that may be associated with the surgical instrument 22422 and its trigger 22452. The trigger activation limit is defined as a percentage of opening of the trigger, with zero percent corresponding to the trigger being fully closed and one hundred percent corresponding to the trigger being fully open. The trigger activation limit for jaw clamping is depicted by line 22472. The trigger activation limit for jaw unclamping is depicted by line 22740. The surgical computing system 20006 may determine to modify the jaw clamping and unclamping limits based upon the hand/wrist posture and body posture and whether they remain within defined thresholds.

As shown, in the time period before time t1, the arm/wrist posture is within the area defined by the thresholds $A_{Tlimit}$. The body balance is similarly within the values defined by the $B_{Tlimit}$ thresholds. Prior to time t1, the trigger activation limit for jaw clamping 22472 has a value between 75 percent open and 100 percent open. The trigger activation limit 22472 may be configured to activate (e.g., close endocutter jaws) at 90% open (e.g., 10% trigger stroke), for example, if/when the user's arm/wrist posture is within the ergonomic arm/wrist range and the user's body balance is within the ergonomic body balance range. The trigger activation limit for jaw unclamping 22470 has a value of approximately 75 percent open. The trigger deactivation limit 22470 may be configured to deactivate (e.g., open endocutter jaws) at 75% open (e.g., 25% trigger stroke), for example, if/when the user's arm/wrist posture is within the ergonomic arm/wrist range and the user's body balance is within the ergonomic body balance range.

Prior to the time t1, the arm/wrist posture value begins moving toward the upper limit $A_{Tlimit}$. At time t1, the value crosses over the $A_{Tlimit}$ threshold. The surgical computing system 20006 may monitor the arm/wrist posture and may determine, based on the arm/wrist posture exceeding threshold $A_{Tlimit}$, to modify the operation of the surgical instrument 22422. As shown, the surgical computing system 20006 may determine, at time t1, to reduce the trigger activation limit 22472 for jaw clamping from between 75 percent and 100 percent to between 50 percent and 75 percent. The trigger activation limit 22472 may be configured to activate (e.g., close endocutter jaws) at 60% open (e.g., 40% trigger stroke), for example, if/when the user's arm/wrist posture is outside the ergonomic arm/wrist range and the user's body balance is within the ergonomic body balance range.

The surgical computing system 20006 may determine to modify the trigger activation limit 22470 for jaw unclamping. As show, at time t1, the surgical computing system 20006 may determine to increase the jaw unclamping activation limit 22470 from 75 percent to between 75 percent and 100 percent. The trigger deactivation limit 22470 may be configured to deactivate (e.g., open endocutter jaws) at 85% open (e.g., 15% trigger stroke), for example, if/when the user's arm/wrist posture is outside the ergonomic arm/wrist range and the user's body balance is within the ergonomic body balance range.

The surgical computing system 20006 may communicate operational parameters corresponding to the modified limits to the surgical instrument 22422 which modifies its clamping and unclamping activation limits. Accordingly, in response to the healthcare professional assuming an arm/wrist posture that is outside the range considered ergonomically acceptable, the surgical computing system 20006 may adjust the operational parameters of the surgical instrument 22422 to accommodate the healthcare professional.

Between time t1 and t2, the posture of the healthcare professional's arm/wrist continues to exceed the $A_{Tlimit}$. The surgical computing system 20006 may maintain the modified trigger activation limits for the surgical instrument 22422. The surgical computing system 20006 may monitor the body posture and may determine, based on the body posture exceeding threshold $B_{Tlimit}$, to modify the operation of the surgical instrument 22422. As shown, the surgical computing system 20006 may determine, at time t2, to further reduce the trigger activation limit 22472 for jaw clamping from below 75 percent to 50 percent. The trigger activation limit 22472 may be configured to activate (e.g., close endocutter jaws) at 50% open (e.g., 50% trigger stroke), for example, if/when the user's arm/wrist posture is outside the ergonomic arm/wrist range and the user's body balance is outside the ergonomic body balance range.

The surgical computing system may determine to modify the trigger activation limit 22470 for jaw unclamping. As show, at time t1, the surgical computing system 20006 may determine to increase the jaw unclamping activation limit 22470 to approximately 99 percent. The trigger deactivation limit 22470 may be configured to deactivate (e.g., open endocutter jaws) at 99% open (e.g., 1% trigger stroke), for example, if/when the user's arm/wrist posture is outside the ergonomic arm/wrist range and the user's body balance is outside the ergonomic body balance range.

The surgical computing system 20006 may determine to communicate operational parameters to the surgical instrument 22422 so that trigger 22452 activates clamping or closure at 50 percent closure of the trigger 22452 and unclamping or release at 99 percent opening of the trigger 22452.

As shown in FIG. 24, at time t3, the body balance or posture of the healthcare professional may move below $B_{Tlimit}$ corresponding to the healthcare professional assuming a position that is more ergonomically correct. The surgical computing system 20006 may determine, at time t3, based on the data indicating improved posture, to modify operational parameters of the surgical instrument 22422 to increase the jaw clamping trigger activation limit 22472 to a value between 50 percent and seventy five percent. The surgical computing system 20006 may determine, based on the data indicating improved posture, to modify operational parameters of the surgical instrument 22422 to decrease the jaw unclamping limit 22470 to a value of 75 percent. The surgical computing system 20006 may determine to communicate operational parameters to the surgical instrument 22422 to modify the activation limits of the trigger 22452.

At time t4, the arm/wrist posture of the healthcare professional may move below $A_{Tlimit}$ corresponding to the arm/wrist of the healthcare professional assuming a posture that is more ergonomically sustainable. The surgical computing system 20006 may determine, at time t4, based on the data indicating improved arm/wrist posture, to modify operational parameters of the surgical instrument 22422 to restore the trigger activation limit for jaw clamping 22472 and jaw unclamping 22470 to their initial values. The surgical computing system 20006 may communicate the operational parameters to the surgical instrument 22422 which may implement the modifications.

Accordingly, systems and techniques are disclosed for adaptively adjusting operation and/or control of a surgical instrument and/or adaptively communicating information to a healthcare professional (e.g., surgeon, assistant). Adaptation of operation, control and/or communication may be based on, for example, situational awareness (e.g., of a surgical procedure). Situational awareness may include, for example, an importance level (e.g., a stress level) of a health care provider, possession of a controllable surgical instrument by a health care provider, and/or body positioning of a health care provider. Situational awareness may be determined, for example, based on information provided by one or more personnel (e.g., wearable) sensing systems, environmental sensing systems, and/or surgical instruments, such as one or more of healthcare provider data (e.g., position, posture, balance, motion, attention, physiologic states), environmental data (e.g., operating room noise level, patient data, healthcare provider data), and/or surgical instrument data (e.g., position, possession, motion, and/or usage). A surgical computing system (e.g., a hub) and/or a surgical instrument may receive (e.g., sensed) information, determine situational awareness and adapt instrument operation, control and/or information communication based on situational awareness.

The invention claimed is:

1. A surgical computing system comprising:

a processor configured to:

receive biomarker data from one or more sensing systems, the biomarker data associated with a healthcare professional operating a surgical instrument during a surgical procedure in an operating room;

determine, based at least in part on the biomarker data, an importance level associated with a task during the surgical procedure;

receive usage data associated with user inputs to the surgical instrument;

receive environmental data from one or more environmental sensing systems, the environmental data associated with environmental characteristics in the operating room;

determine, based at least in part on the biomarker data, usage data, and environmental data, an evaluation of body positioning of the healthcare professional and positioning of the surgical instrument, the evaluation of body positioning of the healthcare professional and positioning of the surgical instrument indicating the surgical instrument is at a limit of an arm reach of the healthcare professional;

determine, based on the evaluation of the body positioning of the healthcare professional and positioning of the surgical instrument indicating the surgical instrument is at a limit of an arm reach of the healthcare professional, one or more operational parameters for the surgical instrument, the one or more operational parameters comprising adjusted activation limits and deactivation limits of the surgical instrument; and communicate the one or more operational parameters to the surgical instrument, causing the adjusted activation limits and deactivation limits to be implemented in the surgical instrument.

2. The surgical computing system of claim 1, wherein the biomarker data is associated with one or more of heart rate, blood pressure, sweat, physical activity, body movement, or eye movement.

3. The surgical computing system of claim 1, wherein the processor configured to determine an importance level is configured to determine an importance level based at least in part on the environmental data and the biomarker data.

4. The surgical computing system of claim 3, wherein the environmental data is associated with one or more of noise level, healthcare professional attention location, or patient biomarkers.

5. The surgical computing system of claim 3, wherein the processor configured to determine an importance level is configured to determine an importance level based at least in part on the environmental data, the biomarker data, and data associated with steps of surgical procedures.

6. The surgical computing system of claim 5, wherein the processor configured to determine an importance level based at least in part on the environmental data, the biomarker data, and data associated with steps of surgical procedures is configured to determine for a step in a surgical procedure whether the biomarker data is within an expected range.

7. The surgical computing system of claim 6, wherein the processor is further configured to:

if the biomarker data is outside the expected range, determine to modify the one or more operational parameters.

8. The surgical computing system of claim 3, wherein the environmental data comprises data associated with eye tracking of the healthcare professional.

9. The surgical computing system of claim 8, wherein the data associated with eye tracking of the healthcare professional comprises data associated with at least one of location of attention or time of attention.

10. The surgical computing system of claim 8, wherein the processor is further configured to:

determine a task associated with attention of the healthcare professional; and determine based on the task operational parameters for the surgical instrument.

11. The surgical computing system of claim 1, wherein the evaluation of body positioning of the healthcare professional comprises an evaluation of at least one of posture or balance, and wherein the one or more operational parameters comprise parameters associated with at least one of: controls of the surgical instrument; stoke trigger points; an activation limit or a deactivation limit; or activating secondary controls.

* * * * *